US009241917B2

(12) United States Patent
DeGrado et al.

(10) Patent No.: US 9,241,917 B2
(45) Date of Patent: *Jan. 26, 2016

(54) FACIALLY AMPHIPHILIC POLYMERS AND OLIGOMERS AND USES THEREOF

(75) Inventors: William F. DeGrado, Moylan, PA (US); Gregory N. Tew, Amherst, MA (US); Michael L. Klein, Ocean City, NJ (US); Dahui Liu, Wynnewood, PA (US); Jing Yuan, Lansdale, PA (US); Sungwook Choi, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 274 days.

This patent is subject to a terminal disclaimer.

(21) Appl. No.: 10/801,951

(22) Filed: Mar. 17, 2004

(65) Prior Publication Data

US 2006/0041023 A1  Feb. 23, 2006

Related U.S. Application Data

(60) Provisional application No. 60/455,479, filed on Mar. 17, 2003, provisional application No. 60/530,630, filed on Dec. 19, 2003, provisional application No. 60/536,980, filed on Jan. 20, 2004.

(51) Int. Cl.
| | |
|---|---|
| *C08G 18/00* | (2006.01) |
| *A61K 31/16* | (2006.01) |
| *A61K 31/165* | (2006.01) |
| *A61K 31/495* | (2006.01) |
| *C07C 233/64* | (2006.01) |
| *C07C 323/42* | (2006.01) |
| *C07C 323/44* | (2006.01) |
| *C08G 18/32* | (2006.01) |
| *C08G 73/02* | (2006.01) |
| *C08L 75/02* | (2006.01) |

(52) U.S. Cl.
CPC ............... *A61K 31/16* (2013.01); *A61K 31/165* (2013.01); *A61K 31/495* (2013.01); *C07C 233/64* (2013.01); *C07C 323/42* (2013.01); *C07C 323/44* (2013.01); *C08G 18/3225* (2013.01); *C08G 73/028* (2013.01); *C08L 75/02* (2013.01)

(58) Field of Classification Search
CPC ...................................... C08G 18/00
USPC ......................... 528/322; 424/422
See application file for complete search history.

(56) References Cited

U.S. PATENT DOCUMENTS

| | | |
|---|---|---|
| 3,409,662 A | 11/1968 | Larsen |
| 3,444,156 A | 5/1969 | de Montmollin et al. |
| 3,484,407 A | 12/1969 | Preston |
| 3,829,563 A | 8/1974 | Barry et al. |
| 4,038,416 A | 7/1977 | Mori et al. |
| 4,118,232 A | 10/1978 | Piller et al. |
| 4,252,951 A | 2/1981 | Jackson et al. |
| 4,343,788 A | 8/1982 | Mustacich et al. |
| 4,392,848 A | 7/1983 | Lucas et al. |
| 4,508,639 A | 4/1985 | Camps et al. |
| 4,515,910 A | 5/1985 | Rawls et al. |
| 4,762,899 A | 8/1988 | Shikinami |
| 4,826,829 A | 5/1989 | Eurkart et al. |
| 4,847,353 A | 7/1989 | Watanabe |
| 4,943,624 A | 7/1990 | Regen |
| 5,021,311 A | 6/1991 | Kato et al. |
| 5,071,648 A | 12/1991 | Rosenblatt |
| 5,073,564 A | 12/1991 | Roush et al. |
| 5,077,281 A | 12/1991 | Reinmüller |
| 5,219,965 A | 6/1993 | Valint, Jr. et al. |
| 5,520,910 A | 5/1996 | Hashimoto et al. |
| 5,543,448 A | 8/1996 | Laughner |
| 5,648,070 A | 7/1997 | Brian, III et al. |
| 5,847,047 A | 12/1998 | Haynie |
| 5,856,245 A | 1/1999 | Caldwell et al. |
| 5,874,164 A | 2/1999 | Caldwell |
| 5,912,116 A | 6/1999 | Caldwell |
| 5,967,714 A | 10/1999 | Ottersbach et al. |
| 5,989,295 A | 11/1999 | de la Mettrie et al. |
| 5,994,340 A | 11/1999 | Maiti et al. |
| 6,034,129 A | 3/2000 | Mandeville, III et al. |
| 6,040,251 A | 3/2000 | Caldwell |
| 6,083,602 A | 7/2000 | Caldwell et al. |
| 6,107,397 A | 8/2000 | Blankenburg et al. |
| 6,121,255 A | 9/2000 | Hwu et al. |
| 6,166,172 A | 12/2000 | McCullough et al. |
| 6,290,973 B1 | 9/2001 | Hawkins et al. |
| 6,309,633 B1 | 10/2001 | Ekwuribe et al. |

(Continued)

FOREIGN PATENT DOCUMENTS

| | | |
|---|---|---|
| CH | 520 657 A | 3/1972 |
| CH | 525 898 A | 7/1972 |

(Continued)

OTHER PUBLICATIONS

Patent Abstracts of Japan, English language abstract of JP 63-108019 A.

(Continued)

*Primary Examiner* — Yong Chong

(74) *Attorney, Agent, or Firm* — Sterne, Kessler, Goldstein & Fox PLLC

(57) ABSTRACT

The present invention discloses methods of use of facially amphiphilic polymers and oligomers, including pharmaceutical uses of the polymers and oligomers as antimicrobial agents and antidotes for hemorrhagic complications associated with heparin therapy. The present invention also discloses novel facially amphiphilic polymers and oligomers and their compositions, including pharmaceutical compositions. The present invention further discloses the design and synthesis of facially amphiphilic polymers and oligomers.

44 Claims, 21 Drawing Sheets

(56) References Cited

U.S. PATENT DOCUMENTS

| | | |
|---|---|---|
| 6,399,629 B1 | 6/2002 | Chamberland et al. |
| 6,537,961 B1 | 3/2003 | Koch |
| 6,552,142 B1 | 4/2003 | Meffert et al. |
| 6,686,345 B2 | 2/2004 | Kerwin et al. |
| 6,878,387 B1 | 4/2005 | Petereit et al. |
| 7,173,102 B2 * | 2/2007 | DeGrado et al. ............. 528/322 |
| 7,332,623 B2 | 2/2008 | Wu et al. |
| 7,378,479 B2 | 5/2008 | Tamareselvy et al. |
| 7,465,820 B2 | 12/2008 | Cunsolo et al. |
| 7,553,876 B2 | 6/2009 | Shaker |
| 7,590,517 B2 | 9/2009 | Doerksen et al. |
| 7,745,662 B2 | 6/2010 | Shaker |
| 7,781,498 B2 | 8/2010 | Krishnan |
| 8,129,566 B2 | 3/2012 | Mousa et al. |
| 8,222,456 B2 | 7/2012 | DeGrado et al. |
| 8,232,428 B2 | 7/2012 | Mousa et al. |
| 8,236,800 B2 | 8/2012 | DeGrado et al. |
| 8,455,490 B2 | 6/2013 | DeGrado et al. |
| 8,507,723 B2 | 8/2013 | Mousa et al. |
| 8,716,530 B2 | 5/2014 | DeGrado et al. |
| 2001/0044459 A1 | 11/2001 | Jackson et al. |
| 2003/0130454 A1 | 7/2003 | Seya et al. |
| 2004/0102941 A1 | 5/2004 | Lopez et al. |
| 2004/0107056 A1 | 6/2004 | Doerksen et al. |
| 2004/0185257 A1 | 9/2004 | DeGrado et al. |
| 2004/0202639 A1 | 10/2004 | DeGrado et al. |
| 2005/0004211 A1 | 1/2005 | Wu et al. |
| 2006/0024264 A1 | 2/2006 | Kuroda et al. |
| 2006/0241052 A1 | 10/2006 | DeGrado et al. |
| 2007/0173752 A1 | 7/2007 | Schonfeldt |
| 2012/0202887 A1 | 8/2012 | DeGrado et al. |

FOREIGN PATENT DOCUMENTS

| | | |
|---|---|---|
| CN | 1181926 A | 5/1998 |
| CN | 1270625 A | 10/2000 |
| CN | 1335303 A | 2/2002 |
| EP | 0 230 539 A2 | 8/1987 |
| GB | 1 324 087 A | 7/1973 |
| GB | 1 566 512 A | 4/1980 |
| GB | 2 188 585 A | 10/1987 |
| JP | 52-034935 A | 3/1977 |
| JP | 52-085133 A | 7/1977 |
| JP | 56-123903 A | 9/1981 |
| JP | 59-177558 U | 11/1984 |
| JP | 63-108019 A | 5/1988 |
| JP | 02-029436 A | 1/1990 |
| JP | 63-22067 A | 11/1994 |
| JP | 7-2808 A | 1/1995 |
| JP | 10-505592 T | 6/1998 |
| JP | 11152329 | 6/1999 |
| JP | 2001-133975 A | 5/2001 |
| JP | 2002-363261 A | 12/2002 |
| JP | 2003-165805 A | 6/2003 |
| JP | 2004-168802 A | 6/2004 |
| JP | 2004-323688 A | 11/2004 |
| JP | 2005-507953 A1 | 3/2005 |
| JP | 2007-516741 A1 | 6/2007 |
| WO | WO 87/01591 A2 | 3/1987 |
| WO | WO 90/04401 | 5/1990 |
| WO | WO 93/14146 A1 | 7/1993 |
| WO | WO 95/00547 | 1/1995 |
| WO | WO 95/19974 A2 | 7/1995 |
| WO | WO 96/09285 | 3/1996 |
| WO | WO 97/29160 | 8/1997 |
| WO | WO 97/49413 | 12/1997 |
| WO | WO 98/17625 A1 | 4/1998 |
| WO | WO 99/48461 | 9/1999 |
| WO | WO 00/37541 A1 | 6/2000 |
| WO | WO 00/44348 A2 | 8/2000 |
| WO | WO 00/69937 A1 | 11/2000 |
| WO | WO 01/51456 A2 | 7/2001 |
| WO | WO 01/055085 A1 | 8/2001 |
| WO | WO 01/72715 A2 | 10/2001 |
| WO | WO 02/072007 | 9/2002 |
| WO | WO 02/095044 A2 | 11/2002 |
| WO | WO 02/100295 | 12/2002 |
| WO | WO 03/009807 A2 | 2/2003 |
| WO | WO 2004/014903 A1 | 2/2004 |
| WO | WO 2004/026958 A1 | 4/2004 |
| WO | WO 2004/082634 | 9/2004 |
| WO | WO 2005/028422 A1 | 3/2005 |
| WO | WO 2005/072246 A2 | 8/2005 |
| WO | WO 2005/123660 A2 | 12/2005 |
| WO | WO 2006/042104 A2 | 4/2006 |
| WO | WO 2006/093813 A2 | 9/2006 |
| WO | WO 2006/132647 A2 | 12/2006 |

OTHER PUBLICATIONS

Patent Abstracts of Japan, English language abstract of JP 2003-165805 A.

Patent Abstracts of Japan, English language abstract of JP 2004-168802 A.

Patent Abstracts of Japan, English language abstract of JP 2004-323688 A.

Office Action for U.S. Appl. No. 10/471,028, DeGrado, W., et al., filed May 11, 2004 (35 U.S.C. § 371(c) date), mailed Oct. 11, 2005.

Final Office Action for U.S. Appl. No. 10/471,028, DeGrado, W., et al., filed May 11, 2004 (35 U.S.C. § 371(c) date), mailed May 8, 2006.

Co-pending U.S. Appl. No. 11/361,050, DeGrado, W., et al., filed Feb. 24, 2006 (Not Published).

Andersen, J.H., et al., "Lactoferrin and cyclic lactoferricin inhibit the entry of human cytomegalovirus into human fibroblasts," *Antiviral Res.* 51:141-149, Elsevier (2001).

Barany, G., et al., "Solid-phase peptide synthesis: a silver anniversary report," *Int. J. Pept. Protein Res.* 30:705-739, Munksgaard International Publishers (1987).

Barron, A.E., and Zuckerman, R.N., "Bioinspired polymeric materials: in-between proteins and plastics," *Curr. Opin. Chem. Biol.* 3:681-687, Current Biology Ltd. (1999).

Bastian, A., and Schafer, H., "Human α-defensin 1 (HNP-1) inhibits adenoviral infection in vitro," *Regul. Pept.* 101:157-161, Elsevier (2001).

Belaid, A., et al., "In Vitro Antiviral Activity of Dermaseptins Against Herpes Simplex Virus Type 1," *J. Med. Virol.* 66:229-234, Wiley-Liss (Feb. 2002).

Bjørnholm, T., et al., "Self-Assembly of Regioregular, Amphiphilic Polythiophenes into Highly Ordered π-Stacked Conjugated Polymer Thin Films and Nanocircuits," *J. Am. Chem. Soc.* 120:7643-7644, American Chemical Society (1998).

Boman, H.G., "Innate immunity and the normal microflora," *Immunol. Rev.* 173:5-16, Munksgaard International Publishers (2000).

Boman, H.G., et al., "Cell-free immunity in Cecropia. A model system for antibacterial proteins," *Eur. J. Biochem.* 201:23-31, Blackwell Science Ltd. (1991).

Bradley, J.S., and Scheld, W.M., "The Challenge of Penicillin-Resistant *Streptococcus pneumoniae* Meningitis: Current Antibiotic Therapy in the 1990s," *Clin. Infect. Dis.* 24 (Suppl. 2):S213-221, University of Chicago Press (1997).

Broekaert, W.F., et at, "An automated quantitative assay for fungal growth inhibition," *FEMS Microbiol. Lett.* 69:55-60, Elsevier (1990).

Butler, J.C., et al., "The Continued Emergence of Drug-Resistant *Streptococcus pneumoniae* in the United States: An Update from the Centers for Disease Control and Prevention's Pneumococcal Sentinel Surveillance System," *J. Infect. Dis.* 174:986-993, University of Chicago Press (1996).

Chen, J., et al., "Development of Protegrins for the Treatment and Prevention of Oral Mucositis: Structure-Activity Relationships of Synthetic Protegrin Analogues," *Biopolymers* 55:88-98, Wiley Interscience (2000).

Cole, A.M., et al., "Retrocyclin: A primate peptide that protects cells from infection by T-and M-tropic strains of HIV-1," *Proc. Natl. Acad. Sci USA* 99:1813-1818, National Academy of Sciences (Feb. 2002).

Debono, M., and Gordee, R.S., "Antibiotics that Inhibit Fungal Cell Wall Development," *Annu. Rev. Microbiol.* 48:471-497, Annual Reviews (1994).

(56) References Cited

OTHER PUBLICATIONS

DeGrado, W.F., "Design of Peptides and Proteins," in *Advances in Protein Chemistry*, vol. 39, Anfinsen, C.B., et al., eds., Academic Press, Inc., San Diego, CA, pp. 51-124 (1988).

DeGrado, W.F., et al., "Design, Synthesis, and Characterization of a Cytotoxic Peptide with Melittin-Like Activity," *J. Amer. Chem. Soc.* 103:679-681, American Chemical Society (1981).

DeGrado, W.F., et al, "Kinetics and Mechanism of Hemolysis Induced by Melittin and by a Synthetic Melittin Analogue," *Biophys. J.* 37:329-338, Rockefeller University Press (1982).

DeLucca, A.J., and Walsh, T.J., "Antifungal Peptides: Novel Therapeutic Compounds against Emerging Pathogens," *Antimicrob. Agents Chemother.* 43:1-11, American Society for Microbiology (1999).

Dempsey, C.E., "The actions of melittin on membranes," *Biochim. Biophys. Acta* 1031:143-161, Elsevier (1990).

Diness, V., and Østergaard, P.B., "Neutralization of a Low Molecular Weight Heparin (LHN-1) and Conventional Heparin by Protamine Sulfate in Rats," *Thromb. Haemost.* 56:3:8-322, Schutteuer (1986).

Edwards, J.R., et al., "In Vitro Antibacterial Activity of SM-7338, a Carbapenem Antibiotic with Stability to Dehydropeptidase I," *Antimicrob. Agents Chemother.* 33:215-222, American Society for Microbiology (1989).

Egal, M., et al., "Antiviral effects of synthetic membrane-active peptides on Herpes Simplex Virus, Type 1," *Int. J. Antimicrob. Agents* 13:57-60, Elsevier (1999).

Ganz, T., et al., "Defensins," *Eur. J. Haematol.* 44:1-8, Munksgaard (1990).

Ganz, T., et al., "Defensins. Natural Peptide Antibiotics of Human Neutrophils," *J. Clin. Invest.* 76:1427-1435, American Society for Clinical Investigation (1985).

Gazit, E., et al., "Interaction of the Mammalian Antibacterial Peptide Cecropin P1 with Phospholipid Vesicles," *Biochemistry* 34:11479-11488, American Chemical Society (1995).

Gellman, S.H., "Foldamers: A Manifesto," *Acc. Chem. Res.* 31:173-180, American Chemical Society (1998).

Gennaro, R., and Zanetti, M., "Structural Features and Biological Activities of the Cathelicidin-Derived Antimicrobial Peptides," *Biopolymers* 55:31-49, Wiley Interscience (2000).

Hamuro, Y., et al., "De Novo Design of Antibacterial β-Peptides," *J. Am. Chem. Soc.* 121:12200-12201, American Chemical Society (1999).

Hamuro, Y., et al., "Novel Folding Patterns in a Family of Oligoanthranilamides: Non-Peptide Oligomers That Form Extended Helical Secondary Structures," *J. Am. Chem. Soc.* 119:10587-10593, American Chemical Society (1997).

Hancock, R.E.W., and Lehrer, R., "Cationic peptides: a new source of antibiotics," *Trends Biotechnol.* 16:82-88, Elsevier Science Publishers B.V. (1998).

Haynie, S.L., et al., "Antimicrobial Activities of Amphiphilic Peptides Covalently Bonded to a Water-Insoluble Resin," *Antimicrob. Agents Chemother.* 39:301-307, American Society for Microbiology (1995).

Hiramatsu, K., et al., "Methicillin-resistant *Staphylococcus aureus* clinical strain with reduced vancomycin susceptibility," *J. Antimicrob. Chemother.* 40:135-136, Oxford University Press (1997).

Hirsh, J., and Levine, M.N., "Low Molecular Weight Heparin," *Blood* 79:1-17, American Society of Hematology (1992).

Javadpour, M.M., et al., "De Novo Antimicrobial Peptides with Low Mammalian Cell Toxicity," *J. Med. Chem.* 39:3107-3113, American Chemical Society (1996).

Kandrotas, R.J., "Heparin Pharmacokinetics and Pharmacodynamics," *Clin. Pharmacokinet.* 22:359-374, Adis Intrnational Ltd. (1992).

Landon, C., et al., "Solution structure of drosomycin, the first inducible antifungal protein from insects," *Protein Sci.* 6:1878-1884, Cambridge University Press (1997).

Liu, D. et al., "Nontoxic Membrane-Active Antimicrobial Arylamide Oligomers," *Angew. Chem. Mt. Ed. Engl.* 43:1158-1162, Verlag Chemie (Feb. 2004).

Liu, D., and DeGrado, W.F., "De Novo Design, Synthesis, and Characterization of Antimicrobial β-Peptides," *J. Amer. Chem. Soc.* 123:7553-7559, American Chemical Society (2001).

Lyytikäinen, O., et al., "Outbreak caused by two multi-resistant Acinetobacter baumannii clones in a burns unit: emergence of resistance to imipenem," *J. Hosp. Infect.* 31:41-54, W.B. Saunders (1995).

Maloy, W.L., and Kari, U.P., "Structure-Activity Studies on Magainins and Other Host Defense Peptides," *Biopolymers* 37:105-122, Wiley (1995).

Margel, S., et al., "Peptide, protein, and cellular interactions with self-assembled monolayer model surfaces," *J. Biomed. Mater. Res.* 27:1463-1476, Wiley Interscience (1993).

Merrifield, E.L., et al., "D-Enantiomers of 15-residue cecropin A-melittin hybrids," *Int. J. Pept. Protein Res.* 46:214-220, Munksgaard International Publishers (1995).

Merrifield, R.B., et al., "Design and synthesis of antimicrobial peptides," *Ciba Found. Symp.* 186:5-26, Wiley (1994).

Merrifield, R.B., et al., "Retro and retroenantio analogs of cecropin-melittin hybrids," *Proc. Natl. Acad. Sci. USA* 92:3449-3453, National Academy of Sciences (1995).

Montecalvo, M.A., et al., "Outbreak of Vancomycin-, Ampicillin-, and Aminoglycoside-Resistant *Enterococcus faecium* Bacteremia in an Adult Oncology Unit," *Antimicro. Agents Chemother.* 38:1363-1367, American Society for Microbiology (1994).

Oren, Z., and Shai, Y., "Mode of Action of Linear Amphipathic α-Helical Antimicrobial Peptides," *Biopolymers* 47:451-463, Wiley Interscience (1998).

Peggion, E., et al., "Conformation and Interactions of Bioactive Peptides from Insect Venoms: The Bombolitins," *Biopolymers* 43:419-431, Wiley Interscience (1997).

Porter, E.A., et al., "Antibiotics: Non-haemolytic β-amino-acid oligomers," *Nature* 404:565, Nature Publishing Group (2000).

Pouny, Y., et al., "Interaction of Antimicrobial Dermaseptin and Its Fluorescently Labeled Analogs with Phospholipid Membranes," *Biochemistry* 31:12416-12423, American Chemical Society (1992).

Samson, N., et al., "Relationships Between Synthesis and Mechanical Properties of New Polyurea Materials," *J. Appl. Polym. Sci.* 65:2265-2280, Wiley (1997).

Sinha, S., et al., "NP-1, a Rabbit α-Defensin, Prevents the Entry and Intercellular Spread of Herpes Simplex Virus Type 2," *Antimicrob. Agents Chemother.* 47:494-500, American Society for Microbiology (Feb. 2003).

Steiner, H., et al., "Sequence and specificity of two antibacterial proteins involved in insect immunity," *Nature* 292:246-248, Nature Publishing Group (1981).

Stigers, K.D., et al., "Designed molecules that fold to mimic protein secondary structures," *Curr. Opin. Chem. Biol.* 3:714-723, Current Biology Ltd. (1999).

Tang, Y-Q., et al., "A Cyclic Antimicrobial Peptide Produced in Primate Leukocytes by the Ligation of Two Truncated α-Defensins," *Science* 286:498-502, American Association for the Advancement of Science (1999).

Tew, G.N., et al., "*De novo* design of biomimetic antimicrobial polymers," *Proc. Natl. Acad. Sci. USA* 99:5110-5114, National Academy of Sciences (Apr. 2002).

Threlfall, E.J., et al., "Increasing spectrum of resistance in multiresistant *Salmonella typhimurium*," *Lancet* 347:1053-1054, Lancet Publishing Group (1996).

Tiller, J.C., et at., "Designing surfaces that kill bacteria on contact," *Proc. Natl. Acad. Sci. USA* 98:5981-5985, National Academy of Sciences (2001).

Tossi, A., et al., "Amphipathic, α-Helical Antimicrobial Peptides," *Biopolymers* 55:4-30, Wiley Interscience (2000).

Turpie, A.G.G., "Pharmacology of the low-molecular-weight heparins," *Am. Heart J.* 135:S329-S335, Mosby (1998).

Van Ryn-McKenna, J., et al., "Neutralization of Enoxaparine-Induced Bleeding by Protamine Sulfate," *Thromb. Haemost.* 63:271-274, Schattauer (1990).

(56) References Cited

OTHER PUBLICATIONS

Wachinger, M., et al., "Antimicrobial peptides melittin and cecropin inhibit replication of human immunodeficiency virus 1 by suppressing viral gene expression," *J. Gen. Virol.* 79:731-740, Cambridge University Press (1998).
Wakefield, T.W., et al., "A [+18RGD] Protamine Variant for Nontoxic and Effective Reversal of Conventional Heparin and Low-Molecular-Weight Heparin Anticoagulation," *J. Surg. Res.* 63:280-286, Academic Press (1996).
Wong, P.C., et al., "Nonpeptide Factor Xa Inhibitors: I. Studies with SF303 and SK549, a New Class of Potent Antithrombotics," *J. Pharmacol. Exp. Therap.* 292:351-357, American Society for Pharmacology and Experimental Therapeutics (2000).
Woo, G.L.Y., et al., "Synthesis and characterization of a novel biodegradable antimicrobial polymer," *Biomaterials* 21:1235-1246, Elsevier (2000).
Yamaguchi, I., et al., "Synthesis of polyurea rotaxanes using a cyclodextrin complex of α,w-diamine," *Polym. Bull.* 44:247-253, Springer-Verlag (2000).
Zasloff, M., "Antibiotic peptides as mediators of innate immunity," *Curr. Opin. Immunol.* 4:3-7, Current Biology Ltd. (1992).
Zasloff, M., "Antimicrobial peptides of multicellular organisms," *Nature* 415:389-395, Nature Publishing Group (Jan. 2002).
Zasloff, M., "Reconstructing one of nature's designs," *Trends Pharmacol. Sci.* 21:236-238, Elsevier (2000).
Zhang, L., et al., "Contribution of Human α-Defensin 1, 2, and 3 to the Anti-HIV-1 Activity of CD8 Antiviral Factor," *Science* 298:995-1000, American Association for the Adancement of Science (Nov. 2002).
Zhao, C., et al., "Identification of a new member of the protegrin family by cDNA cloning," *FEBS Lett.* 346:285-288, Elsevier (1994).
U.S. Patent Application entitled "Facially Amphiphilic Polyaryl and Polyarylalkynyl Polymers and Oligomers and Uses Thereof," filed Jan. 21, 2005, naming as inventors William F. DeGrado, Dahui Liu, Gregory N. Tew, and Michael L. Klein.
English abstract for Japanese patent application JP 11152329, dated Jun. 8, 1999.
Office Action for U.S. Appl. No. 10/471,028, DeGrado, W.F., et al., filed May 11, 2004, mailed on May, 8, 2006.
Office Action for U.S. Appl. No. 10/471,028, DeGrado, W.F., et al., filed May 11, 2004, mailed on Oct. 11, 2005.
Notice of Allowance for U.S. Appl. No. 10/471,028, DeGrado, W.F., et al., filed May 11, 2004, mailed on Sep. 12, 2006.
Supplementary Partial European Search Report for European Patent Application No. EP 04 74 9404, completed on Mar. 27, 2009, European Patent Office, The Hague, Netherlands.
Appella, D., et al., "Formation of Short, Stable Helices in Aqueous Solution by β-Amino Acid Hexamers," *J. Am. Chem. Soc.* 121:2309-2310, American Chemical Society, United States (1999).
Arnt, L. and Tew, G., "New Poly(phenyleneethynylene)s with Cationic, Facially Amphiphilic Structures", *J. Am. Chem. Soc.* 124:7664-7665, American Chemical Society, United States (2002).
Arnt, L. and Tew G., "Phenylene Ethynylene Polymers with Amphiphilic Structures," *Polymer Preprints* 43:445, Division of Polymer Chemistry, Inc. American Chemical Society, United States (2002).
Arnt, L., et al. "Nonhemolytic Abiogenic Polymers as Antimicrobial Peptides Mimics," *J Polym. Sci. A Polym. Chem*.42:3860-3864, John Wiley and Sons, United States (2004).
Arnt, L., et al., "Amphiphilic Secondary Structure in Phenylene Ethynylenes," *Polymer Preprints* 44:1266-1267, Division of Polymer Chemistry, Inc., American Chemical Society, United States (2003).
Atwell, G., et al., "Synthesis, DNA Interactions and Biological Activity of DNA Minor Groove Targeted Polybenzamide-Linked Nitrogen Mustards," *Bioorg. Med. Chem.* 3:679-691, Pergamon Press, United Kingdom (1995).
Baker, M., et al., "Anticancer Efficacy of Magainin2 and Analogue Peptides", *Cancer Res.* 53:3052-3057, American Association for Cancer Research, Inc., United States (1993).

Berresheim, A., et al., "Polyphenylene Nanostructures," *Chem. Rev.* 99:1747-1785, American Chemical Society, United States (1999).
Borsche, W., "Über die Reaktionsfähigkeit der Seitenketten in den kernnitrierten Homologen des Benzols," in *Justus Liebig's Annalen Der Chemie*, vol. 386, pp. 351-373, C.F. Winter'sche Verlagshandlung, Germany (1912).
Braga, D. and Grepioni, F., "Making Crystals from Crystals: A Green Route to Crystal Engineering and Polymorphism," *Chem. Commun.* 29: 3635-3645, The Royal Society of Chemistry, United Kingdom (2005).
Breitenkamp, R. and Tew, G., "Aggregation Studies of Novel, Facially Amphiphilic Phenylene Ethynylenes," *Polymer Preprints* 44:673-674, Division of Polymer Chemistry, Inc., American Chemical Society, United States (2003).
Brooks, B., et al., "Charmm: A Program for Macromolecular Energy, Minimization, and Dynamics Calculations," *J. Comp. Chem.* 4:187-217, John Wiley & Sons Inc., United States (1983).
Bunz, U., "Poly(aryleneethynylene)s: Synthesis, Properties, Structures, and Applications," *Chem. Rev.* 100:1605-1644, American Chemical Society, United States (2000).
Calzia, K. and Tew, G., "Copolymers Containing Metal Binding Ligands for Use in Supramolecular Materials: Toward Metal Induced Reversible Networks," *Polmer Preprints* 43:408-409, Division of Polymer Chemistry, Inc., American Chemical Society, United States (2002).
Car, R. and Parrinello, M., "Unified Approach for Molecular Dynamics and Density-Functional Theory," *Phys. Rev. Lett.* 55:2471-2474, American Physical Society, United States (1985).
Chapman, R., et al., "Small molecule modulators of HIV Rev/Rev response element interaction identified by random screening," *Antiviral Res.* 54:149-162, Elsevier, Netherlands (2002).
Chattaway, F. and Evans, R., "LXIX. The Diphenylbenzens. I. Metadiphenylbenzene," *J. Chem. Soc. Trans.* 69:980-985, Harrison and Sons, United Kingdom (1896).
Cruciani, R., et al., "Antibiotic Magainins Exert Cytolytic Activity Against Tranformed Cell Lines Through Channel Formation," *Proc. Natl. Acad. Sci. USA* 88:3792-3796, The National Academy of Sciences, United States (1991).
Decosterd, L. et al., "High-performance liquid chromatography of the renal blood flow marker p-aminohippuric acid (PAH) and its metabolite N-acetyl PAH improves PAH clearance measurements," *J. Chromatogr. B*. 703:25-36, Elsevier, Netherlands (1997).
Dermer, G., "Another Anniversary for the War on Cancer," *Bio/Technology* 12:320, Nature Publishing Group, United Kingdom (1994).
Freshney, R., "Culture of Animal Cells: A manual of basic technique," p. 4, Alan R. Liss, Inc., New York, United States (1983).
Ge, P., et al., "Structural Characterization of a Cyclohexameric *meta*-Phenyleneethynylene Made by Alkyne Metathesis with In Situ Catalysts," *Agnew. Chem. Int. Ed.* 39:3607-3610 Wiley-VCH Verlag GmbH, Germany (2000).
Guillemot, D., et al., "Low Dosage and Long Treatment Duration of β-Lactam," *JAMA* 279:365-370, American Medical Association, United States (1998).
Gura, T., "Systems for Identifying New Drugs Are Often Faulty," *Science* 278:1041-1042, American Association for the Advancement of Science, United States (1997).
Haugwitz, R., et al., "Antiparisitic agents. 6. Synthesis and Anthelmintic Activities of Novel Isothiocyanatophenyl-1,2,4-Oxadiazoles," *J. Med. Chem.* 28:1234-1241, American Chemical Society, United States (1985).
Höger, S., et al., "Synthesis and Properties of Shape-Persistent Macrocyclic Amphiphiles with Switchable Amphiphilic Portions," *Chem. Eur. J.* Wiley-VCH Verlag GmbH, Germany (1998).
Houseman, B. and Mrksich, M., "The Microenvironment of Immobilized Arg-Gly-Asp Peptides is an Important Determinant of Cell Adhesion," *Biomaterials* 22:943-955, Elsevier Science, Netherlands (2001).
Hsu, S. and Chen, W-C., "Improved Cell Adhesion by Plasma-Induced Grafting of L-Lactide Onto Polyurethane Surface," *Biomaterials* 21:359-367, Elsevier Science, Netherlands (2000).

(56) References Cited

OTHER PUBLICATIONS

Hwu, J., et al., "Cephalosporin 3'-Phloroglucide Esters and 7-(Phloroglucidamido)cephalosporins as Novel Antibacterial Agents," *J. Med. Chem.* 40:3434-3441, American Chemical Society, United States (1997).

Kelly, T., et al., "Emission Rates of Formaldehyde from Materials and Consumer Products Found in California Homes," *Environ. Sci. Technol.* 33:81-88, American Chemical Society, United States (1999).

Kim, J. and Swager, T., "Control of Conformational and Interpolymer Effects in Conjugated Polymers," *Nature* 411:1030-1034, Nature Publishing Group, United Kingdom (2001).

Kim, J., et al., "Nanoscale Fibrils and Grids: Aggregated Structures from Rigid-Rod Conjugated Polymers," *Macromolecules* 32:1500-1507, American Chemical Society, United States (1999).

Kim, J., et al., "Structural Control in Thin Layers of Poly(p-phenyleneethynylene)s: Photophysical Studies of Langmuir and Langmuir-Blodgett Films," *J. Am. Chem. Soc.* 124:7710-7718, American Chemical Society, United States (2002).

Klok, H-A., et al., "Self-Assembling Biomaterials," *Polymer Preprints* 39:166-167, Division of Polymer Chemistry, Inc., American Chemical Society, United States (1998).

Kochendoerfer, G., et al., "Total Chemical Synthesis of the Integral Membrane Protein Influenza A Virus M2: Role of Its C-Terminal Domain in Tetramer Assembly," *Biochemistry* 38:11905-11913, American Chemical Society, United States (1999).

Lathers, C., "Clinical Pharmacology of Antimicrobial Use in Humans and Animals," *J. Clin. Pharmacol.* 42:587-600, Sage Science Press, United States (2002).

Markovac, A., et al., "Antimalarials. 12. Preparation of Carbon Isosteres of Selected 4-Pyridinemethanols as Suppressive Antimalarials," *J Med. Chem.* 23:1198-1201, American Chemical Society, United States (1980).

Martin, M. and Siepmann, J., "Novel Configurational-Bias Monte Carlo Method For Branched Molecules. Transferable Potentials for Phase Equilibria. 2. United-Atom Description of Branched Alkanes," *J. Phys. Chem. B* 103:4508-4517, American Chemical Society, United States (1999).

Massia, S. and Hubbell, J., "An RGD Spacing of 440 nm Is Sufficient for Integrin $\alpha_v\beta_3$ Mediated Fibroblast Spreading and 140 nm for Focal Contact and Stress Fiber Formation," *J Cell Biol.* 114:1089-1100, Rockefeller University Press, United States (1991).

Massia, S. and Hubbell, J., "Covalent Surface Immobilization of Arg-Gly-Asp-and Tyr-Ile-Gly-Ser-Arg-Containing Peptides to Obtain Well-Defined Cell-Adhesive Substrates," *Anal. Biochem.* 187:292-301, Academic Press, Inc., United States (1990).

Massia, S. and Stark, J., "Immobilized RGD Peptides on Surface-Grafted Dextran Promote Biospecific Cell Attachment,"*J. Biomed. Mater. Res.* 56:390-399, Wiley Interscience, United States (2001).

Monroe, S. and Polk, R., "Antimicrobial use and bacterial resistance," *Curr. Opin. Microbiol.* 3:496-501, Elsevier Science Ltd., Netherlands (2000).

Mrksich, M., "Tailored Substrates for Studies of Attached Cell Culture," *Cell Mol. Life Sci.* 54:653-662, Birkhauser Verlag, Switzerland (1998).

Mrksich, M. and Whitesides, G., "Using Self-Assembled Monolayers to Understand the Interactions of Man-Made Surfaces with Proteins and Cells," *Annu. Rev. Biophys. Biomol. Struct.* 25:55-78, Annual Reviews, Inc., United States (1996).

Muir, T., et al., "Protein Synthesis by Chemical Ligation of Unprotected Peptides in Aqueous Solution," *Methods Enzymol.* 289:266-298, Academic Press (1997).

Nelson, J., et al., "Solvophobically Driven Folding of Nonbiological Oligomers," *Science* 277:1793-1796, American Association for the Advancement of Science (1997).

Nicolaus, B., "Symbiotic Approach to Drug Design," in *Decision Making in Drug Research*, pp. 173-186, Gross, F., ed., Raven Press, United States (1983).

Okumura, K., et al., "C-Terminal Domain of Human CAP18 Antimicrobial Peptide Induces Apoptosis in Oral Squamous Cell Carcinoma SAS-H1 cells," *Cancer Lett.* 212:185-194, Elsevier Ireland Ltd., Ireland (2004).

Orita, A., et al., "Double Elimination Protocol for Access to Unsymmetrical Di(phenylethynyl)benzenes," *Chemistry Letters* 32:104-105, The Chemical Society of Japan, Japan (2003).

Papo, N. and Shai, Y., "New Lytic Peptides Based on the D,L-Amphipathic Helix Motif Preferentially Kill Tumor Cells Compared to Normal Cells," *Biochemistry* 42:9346-9354, American Chemical Society, United States (2003).

Papo, N., et al., "Suppression of Human Prostate Tumor Growth in Mice by a Cytolytic D-, L-Amino Acid Peptide: Membrane Lysis, Increased Necrosis, and Inhibition of Prostate-Specific Antigen Secretion," *Cancer Res.* 64:5779-5786, The American Association of Cancer Research, United States (2004).

Patch, J. and Barron, A., "Helical Peptoid Mimics of Magainin-2 Amide," *J. Am. Chem. Soc.* 125:12092-12093, American Chemical Society, United States (2003).

Piskin, E., "Plasma processing of biomaterials," *J. Biomater. Sci. Polymer Edu.* 4:45-60, VSP BV, Netherlands (1992).

Polymedix, Low Molecular Weight Heparin Antagonist (2003), website http://www.polymedix.com/03_03_low-molecular.htm, accessed on Apr. 27, 2007, pp. 1-2, entire document.

Porter, E., et al., "Mimicry of Host-Defense Peptides by Unnatural Oligomers: Antimicrobial β-Peptides," *J. Am. Chem. Soc.* 124:7324-7330, American Chemical Society, United States (2002).

Pralle, M., et al., "Self Assembled Phenylene Vinylene Materials," *Microsc. Microanal.* 8 (*Suppl. 2*):318-319, Cambridge University Press, United States (2002).

Prince, R., et al., "Twist Sense Bias Induced by Chiral Side Chains in Helically Folded Oligomers," *Angew. Chem. Int. Ed.* Wiley-VCH Verlag GmbH, Germany (2000).

Prince, R., et al., "Cooperative Conformational Transitions in Phenylene Ethynylene Oligomers: Chain-Length Dependence," *J. Am. Chem. Soc.* 121:3114-3121, American Chemical Society, United States (1999).

Ridgway, G., "Treatment of chlamydial genital infection," *J. Antimicrob. Chemother.* 40:311-314, The British Society for Antimicrobial Chemotherapy, United Kingdom (1997).

Röthlisberger, U., et al., "The torsional potential of perfluoro n-alkanes: A density functional study," *J. Chem. Phys.* 104:3692-3700, American Institute of Physics, United States (1996).

Rusanov, A., et al., "The use of palladium-catalysed cross-coupling for the synthesis of polymers incorporating vinylene and ethynylene groups," *Russian Chemical Reviews* 66:1053-1068, Russian Academy of Sciences and Turpion Ltd., Russia (1997).

Salamone J., "Polymeric Materials Encyclopedia", (CD Rom Version) vol. 8, CRC Press, LLC, United States 1996, 4 pages.

Scherf, U., "Oligo- and polyarylenes, oligo- and polyarylenevinylenes," in *Carbon Rich Compounds II: Macrocyclic Oligoacetylenes and Other Linearly Conjugated Systems, Topics in Current Chemistry*, de Meijere, A., ed. vol. 201, pp. 163-222, Springer-Verlag, Germany (1999).

Seebach, D, and Matthews, J., "β-Peptides: A Surprise At Every Turn," *Chem. Commun.* 21:2015-2022, Royal Society of Chemistry, United Kingdom (1997).

Sekaran, G., et al., "Physicochemical and Thermal Properties of Phenol-Formaldehyde-Modified Polyphenol Impregnate," *J. Applied Polymer Sci.* 81:1567-1571, John Wiley & Sons, Inc., United States (2001).

Seurynck, S., et al., "Design, Synthesis, and Testing of Peptoid-Based Lung Surfactant Protein Mimics," *Biophysical J.* 84:298A, 1450-Pos Board # B705, Biophysical Society, United States (2003).

Shin, S., et al., "Effects of the hinge region of cecropin A(1-8)-magainin 2(1-12), a synthetic antimicrobial peptide, on liposomes, bacterial and tumor cells," *Biochem. Biophys. Acta* 1463: 209-218, Elsevier, Netherlands (2000).

Shortell, D., et al., "Solid-Phase Approaches Toward Cyclic Oligomers," *Tetrahedron* 57:9055-9065, Elsevier Science Ltd., Netherlands (2001).

(56) References Cited

OTHER PUBLICATIONS

Siepmann, J.J., and Frenkel, D., "Configurational Bias Monte Carlo: A New Sampling Scheme For Flexible Chains," *Mol. Phys.* 75:59-70, Taylor & Francis Ltd., United Kingdom (1992).

Sondossi, M., et al., "Factors Involved in Bactericidal Activities of Formaldehyde and Formaldehyde Condensate/Isothiazolone Mixtures," *Int. Biodeter. Biodegradation* 32:243-261, Elsevier Science Limited, United Kingdom (1993).

Stevens, M., Polymer Chemistry: An Introduction, 3rd ed., pp. 409-424, Oxford University Press, New York (1999).

Stupp, S., et al., "Functionalized Supramolecular Materials," *Polymer* 39:4505-4508, Elsevier Science Limited, United Kingdom (1998).

Tecilla, P., et al., "Hydrogen-bonding self-assembly of multichromophore structures," *J. Am. Chem. Soc.* 112:9408-9410, American Chemical Society, United States (1990).

Tew, G., and Stupp S., "Multifunctional Supramolecular Materials," *ACS Symp. Ser.* 704:218-226, American Chemical Society, United States (1998).

Tew, G., "Amphiphilic Phenylene Ethynylenes," *Polymer Preprints* 44:452, Division of Polymer Chemistry, Inc., American Chemical Society, United States (2003).

Tew, G., et al., "Antimicrobial Activity of an Abiotic Host Defense Peptide Mimic," *Biochim. Biophys. Acta* 1758:1387-1392, Elsevier B.V., Netherlands (2006).

Tew, G., et al., "Simple Facially Amphiphilic Polymers as Peptide Mimics," *224th ACS National Meeting, Boston, MA, Aug. 18-22, 2002, Abstract 4*, American Chemical Society, United States (2002).

Tew, G., et al., "Supramolecular Materials with Electroactive Chemical Functions," *Angew. Chem. Int. Ed.* 39:517-521, Wiley-VCH Verlag GmbH, Germany (2000).

Turner, P., et al., "Polybenzamide mustards: structure-activity relationships for DNA sequence-specific alkylation," *Anti-Cancer Drug Des.* 14:61-70, Oxford University Press, United Kingdom (1999).

Turner, P., et al., "Role of DNA minor groove alkylation and DNA cross-linking in the cytotoxicity of polybenzamide mustards," *Anti-Cancer Drug Des.* 15:245-253, Oxford University Press, United Kingdom (2000).

Vlugt, T., et al., "Improving the Efficiency of the Configurational-Bias Monte Carlo Algorithm," *Mol. Phys.* 94:727-733, Taylor & Francis Ltd., United Kingdom (1998).

Weder, C., et al., "Effect of the Solid State Structure on the Third-Order Nonlinear Optical Response of Poly(2,5-dialkoxy-p-phenyleneethynylene)s," *J. Phys. Chem.* 100:18931-18936, American Chemical Society, United States (1996).

Wick, C., et al., "Transferable Potentials for Phase Equilibria. 4. United-Atom Description of Linear and Branched Alkenes and Alkylbenzenes," *J. Phys. Chem. B* 104:8008-8016, American Chemical Society, United States (2000).

Zushun, X., et al., "Development of the Study on Solution Properties of Amphipathic Polymers and Their Emulsion Polymerization," *Polymer Materials Science and Engineering* 14:1-4, American Chemical Society, United States (1998).

Atwell, G. and Cain, B., "Potential Antitumor Agents. 13. Bisquaternary Salts," *J. Med Chem.* 16:673-678, American Chemical Society, United States (1973).

Denny, W., et al., "Potential Antitumor Agents. 36. Quantitative Relationships Between Experimental Antitumor Activity, Toxicity, and Structure for the General Class of 9-Anilinoacridine Antitumor Agents," *J. Med Chem.* 25:276-315, American Chemical Society, United States (1982).

Hudson, J. and Towers, G. "Antiviral properties of acetylenes and thiophenes,"*Bioactive Molecules* 7:315-338, Elsevier, Amsterdam (1988).

Hudson, J., et al., "Photoactive antiviral and cytotoxic activities of synthetic thiophenes and their acetylenic derivatives," *Chemosphere* 19:1329-1343, Pergamon Press, Great Britain (1989).

Lin, C., et al., "Cytotoxicities, cell cycle, and caspase evaluations of 1,6-diaryl-3(Z)-hexen-1,5-diynes, 2-(6-aryl-3(Z)-hexen-1,5-diynyl)anilines and their derivatives," *Bioorg. Med. Chem.* 13:3565-3575, Elsevier Ltd., England (2005).

Vippagunta, S., et al., "Crystalline solids," *Adv. Drug Deliv. Rev.* 48:3-26, Elsevier Science B.V, Netherlands (2001).

Ishitsuka, Y., et al., "Amphiphilic poly(phenyleneethynylene)s can mimic antimicrobial peptide membrane disordering effect by membrane insertion," *J. Am. Chem. Soc.*, 128(40):13123-13129, American Chemical Society, United States (2006).

Ulrich, J. and Stelzer, T., Chapter 4 in Crystallization, Kirk-Othmer Encyclopedia of Chemical Technology, John Wiley & Sons, pp. 1-63, United States (2007).

West, A.R., "Solid State Chemistry and Its Applications," pp. 358 and 365, John Wiley & Sons, India (1989).

Pugsley, M.K., et al., "Protamine is a low molecular weight polycationic amine that produces actions on cardiac muscle," *Life Sci.* 72(3):293-305, Elsevier, Netherlands (2002).

Tang, H., et al., "Synthesis of urea oligomers and their antibacterial activity," *Chem. Commun.*, pp. 1537-1539, Royal Society of Chemistry, England (2005).

Pearce, H.L., et al., "Chapter 18: Failure modes in anticancer drug discovery and development," in *Cancer Drug Design and Discovery*, Neidle, S., ed., pp. 424-435, Elsevier Inc., United States (2008).

Roberts, T.G., et al., "Trends in the Risks and Benefits to Patients With Cancer Participating in Phase 1 Clinical Trials,"*JAMA* 292(17):2130-2140, American Medical Association, United States (2004).

Dialog® File No. 351 Accession No. 9688439, Derwent WPI English Language Abstract for Chinese Patent Application No. CN 1270625 A (2000).

Patent Abstract of Japan, English Language abstract for JP 52-085133 A, Patent & Utility Model Gazette DB, Japanese Patent Office, 2 pages (1977).

Patent Abstract of Japan, English Language abstract for JP 56-123903 A, Patent & Utility Model Gazette DB, Japanese Patent Office, 2 pages (1981).

Patent Abstract of Japan, English Language abstract for JP 59-177558 U, Patent & Utility Model Gazette DB, Japanese Patent Office, 2 pages (1984).

Patent Abstract of Japan, English Language abstract for JP 02-029436 A, Patent & Utility Model Gazette DB, Japanese Patent Office, 1 page (1990).

Patent Abstract of Japan, English Language abstract for JP 63-22067 A, Patent & Utility Model Gazette DB, Japanese Patent Office, 2 pages (1988).

Esp@cenet Database, English language abstract of JP 7-2808 A, espacenet, European Patent Office, 2 pages (1995).

Esp@cenet Database, English language abstract of JP 10-505592 T, espacenet, European Patent Office, 1 page (1998).

Esp@cenet Database, English language abstract of CN 1335303 A, espacenet, European Patent Office, 1 page (2002).

Patent Abstract of Japan, English Language abstract for JP 2001-133975 A, Patent & Utility Model Gazette DB, Japanese Patent Office, 2 pages (2001).

Patent Abstract of Japan, English Language abstract for JP 2002-363261 A, Patent & Utility Model Gazette DB, Japanese Patent Office, 2 pages (2002).

Unverified machine generated English translation of Swiss Patent No. CH 520 657 A, published Mar. 31, 1972.

Unverified machine generated English translation of Swiss Patent No. CH 525 898 A, published Jul. 31, 1972.

CAS Registry No. 495410-77-0; Entry date: Feb. 27, 2003.

CAS Registry No. 87774-34-3; Entry date: Nov. 16, 1984.

CAS Registry No. 92-06-8; Entry date: Nov. 16, 1984.

STN Database CAPLUS, "1,2-bis[2-(2,6-difluorophenyl) ethynyl]-benzene" Registry No. 27286-86-8, entered Nov. 16, 1984.

STN Database CAPLUS, "2,6-bis(2-phenylethynyl)-phenol" Registry No. 478551-27-8, entered Jan. 9, 2003.

STN Database CAPLUS, "3,5-bis(2-phenylethynyl)-benzoic acid methyl ester," Registry No. 272128-90-2, entered Jun. 22, 2000.

STN Database CAPLUS, "1,4-dibromo-2,5-bis[2-(2-bromophenyl)ethynyl]-benzene," Registry No. 625389-87-9, entered Dec. 10, 2003.

(56) References Cited

OTHER PUBLICATIONS

STN Database CAPLUS, "4,4'-(1,2-phenylenedi-2,1-ethynediyl)bis [2,3,5,6-tetrafluoropyridine]," Registry No. 459457-30-8, entered Oct. 7, 2002.
STN Database CAPLUS, "1,2,4,5-tetrafluoro-3,6-bis[2-(4-fluorophenyl)ethynyl]-benzene" Registry No. 332148-91-1, entered Apr. 24, 2001.
STN Database CAPLUS, "1,4-bis[2-(2,3,4,5,6-pentafluorophenyl)ethynyl]-benzene" Registry No. 258506-15-9, entered Mar. 8, 2000.
Office Action mailed on Mar. 9, 2009 in U.S. Appl. No. 10/471,029, inventors DeGrado, W., et al., filed Jun. 7, 2004.
Office Action mailed on Nov. 17, 2009 in U.S. Appl. No. 10/471,029, inventors DeGrado, W., et al., filed Jun. 7, 2004.
Advisory Action mailed on Apr. 7, 2010 in U.S. Appl. No. 10/471,029, inventors DeGrado, W., et al., filed Jun. 7, 2004.
Office Action mailed on Jul. 27, 2010 in U.S. Appl. No. 10/471,029, inventors DeGrado, W., et al., filed Jun. 7, 2004.
Office Action mailed on Jan. 3, 2011 in U.S. Appl. No. 10/471,029, inventors DeGrado, W., et al., filed Jun. 7, 2004.
Advisory Action mailed on Apr. 18, 2011 in U.S. Appl. No. 10/471,029, inventors DeGrado, W., et al., filed Jun. 7, 2004.
Office Action mailed on May 21, 2009 in U.S. Appl. No. 11/038,787, inventors DeGrado, W., et al., filed Jan. 21, 2005.
Office Action mailed on Oct. 20, 2009 in U.S. Appl. No. 11/038,787, inventors DeGrado, W., et al., filed Jan. 21, 2005.
Office Action mailed on Jan. 12, 2010 in U.S. Appl. No. 11/038,787, inventors DeGrado, W., et al., filed Jan. 21, 2005.
Office Action mailed on Oct. 25, 2010 in U.S. Appl. No. 11/038,787, inventors DeGrado, W., et al., filed Jan. 21, 2005.
Supplemental Office Action mailed on Mar. 22, 2010 in U.S. Appl. No. 11/038,787, inventors DeGrado, W., et al., filed Jan. 21, 2005.
Office Action mailed on Jul. 1, 2010 in U.S. Appl. No. 11/038,787, inventors DeGrado, W., et al., filed Jan. 21, 2005.
Advisory Action mailed on May 17, 2011 in U.S. Appl. No. 11/038,787, inventors DeGrado, W., et al., filed Jan. 21, 2005.
Office Action mailed on Feb. 22, 2011 in U.S. Appl. No. 11/038,787, inventors DeGrado, W., et al., filed Jan. 21, 2005.
Office Action mailed on Nov. 9, 2011 in U.S. Appl. No. 11/038,787, inventors DeGrado, W., et al., filed Jan. 21, 2005.
Office Action mailed on Jan. 23, 2012, in U.S. Appl. No. 11/038,787, inventors Degrado, W., et al., filed Jan. 21, 2005.
Notice of Allowance mailed Feb. 21, 2012 in U.S. Appl. No. 11/038,787, inventors DeGrado, W., et al., filed Jan. 21, 2005.
Office Action mailed on Feb. 5, 2009 in U.S. Appl. No. 11/361,050, inventors DeGrado, W., et al., filed Feb. 24, 2006.
Office Action mailed on Aug. 6, 2009 in U.S. Appl. No. 11/361,050, inventors DeGrado, W., et al., filed Feb. 24, 2006.
Office Action mailed on Feb. 24, 2010 in U.S. Appl. No. 11/361,050, inventors DeGrado, W., et al., filed Feb. 24, 2006.
Office Action mailed on Sep. 9, 2010 in U.S. Appl. No. 11/361,050, inventors DeGrado, W., et al., filed Feb. 24, 2006.
Advisory Action mailed on Feb. 14, 2011 in U.S. Appl. No. 11/361,050, inventors DeGrado, W., et al., filed Feb. 24, 2006.
Office Action mailed on Jun. 17, 2013 in U.S. Appl. No. 11/361,050, inventors DeGrado et al., filed Feb. 24, 2006.
Office Action mailed on Nov. 10, 2011, in U.S. Appl. No. 11/980,785, inventors DeGrado et al., filed Oct. 31, 2007.
Notice of Allowance mailed Mar. 6, 2012 in U.S. Appl. No. 11/980,785, inventors DeGrado, W., et al., filed Oct. 31, 2007.
Office Action mailed Nov. 28, 2012, in U.S. Appl. No. 13/365,840, inventors DeGrado et al., filed Feb. 3, 2012.
Office Action mailed Apr. 30, 2013, in U.S. Appl. No. 13/365,840, inventors DeGrado et al., filed Feb. 3, 2012.
Notice of Allowance mailed Aug. 7, 2013, in U.S. Appl. No. 13/365,840, inventors DeGrado et al., filed Feb. 3, 2012.
Notice of Allowance mailed Jan. 25, 2013, in U.S. Appl. No. 13/559,065, inventors DeGrado et al., filed Jul. 26, 2012.
Office Action mailed on Jan. 29, 2014, in U.S. Appl. No. 11/361,050, inventors Degrado et al., filed Feb. 24, 2006.
Dialog File 351, Accession No. 11931138, English language abstract of WO 98/17625 A1 (Document AU2 on accompanying Form PTO/SB/08A).

* cited by examiner

| -x-y- | R$^1$ | n | M$_p^7$ | K91$^1$ | K91$^2$ | D31$^3$ | K.p.$^4$ | B.s.$^5$ | rbc$^6$ |
|---|---|---|---|---|---|---|---|---|---|
| -CONH- | H | 2 | 756$^8$ | | <18 | 19 | 66 | 12 | 50 |
| | H | 3 | 1125$^8$ | | <19 | | 19 | | 20 |
| | H | 10 | 6000$^9$ | <25 | 12-50 | 7.5-15 | 31-50 | | 1 |
| | H | >30 | 20,000 | >200 | | | | | 5 |
| | C(=NH)NH$_2$ | 2 | 6000 | | | 25 | 100 | 12.5 | 8 |
| -NHCONH- | H | 2 | 745$^8$ | <12.5 | | | | | 15 |
| | H | 10 | 6000 | | <50 | | | | 5 |
| | H | >30 | 20000 | | 100 | | | | 20 |

ANTIMICROBIAL ACTIVITY MIC (μg/mL)

FIG. 10

¹ *E. coli* K91 (M9 MEDIUM)
² *E. coli* K91 (LB MEDIUM)
³ *E. coli* D31 (MH MEDIUM)
⁴ *Klebsiella pneumoniae* 10 (MH MEDIUM)
⁵ *Bacteria subtilis* (LB MEDIUM)
⁶ HEMOLYTIC ACTIVITY-ERYTHROCYTES $HC_{50}$ (μg/mL)
⁷ THE AVERAGE CHAIN LENGTH IS DETERMINED BY THE FLORY EQUATION AND THE POLYMER SIZE IS CONFIRMED BY GEL CHROMATOGRAPHY WITH WATERS STYRYL-GEL COLUMNS WERE CONNECTED IN SERIES TO GIVE A MW RANGE FROM 1,000,000 TO 300. THE PEAK WAS ELUTED WITH THF AND THE PEAK CENTER AT MAXIMUM HEIGHT USING A SIZE EXCLUSION COLUMN. AVERAGE POLYDISPERSITY FOR THESE CONDENSATION POLYMERS IS ~2.5.
⁸ HOMOGENOUS COMPOUND PREPARED BY SOLID PHASE SYNTHESIS.
⁹ *Pseudomonus aeruginosa* 10 $IC_{50}$ 31-62; *Salmonella typhimunium*, S5 $IC_{50}$ <3.75; *Enterococcus faecium* $IC_{50}$ 15-25 (μg/mL).

FIG.10A

COMPOUND STRUCTURES
14. 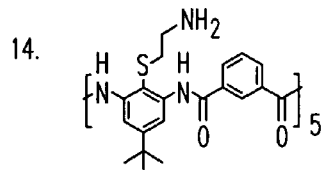
15. 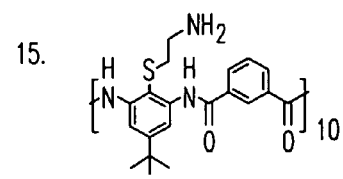
16. 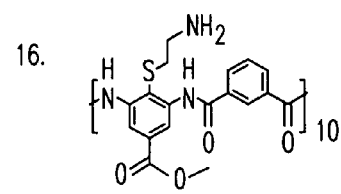
17. 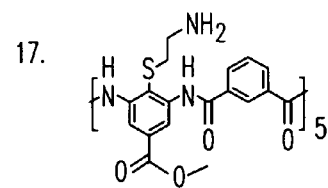
18. 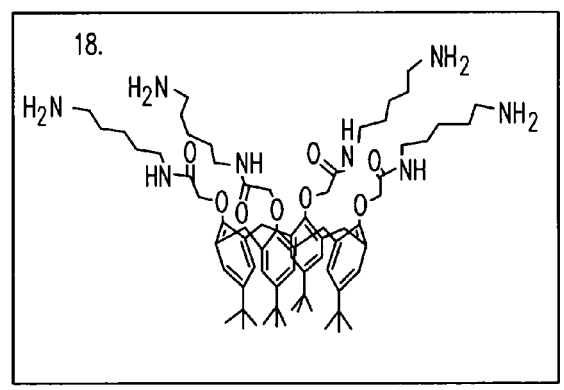
19. 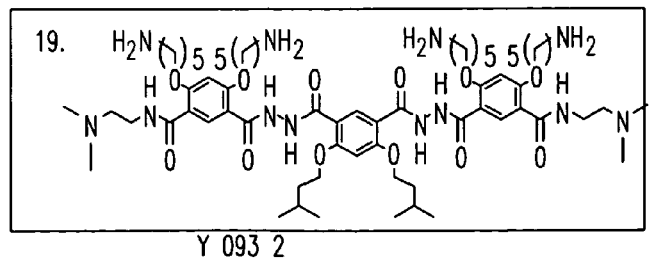
FIG.15A Pmx10073

TABLE 1. ANTIBACTERIAL ACTIVITY AND SELECTIVITY.

| COMPOUND | R₁ | MIC ($\mu$g/mL) | | HC50 ($\mu$g/mL) | SELECTIVITY (HC50/MIC) | | RELATIVE HYDROPHOBICITY $LogK_{ow}$ |
|---|---|---|---|---|---|---|---|
| | | E.coli | S.aureus | | E.coli | S.aureus | |
| 1 | H | 12.5 | 50 | 12 | 0.96 | 0.24 | 3.51 |
| 2 | | 6.25 | 12 | 40 | 6.4 | 3.3 | 3.12 |
| 3 | | 6.25 | 6.25 | 9 | 1.4 | 1.4 | 3.74 |
| 4 | | 6.25 | 6.25 | 7 | 1.1 | 1.1 | 3.86 |
| 5 | | 25 | 50 | 790 | 32 | 16 | 1.45 |
| 6 | | 25 | 100 | 1230(*) | 49 | 12 | 2.99 |
| 7 | | 50 | | 370 | 7.4 | | 0.33 |
| 8 | | 6.25 | 12.5 | 715 | 110 | 57 | −1.71 |
| MSI-78 | | 12.5 | | 120 | 9.6 | | |

(*)HC50 WAS OBTAINED FROM EXTRAPOLATING THE FITTED CURVE TO 50% LYSIS

TABLE 2. ANTIBACTERIAL ACTIVITY AND SELECTIVITY (CONTINUED).

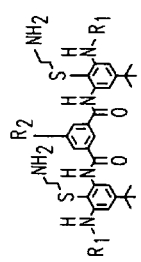

| COMPOUND | R1 | R2 | MIC (µg/mL) E.coli | MIC (µg/mL) S.aureus | HC50 (µg/mL) | SELECTIVITY (HC50/MIC) E.coli | SELECTIVITY (HC50/MIC) S.aureus | RELATIVE HYDROPHOBICITY Log$K_{OW}$ |
|---|---|---|---|---|---|---|---|---|
| 1 | H | H | 12.5 | 50 | 12 | 0.96 | 0.24 | 3.51 |
| 9 | H | H$_2$N$\sim$O- | 25 | 25 | 110(*) | 4.4 | 4.4 | 2.61 |
| 10 | H$_2$N$\sim$O- | H$_2$N$\sim$O- | 50 | 200 | 400 | 8.0 | 2.0 | 1.53 |
| 3 | (benzyl-amide) | H | 6.25 | 6.25 | 9 | 1.4 | 1.4 | 3.74 |
| 11 | (benzyl-amide) | H$_2$N$\sim$O- | 12.5 | 12.5 | 61 | 4.9 | 4.9 | 2.84 |
| 8 | (lys-amide) | H | 6.25 | 12.5 | 715 | 110 | 57 | -1.71 |
| 12 | (lys-amide) | H$_2$N$\sim$O- | 12.5 | 12.5 | >800 | >64 | >64 | -2.61 |
| MSI-78 | | | 12.5 | | 120 | 9.6 | | |

(*) HC50 WAS OBTAINED FROM EXTRAPOLATING THE FITTED CURVE TO 50% LYSIS

FIG. 19

AMPHIPHILIC OLIGOMER 8 INDUCES VESICLE LEAKAGE.

FACIALLY AMPHIPHILIC POLYMERS AND OLIGOMERS AND USES THEREOF

CROSS-REFERENCE TO RELATED APPLICATIONS

This applications claims the benefit, under 35 U.S.C. §119 (e), of the earlier filing dates of U.S. Provisional Application No. 60/455,479, filed on Mar. 17, 2003, U.S. Provisional Application No. 60/530,630, filed on Dec. 19, 2003, and U.S. Provisional Application No. 60/536,980, filed on Jan. 20, 2004. The contents of each of these applications are incorporated herein by reference in their entirety.

STATEMENT REGARDING FEDERALLY-SPONSORED RESEARCH

This invention was made with government support under Grant No. GM-65803 awarded by the National Institutes of Health. The U.S. Government has certain rights in this invention.

BACKGROUND OF THE INVENTION

1. Field of the Invention

The present invention relates to methods of use of facially amphiphilic polymers and oligomers, including pharmaceutical uses of the polymers and oligomers as antimicrobial agents and antidotes for hemorrhagic complications associated with heparin therapy. The present invention also relates to novel facially amphiphilic polymers and oligomers and their compositions, including pharmaceutical compositions. The present invention further relates to the design and synthesis of facially amphiphilic polymers and oligomers.

2. Related Art

Amphiphilic molecules exhibit distinct regions of polar and nonpolar character. These regions can result from substitution of hydrophobic and hydrophilic substituents into specific and distinct regions of conformationally defined molecules. Alternatively, a conformationally flexible molecule or macromolecule can adopt an ordered structure in which the hydrophobic and hydrophilic substituents on the molecule segregate to different areas or faces of the molecule. Commonly occurring amphiphilic molecules include surfactants, soaps, detergents, peptides, proteins and copolymers. These molecules have the capacity to self-assemble in appropriate solvents or at interfaces to form a variety of amphiphilic structures. The size and shape of these structures varies with the specific composition of the amphiphilic molecule and solvent conditions such as pH, ionic strength and temperature.

Amphiphilic peptides with unique broad-spectrum antimicrobial properties have been isolated from a variety of natural sources including plants, frogs, moths, silk worms, pigs and humans (H. G. Boman *Immunol Rev.* 2000 173:5-16; R. E. Hancock and R. Lehrer, *Trends Biotechnol.* 1998 16:82-88). These compounds include the magainin 1 and dermaseptin S1 isolated from the skin of frogs and the cecropin A isolated from the cecropia moth. These naturally occurring compounds have broad-spectrum antibacterial activity and they do not appear prone to the development of bacteria resistance. These compounds are of relatively low molecular weight and have a propensity to adopt an α-helical conformation in hydrophobic media or near a hydrophobic surface and as a result are facially amphiphilic, with one-third to two-thirds of the cylinder generated by the helical peptide has hydrophobic side chains while the remainder has hydrophilic side chains. The hydrophilic side chains are primarily positively-charged at neutral pH.

Hydrophobic amino acids compose 40-60% of the total number of residues in most anti-microbial peptides. The selectivity of the amphiphilic peptides (e.g. for bacteria vs. human erythrocytes) depends on the overall hydrophobicity. The biological activity of the compounds depends on the ratio of charged (c) to hydrophobic (h) residues. When the ratio is varied from 1:1 (c:h) to 1:2 (c:h) peptides with more hydrophobic residues tend to be more active toward erythrocyte membranes. Related peptides have been isolated from mammals and these anti-microbial peptides have been suggested to be an important component of the innate immune response. (Gennaro, R. et al. *Biopoylmers (Peptide Science)* 2000, 55, 31)

Secondary structures other than helices may also give rise to amphiphilic compounds. The protegrins are a related series of anti-microbial peptides. (J. Chen et al., *Biopolymers (Peptide Science)*, 2000 55 88) The presence of a pair of disulfide bonds between $Cys^6$-$Cys^5$ and $Cys^8$-$Cys^{13}$ results in a monomeric amphiphilic anti-parallel β-sheet formed by the chain termini and linked by a β-turn. The amphiphilic β-sheet conformation is essential for anti-microbial activity against both gram-positive and gram-negative bacteria.

Following the initial discovery of cecropins and magainins, antimicrobial peptides have become a large and growing class of biologically interesting compounds (Zasloff, M., *Curr. Opin. Immunol.* 4:3-7 (1992); Zasloff, M., *Trends Pharmacol. Sci.* 21:236-238 (2000)). These compounds represent the first line of defense against microbes for many species, including plants, insects, worms, and mammals (Boman, H. G., *Immunol. Rev.* 173:5-16 (2000); Hancock, R. E., and Lehrer, R., *Trends Biotechnol.* 16:82-88 (1998)). In mammals, the peptides are produced and secreted by skin, mucosal surfaces and neutrophils. There are many different classes of natural host defense peptides (Zasloff, M., *Curr. Opin. Immunol.* 4:3-7 (1992); Zasloff, M., *Trends Pharmacol. Sci.* 21:236-238 (2000); Steiner, H., et al., *Nature,* 292:246-248 (1981); Ganz, T., et al., *Eur. J. Haematol.* 44:1-8 (1990); Tang, Y. Q., et al., *Science* 286:498-502 (1999); Ganz, T., et al., *J. Clin. Invest.* 76:1427-1435 (1985); Landon, C., et al., *Protein Sci.* 6:1878-1884 (1997); Zhao, C., et al., *FEBS Lett.* 346:285-288 (1994); Peggion, E., et al., *Biopolymers* (Peptide Science) 43:419-431 (1998); Dempsey, C. E., *Biochim. Biophys. Acta* 1031:143-161 (1990)), but, in general, most contain between 20-40 amino acid residues and adopt an amphiphilic secondary structure as shown in FIG. 2.

The cytotoxic activity of the cationic and amphiphilic host defense peptides is also specific for bacteria over mammalian cells. This specificity is most likely related to fundamental differences between the two membrane types. For example, bacteria have a large proportion of negatively charged phospholipid headgroups on their surface, while, in contrast, the outer leaflet of animal cells is composed mainly of neutral lipids (Zasloff, M., *Nature* 415:389-395 (2002)). The presence of cholesterol in the animal cell membrane also appears to reduce the activity of the antimicrobial peptides.

The bactericidal activity of the host defense peptides is very rapid, occurring within minutes after exposure of bacteria to lethal doses of peptide. Several mechanisms have been proposed for the process of cell killing. According to the carpet mechanism, host defense peptides aggregate parallel to the membrane surface (Gazit, E., et al., *Biohemistry* 34:11479-11488 (1995); Pouny, Y., et al., *Biochemistry* 31:12416-12423 (1992)), leading to thinning and, ultimately, rupture of the membrane. In the so-called barrel-stave mechanism, the bound peptides on the cell surface self-associate into transmembrane helical bundles that form stable aqueous pores in the membrane (Merrifield, R. B., et al., *Ciba Found. Symp.* 186:5-20 (1994)). According to a third possible mechanism (DeGrado, W. F., et al., *Biophys. J.* 37:329-338 (1982)), the peptides initially bind only to the outer leaflet of the bilayer, leading to an increase in the lateral surface pressure of the outer leaflet relative to the inner leaflet of the bilayer. This pressure imbalance results in translocation of the peptides into the interior of the bilayer, with concomitant formation of transient openings in the membrane that allow hydration of the polar sidechains of the peptide and leakage of cellular contents. Most antimicrobial peptides probably act by more than one of these mechanisms. Additionally, some classes may interact with periplasmic or intercellular targets (Zasloff, M., *Trends Pharmacol. Sci.* 21:236-238 (2000)).

In addition to antibacterial activity, several of the host defense peptides possess antifungal activity. Examples of mammalian, insect and amphibian peptides with demonstrated antifungal activities include defensins, protegrins, lactoferrin-B, cecropins, and dermaseptins (DeLucca, A. J., and Walsh, T. J., *Antimicob. Agents Chemother.* 43:1-11 (1999)). The mechanism of cytotoxic action appears to be similar to that for bacteria, leading to rapid lysis of the fungal membrane.

Several host defense peptides also possess antiviral activity and inhibit the replication of both DNA and RNA viruses. See, for example, Sinha, S., et al., *Antimicrob. Agents Chemother.* 47:494-500 (2003); Belaid, A., et al., *J. Med. Virol.* 66:229-234 (2002); Egal, M., et al., *Int. J. Antimicrob. Agents* 13:57-60 (1999); Andersen, J. H., et al., *Antiviral Rs.* 51:141-149 (2001); and Bastian, A., and Schafer, H., *Regul. Pept.* 15:157-161 (2001).

The human alpha-defensins have also been shown to inhibit the replication of HIV-1 isolates in vitro (Zhang, L., et al., *Science* 298: 995-1000 (2002). The antimicrobial peptides melittin and cecropin have also been reported to inhibit HIV-1 replication and it is suggested that they exert their activity by suppressing HIV gene expression (Wachinger, M., et al., *J. Gen. Virol.* 79:731-740 (1998)).

Although host defense peptides are found in a wide variety of species and are composed of many different sequences, their physiochemical properties are remarkably similar. They adopt an amphiphilic architecture with positively charged groups segregated to one side of the secondary structure and hydrophobic groups on the opposite surface. For example, magainin and some of the other naturally occurring antibacterial peptides contain positively charged amino acids and a large hydrophobic moment. Although these peptides exhibit considerable variation in their chain length, hydrophobicity and distribution of charges, they have a high propensity to adopt α-helical conformations in a hydrophobic environment, e.g., a cell surface or a natural or synthetic membrane (Oren, Z., and Shai, Y., *Biopolymers (Peptide Science)* 47:451-463 (1998)). The periodic distribution of hydrophobic and hydrophilic side chains in their amino acid sequences allows the segregation of the hydrophobic and hydrophilic side chains to opposite faces of the cylinder formed by the helix. These structures can be described as facially amphiphilic regardless of whether the secondary structure is a helix or sheet type fold. In fact, it is the overall physiochemical properties that are responsible for the biological activity of these peptides and not the precise sequence (Zasloff, M., *Curr. Opin. Immunol.* 4:3-7 (1992); Zasloff, M., *Trends Pharmacol. Sci.* 21:236-238 (2000); Hancock, R. E., and Lehrer, R., *Trends Biotechnol.* 16:82-88 (1998); DeGrado, W. F., et al., *J. Amer. Chem. Soc.* 103:679-681 (1981); DeGrado, W. F., *Adv. Prot. Chem.* 39:51-124 (1988); Tossi, A., et al., *Biopolymers* 55:4-30 (2000); Merrifield, E. L., et al., *Int. J. Pept. Protein Res.* 46:214-220 (1995); Merrifield, R. B., et al., *Proc Natl Acad Sci (USA)* 92:3449-3453 (1995)). Thus, facial amphiphilicity, i.e., the alignment of polar (hydrophilic) and nonpolar (hydrophobic) side chains on opposite faces of a secondary structural element formed by the peptide backbone, and not amino acid sequence or any particular secondary/tertiary structure, chirality or receptor specificity, is responsible for the biological activity of these peptides.

The design of non-biological polymers with well-defined secondary and tertiary structures has received considerable attention in the past few years (Gellman, S. H., *Acc. Chem. Res.* 31:173-180 (1998); Barron, A. E., and Zuckermann, R. N., *Curr. Opin. Chem. Biol.* 3:681-687 (1999); Stigers, K. D., et al., *Curr. Opin. Chem. Biol.,* 3:714-723 (1999)). Using these principles, investigators have designed synthetic antimicrobial peptides by idealizing the amphiphilic α-helical arrangement of sidechains observed in the natural host defense peptides, leading to a large number of potent and selective antimicrobial compounds (Tossi, A., et al., *Biopolymers* 55:4-30 (2000); DeGrado, W. F., *Adv. Protein. Chem.* 39:51-124 (1988); Maloy, W. L., and Kari, U. P., *Biopolymers* 37:105-122 (1995); Zasloff, M., *Curr. Opin. Immunol.* 4:3-7 (1992); Boman, H. G., et al., *Eur. J. Biochem.* 201:23-31 (1991); Oren, Z., and Shai, Y., *Biopolymers* 47:451-463 (1998)).

β-peptides have also provided another avenue to test and further elucidate the features required for the construction of bactericidal agents. β-peptides adopt L+2 helices, which have an approximate 3-residue geometric repeat. Thus, if polar and apolar sidechains are arranged with precise three-residue periodicity in the sequence of a β-peptide, they should segregate to opposite sides of the helix. Using this approach, DeGrado and co-workers (Hamuro, Y., et al., *J. Amer. Chem. Soc.* 121:12200-12201 (1999); Liu, D., and DeGrado, W. F., *J. Amer. Chem. Soc.,* 123:7553-7559 (2001)) have designed synthetic β-peptide oligomers that are roughly equipotent in antimicrobial activity to many naturally occurring peptide antibiotics. The antimicrobial activities of these β-peptides and their specificities for bacterial cells over mammalian cells can be controlled by fine-tuning their hydrophobicities and chain lengths. Gellman and coworkers have also synthesized cyclically constrained β-peptides possessing potent antimicrobial activity and minimal activity against mammalian cells (Porter, E. A., et al., *Nature* 404:565 (2000)).

Non-peptidic antimicrobial polymers have also been developed. For example, suitably substituted polymers lacking polyamide linkages that are capable of adopting amphiphilic conformations have been designed and synthesized. Solid phase chemistry technology has been utilized to synthesize a class of meta substituted phenylacetylenes that fold into helical structures in appropriate solvents (Nelson, J. C., et al, *Science* 277:1793-1796 (1997); Prince, R. B., et al., *Angew. Chem. Int. Ed.* 39:228-231 (2000)). These molecules contain an all hydrocarbon backbone with ethylene oxide side chains such that when exposed to a polar solvent (acetonitrile), the backbone collapses to minimize its contact with this polar solvent. As a result of the meta substitution, the preferred folded conformation is helical. This helical folding is attributed to a "solvophobic" energy term; although, the importance of favorable π-π aromatic interactions in the folded state are also likely to be important. Furthermore, addition of a less polar solvent ($CHCl_3$) results in an unfolding of the helical structure demonstrating that this folding is reversible.

Regioregular polythiophenes (5 and 6) have been shown to adopt amphiphilic conformations in highly ordered π-stacked arrays with hydrophobic side chains on one side of the array and hydrophilic side chains on the other side. These polymers form thin films useful in the construction of nanocircuits. (Bjørnholm et al., *J. Am. Chem. Soc.*, 1998 120, 7643) These materials would be facially amphiphilic as defined herein; however, no biological properties have been reported for these compounds.

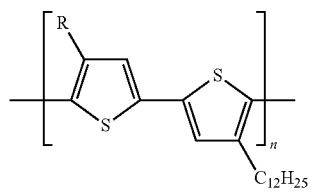

5: R = CH$_2$CO$_2^-$NMe$_4^+$
6: R = (CH$_2$CH$_2$O)$_3$Me

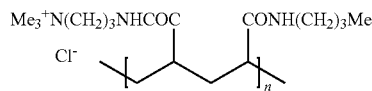

Antimicrobial peptides have been incorporated onto surfaces or bulk materials, with some retention of antimicrobial properties. Haynie and co-workers at DuPont have investigated the activity of antibacterial peptides that have been covalently attached to solid surfaces (S. L. Haynie et al., *Antimicrobial Agents Chemother.*, 1995 39:301-7; S. Margel et al., *J. Biomed. Mater. Res.*, 1993, 27:1463-76). A variety of natural and de novo designed peptides were synthesized and tested for activity while still attached to the solid support. The activity of the peptides decreased when attached to the solid support although the peptides retained their broad spectrum of activity. For example, a de novo designed peptide referred to as E14LKK was reported to have a MBC (minimum bactericidal activity) of 31 µg/ml in solution as opposed to 1.5 mg/ml when attached to a solid phase bead. The peptides were attached to the resin with a 2 to 6-carbon alkyl linker. The porosity of Pepsyn K, the resin used in the synthesis, is small (0.1 to 0.2 µm) compared to the bacteria, so the microbes may have been unable to penetrate into the interior of the resin. Thus the great majority of the peptide would not be available for binding to cells. The antimicrobial activity did not arise from a soluble component; no leached or hydrolyzed peptide was observed and the soluble extracts were inactive. These studies indicate quite convincingly that antimicrobial peptides retain their activity even when attached to a solid support. However, there is a need to optimize the presentation of the peptides to increase their potency.

Other antimicrobial polymeric materials have been reported which contain chemical functionalities known to be antimicrobial (J. C. Tiller et al., *Proc Natl Acad Sci USA*, 2001 98:5981-85). A large portion of this work uses chemical functions such as alkylated pyridinium derivatives, which are known to be toxic to mammalian cells. The antibiotic ciprofloxacin has been grafted into a degradable polymer backbone (G. L. Y. Woo, et al., *Biomaterials* 2000 21:1235-1246). The activity of this material relies on cleavage of the active component from the polymer backbone.

In addition, Mandeville et al., U.S. Pat. No. 6,034,129, disclose anti-infective vinyl copolymers, wherein monomers with hydrophobic and hydrophilic side chains have been randomly polymerized to produce polymers with amphiphilic properties. These materials are produced by polymerization of hydrophobic and hydrophilic acrylate monomers. Alternately, the hydrophobic side chain is derived from a styrene derivative which is copolymerized with a hydrophilic acrylate monomer wherein an ionic group is linked to the carboxylic acid.

Tew et al (Tew, G. N., et al., *Proc. Natl. Acad. Sci. (USA)* 99:5110-5114 (2002)) disclose the design and synthesis of a series of biomimetic, facially amphiphilic arylamide polymers possessing antimicrobial activity. The arylamide polymers were designed using de novo computational design techniques.

WIPO Publ. No. WO 02/100295 discloses facially amphiphilic polyamide, polyester, polyurea, polycarbonate, and polyurethane polymers with anti-infective activity, and articles made from them having biocidal surfaces. WIPO Publ. No. WO 02/100295 is fully incorporated by reference herein in its entirety.

WIPO Publ. No. WO 02/072007 discloses a number of facially amphiphilic polyphenylene and heteroarylene polymers, including polyphenylalkynyl polymers, with anti-infective activity and articles made therefrom having biocidal surfaces. WIPO publication no. WO 02/072007 is fully incorporated by reference herein in its entirety.

An alternative method to make amphiphilic polymers is to produce block copolymers comprised of hydrophobic blocks (A) and hydrophilic blocks (B), commonly polypropyleneoxy and polyethylenoxy segments respectively, into A-B, A-B-A or similar copolymers. These copolymers also are not facially amphiphilic as defined herein.

BRIEF DESCRIPTION OF THE DRAWINGS

Specific embodiments of the invention have been chosen for the purpose of illustration and description but are not intended in any way to restrict the scope of the invention. These embodiments are shown in the accompanying drawings wherein:

FIG. 10 shows antimicrobial data for polyamide oligomers of Formulae II and II' Antimicrobial data for polyurea oligomers of Formulae IV and IV' (structures not shown) are also presented.

FIG. 19 shows the antibacterial activities and selectivities for additional arylamide oligomers described in Example 12.

BRIEF SUMMARY OF THE INVENTION

Figure 1:
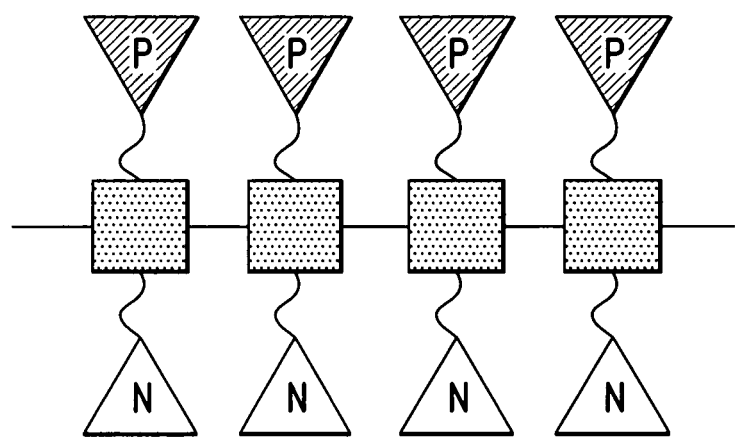
FIG. 1 shows a cartoon depicting the separation of hydrophobic and hydrophilic side chains onto opposite faces of the polymer backbone.
Figure 2:
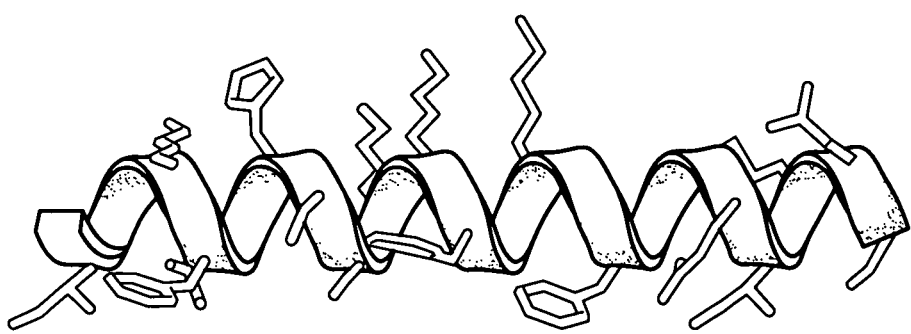
FIG. 2 shows a schematic representation of the structure for the cationic and amphiphilic α-helical host defense peptide, magainin 1.

The present invention provides methods of use of facially amphiphilic polymers and oligomers, including pharmaceutical uses of the polymers and oligomers as antimicrobial agents and antidotes for hemorrhagic complications associated with heparin therapy. The present invention is also provides novel facially amphiphilic polymers and oligomers and their compositions, including pharmaceutical compositions. The present invention further provides methods for the design and synthesis of facially amphiphilic polymers and oligomers.

$$R^1\text{-}[\text{-}x\text{-}A_1\text{-}y\text{-}x\text{-}A_2\text{-}y\text{-}]_m\text{-}R^2 \quad (I)$$

$$R^1\text{-}[\text{-}x\text{-}A_1\text{-}x\text{-}y\text{-}A_2\text{-}y\text{-}]_m\text{-}R^2 \quad (II)$$

$$R^1\text{-}[\text{-}x\text{-}A_1\text{-}x\text{-}z\text{-}y\text{-}A_2\text{-}y\text{-}z\text{-}]_m\text{-}R^2 \quad (IV)$$

The facially amphiphilic polymers and oligomers of the present invention include polyamide and polyester compounds of Formulae I and II wherein x is O, $NR^3$ or S, y is C=O, C=S or $SO_2$, and $A_1$ and $A_2$ are aromatic, heteroaromatic or aliphatic moieties appropriately substituted with polar and nonpolar groups; and polyurea, polycarbamate, and polycarbonate compounds of Formula IV wherein x and y are O, $NR^3$ or S, z is C=O, C=S or $SO_2$, and $A_1$ and $A_2$ are aromatic, heteroaromatic or aliphatic moieties appropriately substituted with polar and nonpolar groups. $R^1$ and $R^2$ are end groups appropriate for the specific polymer chain and their design is well know in the art of designing and synthesizing polymers and oligomers.

These facially amphiphilic polymers and oligomers are capable of adopting repeating secondary structural motifs that allow for the segregation of polar and nonpolar regions of the molecule into different spatial regions. The polymers and oligomers adopt amphiphilic conformations when placed in contact with the cell walls of microorganisms, and the amphiphilic molecules are capable of disrupting essential cell wall functions resulting in the death of the microorganism.

Thus, the present invention is directed to a method of treating a microbial infection in an animal in need thereof, the method comprising administering to the animal an effective amount of a pharmaceutical composition comprising a polymer or oligomer of the invention, or an acceptable salt or solvate thereof, and a pharmaceutically acceptable carrier or diluent.

The invention is also directed to a method of treating a viral infection in an animal in need thereof, the method comprising administering to the animal an effective amount of a pharmaceutical composition comprising a polymer or oligomer of the invention, or an acceptable salt or solvate thereof, and a pharmaceutically acceptable carrier or diluent.

The invention is further directed to a method of treating a fungal infection in an animal in need thereof, the method comprising administering to the animal an effective amount of a pharmaceutical composition comprising a polymer or oligomer of the invention, or an acceptable salt or solvate thereof, and a pharmaceutically acceptable carrier or diluent.

The invention is also directed to a method of providing an antidote to low molecular weight heparin overdose in an animal in need thereof, the method comprising administering to the animal an effective amount of a pharmaceutical composition comprising a polymer or oligomer of the invention, or an acceptable salt or solvate thereof, and a pharmaceutically acceptable carrier or diluent.

The invention is further directed to polymers and oligomers of the invention.

The present invention is also directed to a method of killing or inhibiting the growth of a microorganism, the method comprising contacting the microorganism with an effective amount of a polymer or oligomer of the invention, or an acceptable salt or solvate thereof.

The present invention further provides a computational technique to evaluate the energy of polymer conformations and identify polymers which have the capability of exhibiting amphiphilic behavior and aid in identifying optimal sites for substitution of polar and nonpolar substituents that confer amphiphilic properties.

DETAILED DESCRIPTION OF THE INVENTION

Bacterial drug resistance is a significant current health problem throughout the world. Multiple drug resistance is being commonly seen in a number of human pathogens (Hiramatsu, K., et al., *J. Antimicrob. Chemother.* 40:311-313 (1998); Montecalvo, M. A., et al., *Antimicro. Agents Chemother.* 38:1363-1367 (1994); Butler, J. C., et al., *J. Infect. Dis.* 174:986-993 (1996); Lyytikainen, O., et al., *J. Hosp. Infect.* 31:41-54 (1995)), and the incidence of drug-resistant hospital infections is growing at a rapid rate. For example, in some U.S. hospitals, nosocomial pathogens, such as *E. faecium* and *Acinetobacter* species, have acquired multiple resistance determinants and are virtually untreatable with current antimicrobial agents (Threlfall, E. J., et al., *Lancet* 347:1053-1054 (1996); Bradley, J. S., and Scheld, W. M., *Clin. Infect. Dis.* 24 (*Suppl.* 2):S213-221 (1997)). Moreover, the threat of bio-terrorism is a further impetus for development of novel classes of antibiotics, particularly ones against which it will be difficult to develop resistant bacterial strains.

The pharmaceutical scientific community is responding to this challenge by focusing on the development of new antibiotic drugs. Much of this work, however, is directed to synthesizing analogs of known drugs, such as cephalosporins and quinolones, that, while potentially useful for a short time, will inevitably also encounter bacterial drug resistance and become ineffective. Thus, therapeutically effective antimicrobial drugs that act by novel mechanisms would provide an economc as well as a human health benefit.

The defense host peptides are potentially exciting therapeutic agents because of their broad spectrum of activity, rapid bactericidal activity and very low incidence of development of bacterial resistance. However, significant pharmaceutical issues, including systemic toxicity and difficulty and expense of manufacturing, have severely hampered clinical progress.

The non-peptidic polymers and oligomers of the present invention directly address these issues. These non-peptidic mimetics are significantly smaller and easier to prepare than their naturally occurring counterparts. They have the same mechanism of action as magainin (a naturally occurring host defense peptide), and are approximately equipotent and as broad in their spectrum of action as magainin. However, the non-peptidic mimetics are significantly less toxic towards human erythrocytes, much less expensive to prepare, and are expected to be much more stable in vivo. Importantly, because these compounds mimic the structure and biological activity of host defense peptides, the appearance of bacterial resistant strains is very unlikely to occur.

Thus, the present invention provides non-peptidic, facially amphiphilic polymers and oligomers and methods of using of the polymers and oligomers in a number of applications, including their use in pharmaceutical applications as antimicrobial agents and as antidotes for hemorrhagic complications associated with heparin therapy.

The polymers and oligomers of the present invention are compounds of Formulae I, II, and IV:

$$R^1\text{-}[\text{-}x\text{-}A_1\text{-}y\text{-}x\text{-}A_2\text{-}y\text{-}]_m\text{-}R^2 \qquad \text{(I)}$$

$$R^1\text{-}[\text{-}x\text{-}A_1\text{-}x\text{-}y\text{-}A_2\text{-}y\text{-}]_m\text{-}R^2 \qquad \text{(II)}$$

$$R^1\text{-}[\text{-}x\text{-}A_1\text{-}x\text{-}z\text{-}y\text{-}A_2\text{-}y\text{-}z\text{-}]_m\text{-}R^2 \qquad \text{(IV)}$$

or acceptable salts or solvates thereof, wherein $R^1$, $R^2$, $A_1$, $A_2$, x, y, z and m are as defined below.

The polymers and oligomers of the present invention are capable of adopting amphiphilic conformations that allow for the segregation of polar and nonpolar regions of the molecule into different spatial regions and provide the basis for a number of uses. For example, polymers and oligomers of the invention adopt amphiphilic conformations that are capable of disrupting the integrity of the cell membrane of microorganisms, resulting in the inhibition of growth or the death of the microorganisms. As a consequence, the polymers and oligomers have a broad range of antimicrobial activity and are effective against a variety of microorganisms, including gram-positive and gram-negative bacterial, fungi, yeast, mycoplasmas, mycobacteria, protozoa, and the like.

The polymers and oligomers of the present invention are useful as antimicrobial agents in a number of applications. For example, polymers and oligomers of the present invention, especially oligomers, can be used therapeutically to treat microbial infections in animals, including humans and non-human vertebrates such as wild, domestic and farm animals. The microbial infection in an animal is treated by administering to the animal an effective amount of a pharmaceutical composition of a polymer or oligomer of the invention. The polymer or oligomer compositions can be administered systemically or topically and can be administered to any body site or tissue. Because the polymers and oligomers have a broad range of antimicrobial activity, they are useful in treating a variety of infections in an animal.

The facially amphiphilic conformations adopted by the polymers and oligomers of the present invention form the basis for another therapeutic use, the use of the polymers and oligomers as antidotes for hemorrhagic complications associated with heparin therapy. Thus, the polymers and oligomers, especially the oligomers, can be used in a method of providing an antidote to heparin overdose in an animal by administering to the animal an effective amount of a pharmaceutical composition of the polymer or oligomer.

The polymers and oligomers of the present invention can also be used as disinfectants or as preservatives. The polymers and oligomers can thus be used in a method of killing or inhibiting the growth of a microorganism by contacting the microorganism with an effective amount of the polymer or oligomer. For example, the polymers and oligomers of the invention can be used as disinfectants or preservatives in, for example, soaps, hand lotions, paints, cleansers, and polishers, and the like, or in, for example, foodstuffs, food containers, and food-handling implements, and are often administered for these purposes as a solution, dispersion, or suspension. The polymers and oligomers can also be incorporated into plastics that can be molded or shaped into articles, or attached or immobilized on a surface, to provide a surface-mediated microbicide that kills or inhibits the growth of microorganisms in contact with the surface.

Facially amphiphilic polymers and oligomers of the present invention can be homopolymers wherein one monomer is substituted, with both a nonpolar and a polar substituent or copolymers wherein one monomer is substituted with a polar substituent and the other monomer is substituted with a nonpolar substituent. Since the antimicrobial activity arises from the amphiphilic character conferred by a periodic pattern of side chains rather than the precise spatial arrangement of side chains, other substitution patterns are also expected to produce facially amphiphilic polymers and oligomers and they all are encompassed by the present invention. (See FIG. 1.)

Figure 3:
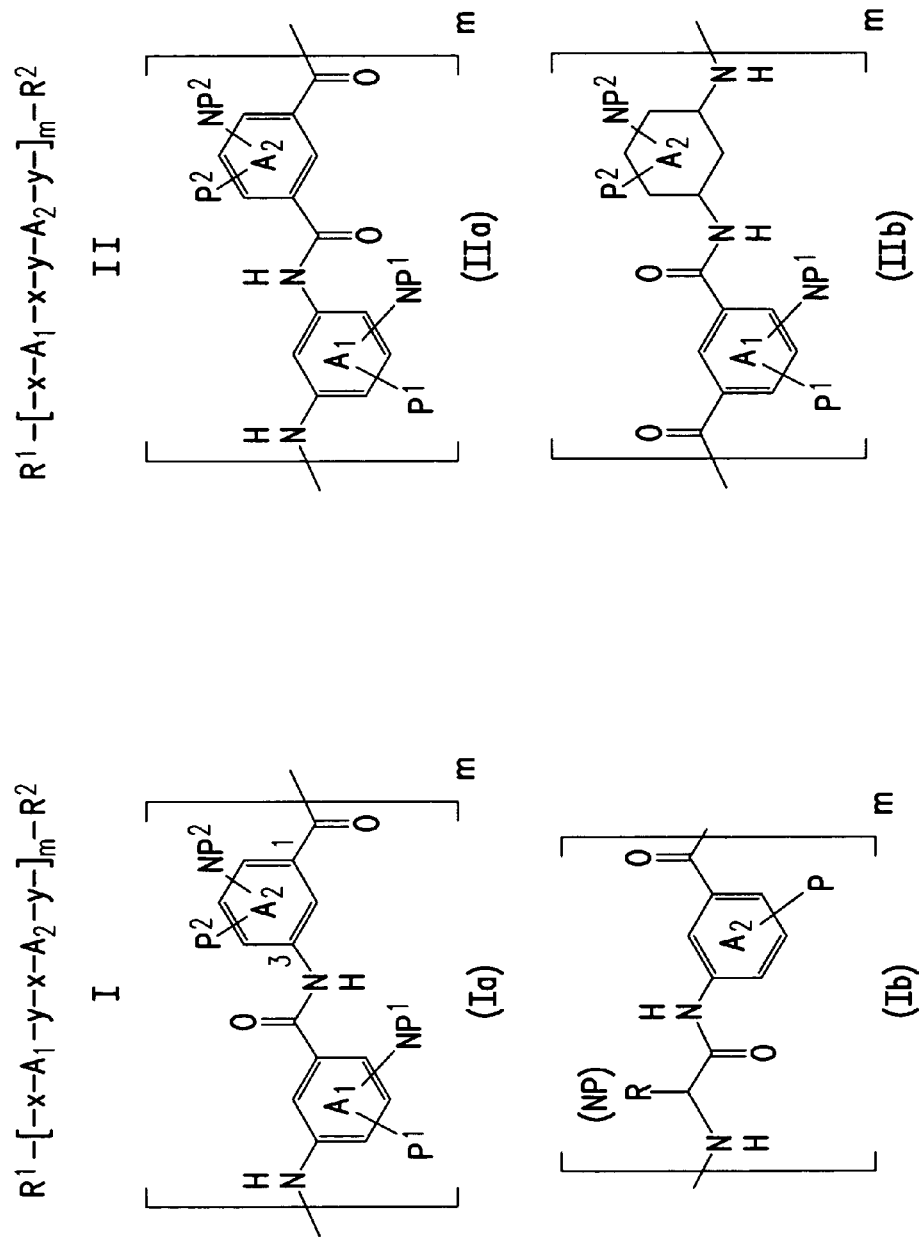
FIG. 3 shows the general structure of facially amphiphilic polyamide or polyester copolymers of Formulae I and II, with representative monomer units for polyamides having aromatic components (Ia and IIa), and with representative monomer units for polyamides having both aromatic and aliphatic components (Ib and IIb).
Figure 4:
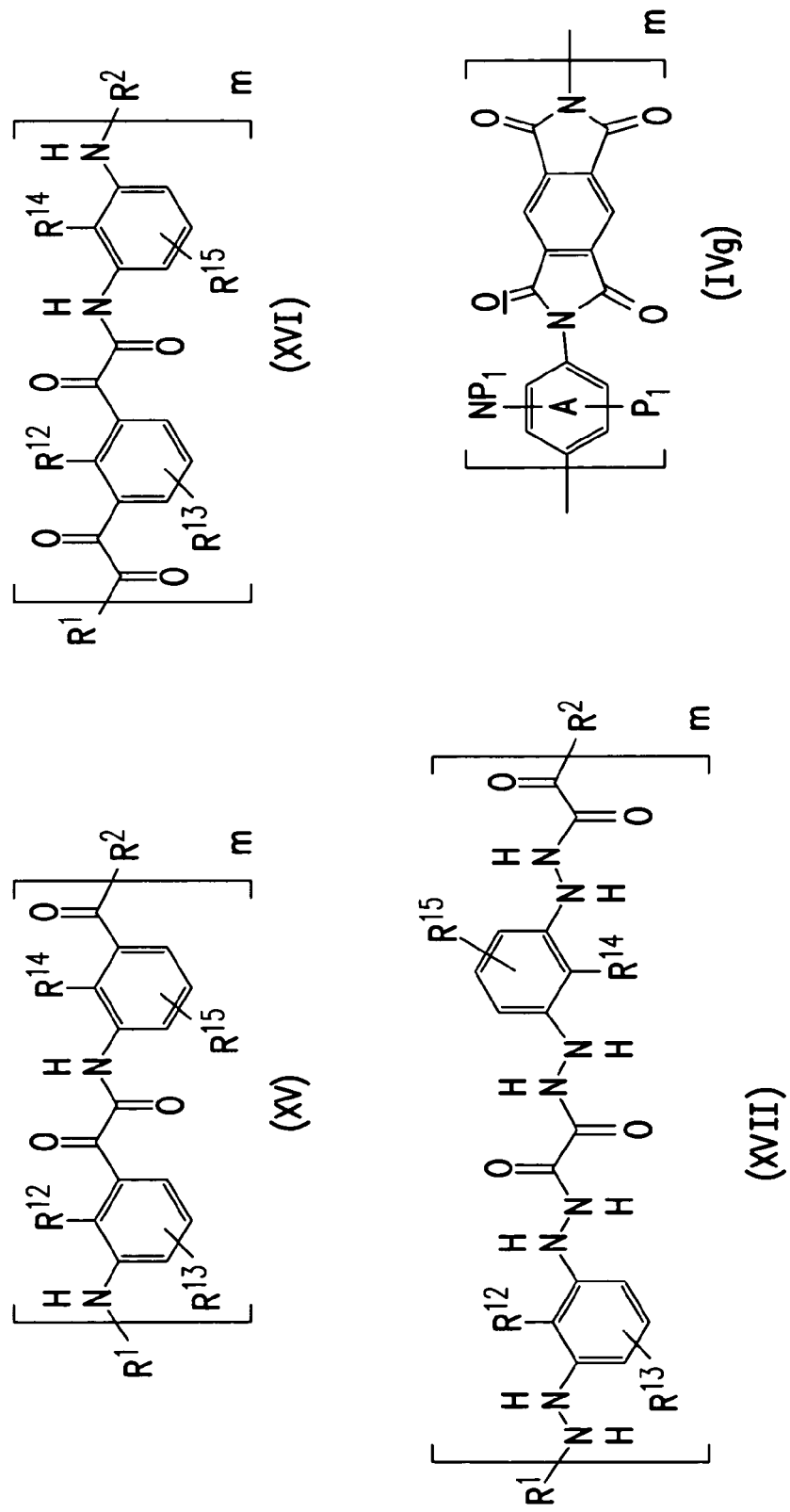
FIG. 4 shows the general structure of polyamides with extended linking groups between aromatic monomer components.

Polyamide and polyester polymers and oligomers of the present invention (FIG. 3) can be comprised solely of aromatic or heteroaromatic monomers or may include both aromatic and aliphatic monomers. One embodiment of the present invention is a copolymer with aromatic monomers and α-amino acid monomers. The polyamides and polyesters can be constructed either by repetitively linking amino (or hydroxy) acid monomers (FIG. 3, I) or by alternating diamine (or dihydroxy) and dicarboxylic acid monomers (FIG. 3, II). While the majority of aromatic rings in the examples depicted in FIGS. 3 and 4 have a meta substitution pattern, one skilled in the art would immediately appreciate that equivalent polymers could be designed with an ortho or a para orientation and these modifications can alter the conformation and the physical properties of the resulting polymer. Furthermore, although the copolymers in FIG. 3 (Ia, IIa, and IIb) are depicted with one polar and one nonpolar substituent, other substitution patterns are equally plausible. The optimal substitution patterns are determined by the conformational properties of the polymer or oligomer backbone.

Although polyamides and polyesters are the most commonly occurring examples of the present invention, other functional groups can be incorporated into the polymer or oligomer backbone with similar results. In particular, thioamides and thioesters are anticipated to have very similar properties. The distance between aromatic rings can significantly impact the geometrical pattern of the polymer and this distance can be altered by incorporating aliphatic chains of varying length, which can be optionally substituted or can comprise an amino acid, a dicarboxylic acid or a diamine. The distance between and the relative orientation of monomers also can altered by replacing the amide bond with a surrogate having additional atoms (see, for example, FIG. 4). Thus, replacing the carbonyl group with a dicarbonyl alters the distance between the monomers and the propensity of dicarbonyl unit to adopt an anti arrangement of the two carbonyl moiety and alter the periodicity of the polymer. Pyromellitic anhydride (FIG. 4, IVg) represents still another alternative to simple amide linkages which can significant alter the conformation and physical properties of the copolymer.

For polymers of the present invention, the synthetic processes can be modified to produce different ranges in molecular weights and the anti-microbial polymers of the present invention will have a molecular weight selected to impart physical and chemical properties optimized for the particular application being contemplated. Traditional polymer syntheses produce a product with a range of molecular weights. The polymer chemist will readily appreciate that the chain length of these polymers can be varied by techniques know in the polymer art. Polymers of the present invention can range in molecular weight from about 300 Daltons up to about 1,000 kiloDaltons. Advancements in solid-phase and solution phase synthesis of amino acid oligomers have made available techniques to prepare homogeneous polymers or oligomers with defined sequence and size and these techniques can be adapted to the present invention. Modern methods of solid phase organic chemistry (E. Atherton and R. C. Sheppard, *Solid Phase Peptide Synthesis A Practical Approach* IRL Press Oxford 1989) now allow the synthesis of homodisperse, sequence-specific oligomers with molecular weights approaching 5,000 Daltons.

Figure 5:
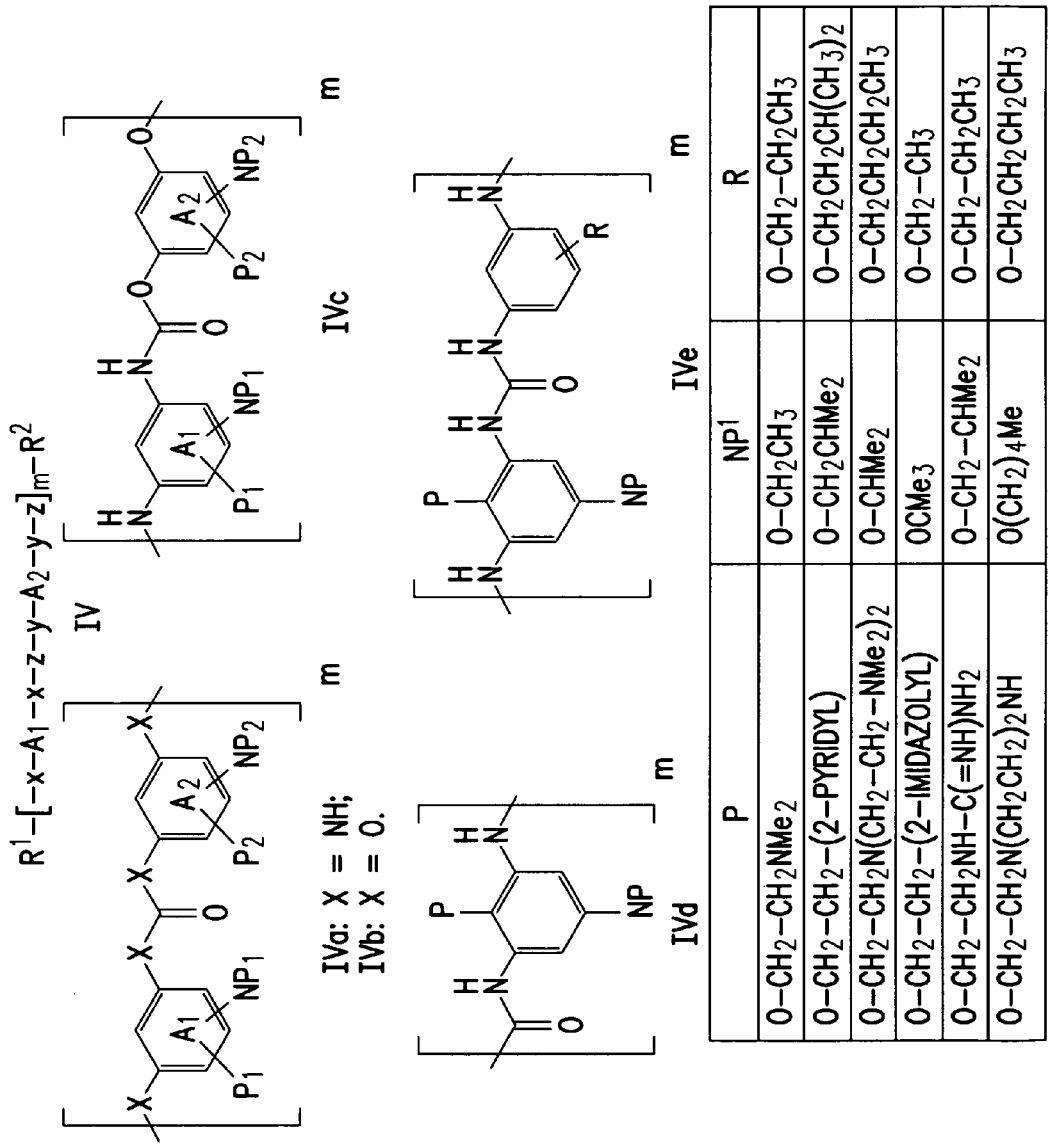
FIG. 5 shows the general structure of facially amphiphilic polyurea, polycarbonate and polyurethane copolymers of Formula IV, with corresponding representative monomer units (IVa, IVb and IVc, respectively). Two typical polyurea monomer units are exemplified in IVd and IVe.
Figure 6:
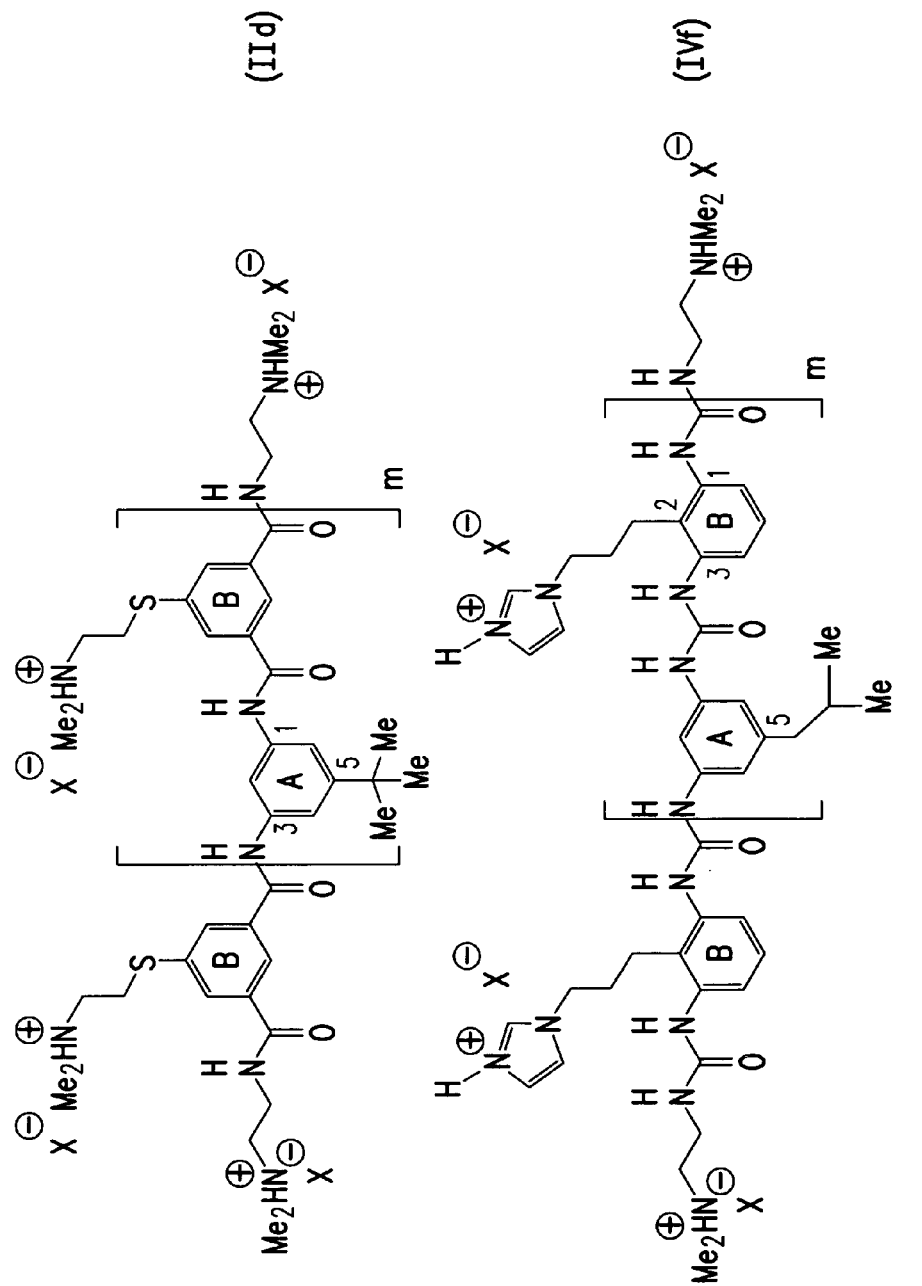
FIG. 6 shows the complete structure of a facially amphiphilic polyamide (IId) and polyurethane (IVf).
Figure 7:
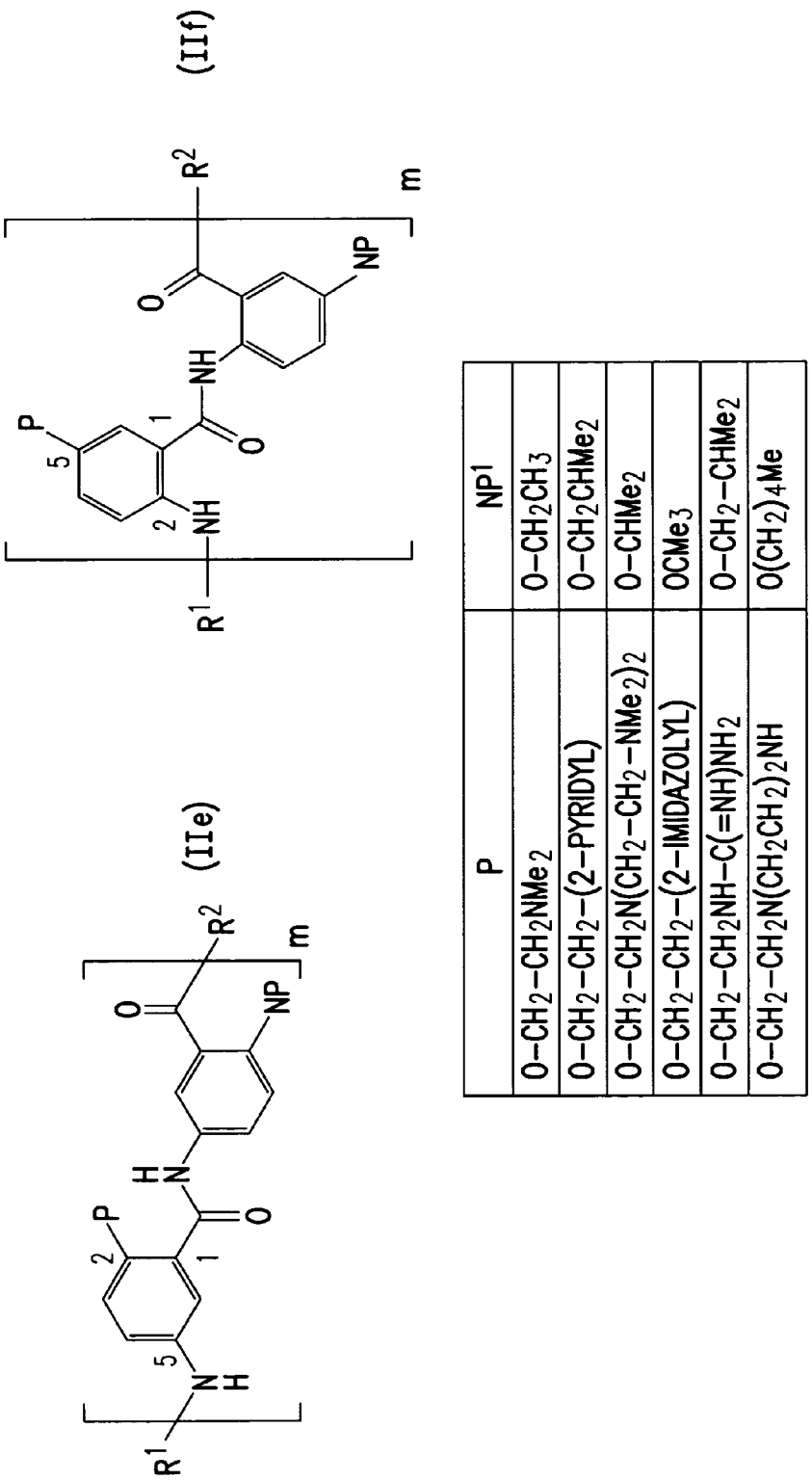
FIG. 7 shows two examples of meta- and ortho-phenylene facially amphiphilic polyamide polymers (IIe and IIf, respectively).

Polyureas (FIG. 5, IVa), polycarbonates (FIG. 5, IVb) or polyurethanes (FIG. 5, IVc) are carbonic acid derivatives and exhibit properties similar to polyamides (N. Samson et al. *J. Appl. Polym. Sci.* 65, 2265 (1997)). FIG. 5, IVd and IVe, depict two different substitution patterns that can be utilized. Other substitution patterns are equally effective.

The process for designing polymers and oligomers of the present invention simply requires a structure in which the repeating sequence of monomers matches the secondary structure adopted by the backbone. Once the periodicity is observed, monomers substituted with polar and nonpolar groups monomers must be prepared and introduced to produce a cationic, amphiphilic secondary. Aromatic polyamides and ureas frequently have only a few torsional degrees of freedom per repeat (typically two or four). In this case, the secondary structure adopted by these polymers and oligomers is most likely planar with polar and nonpolar groups extended from opposite sides of the backbone. In some cases, the desired facial amphiphilicity can be achieved through a simple design principal.

Additional molecular features can be added to the macromolecular backbone to promote the desired secondary structure and disfavor other structures thereby combining elements of both positive and negative design. Conformational studies on biofoldamers (proteins and RNA), and early work with a variety of sequence-specific polymers, have shown that several elements are crucial in order for the polymers to adopt the desired folded conformation. Key elements include strong electrostatic interactions (i.e., intramolecular hydrogen bonding) between adjacent or more distant monomers and rigidification caused by the backbone torsions or by bulky functional groups. For example, the presence of multiple hydrogen bond donors and acceptors along the macromolecular backbone can lead to extensive intermolecular backbone interactions. Precise placement of well designed intramolecular interactions can stabilize desired secondary structures while at the same time blocking the backbone hydrogen bond donors which limits intermolecular aggregation problems. For example, in polyamide and polyurea polmers, a thioether was positioned between two amide nitrogens to form an internal hydrogen bond between the sulfur and amide nitrogens. This limits the torsional angle of the aromatic carbon-amide NH bond by forcing the NH group to be on the same side as the heteroatom, thereby helping to define the overall sheet-like secondary structure. The secondary structure for this backbone is predicted to be nearly planar. Similarly, the polyanthranilate polymer (XIII) is designed based on the finding of Hamuro and Hamilton (Y. Hamuro et al, *J. Am. Chem. Soc.* 1996 119:10587-93) that intramolecular hydrogen-bonding defines the secondary structure of this class of polyarylamides.

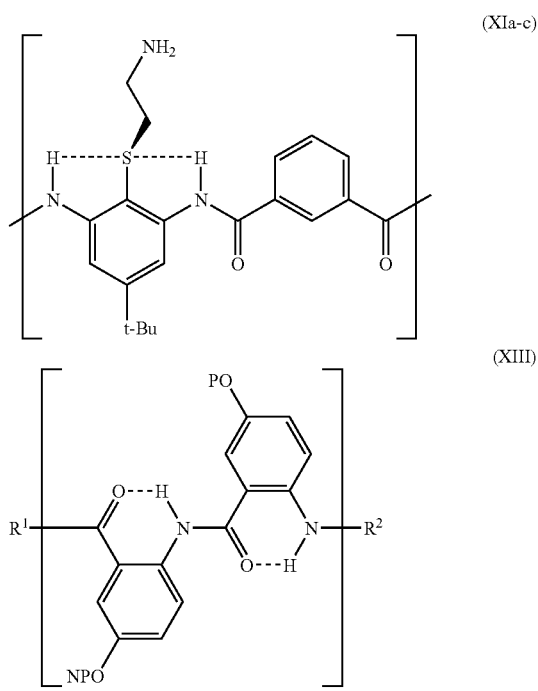

De novo design can provide a systematic approach to studying the important principles regarding biological potency and selectivity (24, 25). It is clear from the diversity of naturally occurring antimicrobial peptides that facial amphiphilicity is the key physiochemical property responsible for the biological activity of this class of peptides. Furthermore, the charge density, hydrophobicity, and degree of amphiphilicity, are a critically important parameters to maximize lethal activity against microbes while minimizing activity against mammalian cells.

The present invention discloses facially amphiphilic polymers and oligomers. Polymers are generally defined as synthetic compounds assembled from monomer subunits that are polydisperse in molecular weight, and are most commonly prepared by one-pot synthetic procedures. The term "polymer" as used herein refers to a macromolecule comprising a plurality of repeating monomers or monomer units. The term includes homopolymers, which are formed from a single type of monomer, and copolymers, which are formed from two or more different monomers. In copolymers, the monomers may be distributed randomly (random copolymer), in alternating fashion (alternating copolymers), or in blocks (block copolymer). The polymers of the present invention are either homopolymers or alternating copolymers having about 2 monomer units to about 500 monomer units, with average molecular weights that range from about 300 Daltons to about 1,000,000 Daltons, or from about 400 Daltons to about 120,000 Daltons. Preferred polymers are those having about 5 to about 100 monomer units, with average molecular weights that range from about 1,000 Daltons to about 25,000 Daltons.

The term "oligomer" as used herein refers to as a homogenous polymer with a defined sequence and molecular weight. Modern methods of solid phase organic chemistry have allowed the synthesis of homodisperse, sequence-specific oligomers with molecular weights approaching 5,000 Daltons. An oligomer, in contrast to a polymer, has a defined sequence and molecular weight and is usually synthesized either by solid phase techniques or by step-wise solution chemistry and purified to homogeneity. Oligomers of the present invention are those having about 1 monomer unit to about 25 monomer units, with molecular weights that range from about 300 Daltons to about 6,000 Daltons. Preferred oligomers are those having about 1 monomer unit (2 monomers) to about 10 monomer units, with molecular weights that range from about 300 Daltons to about 2,500 Daltons.

The term "polymer backbone," "oligomer backbone," or "backbone" as used herein refers to that portion of the polymer or oligomer which is a contiuous chain comprising the bonds formed between monomers upon polymerization. The composition of the polymer or oligomer backbone can be described in terms of the identity of the monomers from which it is formed without regard to the composition of branches, or side chains, of the polymer or oligomer backbone.

The term "polymer side chain," "oligomer side chain," or "side chain" refers to portions of the monomer which, following polymerization, forms an extension of the polymer or oligomer backbone. In homopolymers and homooligomers, all the side chains are derived from the same monomer.

The term "microorganism" as used herein includes bacteria, algae, fungi, yeast, mycoplasmas, mycobacteria, parasites and protozoa.

The term "antimicrobial," "microbiocidal," or "biocidal" as used herein means that the materials inhibit, prevent, or destroy the growth or proliferation of microorganisms. This activity can be either bacteriocidal or bacteriostatic. The term "bactoriocidal" as used herein means the killing of microorganisms. The term "bacteriostatic" as used herein means inhibiting the growth of microorganisms which can be reversible under certain conditions.

The term "alkyl" as used herein by itself or as part of another group refers to both straight and branched chain radicals from 1 to 12 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl.

The term "alkenyl" as used herein refers to a straight or branched chain radical of 2-20 carbon atoms, unless the chain length is limited thereto, including, but not limited to, ethenyl, 1-propenyl, 2-propenyl, 2-methyl-1-propenyl, 1-butenyl, 2-butenyl, and the like. Preferably, the alkenyl chain is 2 to 10 carbon atoms in length, more preferably, 2 to 8 carbon atoms in length most preferably from 2 to 4 carbon atoms in length.

The term "alkynyl" as used herein refers to a straight or branched chain radical of 2-20 carbon atoms, unless the chain length is limited thereto, wherein there is at least one triple bond between two of the carbon atoms in the chain, including, but not limited to, acetylene, 1-propylene, 2-propylene, and the like. Preferably, the alkynyl chain is 2 to 10 carbon atoms in length, more preferably, 2 to 8 carbon atoms in length, most preferably from 2 to 4 carbon atoms in length.

The term "alkylene" as used herein refers to an alkyl linking group, i.e., an alkyl group that links one group to another group in a molecule.

The term "alkoxy" as used herein refers to mean a straight or branched chain radical of 1 to 20 carbon atoms, unless the chain length is limited thereto, bonded to an oxygen atom, including, but not limited to, methoxy, ethoxy, n-propoxy, isopropoxy, and the like. Preferably the alkoxy chain is 1 to 10 carbon atoms in length, more preferably 1 to 8 carbon atoms in length, and even more preferred 1 to 6 carbon atoms in length.

The term "aryl" as used herein by itself or as part of another group refers to monocyclic or bicyclic aromatic groups containing from 6 to 12 carbons in the ring portion, preferably 6-10 carbons in the ring portion, such as the carbocyclic groups phenyl, naphthyl or tetrahydronaphthyl.

The term "arylene" as used herein by itself or as part of another group refers to an aryl linking group, i.e., an aryl group that links one group to another group in a molecule.

The term "cycloalkyl" as used herein by itself or as part of another group refers to cycloalkyl groups containing 3 to 9 carbon atoms, more preferably, 3 to 8 carbon atoms. Typical examples are cyclopropyl, cyclobutyl, cyclopentyl, cyclohexyl, cycloheptyl, cyclooctyl and cyclononyl.

The term "halogen" or "halo" as used herein by itself or as part of another group refers to chlorine, bromine, fluorine or iodine.

The term "hydoxy" or "hydroxyl" as used herein by itself or as part of another group refers to an —OH group.

The term "heteroaryl" as used herein refers to groups having 5 to 14 ring atoms; 6, 10 or 14 $7\pi$-electrons shared in a cyclic array; and containing carbon atoms and 1, 2 or 3 oxygen, nitrogen or sulfur heteroatoms. Examples of heteroaryl groups include thienyl, imadizolyl, oxadiazolyl, isoxazolyl, triazolyl, pyridyl, pyrimidinyl, pyridazinyl, furyl, pyranyl, thianthrenyl, pyrazolyl, pyrazinyl, indolizinyl, isoindolyl, isobenzofuranyl, benzoxazolyl, xanthenyl, 2H-pyrrolyl, pyrrolyl, 3H-indolyl, indolyl, indazolyl, purinyl, 4H-quinolizinyl, isoquinolyl, quinolyl, phthalazinyl, naphthyridinyl, quinazolinyl, phenanthridinyl, acridinyl, perimidinyl, phenanthrolinyl, phenazinyl, isothiazolyl, phenothiazinyl, isoxazolyl, furazanyl, and phenoxazinyl groups. Especially preferred heteroaryl groups include 1,2,3-triazole, 1,2,4-triazole, 5-amino 1,2,4-triazole, imidazole, oxazole, isoxazole, 1,2,3-oxadiazole, 1,2,4-oxadiazole, 3-amino-1,2, 4-oxadiazole, 1,2,5-oxadiazole, 1,3,4-oxadiazole, pyridine, and 2-aminopyridine.

The term "heteroarylene" as used herein by itself or as part of another group refers to a heteroaryl linking group, i.e., a heteroaryl group that links one group to another group in a molecule.

The term "heterocycle" or "heterocyclic ring", as used herein except where noted, represents a stable 5- to 7-membered mono- or bicyclic or stable 7- to 10-membered bicyclic heterocyclic ring system any ring of which may be saturated or unsaturated, and which consists of carbon atoms and from one to three heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Especially useful are rings containing one oxygen or sulfur, one to three nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, thienyl, benzothienyl, thiamorpholinyl, thiamorpholinyl sulfoxide, thiamorpholinyl sulfone, and oxadiazolyl. Morpholino is the same as morpholinyl.

The term "alkylamino" as used herein by itself or as part of another group refers to an amino group which is substituted with one alkyl group having from 1 to 6 carbon atoms. The term "dialkylamino" as used herein by itself or as part of another group refers to an amino group which is substituted with two alkyl groups, each having from 1 to 6 carbon atoms.

The term "alkylthio" as used herein by itself or as part of an other group refers to an thio group which is substituted with one alkyl group having from 1 to 6 carbon atoms.

The term "lower acylamino" as used herein by itself or as part of an other group refers to an amino group substituted with a $C_1$-$C_6$ alkylcarbonyl group.

The phrase "groups with chemically nonequivalent termini" refers to functional groups such as esters amides, sulfonamides and N-hydroxyoximes where reversing the orientation of the substituents, e.g. $R^1C(=O)OR^2$ vs. $R^1O(O=)CR^2$, produces unique chemical entities.

The term "basic heterocycle" as used herein denotes cyclic atomic array which includes a nitrogen atom that has a pKa greater than about 5 and that is protonated under physiological conditions. Representative basic heterocycles are pyridine, quinoline, imidazole, imidazoline, cyclic guanidines, pyrazole, pyrazoline, dihydropyrazoline, pyrrolidine, piperidine, piperazine, 4-alkylpiperazine, and derivatives thereof, such as 2-aminopyridine, 4-aminopyridine, 2-aminoimidazoline, 4-aminoimidazoline or VII, where $X^1$ is O, N, S or absent and i is 2 to 4.

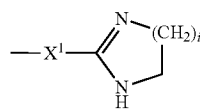

(VII)

The term "amphiphilic" as used herein describes a three-dimensional structure having discrete hydrophobic and hydrophilic regions. An amphiphilic polymer or oligomer requires the presence of both hydrophobic and hydrophilic elements along the polymer backbone. The presence of hydrophobic and hydrophilic groups is a necessary, but not sufficient, condition to produce an amphiphilic oligomer or polymer. Polymers frequently adopt a random or disordered conformation in which the side chains are located randomly in space and there are no distinctive hydrophobic and hydrophilic regions.

The term "facially amphiphilic" or "facial amphiphilicity" as used herein describes polymers and oligomers with polar (hydrophilic) and nonpolar (hydrophobic) side chains that adopt conformation(s) leading to segregation of polar and nonpolar side chains to opposite faces or separate regions of the structure. This structure can comprise any of the energetically accessible low-energy conformations for a given polymer or oligomer backbone. Additionally random or block copolymers may adopt random backbone conformations that do not lead to distinct hydrophilic and hydrophobic regions or which do not segregate along different faces of the polymer. These copolymers are not facially amphiphilic as defined herein.

The term "naturally occurring amino acids" refers to the L-isomers of the naturally occurring amino acids, The naturally occurring amino acids are glycine, alanine, valine, leucine, isoleucine, serine, methionine, threonine, phenylalanine, tyrosine, tryptophan, cysteine, proline, histidine, aspartic acid, asparagine, glutamic acid, glutamine, carboxyglutamic acid, arginine, ornithine and lysine. Unless specifically indicated, all amino acids referred to in this application are in the L-form.

The term "side chain of a naturally occurring amino acid" as used herein refers to the substituent on the α-carbon of a amino acid. The term "polar side chain of a naturally occurring amino acid" refers to the side chain of a positively charged, negatively charged or hydrophilic amino acid. The term "nonpolar side chain of a naturally occurring amino acid" refers to the side chain of a hydrophobic amino acid.

The term "positively charged amino acid" or "cationic amino acid" as used herein includes any naturally occurring or unnatural amino acid having a positively charged side chain under normal physiological conditions. Examples of positively charged naturally occurring amino acids are arginine, lysine and histidine.

The term "hydrophilic amino acid" means any amino acid having an uncharged, polar side chain that is relatively soluble in water. Examples of naturally occurring hydrophilic amino acids are serine, threonine, tyrosine, asparagine, glutamine, and cysteine.

The term "hydrophobic amino acid" means any amino acid having an uncharged, nonpolar side chain that is relatively insoluble in water. Examples of naturally occurring hydrophobic amino acids are alanine, leucine, isoleucine, valine, proline, phenylalanine, tryptophan and methionine.

The terms "treat," "treated," or "treating" as used herein refers to both therapeutic treatment and prophylactic or preventative measures, wherein the object is to prevent or slow down (lessen) an undesired physiological condition, disorder or disease, or obtain beneficial or desired clinical results. For purposes of this invention, beneficial or desired clinical results include, but are not limited to, alleviation of symptoms; diminishment of extent of condition, disorder or disease; stabilized (i.e., not worsening) state of condition, disorder or disease; delay in onset or slowing of condition, disorder or disease progression; amelioration of the condition, disorder or disease state, remission (whether partial or total), whether detectable or undetectable; or enhancement or improvement of condition, disorder or disease. Treatment includes eliciting a clinically significant response, without excessive levels of side effects. Treatment also includes prolonging survival as compared to expected survival if not receiving treatment.

The term "animal" as used herein includes, but is not limited to, humans and non-human vertebrates such as wild, domestic and farm animals.

The polymers and oligomers of the present invention have been shown to possess antimicrobial activity. Thus, the polymers and oligomers of the present invention can be used as antimicrobial agents and, for example, can be used in a method of treating microbial infections in an animal.

Thus, the invention is directed to a method of treating a microbial infection in an animal in need thereof, by administering to the animal a polymer or oligomer of the invention.

For example, in some aspects, the invention is directed to a method of treating a microbial infection in an animal in need thereof, the method comprising administering to the animal an effective amount of a pharmaceutical composition comprising a polymer or oligomer of Formula I:

$$R^1\text{-}[\text{-}x\text{-}A_1\text{-}y\text{-}x\text{-}A_2\text{-}y\text{-}]_m\text{-}R^2 \quad (I)$$

or an acceptable salt or solvate thereof,
wherein:
x is $NR^8$, $—N(R^8)N(R^8)—$, O, or S; y is C=O, C=S, O=S=O, or —C(=O)C(=O)—;
and $R^8$ is hydrogen or alkyl;
$A_1$ and $A_2$ are independently optionally substituted arylene or optionally substituted heteroarylene, wherein:
  (i) $A_1$ and $A_2$ are independently optionally substituted with one or more polar (PL) group(s), one or more non-polar (NPL) group(s), or a combination of one or more polar (PL) group(s) and one or more non-polar (NPL) group(s); or
  (ii) $A_1$ is optionally substituted arylene or optionally substituted heteroarylene and $A_2$ is a $C_3$ to $C_8$ cycloalkyl or $—(CH_2)_q—$, wherein q is 1 to 7, wherein $A_1$ and $A_2$ are independently optionally substituted with one or more polar (PL) group(s), one or more non-polar (NPL) group(s), or a combination of one or more polar (PL) group(s) and one or more non-polar (NPL) group(s); or
  (iii) $A_2$ is optionally substituted arylene or optionally substituted heteroarylene, and $A_1$ is a $C_3$ to $C_8$ cycloalkyl or $—(CH_2)_q—$, wherein q is 1 to 7, wherein $A_1$ and $A_2$ are independently optionally substituted with one or more polar (PL) group(s), one or more non-polar (NPL) group(s), or a combination of one or more polar (PL) group(s) and one or more non-polar (NPL) group(s);
$R^1$ is
  (i) hydrogen, a polar (PL) group, or a non-polar (NPL) group, and $R^2$ is $-x-A_1-y-R^{11}$, wherein $R^{11}$ is hydrogen, a polar (PL) group, or a non-polar (NPL) group; or
  (ii) $R^1$ and $R^2$ are independently hydrogen, a polar (PL) group, or a non-polar (NPL) group; or
  (iii) $R^1$ and $R^2$ together are a single bond;
NPL is a nonpolar group independently selected from the group consisting of $—B(OR^4)_2$ and $—(NR^3)_{q1NPL}—U^{NPL}—(CH_2)_{pNPL}—(NR^{3''})_{q2NPL}—R^{4'}$, wherein:
$R^3$, $R^{3'}$, and $R^{3''}$ are independently selected from the group consisting of hydrogen, alkyl, and alkoxy;
$R^4$ and $R^{4'}$ are independently selected from the group consisting of hydrogen, alkyl, alkenyl, alkynyl, cycloalkyl, aryl, and heteroaryl, any of which is optionally substituted with one or more alkyl or halo groups;
$U^{NPL}$ is absent or selected from the group consisting of O, S, S(=O), S(=O)$_2$, $NR^3$, —C(=O)—, —C(=O)—N=N—$NR^3$—, —C(=O)—$NR^3$—N=N—, —N=N—$NR^3$—, —C(=N—N($R^3$)$_2$)—, —C(=$NR^3$)—, —C(=O)O—, —C(=O)S—, —C(=S)—, —O—P(=O)$_2$O—, —$R^3$O—, —$R^3$S—, —S—C=N— and —C(=O)—$NR^3$—O—, wherein groups with two chemically nonequivalent termini can adopt both possible orientations;
the $—(CH_2)_{pNPL}—$ alkylene chain is optionally substituted with one or more amino or hydroxy groups, or is unsaturated;
pNPL is 0 to 8;
q1NPL and q2NPL are independently 0, 1 or 2;
PL is a polar group selected from the group consisting of halo, hydroxyethoxymethyl, methoxyethoxymethyl, polyoxyethylene, and $—(NR^{5'})_{q1PL}—U^{PL}—(CH_2)_{pPL}—(NR^{5'})_{q2PL}—V$, wherein:
$R^5$, $R^{5'}$, and $R^{5''}$ are independently selected from the group consisting of hydrogen, alkyl, and alkoxy;
$U^{PL}$ is absent or selected from the group consisting of O, S, S(=O), S(=O)$_2$, $NR^5$, —C(=O)—, —C(=O)—N=N—$NR^5$—, —C(=O)—$NR^5$—N=N—, —N=N—$NR^5$—, —C(=N—N($R^5$)$_2$)—, —C(=$NR^5$)—, —C(=O)O—, —C(=O)S—, —C(=S)—, —O—P(=O)$_2$O—, —$R^5$O—, —$R^5$S—, —S—C=N— and —C(=O)—$NR^5$—O—, wherein groups with two chemically nonequivalent termini can adopt both possible orientations;
V is selected from the group consisting of nitro, cyano, amino, hydroxy, alkoxy, alkylthio, alkylamino, dialkylamino, $—NH(CH_2)_pNH_2$ wherein p is 1 to 4, $—N(CH_2CH_2NH_2)_2$, diazamino, amidino, guanidino, guanyl, semicarbazone, aryl, heterocycle and heteroaryl, any of which is optionally substituted with one or more of amino, halo, cyano, nitro, hydroxy, $—NH(CH_2)_pNH_2$ wherein p is 1 to 4, $N(CH_2CH_2NH_2)_2$, amidino, guanidino, guanyl, aminosulfonyl, aminoalkoxy, aminoalkythio, lower acylamino, or benzyloxycarbonyl, wherein p is 1 to 4;
the $—(CH_2)_{pPL}—$ alkylene chain is optionally substituted with one or more amino or hydroxy groups, or is unsaturated;
pPL is 0 to 8;
q1PL and q2PL are independently 0, 1 or 2; and
m is 1 to about 500;
and a pharmaceutically acceptable carrier or diluent.

Polymers and oligomers of Formula I that are preferred for use in the disclosed method are those wherein x is $NR^8$, O, or $—N(R^8)N(R^8)—$, and $R^8$ is hydrogen or $C_1$-$C_6$ alkyl. Also preferred are those polymers and oligomers wherein y is C=O, C=S, or O=S=O. Especially preferred are those polymers and oligomers wherein x is $NR^8$ and y is C=O. For example, oligomers of Formula I wherein x is NH and y is C=O are especially preferred. Also preferred are oligomers of Formula I wherein x is O and y is C=O, or wherein x is $—N(R^8)N(R^8)—$ and $R^8$ is hydrogen, and y is C=O.

Preferred are those polymers and oligomers of Formula I wherein $A_1$ or $A_2$ are independently optionally substituted o-, m-, or p-phenylene. Those oligomers wherein $A_1$ or $A_2$ are optionally substituted m-phenylene are especially preferred.

Preferred polymers and oligomers of Formula I are also those wherein $A_1$ is optionally substituted arylene or optionally substituted heteroarylene and $A_2$ is a $C_3$ to $C_8$ cycloalkyl or $—(CH_2)_q—$, wherein q is 1 to 7, and wherein $A_1$ and $A_2$ are independently optionally substituted with one or more polar (PL) group(s), one or more non-polar (NPL) group(s), or a combination of one or more polar (PL) group(s) and one or more non-polar (NPL) group(s). Especially preferred are oligomers of Formula I wherein $A_1$ is substituted arylene and $A_2$ is $—(CH_2)_q—$, wherein q is 1 or 2, and wherein one of $A_1$ and $A_2$ is substituted with one or more polar (PL) group(s), and the other of $A_1$ and $A_2$ is substituted with one or more non-polar (NPL) group(s).

Also preferred are polymers and oligomers of Formula I wherein $A_2$ is optionally substituted arylene or optionally substituted heteroarylene, and $A_1$ is a $C_3$ to $C_8$ cycloalkyl or —$(CH_2)_q$—, wherein q is 1 to 7, and wherein $A_1$ and $A_2$ are independently optionally substituted with one or more polar (PL) group(s), one or more non-polar (NPL) group(s), or a combination of one or more polar (PL) group(s) and one or more non-polar (NPL) group(s). Especially preferred are oligomers of Formula I wherein $A_2$ is substituted arylene and $A_1$ is —$(CH_2)_q$—, wherein q is 1 or 2, and wherein one of $A_1$ and $A_2$ is substituted with one or more polar (PL) group(s), and the other of $A_1$ and $A_2$ is substituted with one or more non-polar (NPL) group(s).

In some aspects of the invention, preferred polymers and oligomers of Formula I are those wherein (i) $R^1$ is hydrogen, a polar (PL) group, or a non-polar (NPL) group, and $R^2$ is -x-$A_1$-y-$R^{11}$, wherein $R^{11}$ is hydrogen, a polar (PL) group, or a non-polar (NPL) group. Especially preferred are oligomers of Formula I wherein $R^1$ is hydrogen, $R^2$ is -x-$A_1$-y-$R^{11}$, and $R^{11}$ is a polar (PL) group, for example, hydroxy.

In other aspects, preferred polymers and oligomers of Formula I are those wherein $R^1$ and $R^2$ are independently hydrogen, a polar (PL) group, or a non-polar (NPL) group. Especially preferred are oligomers of Formula I wherein $R^1$ is hydrogen, and $R^2$ is a polar group, for example, amino or hydroxy.

In some aspects of the invention, preferred polymers and oligomers of Formula I are those wherein NPL is —$B(OR^4)_2$. Preferred values of $R^4$ are hydrogen, $C_1$-$C_{10}$ alkyl, $C_3$-$C_{18}$ branched alkyl, $C_2$-$C_{10}$ alkenyl, $C_2$-$C_{10}$ alkynyl, $C_3$-$C_8$ cycloalkyl, $C_6$-$C_{10}$ aryl, and heteroaryl, any of which is optionally substituted with one or more $C_1$-$C_6$ alkyl or halo groups.

In other aspects, preferred polymers and oligomers of Formula I are those wherein NPL is —$(NR^{3'})_{q1NPL}$—$U^{NPL}$—$(CH_2)_{pNPL}$—$(NR^{3''})_{q2NPL}$—$R^{4'}$, and $R^3$, $R^{3'}$, $R^{3''}$, $R^{4'}$, $U^{NPL}$, pNPL, q1NPL and q2NPL are as defined above.

Preferred values for each of $R^3$, $R^{3'}$, and $R^{3''}$ are hydrogen, $C_1$-$C_6$ alkyl, and $C_1$-$C_6$ alkoxy. Hydrogen is an especially preferred value for $R^3$, $R^{3'}$, and $R^{3''}$.

Preferred values of $R^{4'}$ are hydrogen, $C_1$-$C_{10}$ alkyl, $C_3$-$C_{18}$ branched alkyl, $C_2$-$C_{10}$ alkenyl, $C_2$-$C_{10}$ alkynyl, $C_3$-$C_8$ cycloalkyl, $C_6$-$C_{10}$ aryl, and heteroaryl, any of which is optionally substituted with one or more $C_1$-$C_6$ alkyl or halo groups. Values of $R^{4'}$ that are more preferred are $C_1$-$C_{10}$ alkyl, $C_3$-$C_{18}$ branched alkyl, $C_2$-$C_{10}$ alkenyl, $C_2$-$C_{10}$ alkynyl, and $C_6$-$C_{10}$ aryl, especially phenyl. Especially preferred values of $R^{4'}$ are $C_1$-$C_{10}$ alkyl and $C_3$-$C_{18}$ branched alkyl. Suitable $C_1$-$C_{10}$ alkyl and $C_3$-$C_{18}$ branched alkyl groups are methyl, ethyl, n-propyl, isopropyl, n-butyl, tert-butyl, n-pentyl, and isopentyl.

Preferred values of $U^{NPL}$ are O, S, S(=O), S(=O)$_2$, NH, —C(=O)—, —C(=O)—N=N—NH—, —C(=O)—NH—N=N—, —N=N—NH—, —C(=N—N($R^3$)$_2$)—, —C(=N$R^3$)—, —C(=O)O—, —C(=O)S—, —C(=S)—, —O—P(=O)$_2$O—, —$R^3$O—, —$R^3$S—, —S—C=N— and —C(=O)—N$R^3$—O—, wherein groups with two chemically nonequivalent termini can adopt both possible orientations.

Values of $U^{NPL}$ that are more preferred are O, S, NH, —C(=O)—, —C(=O)—N=N—NH—, —C(=O)—NH—N=N—, —N=N—NH—, —C(=N—N($R^3$)$_2$)—, —C(=N$R^3$)—, —C(=O)O—, —$R^3$S— and —$R^3$O—. Especially preferred values of $U^{NPL}$ are NH, —C(=O)—, O and S. Especially preferred polymers and oligomers of Formula I also are those wherein $U^{NPL}$ is absent.

In some aspects of the invention, preferred polymers and oligomers of Formula I are those wherein $U^{NPL}$ is —O—P(=O)$_2$O—.

Preferred values of pNPL are 0 to 6; values of pNPL of 0 to 4 are especially preferred, with values of pNPL of 0 to 2 most preferred.

Preferred values of q1NPL and q2NPL are 0 or 1. Values of q1NPL and q2NPL of 0 or 1 are especially preferred, with a value of 0 being the most preferred for each of q1NPL and q2NPL.

In preferred polymers and oligomers of Formula I, the —$(CH_2)_{pNPL}$— alkylene chain in NPL is unsubstituted or substituted with one or more amino or hydroxy groups. More preferred are those oligomers of Formula I wherein the —$(CH_2)_{pNPL}$— alkylene chain in NPL is either unsubstituted or substituted with one or more amino groups.

An especially preferred value of NPL for polymers and oligomers of Formula I is $C_1$-$C_6$ alkyl or aryl $C_1$-$C_6$ alkyl. Examples of preferred values for NPL are n-propyl, isopropyl, n-butyl, tert-butyl, and benzyl.

In some aspects of the invention, preferred polymers and oligomers of Formula I are those wherein PL is —$(NR^{5'})_{q1PL}$—$U^{PL}$—$(CH_2)_{pPL}$—$(NR^{5''})_{q2PL}$—V, and $R^5$, $R^{5'}$, $R^{5''}$, V, $U^{PL}$, pPL, q1PL and q2PL are as defined above.

Preferred values for $R^5$, $R^{5'}$, and $R^{5''}$ are hydrogen, $C_1$-$C_6$ alkyl, and $C_1$-$C_6$ alkoxy. Hydrogen is an especially preferred value for each of $R^5$, $R^{5'}$, and $R^{5''}$.

Preferred values of $U^{PL}$ are O, S, S(=O), S(=O)$_2$, NH, —C(=O)—, —C(=O)—N=N—NH—, —C(=O)—NH—N=N—, —N=N—NH—, —C(=N—N($R^5$)$_2$)—, —C(=N$R^5$)—, —C(=O)O—, —C(=O)S—, —C(=S)—, —O—P(=O)$_2$O—, —$R^5$O—, —$R^5$S—, —S—C=N— and —C(=O)—N$R^5$—O—, wherein groups with two chemically nonequivalent termini can adopt both possible orientations. Values of $U^{PL}$ that are more preferred are O, S, NH, —C(=O)—, —C(=O)—N=N—NH—, —C(=O)—NH—N=N—, —N=N—NH—, —C(=N—N($R^5$)$_2$)—, —C(=N$R^5$)—, —C(=O)O—, —$R^5$S— and —$R^5$O—. Especially preferred values of $U^{PL}$ are O, S, NH, and —C(=O)—. Preferred polymers and oligomers of Formula I are also those wherein $U^{PL}$ is absent.

In some aspects of the invention, preferred polymers and oligomers of Formula I are those wherein $U^{PL}$ is —O—P(=O)$_2$O—.

Preferred values of V are nitro, cyano, amino, hydroxy, $C_1$-$C_6$ alkoxy, $C_1$-$C_6$ alkylthio, $C_1$-$C_6$ alkylamino, $C_1$-$C_6$ dialkylamino, —NH$(CH_2)_p$NH$_2$ wherein p is 1 to 4, —N$(CH_2CH_2NH_2)_2$, diazamino, amidino, guanidino, guanyl, semicarbazone, $C_6$-$C_{10}$ aryl, heterocycle, and heteroaryl, preferably any of which is optionally substituted with one or more of amino, halo, cyano, nitro, hydroxy, —NH$(CH_2)_p$NH$_2$, —N$(CH_2CH_2NH_2)_2$, amidino, guanidino, guanyl, aminosulfonyl, aminoalkoxy, lower acylamino, or benzyloxycarbonyl.

Suitable heteroaryl groups include indolyl, 3H-indolyl, 1H-isoindolyl, indazolyl, benzoxazolyl, pyridyl, and 2-aminopyridyl. Suitable heterocycle groups include piperidinyl, piperazinyl, imidazolidinyl, pyrrolidinyl, pyrazolidinyl, and morpholinyl.

Values of V that are more preferred are amino, $C_1$-$C_6$ alkylamino, $C_1$-$C_6$ dialkylamino, —NH$(CH_2)_p$NH$_2$ wherein p is 1 to 4, —N$(CH_2CH_2NH_2)_2$, diazamino, amidino, guanidino, guanyl, and semicarbazone, preferably any of which is optionally substituted with one or more of amino, halo, cyano, nitro, hydroxy, —NH$(CH_2)_p$NH$_2$, —N$(CH_2CH_2NH_2)_2$, amidino, guanidino, guanyl, aminosulfonyl, aminoalkoxy, lower acylamino, or benzyloxycarbonyl.

Especially preferred values of V are amino, $C_1$-$C_6$ alkylamino, —NH(CH$_2$)$_p$NH$_2$ wherein p is 1 to 4, —N(CH$_2$CH$_2$NH$_2$)$_2$, diazamino, amidino, and guanidino, preferably any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanyl, guanidino, or aminoalkoxy. Values of V that are most preferred are amino and guanidino.

Preferred values of pPL are 0 to 6, with values of pPL of 2 to 5 especially preferred.

Preferred values of q1PL and q2PL are 0 or 1. Values of q1PL and q2PL of 0 or 1 are especially preferred, with a value of 0 being especially preferred for each of q1PL and q2PL.

In preferred polymers and oligomers of Formula I, the —(CH$_2$)$_{pPL}$-alkylene chain in PL is optionally substituted with one or more amino groups.

Preferred polymers of Formula I are those in which m is 1 to about 500. Especially preferred are those polymers of Formula I wherein m is 1 to about 100, or wherein m is 1 to about 50.

Oligomers of Formula I that are preferred are those wherein m is 1 to about 30, or m is 1 to about 25; more preferred are those wherein m is 1 to about 20, or those wherein m is 1 to about 10, or wherein m is 1 to about 5.

Thus, the invention is also directed to a method of treating a microbial infection in an animal in need thereof, the method comprising administering to the animal an effective amount of a pharmaceutical composition comprising an oligomer of Formula I, or an acceptable salt or solvate thereof, wherein:

x is NR$^8$, y is C=O, and R$^8$ is hydrogen;

A$_1$ is optionally substituted o-, m-, or p-phenylene and A$_2$ is —(CH$_2$)$_q$—, wherein q is 1 or 2, and wherein A$_1$ and A$_2$ are independently optionally substituted with one or more polar (PL) group(s), one or more non-polar (NPL) group(s), or a combination of one or more polar (PL) group(s) and one or more non-polar (NPL) group(s); or A$_2$ is optionally substituted o-, m-, or p-phenylene and A$_1$ is —(CH$_2$)$_q$—, wherein q is 1 or 2, and wherein A$_1$ and A$_2$ are independently optionally substituted with one or more polar (PL) group(s), one or more non-polar (NPL) group(s), or a combination of one or more polar (PL) group(s) and one or more non-polar (NPL) group(s);

R$^1$ and R$^2$ are independently hydrogen, a polar (PL) group, or a non-polar (NPL) group;

NPL is —(NR$^{3'}$)$_{q1NPL}$—U$^{NPL}$—(CH$_2$)$_{pNPL}$—(NR$^{3''}$)$_{q2NPL}$R$^{4'}$, wherein:

R$^3$, R$^{3'}$, and R$^{3''}$ are independently selected from the group consisting of hydrogen, $C_1$-$C_6$ alkyl, and $C_1$-$C_6$ alkoxy;

R$^{4'}$ is selected from the group consisting of hydrogen, alkyl, alkenyl, alkynyl, cycloalkyl, aryl, and heteroaryl, any of which is optionally substituted with one or more alkyl or halo groups;

U$^{NPL}$ is absent or selected from the group consisting of O, S, S(=O), S(=O)$_2$, NR$^3$, —C(=O)—, —C(=O)—N=N—NR$^3$—, —C(=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$O—, —R$^3$S—, —S—C=N— and —C(=O)—NR$^3$—O—, wherein groups with two chemically nonequivalent termini can adopt both possible orientations;

the —(CH$_2$)$_{pNPL}$— alkylene chain is optionally substituted with one or more amino or hydroxy groups, or the alkylene chain is unsaturated;

pNPL is 0 to 8;

q1NPL and q2NPL are independently 0, 1 or 2;

PL is a polar group selected from the group consisting of halo, hydroxyethoxymethyl, methoxyethoxymethyl, polyoxyethylene, and —(NR$^{5'}$)$_{q1PL}$—U$^{PL}$—(CH$_2$)$_{pPL}$—(NR$^{5''}$)$_{q2PL}$—V, wherein:

R$^5$, R$^{5'}$, and R$^{5''}$ are independently selected from the group consisting of hydrogen, alkyl, and alkoxy;

U$^{PL}$ is absent or selected from the group consisting of O, S, S(=O), S(=O)$_2$, NR$^5$—, —C(=O)—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N— and —C(=O)—NR$^5$—O—, wherein groups with two chemically nonequivalent termini can adopt both possible orientations;

V is selected from the group consisting of nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkythio, lower acylamino, or benzyloxycarbonyl;

the —(CH$_2$)$_{pPL}$— alkylene chain is optionally substituted with one or more amino or hydroxy groups, or the alkylene chain is unsaturated;

pPL is 0 to 8;

q1PL and q2PL are independently 0, 1 or 2; and m is 4 or 5;

and a pharmaceutically acceptable carrier or diluent.

In some aspects, the invention is also directed to a method of treating a microbial infection in an animal in need thereof, the method comprising administering to the animal an effective amount of a pharmaceutical composition comprising a polymer or oligomer of Formula I'

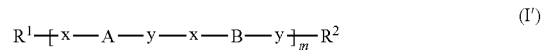

(I')

or an acceptable salt or solvate thereof, wherein:

x is NR$^3$, O, or S; y is C=O, C=S, O=S=O, or —C(=O)C(=O)—; and R$^3$ is hydrogen or alkyl;

A and B are independently optionally substituted o-, m-, or p-phenylene or optionally substituted heteroarylene, wherein:

(i) A and B are independently optionally substituted with one or more polar (P) group(s), one or more non-polar (NP) group(s), or a combination of one or more polar (P) group(s) and one or more non-polar (NP) group(s); or (ii) A is optionally substituted o-, m-, or p-phenylene or optionally substituted heteroarylene and B is a $C_3$ to $C_8$ cycloalkyl or —(CH$_2$)$_q$—, wherein q is 1 to 7, wherein A and B are independently optionally substituted with one or more polar (P) group(s), one or more non-polar (NP) group(s), or a combination of one or more polar (P) group(s) and one or more non-polar (NP) group(s); or (iii) B is optionally substituted o-, m-, or p-phenylene or optionally substituted heteroarylene, and A is a $C_3$ to $C_8$ cycloalkyl or —(CH$_2$)$_q$—, wherein q is 1 to 7, wherein A and B are independently optionally substituted with one or more polar (P) group(s), one or more non-polar (NP)

group(s), or a combination of one or more polar (P) group(s) and one or more non-polar (NP) group(s);

$R^1$ is
(i) -y-C and $R^2$ is OH or $NH_2$ wherein C is selected from a group consisting of $C_1$-$C_6$ alkyl, vinyl, 2-propenyl, H-x-$(CH_2)_p$—, $(C_1$-$C_6$ alkoxy$)C(=O)(CH_2)_p$—, $C_1$-$C_6$ alkoxy, benzyloxy, t-butoxy, pyridine and phenyl, any of which is optionally substituted with one or more substituents independently selected from a group consisting of halo, amino, nitro, cyano, $C_1$-$C_6$ alkoxy, $C_1$-$C_6$ alkoxycarbonyl, and benzyloxycarbonyl, and wherein p is defined below; or
(ii) is H and $R^2$ is -x-$(CH_2)_p$—W wherein x is as defined above, p is as defined below, W is H, N-maleimide, or V as defined below, and —$(CH_2)_p$— is optionally substituted with one or more hydroxyl groups; or
(iii) -y-C and $R^2$ is -x-$(CH_2)_p$—W wherein x is as defined above, p is as defined below, W is H, N-maleimide, or V as defined below, and —$(CH_2)_p$— is optionally substituted with one or more hydroxyl groups; or
(iv) $R^1$ and $R^2$ together are a single bond;

NP is a nonpolar group independently selected from —$B(OR^4)_2$ (wherein B represents in this instance a boron atom), $R^4$ or —$(NR^3)_{q1}$U—$(CH_2)_p$—$(NR^3)_{q2}$—$R^4$, wherein
$R^3$ is selected from the group consisting of hydrogen, alkyl, and alkoxy;
$R^4$ is selected from the group consisting of hydrogen, alkyl, alkenyl, alkynyl, cycloalkyl, aryl, and heteroaryl, any of which is optionally substituted with one or more alkyl, alkoxy, or halo groups;
U is absent or selected from the group consisting of O, S, S(=O), S(=O)$_2$, $NR^3$, —C(=O)—, —C(=O)—N=N—$NR^3$—, —C(=O)—$NR^3$—N=N—, —N=N—$NR^3$—, —C(=N—N($R^3$)$_2$)—, —C(=$NR^3$)—, —C(=O)O—, —C(=O)S—, —C(=S)—, —O—P(=O)$_2$O— (wherein P represents in this instance a phosphorus atom), —$R^3$—O—, —$R^3$—S—, —S—C=N— and —C(=O)—$NR^3$—O—, wherein groups with two chemically nonequivalent termini can adopt both possible orientations;
the —$(CH_2)_p$— alkylene chain is optionally substituted with one or more amino or hydroxyl groups, or the alkylene chain is unsaturated;
p is independently 0 to 8;
q1 and q2 are independently 0 to 2;
P is a polar group selected from the group consisting of halo, hydroxyethoxymethyl, methoxyethoxymethyl, polyoxyethylene, and —$(NR^3)_{q1}$—U—$(CH_2)_p$—$(NR^3)_{q2}$—V, wherein;
U and $R^3$ are as defined above;
V is selected from the group consisting of nitro, cyano, thio, amino, hydroxyl, alkoxy, alkylthio, alkylamino, dialkylamino, —NH$(CH_2)_p$NH$_2$, —N$(CH_2CH_2NH_2)_2$, diazamino, amidino, guanidino, guanyl, semicarbazone, alkoxycarbonyl, aryl, heterocycle and heteroaryl, any of which is optionally substituted with one or more of amino, halo, cyano, nitro, hydroxyl, —NH$(CH_2)_p$NH$_2$, —N$(CH_2CH_2NH_2)_2$, alkylamino, dialkylamino, amidino, guanidino, guanyl, aminosulfonyl, aminoalkoxy, aminoalkylthio, lower acylamino, or benzyloxycarbonyl;
the —$(CH_2)_p$— alkylene chain is optionally substituted with one or more amino or hydroxyl groups, or the alkylene chain is unsaturated;
p, q1 and q2 are as defined above; and
m is 1 to about about 500;
and a pharmaceutically acceptable carrier or diluent.

In some aspects, the invention is also directed to a method of treating a microbial infection in an animal in need thereof, the method comprising administering to the animal an effective amount of a pharmaceutical composition comprising a polymer or oligomer of Formula I', or an acceptable salt or solvate thereof, wherein:
x is $NR^3$ y is C=O; and $R^3$ is hydrogen or alkyl;
A and B are independently optionally substituted o-, m-, or p-phenylene, wherein B is optionally substituted o-, m-, or p-phenylene, and A is —$(CH_2)_q$—, wherein q is 1, and wherein A is optionally substituted with one or more non-polar (NP) group(s) and B is optionally substituted with one or more polar (P) group(s);
$R^1$ is H and $R^2$ is an amino group;
NP is $R^4$, wherein
$R^4$ is alkyl, alkenyl, or alkynyl, any of which is optionally substituted with one or more alkyl, alkoxy, or halo groups;
P is —$(NR^3)_{q1}$—U—$(CH_2)_p$—$(NR^3)_{q2}$—V, wherein:
q1 and q2 are each 0;
p is 0 to 6;
U is absent, O, or C=O;
V is selected from the group consisting amino, alkoxy, alkylamino, dialkylamino, —NH$(CH_2)_p$NH$_2$, —N$(CH_2CH_2NH_2)_2$, diazamino, amidino, guanidino, and guanyl, any of which is optionally substituted with one or more of amino, halo, —NH$(CH_2)_p$NH$_2$—, —N$(CH_2CH_2NH_2)_2$—, alkylamino, dialkylamino, amidino, guanidino, or guanyl, or aminoalkoxy;
the —$(CH_2)_p$— alkylene chain is optionally substituted with one or more amino or hydroxyl groups; and
m is 1 to 5;
and a pharmaceutically acceptable carrier or diluent.

In other aspects, the invention is also directed to a method of treating a microbial infection in an animal in need thereof, the method comprising administering to the animal an effective amount of a pharmaceutical composition comprising a polymer or oligomer of Formula I', or an acceptable salt or solvate thereof, wherein:
x is $NR^3$; y is C=O; and $R^3$ is hydrogen or alkyl;
A and B are independently optionally substituted o-, m-, or p-phenylene, wherein A is optionally substituted o-, m-, or p-phenylene and B is —$(CH_2)_q$—, wherein q is 1, where A is optionally substituted with one polar (P) group or one non-polar (NP) group, and B is optionally substituted with one or more polar (P) group(s) or one or more non-polar (NP) group(s);
$R^1$ is H and $R^2$ is an amino group;
NP is —$(NR^3)_{q1}$—U—$(CH_2)_p$—$(NR^3)_{q2}$—$R^4$, wherein
$R^4$ is selected from the group consisting of hydrogen, alkyl, alkenyl, alkynyl, and aryl, any of which is optionally substituted with one or more alkyl, alkoxy, or halo groups;
U is absent;
the —$(CH_2)_p$— alkylene chain is optionally substituted with one or more amino or hydroxyl groups;
p is independently 0 to 6;
q1 and q2 are each 0;
P is —$(NR^3)_{q1}$—U—$(CH_2)_p$—$(NR^3)_{q2}$—V, wherein:
q1 and q2 are each 0;
p is 0 to 6;
U is absent, O, or C=O;
V is selected from the group consisting amino, alkoxy, alkylamino, dialkylamino, —NH$(CH_2)_p$NH$_2$—, —N$(CH_2CH_2NH_2)_2$, diazamino, amidino, guanidino, and guanyl, any of which is optionally substituted with one or more of amino, halo, —NH(CH$_2$)$_p$NH$_2$—, —N(CH$_2$CH$_2$NH$_2$)$_2$, alkylamino, dialkylamino, amidino, guanidino, or guanyl, or aminoalkoxy;

the —(CH$_2$)$_p$— alkylene chain is optionally substituted with one or more amino or hydroxyl groups;

m is 1 to 5;

and a pharmaceutically acceptable carrier or diluent.

In other aspects, the invention is directed to a method of treating a microbial infection in an animal in need thereof, the method comprising administering to the animal an effective amount of a pharmaceutical composition comprising a polymer or oligomer of Formula VII:

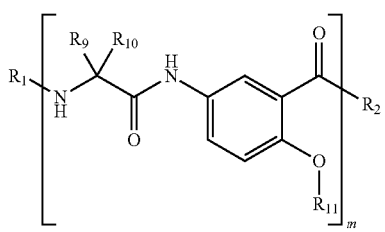

(VII)

wherein one of R$^9$ or R$^{10}$ and R$^{11}$ is a polar (P) group and the other of R$^9$ or R$^{10}$ and R$^{11}$ is a nonpolar (NP) group;

P is a polar group selected from a group consisting of IIIb, hydroxyethoxymethyl methoxyethoxymethyl and polyoxyethylene —(CH$_2$)$_p$—V (IIIb)

wherein:

V is selected from a group consisting of amino, hydroxyl, C$_1$-C$_6$ alkylamino, C$_1$-C$_6$ dialkylamino, NH(CH$_2$)$_p$NH$_2$, N(CH$_2$CH$_2$NH$_2$)$_2$, amidine, guanidine, semicarbazone, imidazole, piperidine, piperazine, 4-alkylpiperazine and phenyl optionally substituted with an amino, C$_1$-C$_6$ alkylamino, C$_1$-C$_6$ dialkylamino or lower acylamino optionally substituted with one or more amino, lower alkylamino or lower dialkylamino; and, the alkylene chain is optionally substituted with an amino or hydroxyl group;

p is independently 0 to 8; and,

NP, R$^1$ and R$^2$ are as defined in Formula I above;

m is 1 to about 30, or is 1 to about 50;

or an acceptable salt or solvate thereof; and a pharmaceutically acceptable carrier or diluent.

In yet other aspects, the invention is directed to a method of treating a microbial infection in an animal in need thereof, the method comprising administering to the animal an effective amount of a pharmaceutical composition comprising a polymer or oligomer of Formula IX:

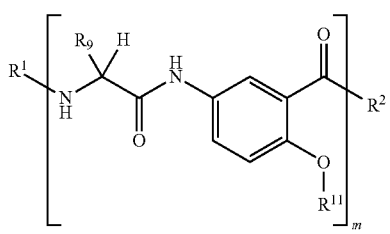

(IX)

wherein:

one of R$^9$ or R$^{11}$ is either a polar (P) group or a nonpolar (NP) group and the other of R$^9$ or R$^{11}$ is the other of a polar (P) group or a nonpolar (NP) group;

NP is —(CH$_2$)$_p$—R$^4$ wherein R$^4$ is selected from a group consisting of hydrogen, C$_1$-C$_4$ alkyl, C$_3$-C$_{12}$ branched alkyl, C$_3$-C$_8$ cycloalkyl, phenyl optionally substituted with one or more C$_1$-C$_4$ alkyl groups, C$_1$-C$_4$ alkoxy, or halo groups and heteroaryl optionally substituted with one or more C$_1$-C$_4$ alkyl group, C$_1$-C$_4$ alkoxy or halo groups, and p is as defined below;

P is a polar group selected from a group consisting of IIIb, hydroxyethoxymethyl, methoxyethoxymethyl and polyoxyethylene —(CH$_2$)$_p$—V (IIIb)

wherein:

V is selected from a group consisting of amino, hydroxyl, C$_1$-C$_6$ alkylamino, C$_1$-C$_6$ dialkylamino, NH(CH$_2$)$_p$NH$_2$, N(CH$_2$CH$_2$NH$_2$)$_2$, amidine, guanidine, semicarbazone, imidazole, piperidine, piperazine, 4-alkylpiperazine and phenyl optionally substituted with an amino, C$_1$-C$_6$ alkylamino, C$_1$-C$_6$ dialkylamino or lower acylamino optionally substituted with one or more amino, lower alkylamino or lower dialkylamino; and, the alkylene chain is optionally substituted with an amino or hydroxyl group;

p is independently 0 to 8;

R$^1$ and R$^2$ are as defined in Formula I' above;

m is 1 to about 500;

or an acceptable salt or solvate thereof; and a pharmaceutically acceptable carrier or diluent.

In some aspects of the invention, in the polymer or oligomer of Formula IX, R$^9$ is a polar side chain of a natural amino acids and R$^{11}$ is selected from a group consisting of methyl, ethyl, n-propyl, iso-propyl, n-butyl iso-butyl, sec-butyl, tert-butyl, n-pentyl, iso-pentyl, sec-pentyl, and benzyl.

In yet other aspects, the invention is directed to a method of treating a microbial infection in an animal in need thereof, the method comprising administering to the animal an effective amount of a pharmaceutical composition comprising a polymer or oligomer of Formula IX, wherein R$^9$ is a nonpolar side chain of a natural amino acids and R$^{11}$ is a polar group selected from a group consisting of IIIb, hydroxyethoxymethyl, methoxyethoxymethyl and polyoxyethylene —(CH$_2$)$_p$—V (IIIb)

wherein:

V is selected from a group consisting of amino, hydroxyl, C$_1$-C$_6$ alkylamino, C$_1$-C$_6$ dialkylamino, NH(CH$_2$)$_p$NH$_2$, N(CH$_2$CH$_2$NH$_2$)$_2$, amidine, guanidine, semicarbazone, imidazole, piperidine, piperazine, 4-alkylpiperazine, and phenyl optionally substituted with an amino, C$_1$-C$_6$ alkylamino, C$_1$-C$_6$ dialkylamino or lower acylamino optionally substituted with one or more amino, lower alkylamino or lower dialkylamino; and, p is independently 0 to 8;

R$^1$ and R$^2$ are as defined in Formula I' above;

m is 1 to about 500;

or an acceptable salt or solvate thereof; and a pharmaceutically acceptable carrier or diluent.

In yet other aspects, the invention is directed to a method of treating a microbial infection in an animal in need thereof, the method comprising administering to the animal an effective amount of a pharmaceutical composition comprising a polymer or oligomer of Formula I':

wherein:
x is NH and y is C=O or C=S;
A and B are independently optionally substituted o-, m-, or p-phenylene, 2,5-thiophenylene or 2,5-pyrrolene;
NP is a nonpolar group independently selected from $R^4$ or U—$(CH_2)_p$—$R^4$ wherein $R^4$ is selected from a group consisting of hydrogen, $C_1$-$C_4$ alkyl, $C_3$-$C_{12}$ branched alkyl, $C_3$-$C_8$ cycloalkyl, phenyl optionally substituted with one or more $C_1$-$C_4$ alkyl groups, $C_1$-$C_4$ alkoxy, or halo groups and heteroaryl optionally substituted with one or more $C_1$-$C_4$ alkyl group, $C_1$-$C_4$ alkoxy, or halo groups, and U and p are as defined below;
P is a polar group selected from a group consisting of IIIa, hydroxyethoxymethyl, methoxyethoxymethyl and polyoxyethylene

—U—$(CH_2)_p$—V     (IIIa)

wherein:
U is absent, O, S, SO, $SO_2$, or NH;
V is selected from a group consisting of amino, hydroxyl, $C_1$-$C_6$ alkylamino, $C_1$-$C_6$ dialkylamino, $NH(CH_2)_pNH_2$, $N(CH_2CH_2NH_2)_2$, amidine, guanidine, semicarbazone, imidazole, piperidine, piperazine, 4-alkylpiperazine and phenyl optionally substituted with an amino, $C_1$-$C_6$ alkylamino, $C_1$-$C_6$ dialkylamino or lower acylamino optionally substituted with one or more amino, lower alkylamino or lower dialkylamino; and,
the alkylene chain is optionally substituted with an amino or hydroxyl group;
p is independently 0 to 8; and,
m is 1 to about 500;
or an acceptable salt or solvate thereof; and
a pharmaceutically acceptable carrier or diluent.
In some aspects, in the polymer or oligomer of Formula I', x is $NR^3$, $R^3$ is hydrogen and y is C=O or C=S;
A and B are independently optionally substituted o-, m-, or p-phenylene;
NP is a nonpolar group independently selected from $R^4$ or —U—$(CH_2)_p$—$R^4$ wherein $R^4$ is selected from a group consisting of hydrogen, methyl, ethyl, n-propyl, iso-propyl, n-butyl, iso-butyl, sec-butyl, tert-butyl, n-pentyl, iso-pentyl, and sec-pentyl, and U and p are as defined below;
P is a polar group U—$(CH_2)_p$— V wherein U is absent or selected from a group consisting of O and S, and V is selected from a group consisting of amino, lower alkyl amino, lower dialkylamino, imidazole, guanidine, $NH(CH_2)_pNH_2$, $N(CH_2CH_2NH_2)_2$, pyridine, piperidine, piperazine, and 4-alkylpiperazine;
p is independently 0 to 8; and
m is 1 to about 500.
In other aspects, in the polymer or oligomer of Formula I', x is $NR^3$, y is CO, and $R^3$ is hydrogen;
A and B are m- or p-phenylene wherein (i) A is substituted at the 2-position with a polar (P) group and B is substituted at the 5-position with a nonpolar (NP) group, (ii) A is substituted at the 2-position with a polar (P) group and at the 5-position with a nonpolar (NP) group and B is substituted at the 2-position with a nonpolar (NP) group and at the 5-position with a polar (P) group or, (iii) A is substituted at the 2-position with one of a polar (P) or nonpolar (NP) group and B is substituted at the 2-position with the other of a nonpolar (NP) or a polar (P) group;
NP is a nonpolar group independently selected from $R^4$ or —U—$R^4$ wherein $R^4$ is selected from a group consisting of methyl, ethyl, n-propyl, iso-propyl, n-butyl, iso-butyl, sec-butyl, tert-butyl, n-pentyl, iso-pentyl, and sec-pentyl, and U and p are as defined below;

p is independently 0 to 8; and,
m is 1 to about 500.
In some aspects, the invention is directed to a method of treating a microbial infection in an animal in need thereof, the method comprising administering to the animal an effective amount of a pharmaceutical composition comprising a polymer or oligomer of Formula XII:

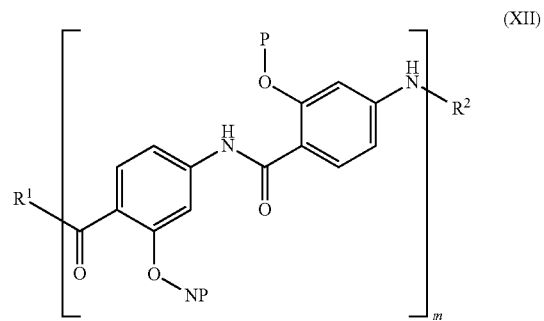

wherein:
NP is a nonpolar group independently selected from a group consisting of methyl, ethyl, n-propyl, iso-propyl, n-butyl, iso-butyl, sec-butyl, tert-butyl, n-pentyl, iso-pentyl, and sec-pentyl, and U and p are as defined below;
P is a polar group U—$(CH_2)_p$—V wherein U is selected from a group consisting of O, S, or no atom and V is selected from a group consisting of amino, lower alkyl amino, lower dialkylamino, imidazole, guanidine, $NH(CH_2)_pNH_2$, and $N(CH_2CH_2NH_2)_2$, piperidine, piperazine, and 4-alkylpiperazine;
p is independently 0 to 8;
m is 1 to about 30, or is 1 to about 50;
or an acceptable salt or solvate thereof; and
a pharmaceutically acceptable carrier or diluent.
In other aspects, the invention is directed to a method of treating a microbial infection in an animal in need thereof, the method comprising administering to the animal an effective amount of a pharmaceutical composition comprising a polymer or oligomer of Formula XIV:

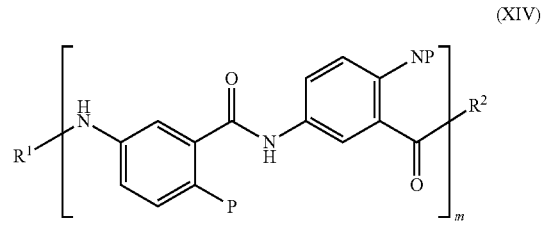

wherein:
NP is a nonpolar group independently selected from $R^4$ or —U—$R^4$ wherein $R^4$ is selected from a group consisting of methyl, ethyl, n-propyl, iso-propyl, n-butyl, iso-butyl, sec-butyl, tert-butyl, n-pentyl, iso-pentyl, and sec-pentyl, and U and p are as defined below;
P is a polar group U—$(CH_2)_p$—V wherein U is selected from a group consisting of O, S, or no atom and V is selected from a group consisting of amino, lower alkyl amino, lower dialkylamino, imidazole, guanidine, $NH(CH_2)_pNH_2$, $N(CH_2CH_2NH_2)_2$, piperidine, piperazine, and 4-alkylpiperazine;

p is independently 0 to 8; and
m is 1 to about 30, or is 1 to about 50;
or an acceptable salt or solvate thereof; and
a pharmaceutically acceptable carrier or diluent.

In some aspects, the invention is directed to a method of treating a microbial infection in an animal in need thereof, the method comprising administering to the animal an effective amount of a pharmaceutical composition comprising a polymer or oligomer of Formula I'
wherein:
x is $NR^3$, y is CO, and $R^3$ is hydrogen;
A and B are o-phenylene wherein A is substituted at the 5-position with a polar (P) group and B is substituted at the 5-position with a nonpolar (NP) group;
NP is a nonpolar group independently selected from $R^4$ or —U—$R^4$ wherein $R^4$ is selected from a group consisting of methyl, ethyl, n-propyl, iso-propyl, iso-butyl, n-butyl, sec-butyl, tert-butyl, n-pentyl, iso-pentyl, and sec-pentyl, and U and p are as defined below;
P is a polar group U—$(CH_2)_p$—V wherein U is selected from a group consisting of O, S, or no atom and V is selected from a group consisting of amino, lower alkyl amino, lower dialkylamino, imidazole, guanidine, $NH(CH_2)_pNH_2$, $N(CH_2CH_2NH_2)_2$, pyridine, piperidine, piperazine, and 4-alkylpiperazine;
p is independently 0 to 8; and
m is 1 to about 500;
or an acceptable salt or solvate thereof; and
a pharmaceutically acceptable carrier or diluent.

In yet other aspects, the invention is directed to a method of treating a microbial infection in an animal in need thereof, the method comprising administering to the animal an effective amount of a pharmaceutical composition comprising a polymer or oligomer of Formula XIII:

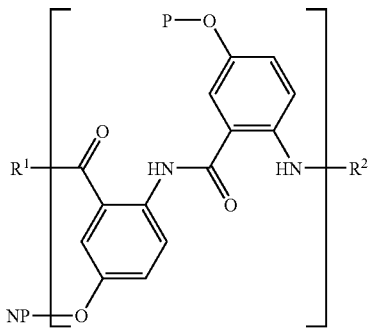

(XIII)

wherein:
NP is a nonpolar group independently selected from a the group consisting of methyl, ethyl, n-propyl, iso-propyl, n-butyl, iso-butyl, sec-butyl, tert-butyl, n-pentyl, iso-pentyl, and sec-pentyl, and U and p are as defined below;
P is a polar group $(CH_2)_p$—V wherein V is selected from a group consisting of amino, lower alkyl amino, lower dialkylamino, guanidine, piperazine, and 4-alkylpiperazine;
p is independently 0 to 8; and
m is 1 to about 30, or is 1 to about 50;
or an acceptable salt or solvate thereof; and
a pharmaceutically acceptable carrier or diluent.

In some aspects, the invention is directed to a method of treating a microbial infection in an animal in need thereof, the method comprising administering to the animal an effective amount of a pharmaceutical composition comprising a polymer or oligomer of Formula XV:

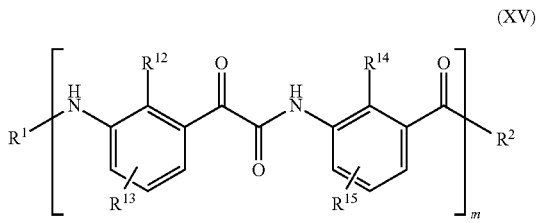

(XV)

wherein
either $R^{12}$ and $R^{14}$ are independently polar (P) groups and $R^{13}$ and $R^{15}$ are independently nonpolar (NP) groups substituted at one of the remaining unsubstituted carbon atoms, or $R^{12}$ and $R^{14}$ are independently nonpolar (NP) groups and $R^{13}$ and $R^{15}$ are independently polar (P) groups;
NP is a nonpolar group independently selected from $R^4$ or —U—$R^4$ wherein $R^4$ is selected from a the group consisting of methyl, ethyl, n-propyl, iso-propyl, n-butyl, iso-butyl, sec-butyl, tert-butyl, n-pentyl, iso-pentyl, and sec-pentyl, and U is defined below;
P is a polar group U—$(CH_2)_p$—V wherein U is selected from a group consisting of O or S and V is selected from a group consisting of amino, lower alkyl amino, lower dialkylamino, guanidine, pyridine, piperazine, and 4-alkylpiperazine;
p is independently 0 to 8; and
m is 1 to about 30, or 1 to about 50;
or an acceptable salt or solvate thereof; and
a pharmaceutically acceptable carrier or diluent.

In some aspects, the invention is also directed to a method of treating a microbial infection in an animal in need thereof, the method comprising administering to the animal an effective amount of a pharmaceutical composition comprising a polymer or oligomer of Formula II:

$$R^1\text{-}[\text{-}x\text{-}A_1\text{-}x\text{-}y\text{-}A_2\text{-}y\text{-}]_m\text{-}R^2 \quad (II)$$

or an acceptable salt or solvate thereof,
wherein:
x is $NR^8$, O, S, —$N(R^8)N(R^8)$—, —$N(R^8)$—(N=N)—, —(N=N)—$N(R^8)$—, —$C(R^7R^{7'})NR^8$—, —$C(R^7R^{7'})$O—, or —$C(R^7R^{7'})S$—; and y is C=O, C=S, O=S=O, —C(=O)C(=O)—, $C(R^6R^{6'})$C=O or $C(R^6R^{6'})$C=S; or
x and y are taken together to be pyromellitic diimide;
wherein $R^8$ is hydrogen or alkyl; $R^7$ and $R^{7'}$ are independently hydrogen or alkyl, or $R^7$ and $R^{7'}$ together are —$(CH_2)_p$—, wherein p is 4 to 8; and $R^6$ and $R^{6'}$ are independently hydrogen or alkyl, or $R^6$ and $R^{6'}$ together are $(CH_2)_2NR^{12}(CH_2)_2$, wherein $R^{12}$ is hydrogen, —C(=N)$CH_3$ or C(=NH)—$NH_2$;
$A_1$ and $A_2$ are independently optionally substituted arylene or optionally substituted heteroarylene, wherein $A_1$ and $A_2$ are independently optionally substituted with one or more polar (PL) group(s), one or more non-polar (NPL) group(s), or a combination of one or more polar (PL) group(s) and one or more non-polar (NPL) group(s);
$R^1$ is
(i) hydrogen, a polar group (PL), or a non-polar group (NPL), and $R^2$ is -x-$A_1$-x-$R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s); or (ii) hydrogen, a polar group (PL), or a non-polar group (NPL), and $R^2$ is -x-A'-x-$R^1$, wherein A' is aryl or heteroaryl and is optionally substituted with one or more polar (PL) group(s), one or more non-polar (NPL) group(s), or a combination of one or more polar (PL) group(s) and one or more non-polar (NPL) group(s);

(iii) -y-$A_2$-y-$R^2$, and $R^2$ is hydrogen, a polar group (PL), or a non-polar group (NPL); or (iv) -y-A' and $R^2$ is -x-A', wherein A' is aryl or heteroaryl and is optionally substituted with one or more polar (PL) group(s), one or more non-polar (NPL) group(s), or a combination of one or more polar (PL) group(s) and one or more non-polar (NPL) group(s); or (v) $R^1$ and $R^2$ are independently a polar group (PL) or a non-polar group (NPL); or (vi) $R^1$ and $R^2$ together form a single bond;

NPL is a nonpolar group independently selected from the group consisting of —B(O$R^4$)$_2$ and —(N$R^3{}'$)$_{q1NPL}$—$U^{NPL}$—(CH$_2$)$_{pNPL}$—(N$R^{3''}$)$_{q2NPL}$—$R^{4'}$, wherein:

$R^3$, $R^{3'}$, and $R^{3''}$ are independently selected from the group consisting of hydrogen, alkyl, and alkoxy;

$R^4$ and $R^{4'}$ are independently selected from the group consisting of hydrogen, alkyl, alkenyl, alkynyl, cycloalkyl, aryl, and heteroaryl, any of which is optionally substituted with one or more alkyl or halo groups;

$U^{NPL}$ is absent or selected from the group consisting of O, S, S(=O), S(=O)$_2$, N$R^3$, —C(=O)—, —C(=O)—N=N—N$R^3$—, —C(=O)—N$R^3$—N=N—, —N=N—N$R^3$—, —C(=N—N($R^3$)$_2$)—, —C(N$R^3$)—, —C(=O)O—, —C(=O)S—, —C(=S)—, —O—P(=O)$_2$O—, —$R^3$O—, —$R^3$S—, —S—C=N— and —C(=O)—N$R^3$—O—, wherein groups with two chemically nonequivalent termini can adopt both possible orientations;

the —(CH$_2$)$_{pNPL}$— alkylene chain is optionally substituted with one or more amino or hydroxy groups, or is unsaturated;

pNPL is 0 to 8;

q1NPL and q2NPL are independently 0, 1 or 2;

PL is a polar group selected from the group consisting of halo, hydroxyethoxymethyl, methoxyethoxymethyl, polyoxyethylene, and —(N$R^{5'}$)$_{q1PL}$—$U^{PL}$—(CH$_2$)$_{pPL}$—(N$R^{5'}$)$_{q2PL}$—V, wherein:

$R^5$, $R^{5'}$, and $R^{5''}$ are independently selected from the group consisting of hydrogen, alkyl, and alkoxy;

$U^{PL}$ is absent or selected from the group consisting of O, S, S(=O), S(=O)$_2$, N$R^5$, —C(=O)—, —C(=O)—N=N—N$R^5$—, —C(=O)—N$R^5$—N=N—, —N=N—N$R^5$—, —C(=N—N($R^5$)$_2$)—, —C(=N$R^5$)—, —C(=O)O—, —C(=O)S—, —C(=S)—, —O—P(=O)$_2$O—, —$R^5$O—, —$R^5$S—, —S—C=N— and —C(=O)—N$R^5$—O—, wherein groups with two chemically nonequivalent termini can adopt both possible orientations;

V is selected from the group consisting of nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkythio, lower acylamino, or benzyloxycarbonyl;

the —(CH$_2$)$_{pPL}$— alkylene chain is optionally substituted with one or more amino or hydroxy groups, or is unsaturated;

pPL is 0 to 8;

q1PL and q2PL are independently 0, 1 or 2; and m is 1 to about 500;

and a pharmaceutically acceptable carrier or diluent.

Polymers and oligomers of Formula II that are preferred for use in the disclosed method are those wherein x is N$R^8$, O, S, or —N($R^8$)N($R^8$)—, and $R^8$ is hydrogen or $C_1$-$C_6$ alkyl Also preferred are those polymers and oligomers wherein y is C=O, C=S, or O=S=O. Especially preferred are those polymers and oligomers wherein x is N$R^8$ and y is C=O. For example, oligomers of Formula II wherein x is NH and y is C=O are especially preferred. Also preferred are oligomers of Formula II wherein x is O and y is C=O, or wherein x is —N($R^8$)N($R^8$)— and $R^8$ is hydrogen, and y is C=O.

Preferred are those polymers and oligomers of Formula II wherein $A_1$ and $A_2$ are independently optionally substituted o-, m-, or p-phenylene. Those oligomers wherein $A_1$ and $A_2$ are optionally substituted m-phenylene are especially preferred. Also preferred are polymers and oligomers of Formula II wherein one of $A_1$ and $A_2$ is o-, m-, or p-phenylene, and the other of $A_1$ and $A_2$ is heteroarylene. Preferred heteroarylene groups include, but are not limited to, pyridinylene, pyrimidinylene, and pyrazinylene.

Also preferred are polymers and oligomers of Formula II wherein $A_1$ and $A_2$ are independently optionally substituted arylene or optionally substituted heteroarylene, and (i) one of $A_1$ and $A_2$ is substituted with one or more polar (PL) group(s) and one or more nonpolar (NPL) group(s) and the other of $A_1$ and $A_2$ is unsubstituted; or (ii) one of $A_1$ and $A_2$ is substituted with one or more polar (PL) group(s) and one or more non-polar (NPL) group(s) and the other of $A_1$ and $A_2$ is substituted with one or more polar (PL) group(s). Polymers and oligomers in which either (i) one of $A_1$ and $A_2$ is substituted with one polar (PL) group and one nonpolar (NPL) group, and the other of $A_1$ and $A_2$ is unsubstituted, or (ii) one of $A_1$ and $A_2$ is substituted with one polar (PL) group and one nonpolar (NPL) group and the other of $A_1$ and $A_2$ is substituted with one or two polar (PL) group(s), are especially preferred.

Thus, polymers and oligomers of Formula II are preferred in which $A_1$ and $A_2$ are optionally substituted m-phenylene, wherein one of $A_1$ and $A_2$ is substituted with one polar (PL) group and one nonpolar (NPL) group and the other of $A_1$ and $A_2$ is unsubstituted.

In some aspects of the invention, preferred polymers and oligomers of Formula II are those wherein (i) $R^1$ is hydrogen, a polar group (PL), or a non-polar group (NPL), and $R^2$ is -x-$A_1$-x-$R^1$, wherein $A_1$ is as defined above and is substituted with one or more polar (PL) group(s), one or more non-polar (NPL) group(s), or a combination of one or more polar (PL) group(s) and one or more non-polar (NPL) group(s), or (ii) $R^1$ is hydrogen, a polar group (PL), or a non-polar group (NPL), and $R^2$ is -x-A'-x-$R^1$, wherein A' is aryl or heteroaryl and is optionally substituted with one or more polar (PL) group(s), one or more non-polar (NPL) group(s), or a combination of one or more polar (PL) group(s) and one or more non-polar (NPL) group(s).

More preferred are those oligomers of Formula II wherein $R^1$ is hydrogen, a polar group (PL), or a non-polar group (NPL), and $R^2$ is -x-$A_1$-x-$R^1$, wherein $A_1$ is as defined above and is substituted with one or more polar (PL) group(s), one or more non-polar (NPL) group(s), or a combination of one or more polar (PL) group(s) and one or more non-polar (NPL) group(s). More preferred still are those oligomers wherein $R^1$ is hydrogen or a polar group (PL), and $R^2$ is -x-$A_1$-x-$R^1$, where $A_1$ is substituted with one or more polar (PL) group(s) or a combination of one or more polar (PL) group(s) and one or more non-polar (NPL) group(s). Especially preferred are those oligomers wherein $R^1$ is a polar (PL) group and $R^2$ is $-x-A_1-x-R^1$, where $A_1$ is substituted with one or two polar (PL) group(s) and one non-polar (NPL) group.

In some aspects of the invention, preferred polymers and oligomers of Formula II are those wherein NPL is $-B(OR^4)_2$. Preferred values of $R^4$ are hydrogen, $C_1$-$C_{10}$ alkyl, $C_3$-$C_{18}$ branched alkyl, $C_2$-$C_{10}$ alkenyl, $C_2$-$C_{10}$ alkynyl, $C_3$-$C_8$ cycloalkyl, $C_6$-$C_{10}$ aryl, and heteroaryl, any of which is optionally substituted with one or more $C_1$-$C_6$ alkyl or halo groups.

In other aspects, preferred polymers and oligomers of Formula II include those wherein NPL is $-(NR^{3'})_{q1NPL}-U^{NPL}-(CH_2)_{pNPL}-(NR^{3''})_{q2NPL}-R^4$ and $R^3$, $R^{3'}$, $R^{3''}$, $R^4$, $U^{NPL}$, pNPL, q1NPL and q2NPL are as defined above.

Preferred values for each of $R^3$, $R^{3'}$, and $R^{3''}$ are hydrogen, $C_1$-$C_6$ alkyl, and $C_1$-$C_6$ alkoxy. Hydrogen is an especially preferred value for $R^3$, $R^{3'}$, and $R^{3''}$.

Preferred values of $R^4$ are hydrogen, $C_1$-$C_{10}$ alkyl, $C_3$-$C_{18}$ branched alkyl, $C_2$-$C_{10}$ alkenyl, $C_2$-$C_{10}$ alkynyl, $C_3$-$C_8$ cycloalkyl, $C_6$-$C_{10}$ aryl, and heteroaryl, any of which is optionally substituted with one or more $C_1$-$C_6$ alkyl or halo groups. Values of $R^4$ that are more preferred are $C_1$-$C_{10}$ alkyl, $C_3$-$C_{18}$ branched alkyl, $C_2$-$C_{10}$ alkenyl, $C_2$-$C_{10}$ alkynyl, and $C_6$-$C_{10}$ aryl, especially phenyl. Especially preferred values of $R^4$ are $C_1$-$C_{10}$ alkyl and $C_3$-$C_{18}$ branched alkyl. Suitable $C_1$-$C_{10}$ alkyl and $C_3$-$C_{18}$ branched alkyl groups are methyl, ethyl, n-propyl, isopropyl, n-butyl, tert-butyl, and n-pentyl.

Preferred values of $U^{NPL}$ are O, S, S(=O), S(=O)$_2$, NH, —C(=O)—, —C(=O)—N=N—NH—, —C(=O)—NH—N=N—, —N=N—NH—, —C(=N—N(R$^3$)$_2$)—, —C(=NR$^3$)—, —C(=O)O—, —C(=O)S—, —C(=S)—, —O—P(=O)$_2$O—, —R$^3$O—, —R$^3$S—, —S—C=N— and —C(=O)—NR$^3$—O—, wherein groups with two chemically nonequivalent termini can adopt both possible orientations.

Values of $U^{NPL}$ that are more preferred are O, S, NH, —C(=O)—, —C(=O)—N=N—NH—, —C(=O)—NH—N=N—, —N=N—NH—, —C(=N—N(R$^3$)$_2$)—, —C(=NR$^3$)—, —C(=O)O—, —R$^3$S— and —R$^3$O—. An especially preferred value of $U^{NPL}$ is —C(=O)—. Preferred polymers and oligomers of Formula II also include those wherein $U^{NPL}$ is absent.

In some aspects of the invention, preferred polymers and oligomers of Formula II are those wherein $U^{NPL}$ is —O—P(=O)$_2$O—.

Preferred values of pNPL are 0 to 6; values of pNPL of 0 to 4 are especially preferred, with values of pNPL of 0, 1 or 2 most preferred.

Preferred values of q1NPL and q2NPL are 0 or 1. Values of q1NPL and q2NPL of 0 or 1 are especially preferred, with a value of 0 being the most preferred for each of q1NPL and q2NPL.

In preferred polymers and oligomers of Formula II, the —(CH$_2$)$_{pNPL}$— alkylene chain in NPL is unsubstituted or substituted with one or more amino or hydroxy groups. More preferred are those oligomers of Formula II wherein the —(CH$_2$)$_{pNPL}$— alkylene chain in NPL is substituted with one or more amino groups.

An especially preferred value of NPL for polymers and oligomers of Formula II is $C_1$-$C_6$ alkyl. Examples of preferred values for NPL are n-propyl, isopropyl, n-butyl, and tert-butyl.

In some aspects of the invention, preferred polymers and oligomers of Formula II are those wherein PL is —(NR$^{5'}$)$_{q1PL}$—U$^{PL}$—(CH$_2$)$_{pPL}$—(NR$^{5''}$)$_{q2PL}$—V and $R^5$, $R^{5'}$, $R^{5''}$, V, $U^{PL}$, pPL, q1PL and q2PL are as defined above.

Preferred values for $R^5$, $R^{5'}$, and $R^{5''}$ are hydrogen, $C_1$-$C_6$ alkyl, and $C_1$-$C_6$ alkoxy. Hydrogen is an especially preferred value for each of $R^5$, $R^{5'}$, and $R^{5''}$.

Preferred values of $U^{PL}$ are O, S, S(=O), S(=O)$_2$, NH, —C(=O)—, —C(=O)—N=N—NH—, —C(=O)—NH—N=N—, —N=N—NH—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N— and —C(=O)—NR$^5$—O—, wherein groups with two chemically nonequivalent termini can adopt both possible orientations. Values of $U^{PL}$ that are more preferred are O, S, NH, —C(=O)—, —C(=O)—N=N—NH—, —C(=O)—NH—N=N—, —N=N—NH—, —C(=N—N(R$^5$)$_2$)—, —C(=NR$^5$)—, —C(=O)O—, —R$^5$S— and —R$^5$O—. Especially preferred values of $U^{PL}$ are O, S, and —C(=O). Preferred polymers and oligomers of Formula II are also those wherein $U^{PL}$ is absent.

In some aspects of the invention, preferred polymers and oligomers of Formula II are those wherein $U^{PL}$ is —O—P(=O)$_2$O—.

Preferred values of V are nitro, cyano, amino, hydroxy, $C_1$-$C_6$ alkoxy, $C_1$-$C_6$ alkylthio, $C_1$-$C_6$ alkylamino, $C_1$-$C_6$ dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, $C_6$-$C_{10}$ aryl, heterocycle, and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, lower acylamino, or benzyloxycarbonyl.

Suitable heteroaryl groups include indolyl, 3H-indolyl, 1H-isoindolyl, indazolyl, benzoxazolyl, pyridyl, and 2-aminopyridyl. Suitable heterocycle groups include piperidinyl, piperazinyl, imidazolidinyl, pyrrolidinyl, pyrazolidinyl, and morpholinyl.

Values of V that are more preferred are amino, $C_1$-$C_6$ alkylamino, $C_1$-$C_6$ dialkylamino, —NH(CH$_2$)$_p$NH$_2$ wherein p is 1 to 4, —N(CH$_2$CH$_2$NH$_2$)$_2$, diazamino, amidino, guanidino, guanyl, and semicarbazone, preferably any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, lower acylamino, or benzyloxycarbonyl.

Especially preferred values of V are amino, $C_1$-$C_6$ alkylamino, —NH(CH$_2$)$_p$NH$_2$ wherein p is 1 to 4, —N(CH$_2$CH$_2$NH$_2$)$_2$, diazamino, amidino, and guanidino, preferably any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanyl, guanidino, or aminoalkoxy. Values of V that are most preferred are amino and guanidino.

Preferred values of pPL are 0 to 6; values of pPL of 0 to 4 are especially preferred, with values of pPL of 2 to 4 especially preferred.

Preferred values of q1PL and q2PL are 0 or 1. Values of q1PL and q2PL of 0 or 1 are especially preferred, with a value of 0 being especially preferred for each of q1PL and q2PL.

In preferred polymers and oligomers of Formula II, the —(CH$_2$)$_{pPL}$-alkylene chain in PL is optionally substituted with one or more amino or hydroxy groups.

Preferred polymers of Formula II are those in which m is 1 to about 500. Especially preferred are those polymers of Formula II wherein m is 1 to about 100, or wherein m is 1 to about 50.

Oligomers of Formula II that are preferred are those wherein m is 1 to about 30, or m is 1 to about 25; more preferred are those wherein m is 1 to about 20, or wherein m is 1 to about 10, or wherein m is 1 to about 5. Especially preferred are those oligomers of Formula II wherein m is 1, 2 or 3.

Thus, in some aspects, the invention is directed to a method of treating a microbial infection in an animal in need thereof, the method comprising administering to the animal an effective amount of a pharmaceutical composition comprising a polymer or oligomer of Formula II, wherein:

x is $NR^8$, y is C=O, and $R^8$ is hydrogen or alkyl;

$A_1$ and $A_2$ are independently optionally substituted o-, m-, or p-phenylene or pyrimidinylene, wherein $A_1$ and $A_2$ are independently optionally substituted with one or more polar (PL) group(s), one or more non-polar (NPL) group(s), or a combination of one or more polar (PL) group(s) and one or more non-polar (NPL) group(s);

$R^1$ is hydrogen, a polar group (PL), or a non-polar group (NPL), and $R^2$ is -x-$A_1$-x-$R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s);

NPL is $—(NR^{3'})_{q1NPL}—U^{NPL}—(CH_2)_{pNPL}—(NR^{3''})_{q2NPL}—R^{4'}$, wherein:

$R^3$, $R^{3'}$, and $R^{3''}$ are independently selected from the group consisting of hydrogen, $C_1$-$C_6$ alkyl, and $C_1$-$C_6$ alkoxy;

$R^{4'}$ is selected from the group consisting of hydrogen, $C_1$-$C_{10}$ alkyl, $C_3$-$C_{18}$ branched alkyl, $C_2$-$C_{10}$ alkenyl, $C_2$-$C_{10}$ alkynyl, $C_3$-$C_8$ cycloalkyl, $C_6$-$C_{10}$ aryl, and heteroaryl, any of which is optionally substituted with one or more $C_1$-$C_6$ alkyl or halo groups;

$U^{NPL}$ is absent or selected from the group consisting of O, S, NH, —C(=O)—, —C(=O)—N=N—NH—, —C(=O)—NH—N=N—, —N=N—NH—, —C(=N—N($R^3$)$_2$)—, —C(=$NR^3$)—, —C(=O)O—, —$R^3$S— and —$R^3$O—, wherein groups with two chemically nonequivalent termini can adopt both possible orientations;

the —$(CH_2)_{pNPL}$— alkylene chain is optionally substituted with one or more amino or hydroxy groups;

pNPL is 0 to 6;

q1NPL and q2NPL are independently 0;

PL is $—(NR^{5'})_{q1PL}—U^{PL}—(CH_2)_{pPL}—(NR^{5'})_{q2PL}—V$ wherein:

$R^5$, $R^{5'}$, and $R^{5'}$ are independently selected from the group consisting of hydrogen, $C_1$-$C_6$ alkyl, and $C_1$-$C_6$ alkoxy;

$U^{PL}$ is absent or selected from the group consisting of O, S, NH, —C(=O)—, —C(=O)—N=N—NH—, —C(=O)—NH—N=N—, —N=N—NH—, —C(=N—N($R^5$)$_2$)—, —C(=$NR^5$)—, —C(=O)O—, —$R^5$O—, and —$R^5$S—, wherein groups with two chemically nonequivalent termini can adopt both possible orientations;

V is selected from the group consisting of nitro, cyano, amino, hydroxy, $C_1$-$C_6$ alkoxy, $C_1$-$C_6$ alkylthio, $C_1$-$C_6$ alkylamino, $C_1$-$C_6$ dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, $C_6$-$C_{10}$ aryl, heterocycle, and heteroaryl, preferably any of which is optionally substituted with one or more amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, lower acylamino, or benzyloxycarbonyl;

the —$(CH_2)_{pPL}$— alkylene chain is optionally substituted with one or more amino or hydroxy groups;

pPL is 0 to 6;

q1PL and q2PL are 0; and m is 1 to 10.

The invention is also directed to a method of treating a microbial infection in an animal in need thereof, the method comprising administering to the animal an effective amount of a pharmaceutical composition comprising an oligomer of Formula Ia:

$$R^1\text{-}x\text{-}A_1\text{-}x\text{-}y\text{-}A_2\text{-}y\text{-}x\text{-}A_1\text{-}x\text{-}R^2 \qquad (IIa)$$

or an acceptable salt or solvate thereof,
wherein:

x is $NR^8$, O, S, or —N($R^8$)N($R^8$)—; and y is C=O, C=S, or O=S=O; wherein $R^8$ is hydrogen or alkyl;

$A^1$ and $A_2$ are independently optionally substituted arylene or optionally substituted heteroarylene, wherein $A_1$ and $A_2$ are independently optionally substituted with one or more polar (PL) group(s), one or more non-polar (NPL) group(s), or a combination of one or more polar (PL) group(s) and one or more non-polar (NPL) group(s);

$R^1$ is a polar group (PL) or a non-polar group (NPL); and $R^2$ is $R^1$;

NPL is a nonpolar group independently selected from the group consisting of —B(O$R^4$)$_2$ and —(NR$^{3'}$)$_{q1NPL}$—$U^{NPL}$—(CH$_2$)$_{pNPL}$—(NR$^{3''}$)$_{q2NPL}$—$R^{4'}$, wherein:

$R^3$, $R^{3'}$, and $R^{3''}$ are independently selected from the group consisting of hydrogen, alkyl, and alkoxy;

$R^4$ and $R^{4'}$ are independently selected from the group consisting of hydrogen, alkyl, alkenyl, alkynyl, cycloalkyl, aryl, and heteroaryl, any of which is optionally substituted with one or more alkyl or halo groups;

$U^{NPL}$ is absent or selected from the group consisting of O, S, S(=O), S(=O)$_2$, NR$^3$, —C(=O)—, —C(=O)—N=N—NR$^3$—, —C(=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$O—, —R$^3$S—, —S—C=N— and —C(=O)—NR$^3$—O—, wherein groups with two chemically nonequivalent termini can adopt both possible orientations;

the —$(CH_2)_{pNPL}$— alkylene chain is optionally substituted with one or more amino or hydroxy groups, or is unsaturated;

pNPL is 0 to 8;

q1NPL and q2NPL are independently 0, 1 or 2;

PL is a polar group selected from the group consisting of halo, hydroxyethoxymethyl, methoxyethoxymethyl, polyoxyethylene, and —(NR$^{5'}$)$_{q1PL}$—$U^{PL}$—(CH$_2$)$_{pPL}$—(NR$^{5'}$)$_{q2PL}$—V, wherein:

$R^5$, $R^{5'}$, and $R^{5''}$ are independently selected from the group consisting of hydrogen, alkyl, and alkoxy;

$U^{PL}$ is absent or selected from the group consisting of O, S, S(=O), S(=O)$_2$, NR$^5$, —C(=O)—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N— and —C(=O)—NR$^5$—O—, wherein groups with two chemically nonequivalent termini can adopt both possible orientations;

V is selected from the group consisting of nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle and heteroaryl, preferably any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkythio, lower acylamino, or benzyloxycarbonyl;

the —(CH$_2$)$_{pPL}$— alkylene chain is optionally substituted with one or more amino or hydroxy groups, or is unsaturated;

pPL is 0 to 8; and q1PL and q2PL are independently 0, 1 or 2;

and a pharmaceutically acceptable carrier or diluent.

Preferred oligomers of Formula Ia are those wherein x is NR$^8$ and y is C=O. For example, oligomers of Formula Ia wherein x is NH and y is C=O are especially preferred. Also preferred are oligomers of Formula IIa wherein x is O and y is C=O, or wherein x is —N(R$^8$)N(R$^8$)— and R$^8$ is hydrogen, and y is C=O.

Preferred are those oligomers of Formula IIa wherein A$_1$ and A$_2$ are independently optionally substituted o-, m-, or p-phenylene, especially m-phenylene. Also preferred are oligomers of Formula Ia wherein one of A$_1$ and A$_2$ is o-, m-, or p-phenylene, and the other of A$_1$ and A$_2$ is heteroarylene. Preferred heteroarylene groups include, but are not limited to, pyridinylene, pyrimidinylene, and pyrazinylene.

As for the polymers and oligomers of Formula II, preferred oligomers of Formula IIa are those wherein A$_1$ and A$_2$ are independently optionally substituted arylene or optionally substituted heteroarylene, and (i) one of A$_1$ and A$_2$ is substituted with one or more polar (PL) group(s) and one or more nonpolar (NPL) group(s) and the other of A$_1$ and A$_2$ is unsubstituted; or (ii) one of A$_1$ and A$_2$ is substituted with one or more polar (PL) group(s) and one or more nonpolar (NPL) group(s) and the other of A$_1$ and A$_2$ is substituted with one or more polar (PL) group(s). Especially preferred are oligomers in which either (i) one of A$_1$ and A$_2$ is substituted with one polar (PL) group and one nonpolar (NPL) group, and the other of A$_1$ and A$_2$ is unsubstituted, or (ii) one of A$_1$ and A$_2$ is substituted with one polar (PL) group and one nonpolar (NPL) group and the other of A$_1$ and A$_2$ is substituted with one or two polar (PL) group(s), are especially preferred.

Preferred oligomers of Formula IIa are those in which R$^1$ and R$^2$ are either hydrogen or a polar (PL) group.

Preferred values of R$^3$, R$^{3'}$, R$^{3''}$, R$^4$, R$^{4'}$, NPL, U$^{NPL}$, pNPL, q1NPL, q2NPL, PL, R$^5$, R$^{5'}$, R$^{5''}$, V, U$^{PL}$, pPL, q1PL and q2PL for the oligomers of Formula Ia are also the same as those listed for polymers and oligomers of Formula II above.

In some aspects, the invention is directed to a method of treating a microbial infection in an animal in need thereof, the method comprising administering to the animal an effective amount of a pharmaceutical composition comprising a polymer or oligomer of Formula II':

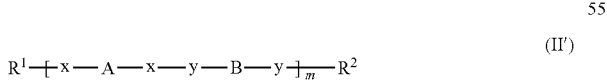

(II')

or an acceptable salt or solvate thereof, wherein:

x is NR$^3$, O, S, —C(R$^7$R$^8$)NR$^3$, —C(R$^7$R$^8$)O, —C(R$^7$R$^8$)S, or —N(R$^3$)(N=N)—; and y is C=O, C=S, O=S=O, —C(=O)C(=O)—, C(R$^5$R$^6$)C=O or C(R$^5$R$^6$)C=S; wherein R$^3$ is hydrogen or alkyl, and R$^7$ and R$^8$ together are (CH$_2$)$_p$—, wherein p is as defined below; or x and y are taken together to be pyromellitic diimide; wherein R$^5$ and R$^6$ together are (CH$_2$)$_2$NR$^{12}$CH$_2$)$_2$, and R$^{12}$ is hydrogen, —C(=N)CH$_3$ or C(=NH)—NH$_2$;

A and B are independently optionally substituted o-, m-, or p-phenylene or optionally substituted heteroarylene, wherein:

A and B are independently optionally substituted with one or more polar (P) group(s), one or more non-polar (NP) group(s), or a combination of one or more polar (P) group(s) and one or more non-polar (NP) group(s);

R$^1$ is (i) —B-y-R$^2$ and R$^2$ is -x-(CH$_2$)$_p$—W, wherein: x is as defined above; W is hydrogen, phenyl optionally substituted with up to three substituents selected from a group consisting of halogen, C$_1$-C$_4$ alkyl, C$_1$-C$_4$ alkoxy, acyl, and carboxyl, N-maleimide, or V as defined below; p is as defined below; and the —(CH$_2$)$_p$— chain is optionally substituted with one or more amino or hydroxyl groups, or the alkylene chain is unsaturated; or (ii) R$^1$ and R$^2$ together are a single bond; or (iii) -y-(CH$_2$)$_p$—W or —U—(CH$_2$)$_p$—W, wherein: W is defined above; U is defined below; the —(CH$_2$)$_p$— alkylene chain is optionally substituted with one or more amino or hydroxyl groups, or the alkylene chain is unsaturated; P is as defined below; and R$^2$ is -x-A-x-R$^1$; or (iv) -y-B-y-R$^2$ and R$^2$ is -x-(CH$_2$)$_p$—W or —U—(CH$_2$)$_p$—W, wherein: W is defined above, U is defined below; and the —(CH$_2$)$_p$— alkylene chain is optionally substituted with one or more amino or hydroxyl groups, or the alkylene chain is unsaturated; and p is as defined below; or (v) is H and R$^2$ is -x-A-x-R$^1$;

NP is a nonpolar group independently selected from —B(OR$^4$)$_2$ (wherein B in this instance represents a boron atom), R$^4$, or —(NR$^3$)$_{q1}$—U—(CH$_2$)$_p$—(NR$^3$)$_{q2}$—R$^4$, wherein R$^3$ is selected from the group consisting of hydrogen, alkyl, and alkoxy;

R$^4$ is selected from the group consisting of hydrogen, alkyl, alkenyl, alkynyl, cycloalkyl, aryl, and heteroaryl, any of which is optionally substituted with one or more alkyl, alkoxy, or halo groups;

U is absent or selected from the group consisting of O, S, S(=O), S(=O)$_2$, NR$^3$, —(C=O)—, —(C=O)—N=N—NR$^3$—, —(C=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O— (wherein P in this instance represents a phosphorus atom), —R$^3$—O—, —R$^3$—S—, —S—C=N— and —(C=O)—NR$^3$—O—, wherein groups with two chemically nonequivalent termini can adopt both possible orientations;

the —(CH$_2$)$_p$— alkylene chain is optionally substituted with one or more amino or hydroxyl groups, or the alkylene chain is unsaturated;

p is independently 0 to 8;

q1 and q2 are independently 0 to 2;

P is a polar group selected from the group consisting of halo, hydroxyethoxymethyl, methoxyethoxymethyl, polyoxyethylene, and —(NR$^3$)$_{q1}$—U—(CH$_2$)$_p$—(NR$^3$)$_{q2}$—V, wherein;

U and R$^3$ are as defined above;

V is selected from the group consisting of nitro, cyano; thio, amino, hydroxyl, alkoxy, alkylthio, alkylamino, dialkylamino, —NH(CH$_2$)$_p$NH$_2$, —N(CH$_2$CH$_2$NH$_2$)$_2$, diazamino, amidino, guanidino, guanyl, semicarbazone, alkoxycarbonyl, aryl, heterocycle and heteroaryl, any which is optionally substituted with one or more of amino, halo, cyano, nitro, hydroxyl, —NH(CH$_2$)$_p$NH$_2$, —N(CH$_2$CH$_2$NH$_2$)$_2$, alkylamino, dialkylamino, amidino, guanidino, guanyl, aminosulfonyl, aminoalkoxy, aminoalkylthio, lower acylamino, or benzyloxycarbonyl;

the —(CH$_2$)$_p$— alkylene chain is optionally substituted with one or more amino or hydroxyl groups, or the alkylene chain is unsaturated;

p, q1 and q2 are as defined above; and m is 1 to about about 500;

and a pharmaceutically acceptable carrier or diluent.

In some aspects, the invention is also directed to a method of treating a microbial infection in an animal in need thereof, the method comprising administering to the animal an effective amount of a pharmaceutical composition comprising an oligomer of Formula II', wherein:

x is NR$^3$ y is C=O; and R$^3$ is hydrogen or alkyl;

A and B are independently optionally substituted o-, m-, or p-phenylene or optionally substituted pyrimidinyl, wherein:

A and B are independently optionally substituted with one or more polar (P) group(s), one or more non-polar (NP) group(s), or a combination of one or more polar (P) group(s) and one or more non-polar (NP) group(s);

R$^1$ is (i) -y-(CH$_2$)$_p$—W or —U—(CH$_2$)$_p$—W, wherein: W is hydrogen, phenyl optionally substituted with up to three substituents selected from a group consisting of halogen, C$_1$-C$_4$ alkyl, C$_1$-C$_4$ alkoxy, acyl, and carboxyl, N-maleimide, or V as defined below; U is defined below; the —(CH$_2$)$_p$— alkylene chain is optionally substituted with one or more amino or hydroxyl groups; and R$^2$ is -x-A-x-R$^1$ or (ii) is H and R$^2$ is -x-A-x-R$^1$;

NP is —(NR$^3$)$_{q1}$—U—(CH$_2$)$_p$—(NR$^3$)$_{q2}$—R$^4$, wherein

R$^4$ is selected from the group consisting of hydrogen, alkyl, alkenyl, alkynyl, and aryl, any of which is optionally substituted with one or more alkyl, alkoxy, or halo groups;

U is absent, O, S, or —(C=O)—;

the —(CH$_2$)$_p$— alkylene chain is optionally substituted with one or more amino or hydroxyl groups;

p is independently 0 to 6;

q1 and q2 are each 0;

P is —(NR$^3$)$_{q1}$—U—(CH$_2$)$_p$—(NR$^3$)$_{q2}$—V, wherein;

U and R$^3$ are as defined above;

V is selected from the group consisting of nitro, cyano, thio, amino, hydroxyl, alkoxy, alkylthio, alkylamino, dialkylamino, —NH(CH$_2$)$_p$NH$_2$, —N(CH$_2$CH$_2$NH$_2$)$_2$, diazamino, amidino, guanidino, guanyl, semicarbazone, alkoxycarbonyl, aryl, heterocycle and heteroaryl, any of which is optionally substituted with one or more of amino, halo, cyano, nitro, hydroxyl, —NH(CH$_2$)$_p$NH$_2$, —N(CH$_2$CH$_2$NH$_2$)$_2$, alkylamino, dialkylamino, amidino, guanidino, guanyl, aminosulfonyl, aminoalkoxy, aminoalkylthio, lower acylamino, or benzyloxycarbonyl;

the —(CH$_2$)$_p$— alkylene chain is optionally substituted with one or more amino or hydroxyl groups, p is independently 0 to 6;

q1 and q2 are each 0; and m is 1 to 5;

and a pharmaceutically acceptable carrier or diluent.

In some aspects, in the polymer or oligomer of Formula II', X is NH, and y is C=O;

A and B are m- or p-phenylene wherein (i) A is substituted at the 2-position with a polar (P) group and B is substituted at the 5-position with a nonpolar (NP) group, or (ii) A is substituted at the 2-position with a polar (P) group and at the 5-position with a nonpolar (NP) group and B is either substituted at the 2-position with a nonpolar (NP) group and at the 5-position with a polar (P) group or B is unsubstituted;

NP is a nonpolar group independently selected from R$^4$ or —U—(CH$_2$)$_p$—R$^4$ wherein R$^4$ is selected from a group consisting of methyl, ethyl, n-propyl, iso-propyl, iso-butyl, sec-butyl, tert-butyl, iso-pentyl, and sec-pentyl, and U and p are as defined below;

P is a polar group U—(CH$_2$)$_p$—V wherein U is absent or selected from a group consisting of O and S and V is selected from a group consisting of amino, lower alkyl amino, lower dialkylamino, imidazole, guanidine, NH(CH$_2$)$_p$NH$_2$, N(CH$_2$CH$_2$NH$_2$)$_2$; piperidine, and 4-alkylpiperazine;

p is independently 0 to 8; and m is 1 to about 500.

In yet other aspects, in the polymer or oligomer of Formula II', A is an optionally substituted 1,3-diaminobenzene and B is an optionally substituted iso-phthalic acid.

In some aspects, the invention is directed to a method of treating a microbial infection in an animal in need thereof, the method comprising administering to the animal an effective amount of a pharmaceutical composition comprising a polymer or oligomer of Formula XI:

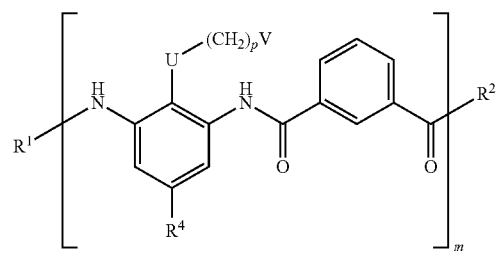

(XI)

wherein

R$^4$ is selected from a group consisting of methyl, ethyl, n-propyl, iso-propyl, n-butyl, iso-butyl, sec-butyl, tert-butyl n-pentyl, iso-pentyl, and sec-pentyl;

U is O or S;

V is amino, lower alkyl amino, lower dialkylamino, or guanidine;

p is independently 0-8; and m is 1 to about 30, or 1 to about 50;

or an acceptable salt or solvate thereof;

and a pharmaceutically acceptable carrier or diluent.

In yet other aspects, the invention is directed to a method of treating a microbial infection in an animal in need thereof, the method comprising administering to the animal an effective amount of a pharmaceutical composition comprising a polymer or oligomer of Formula XVI:

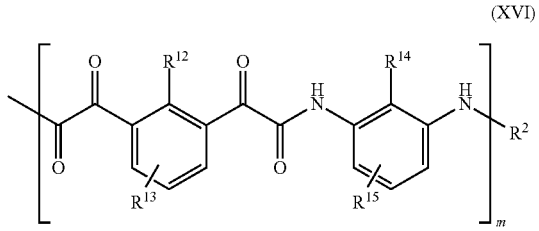

(XVI)

wherein:
either $R^{12}$ and $R^{14}$ are independently polar (P) groups and $R^{13}$ and $R^{15}$ are independently nonpolar (NP) groups substituted at one of the remaining unsubstituted carbon atoms, or $R^{12}$ and $R^{14}$ are independently nonpolar (NP) groups and $R^{13}$ and $R^{15}$ are independently polar (P) groups;

NP is a nonpolar group independently selected from $R^4$ or —U—$R^4$ where $R^4$ is selected from a group consisting of methyl, ethyl, n-propyl, iso-propyl, n-butyl, iso-butyl, sec-butyl, tert-butyl, n-pentyl, iso-pentyl, and sec-pentyl, and U is as defined below;

P is a polar group U—$(CH_2)_p$—V wherein U is absent or selected from a group consisting of O and S, and V is selected from a group consisting of amino, lower alkyl amino, lower dialkylamino, imidazole, guanidine, —NH$(CH_2)_p NH_2$—, —N$(CH_2 CH_2 NH_2)_2$—, piperidine, and 4-alkylpiperazine;

U is O or S;

V is amino, lower alkyl amino, lower dialkylamino, and guanidine;

p is independently 0 to 8; and m is 1 to about 30, or 1 to about 50;

or an acceptable salt or solvate thereof; and a pharmaceutically acceptable carrier or diluent.

In some aspects, the invention is directed to a method of treating a microbial infection in an animal in need thereof; the method comprising administering to the animal an effective amount of a pharmaceutical composition comprising a polymer or oligomer of Formula XX:

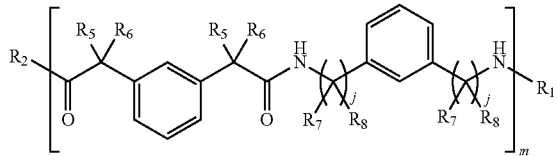

(XX)

wherein j is independently 0 or 1, $R^5$ and $R^6$ together are $(CH_2)_2 NH(CH_2)_2$ and $R^7$ and $R^8$ together are $(CH_2)_p$ wherein p is 4 to 6;

m is 1 to about 30, or 1 to about 50;

or an acceptable salt or solvate thereof; and a pharmaceutically acceptable carrier or diluent.

In some aspects, the invention is directed to a method of treating a microbial infection in an animal in need thereof, the method comprising administering to the animal an effective amount of a pharmaceutical composition comprising a polymer or oligomer of Formula IV:

$$R^1\text{-}[\text{-}x\text{-}A_1\text{-}x\text{-}z\text{-}y\text{-}A_2\text{-}y\text{-}z\text{-}]_m\text{-}R^2 \quad (IV)$$

or an acceptable salt or solvate thereof, wherein:
x is $NR^8$, —$NR^8 NR^8$—, C=O, or O; y is $NR^8$, —$NR^8 NR^8$—, C=O, S, or O; and $R^8$ is hydrogen or alkyl;

z is C=O, C=S, O=S=O, —$NR^8 NR^8$, or —C(=O)C(=O)—;

$A_1$ and $A_2$ are independently optionally substituted arylene or optionally substituted heteroarylene, wherein $A_1$ and $A_2$ are independently optionally substituted with one or more polar (PL) group(s), one or more non-polar (NPL) group(s), or a combination of one or more polar (PL) group(s) and one or more non-polar (NPL) group(s);

$R^1$ is
(i) hydrogen, a polar group (PL), or a non-polar group (NPL), and $R^2$ is -x-$A_1$-x-$R^1$, wherein $A_1$ is as defined above and is optionally substituted with one or more polar (PL) group(s), one or more non-polar (NPL) group(s), or a combination of one or more polar (PL) group(s) and one or more non-polar (NPL) group(s); or (ii) hydrogen, a polar group (PL), or a non-polar group (NPL), and $R^2$ is -x-$A_1$-x-z-y-$A_2$-y-$R^1$, wherein $A_1$ and $A_2$ are as defined above, and each of which is optionally substituted with one or more polar (PL) group(s), one or more non-polar (NPL) group(s), or a combination of one or more polar (PL) group(s) and one or more non-polar (NPL) group(s); or (iii) hydrogen, a polar group (PL), or a non-polar group (NPL), and $R^2$ is -x-A'-x-$R^1$, wherein A' is aryl or heteroaryl and is optionally substituted with one or more polar (PL) group(s), one or more non-polar (NPL) group(s), or a combination of one or more polar (PL) group(s) and one or more non-polar (NPL) group(s); or (iv) hydrogen, a polar group (PL), or a non-polar group (NPL), and $R^2$ is -x-$A_1$-x-z-y-A'-y-$R^1$, wherein A' is as defined above, A' is aryl or heteroaryl, and each of $A_1$ and A' is optionally substituted with one or more polar (PL) group(s), one or more non-polar (NPL) group(s), or a combination of one or more polar (PL) group(s) and one or more non-polar (NPL) group(s); or (v) -z-y-A' and $R^2$ is hydrogen, a polar group (PL), or a non-polar group (NPL), wherein A' is aryl or heteroaryl and is optionally substituted with one or more polar (PL) group(s), one or more non-polar (NPL) group(s), or a combination of one or more polar (PL) group(s) and one or more non-polar (NPL) group(s); or (vi) -z-y-A', and $R^2$ is -x-A", wherein A' and A" are independently aryl or heteroaryl, and each of A' and A" is optionally substituted with one or more polar (PL) group(s), one or more non-polar (NPL) group(s), or a combination of one or more polar (PL) group(s) and one or more non-polar (NPL) group(s); or (vii) $R^1$ and $R^2$ are independently a polar group (PL) or a non-polar group (NPL); or (viii) $R^1$ and $R^2$ together form a single bond;

NPL is a nonpolar group independently selected from the group consisting of —B$(OR^4)_2$ and —$(NR^{3'})_{q1NPL}$—$U^{NPL}$—$(CH_2)_{pNPL}$—$(NR^{3''})_{q2NPL}$—$R^{4'}$, wherein:

$R^3$, $R^{3'}$, and $R^{3''}$ are independently selected from the group consisting of hydrogen, alkyl, and alkoxy;

$R^4$ and $R^{4'}$ are independently selected from the group consisting of hydrogen, alkyl, alkenyl, alkynyl, cycloalkyl, aryl, and heteroaryl, any of which is optionally substituted with one or more alkyl or halo groups;

$U^{NPL}$ is absent or selected from the group consisting of O, S, S(=O), S(=O)$_2$, $NR^3$, —C(=O)—, —C(=O)—N=N—$NR^3$—, —C(=O)—$NR^3$—N=N—, —N=N—$NR^3$—, —C(=N—N$(R^3)_2$)—, —C(=$NR^3$)—, —C(=O)O—, —C(=O)S—, —C(=S)—, —O—P(=O)$_2$O—, —$R^3$O—, —$R^3$S—, —S—C=N— and —C(=O)—NR$^3$—O—, wherein groups with two chemically nonequivalent termini can adopt both possible orientations;

the —(CH$_2$)$_{pNPL}$— alkylene chain is optionally substituted with one or more amino or hydroxy groups, or is unsaturated;

pNPL is 0 to 8;

q1NPL and q2NPL are independently 0, 1 or 2;

PL is a polar group selected from the group consisting of halo, hydroxyethoxymethyl, methoxyethoxymethyl, polyoxyethylene, and —(NR$^{5'}$)$_{q1PL}$—U$^{PL}$—(CH$_2$)$_{pPL}$—(NR$^{5''}$)$_{q2PL}$—V, wherein:

R$^5$, R$^{5'}$, and R$^{5''}$ are independently selected from the group consisting of hydrogen, alkyl, and alkoxy;

U$^{PL}$ is absent or selected from the group consisting of O, S, S(=O), S(=O)$_2$, NR$^5$, —C(=O)—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N— and —C(=O)—NR$^5$—O—, wherein groups with two chemically nonequivalent termini can adopt both possible orientations;

V is selected from the group consisting of nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkythio, lower acylamino, or benzyloxycarbonyl;

the —(CH$_2$)$_{pPL}$— alkylene chain is optionally substituted with one or more amino or hydroxy groups, or is unsaturated;

pPL is 0 to 8;

q1PL and q2PL are independently 0, 1 or 2; and m is 1 to about 500;

and a pharmaceutically acceptable carrier or diluent.

Polymers and oligomers of Formula IV that are preferred for use in the disclosed method are those wherein x and y are independently NR$^8$, C=O, or O; z is C=O or —NR$^8$NR$^8$; and R$^8$ is hydrogen or C$_1$-C$_6$ alkyl. Especially preferred are those polymers and oligomers wherein x and y are each NR$^8$, z is C=O, and R$^8$ is hydrogen. Also preferred are oligomers of Formula IV wherein x is NR$^8$ or O, y is O, and z is C=O, or wherein x and y are each C=O, and z is —N(R$^8$)N(R$^8$)—, especially wherein R$^8$ is hydrogen.

Preferred are those polymers and oligomers of Formula IV wherein A$_1$ and A$_2$ are independently optionally substituted o-, m-, or p-phenylene. Those oligomers wherein A$_1$ and A$_2$ are optionally substituted m-phenylene are especially preferred. Also preferred are polymers and oligomers of Formula IV wherein one of A$_1$ and A$_2$ is o-, m-, or p-phenylene, and the other of A$_1$ and A$_2$ is heteroarylene. Preferred heteroarylene groups include, but are not limited to, pyridinylene, pyrimidinylene, and pyrazinylene.

Also preferred are polymers and oligomers of Formula IV wherein A$_1$ and A$_2$ are independently optionally substituted arylene or optionally substituted heteroarylene, and (i) each of A$_1$ and A$_2$ is substituted with one or more polar (PL) group(s) and one or more nonpolar (NPL) group(s); or (ii) one of A$_1$ and A$_2$ is substituted with one or more polar (PL) group(s) and the other of A$_1$ and A$_2$ is substituted with one or more nonpolar (NPL) group(s). Polymers and oligomers in which (i) each of A$_1$ and A$_2$ is substituted with one polar (PL) group and one nonpolar (NPL) group, or (ii) one of A$_1$ and A$_2$ is substituted with one or two polar (PL) group(s) and the other of A$_1$ and A$_2$ is substituted with one or two nonpolar (NPL) group(s), are especially preferred.

In some aspects of the invention, preferred polymers and oligomers of Formula IV are those wherein (i) R$^1$ is hydrogen, a polar group (PL), or a non-polar group (NPL), and R$^2$ is -x-A$_1$-x-R$^1$, wherein A$_1$ is as defined above and is optionally substituted with one or more polar (PL) group(s), one or more nonpolar (NPL) group(s), or a combination of one or more polar (PL) group(s) and one or more non-polar (NPL) group(s); or (iii) R$^1$ is hydrogen, a polar group (PL), or a non-polar group (NPL), and R$^2$ is -x-A$_1$-x-z-y-A$_2$-y-R$^1$, wherein A$_1$ and A$_2$ are as defined above, and each of which is optionally substituted with one or more polar (PL) group(s), one or more nonpolar (NPL) group(s), or a combination of one or more polar (PL) group(s) and one or more non-polar (NPL) group(s).

More preferred are those oligomers of Formula IV wherein R$^1$ is hydrogen, a polar group (PL), or a non-polar group (NPL), and R$^2$ is -x-A$_1$-x-R$^1$, wherein A$_1$ is as defined above and is substituted with one polar (PL) group and one non-polar (NPL) group; or those oligomers wherein R$^1$ is hydrogen, a polar group (PL), or a non-polar group (NPL), and R$^2$ is -x-A$_1$-x-z-y-A$_2$-y-R$^1$, wherein A$_1$ and A$_2$ are as defined above, and each of which is substituted with one polar (PL) group and one non-polar (NPL) group.

In some aspects, preferred polymers and oligomers of Formula IV are those wherein NPL is (CH$_2$)$_{pNPL}$—(NR$^{3'''}$)$_{q2NPL}$—R$^{4'}$, and R$^3$, R$^{3'}$, R$^{3''}$, R$^{4''}$, U$^{NPL}$, pNPL, q1NPL and q2NPL are as defined above.

Preferred values for each of R$^3$, R$^{3'}$, and R$^{3''}$ are hydrogen, C$_1$-C$_6$ alkyl, and C$_1$-C$_6$ alkoxy. Hydrogen is an especially preferred value for R$^3$, R$^{3'}$, and R$^{3''}$.

Preferred values of R$^4$ are hydrogen, C$_1$-C$_{10}$ alkyl, C$_3$-C$_{18}$ branched alkyl, C$_2$-C$_{10}$ alkenyl, C$_2$-C$_{10}$ alkynyl, C$_3$-C$_8$ cycloalkyl, C$_6$-C$_{10}$ aryl, and heteroaryl, any of which is optionally substituted with one or more C$_1$-C$_6$ alkyl or halo groups. Values of R$^{4'}$ that are more preferred are C$_1$-C$_{10}$ alkyl, C$_3$-C$_{18}$ branched alkyl, C$_2$-C$_{10}$ alkenyl, C$_2$-C$_{10}$ alkynyl, and C$_6$-C$_{10}$ aryl, especially phenyl. Especially preferred values of R$^4$ are C$_1$-C$_{10}$ alkyl and C$_3$-C$_{18}$ branched alkyl. Suitable C$_1$-C$_{10}$ alkyl and C$_3$-C$_{18}$ branched alkyl groups are methyl, ethyl, n-propyl, isopropyl, n-butyl, tert-butyl, and n-pentyl.

Preferred values of U$^{NPL}$ are O, S, NH, —C(=O)—, —C(=O)—N=N—NH—, —C(=O)—NH—N=N—, —N=N—NH—, —C(=N—N(R$^3$)$_2$)—, —C(=NR$^3$)—, —C(=O)O—, —R$^3$S— and —R$^3$O—.

Especially preferred polymers and oligomers of Formula IV are those wherein U$^{NPL}$ is absent.

Preferred values of pNPL are 0 to 6; values of pNPL of 0 to 4 are especially preferred, with values of pNPL of 0, 1 or 2 most preferred.

Preferred values of q1NPL and q2NPL are 0 or 1. Values of q1NPL and q2NPL of 0 or 1 are especially preferred, with a value of 0 being the most preferred for each of q1NPL and q2NPL.

In preferred polymers and oligomers of Formula IV, the —(CH$_2$)$_{pNPL}$— alkylene chain in NPL is unsubstituted or substituted with one or more amino or hydroxy groups. More preferred are those oligomers of Formula IV wherein the —(CH$_2$)$_{pNPL}$— alkylene chain in NPL is substituted with one or more amino groups.

An especially preferred value of NPL for polymers and oligomers of Formula IV is $C_1$-$C_6$ alkyl. Examples of preferred values for NPL are n-propyl, isopropyl, n-butyl, and tert-butyl.

In some aspects of the invention, preferred polymers and oligomers of Formula IV are those wherein PL is —$(NR^{5'})_{q1PL}$—$U^{PL}$—$(CH_2)_{pPL}$—$(NR^{5''})_{q2PL}$—V, and $R^5$, $R^{5'}$, $R^{5''}$, V, $U^{PL}$, pPL, q1PL and q2PL are as defined above.

Preferred values for $R^5$, $R^{5'}$, and $R^{5''}$ are hydrogen, $C_1$-$C_6$ alkyl, and $C_1$-$C_6$ alkoxy. Hydrogen is an especially preferred value for each of $R^5$, $R^{5'}$, and $R^{5''}$.

Preferred values of $U^{PL}$ are O, S, NH, —C(=O)—, —C(=O)—N=N—NH—, —C(=O)—NH—N=N—, —N=N—NH—, —C(=N—N($R^5$)$_2$)—, —C(=$NR^5$)—, —C(=O)O—, —$R^5$S— and —$R^5$O—. Especially preferred values of $U^{PL}$ are O, S, and —C(=O).

In some aspects of the invention, preferred polymers and oligomers of Formula IV are those wherein $U^{PL}$ is —O—P(=O)$_2$O—.

Preferred values of V are nitro, cyano, amino, 1, $C_1$-$C_6$ alkoxy, $C_1$-$C_6$ alkylthio, $C_1$-$C_6$ alkylamino, $C_1$-$C_6$ dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, $C_6$-$C_{10}$ aryl, heterocycle, and heteroaryl, preferably any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, lower acylamino, or benzyloxycarbonyl.

Suitable heteroaryl groups include indolyl, 3H-indolyl, 1H-isoindolyl, indazolyl, benzoxazolyl, pyridyl, and 2-aminopyridyl. Suitable heterocycle groups include piperidinyl, piperazinyl, imidazolidinyl, pyrrolidinyl, pyrazolidinyl, and morpholinyl.

Values of V that are more preferred are amino, $C_1$-$C_6$ alkylamino, $C_1$-$C_6$ dialkylamino, —NH(CH$_2$)$_p$NH$_2$ wherein p is 1 to 4, —N(CH$_2$CH$_2$NH$_2$)$_2$, diazamino, amidino, guanidino, guanyl, and semicarbazone, preferably any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, lower acylamino, or benzyloxycarbonyl.

Especially preferred values of V are amino, $C_1$-$C_6$ alkylamino, —NH(CH$_2$)$_p$NH$_2$ wherein p is 1 to 4, —N(CH$_2$CH$_2$NH$_2$)$_2$, diazamino, amidino, and guanidino, preferably any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanyl, guanidino, or aminoalkoxy. Values of V that are most preferred are amino and guanidino.

Preferred values of pPL are 0 to 6; values of pPL of 0 to 4 are especially preferred, with values of pPL of 2 to 4 especially preferred.

Preferred values of q1PL and q2PL are 0 or 1. Values of q1PL and q2PL of 0 or 1 are especially preferred, with a value of 0 being especially preferred for each of q1PL and q2PL.

In preferred polymers and oligomers of Formula IV, the —(CH$_2$)$_{pPL}$-alkylene chain in PL is optionally substituted with one or more amino or hydroxy groups.

Preferred polymers of Formula IV are those in which m is 1 to about 500. Especially preferred are those polymers of Formula IV wherein m is 1 to about 100, or wherein m is 1 to about 50.

Oligomers of Formula IV that are preferred are those wherein m is 1 to about 30, or m is 1 to about 25; more preferred are those wherein m is 1 to about 20, or wherein m is 1 to about 10, or wherein m is 1 to about 5. Especially preferred are those oligomers of Formula IV wherein m is 1, 2 or 3.

The invention is also directed to a method of treating a microbial infection in an animal in need thereof, the method comprising administering to the animal an effective amount of a pharmaceutical composition comprising an oligomer of Formula IVa, Formula IVb, or Formula IVc:

$$R^1\text{-}x\text{-}A_1\text{-}x\text{-}z\text{-}y\text{-}A_2\text{-}y\text{-}R^2 \qquad \text{(IVa)}$$

$$R^1\text{-}x\text{-}A_1\text{-}x\text{-}z\text{-}y\text{-}A_2\text{-}y\text{-}z\text{-}x\text{-}A_1\text{-}x\text{-}R^2 \qquad \text{(IVb)}$$

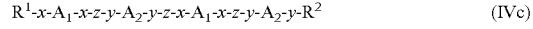

$$R^1\text{-}x\text{-}A_1\text{-}x\text{-}z\text{-}y\text{-}A_2\text{-}y\text{-}z\text{-}x\text{-}A_1\text{-}x\text{-}z\text{-}y\text{-}A_2\text{-}y\text{-}R^2 \qquad \text{(IVc)}$$

or an acceptable salt or solvate thereof,
wherein:
x is $NR^8$, —$NR^8NR^8$—, C=O, or O; y is $NR^8$, —$NR^8NR^8$—, C=O, S, or O; and $R^8$ is hydrogen or alkyl;
z is C=O, C=S, O=S=O, —$NR^8NR^8$—, or —C(=O)C(=O)—;
$A_1$ and $A_2$ are independently optionally substituted arylene or optionally substituted heteroarylene, wherein $A_1$ and $A_2$ are independently optionally substituted with one or more polar (PL) group(s), one or more non-polar (NPL) group(s), or a combination of one or more polar (PL) group(s) and one or more non-polar (NPL) group(s);
$R^1$ is hydrogen, a polar group (PL), or a non-polar group (NPL), and $R^2$ is $R^1$;
NPL is a nonpolar group independently selected from the group consisting of —B(OR$^4$)$_2$ and —(NR$^{3'}$)$_{q1NPL}$—$U^{NPL}$—(CH$_2$)$_{pNPL}$—(NR$^{3''}$)$_{q2NPL}$R$^{4'}$, wherein:
$R^3$, $R^{3'}$, and $R^{3''}$ are independently selected from the group consisting of hydrogen, alkyl, and alkoxy;
$R^4$ and $R^{4'}$ are independently selected from the group consisting of hydrogen, alkyl, alkenyl, alkynyl, cycloalkyl, aryl, and heteroaryl, any of which is optionally substituted with one or more alkyl or halo groups;
$U^{NPL}$ is absent or selected from the group consisting of O, S, S(=O), S(=O)$_2$, $NR^3$, —C(=O)—, —C(=O)—N=N—$NR^3$—, —C(=O)—$NR^3$—N=N—, —N=N—$NR^3$—, —C(=N—N($R^3$)$_2$)—, —C(=$NR^3$)—, —C(=O)O—, —C(=O)S—, —C(=S)—, —O—P(=O)$_2$O—, —$R^3$O—, —$R^3$S—, —S—C=N— and —C(=O)—$NR^3$—O—, wherein groups with two chemically nonequivalent termini can adopt both possible orientations;
the —(CH$_2$)$_{pNPL}$—alkylene chain is optionally substituted with one or more amino or hydroxy groups, or is unsaturated;
pNPL is 0 to 8;
q1NPL and q2NPL are independently 0, 1 or 2;
PL is a polar group selected from the group consisting of halo, hydroxyethoxymethyl, methoxyethoxymethyl, polyoxyethylene, and —(NR$^{5'}$)$_{q1PL}$—$U^{PL}$—(CH$_2$)$_{pPL}$—(NR$^{5''}$)$_{q2PL}$—V, wherein:
$R^5$, $R^{5'}$, and $R^{5''}$ are independently selected from the group consisting of hydrogen, alkyl, and alkoxy;
$U^{PL}$ is absent or selected from the group consisting of O, S, S(=O), S(=O)$_2$, $NR^5$, —C(=O)—, —C(=O)—N=N—$NR^5$—, —C(=O)—$NR^5$—N=N—, —N=N—$NR^5$—, —C(=N—N($R^5$)$_2$)—, —C(=$NR^5$)—, —C(=O)O—, —C(=O)S—, —C(=S)—, —O—P(=O)$_2$O—, —$R^5$O—, —$R^5$S—, —S—C=N— and —C(=O)—$NR^5$O—, wherein groups with two chemically nonequivalent termini can adopt both possible orientations;

V is selected from the group consisting of nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle and heteroaryl, preferably any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkythio, lower acylamino, or benzyloxycarbonyl;

the —(CH$_2$)$_{pPL}$— alkylene chain is optionally substituted with one or more amino or hydroxy groups, or is unsaturated;

pPL is 0 to 8;

q1PL and q2PL are independently 0, 1 or 2; and a pharmaceutically acceptable carrier or diluent.

Preferred values of A$_1$, A$_2$, R$^1$, R$^2$, R$^3$, R$^{3'}$, R$^{3''}$, R$^4$, R$^{4'}$, NPL, U$^{NPL}$, pNPL, q1NPL, q2NPL, PL, R$^5$, R$^{5'}$, R$^{5''}$, V, U$^{PL}$, pPL, q1PL and q2PL for the oligomers of Formula IVa, Formula IVb, and Formula IVc are also the same as those listed for polymers and oligomers of Formula IV above.

In some aspects, the invention is also directed to a method of treating a microbial infection in an animal in need thereof, the method comprising administering to the animal an effective amount of a pharmaceutical composition comprising a polymer or oligomer of Formula IV'

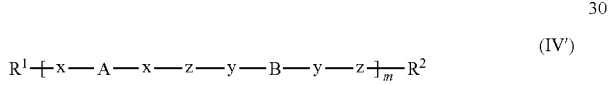

(IV')

or an acceptable salt or solvate thereof,
wherein:

x is NR$^3$, —NR$^3$NR$^3$—, or C═O; y is NR$^3$, —NR$^3$NR$^3$—, C═O; S, or O; and R$^3$ is hydrogen or alkyl;

z is C═O, C═S, O═S═O, —NR$^3$NR$^3$—, or —C(═O)C(═O)—;

A and B are independently optionally substituted o-, m-, or p-phenylene or optionally substituted heteroarylene, wherein:

A and B are independently optionally substituted with one or more polar (P) group(s), one or more non-polar (NP) group(s), or a combination of one or more polar (P) group(s) and one or more non-polar (NP) group(s);

R$^1$ is
(i) —B-y-R$^2$ and R$^2$ is -x-(CH$_2$)$_p$—W, wherein: x is as defined above; W is hydrogen, pyridine, phenyl, said pyridine or phenyl optionally substituted with 1 or 2 substituents independently selected from the group consisting of halo, nitro, cyano, C$_1$-C$_6$ alkoxy, C$_1$-C$_6$ alkoxycarbonyl, and benzyoloxycarbonyl, carboxyl, N-maleimide, or V as defined below; the —(CH$_2$)$_p$- alkylene chain is optionally substituted with one or more amino or hydroxyl groups, or the alkylene chain is unsaturated; and p is as defined below; or
(ii) R$^1$ is H and R$^2$ is -x-(CH$_2$)$_p$—W; wherein: x is as defined above; W is as defined above; the —(CH$_2$)$_p$— alkylene chain is optionally substituted with one or more amino or hydroxyl groups, or the alkylene chain is unsaturated; and p is as defined below; or
(iii) R$^1$ and R$^2$ together are a single bond; or
(iv) —(CH$_2$)$_p$—W or —(CH$_2$)$_p$—U, wherein W is as defined above, U is as defined below, and the —(CH$_2$)$_p$— alkylene chain is optionally substituted with one or more amino or hydroxyl groups, or the alkylene chain is unsaturated, and p is as defined below; and R$^2$ is x-A-x-R$^1$; or
(v) —(CH$_2$)$_p$—W or —(CH$_2$)$_p$—U, wherein W is as defined above, U is as defined below, and the —(CH$_2$)$_p$— alkylene chain is optionally substituted with one or more amino or hydroxyl groups, or the alkylene chain is unsaturated, and p is as defined below; and R$^2$ is -x-A-x-z-y-B-y-R$^1$; or
(vi) -z-y-B-y-R$^2$ and R$^2$ is —(CH$_2$)$_p$—W or —(CH$_2$)—U, wherein W is as defined above, U is as defined below, and the —(CH$_2$)$_p$— alkylene chain is optionally substituted with one or more amino or hydroxyl groups, or the alkylene chain is unsaturated, and p is as defined below;

NP is a nonpolar group independently selected from —B(OR$^4$)$_2$ (wherein B in this instance represents a boron atom), R$^4$, or —(NR$^3$)$_{q1}$—U—(CH$_2$)$_p$—(NR$^3$)$_{q2}$—R$^4$,
wherein R$^3$ is selected from the group consisting of hydrogen, alkyl, and alkoxy;

R$^4$ is selected from the group consisting of hydrogen, alkyl, alkenyl, alkynyl, cycloalkyl, aryl, and heteroaryl, any of which is optionally substituted with one or more alkyl, alkoxy, or halo groups;

U is absent or selected from the group consisting of O, S, S(═O), S(═O)$_2$, NR$^3$, —(C═O)—, —(C═O)—N═N—NR$^3$—, —(C═O)—NR$^3$—N═N—, —N═N—NR$^3$—, —C(═N—N(R$^3$)$_2$)—, —C(═NR$^3$)—, —C(═O)O—, —C(═O)S—, —C(═S)—, —O—P(═O)$_2$O— (wherein P in this instance represents a phosphorus atom), —R$^3$—O—, —R$^3$—S—, —S—C═N— and —(C═O)—NR$^3$—O—, wherein groups with two chemically nonequivalent termini can adopt both possible orientations;

the —(CH$_2$)$_p$— alkylene chain is optionally substituted with one or more amino or hydroxyl groups, or the alkylene chain is unsaturated;

p is independently 0 to 8;

q1 and q2 are independently 0 to 2;

P is a polar group selected from the group consisting of halo, hydroxyethoxymethyl, methoxyethoxymethyl, polyoxyethylene, and —(NR$^3$)$_{q1}$—U—(CH$_2$)$_p$—(NR$^3$)$_{q2}$—V, wherein;

U and R$^3$ are as defined above;

V is selected from the group consisting of nitro, cyano, thio, amino, hydroxyl, alkoxy, alkylthio, alkylamino, dialkylamino, —NH(CH$_2$)$_p$NH$_2$, —N(CH$_2$CH$_2$NH$_2$)$_2$, diazamino, amidino, guanidino, guanyl, semicarbazone, alkoxycarbonyl, aryl, heterocycle and heteroaryl, any of which is optionally substituted with one or more of amino, halo, cyano, nitro, hydroxyl, —NH(CH$_2$)NH$_2$, —N(CH$_2$CH$_2$NH$_2$)$_2$ alkylamino, dialkylamino, amidino, guanidino, guanyl, aminosulfonyl, aminoalkoxy, aminoalkylthio, lower acylamino, or benzyloxycarbonyl;

the —(CH$_2$)$_p$— alkylene chain is optionally substituted with one or more amino or hydroxyl groups, or the alkylene chain is unsaturated;

p, q1 and q2 are as defined above; and m is 1 to about about 500;

and a pharmaceutically acceptable carrier or diluent.

In some aspects, the invention is also directed to a method of treating a microbial infection in an animal in need thereof, the method comprising administering to the animal an effective amount of a pharmaceutical composition comprising a polymer or oligomer of Formula IV', wherein:

x is NR³; y is NR³ z is C=O; and R³ is hydrogen or alkyl;
A and B are independently optionally substituted o-, m-, or p-phenylene,
  wherein:
  A and B are independently optionally substituted with one or more polar (P) group(s), one or more non-polar (NP) group(s), or a combination of one or more polar (P) group(s) and one or more non-polar (NP) group(s);
R¹ is
  (i) —(CH₂)ₚ—W or —(CH₂)ₚ—U, wherein: W is hydrogen, pyridine, phenyl, said pyridine or phenyl optionally substituted with 1 or 2 substituents independently selected from the group consisting of halo, nitro, cyano, C₁-C₆ alkoxy, C₁-C₆ alkoxycarbonyl, and benzyloxycarbonyl, carboxyl, N-maleimide, or V as defined below; U is as defined below; the —(CH₂)ₚ— alkylene chain is optionally substituted with one or more amino or hydroxyl groups; p is as defined below; and R² is -x-A-x-R¹; or
  (ii) —(CH₂)ₚ—W or —(CH₂)ₚ—U, wherein: W is as defined above; U is as defined below; and the —(CH₂)ₚ— alkylene chain is optionally substituted with one or more amino or hydroxyl groups; p is as defined below; and R² is -x-A-x-z-y-B-y-R¹;
NP is —(NR³)_{q1}—U—(CH₂)ₚ—(NR³)_{q2}—R⁴, wherein
  R⁴ is selected from the group consisting of hydrogen, alkyl, alkenyl, alkynyl, and aryl, any of which is optionally substituted with one or more alkyl, alkoxy, or halo groups;
  U is absent, O, S, or —(C=O)—;
  the —(CH₂)ₚ— alkylene chain is optionally substituted with one or more amino or hydroxyl groups;
  p is independently 0 to 6;
  q1 and q2 are each 0;
P is (NR³)_{q1}—U—(CH₂)ₚ—(NR³)_{q2}—V, wherein;
  U and R³ are as defined above;
  V is selected from the group consisting of nitro, amino, hydroxyl, alkoxy, alkylthio, alkylamino, dialkylamino, —NH(CH₂)ₚNH₂, —N(CH₂CH₂NH₂)₂, diazamino, amidino, guanidino, guanyl, semicarbazone, alkoxycarbonyl, aryl, heterocycle and heteroaryl, any of which is optionally substituted with one or more of amino, halo, —NH(CH₂)ₚNH₂, —N(CH₂CH₂NH₂)₂, alkylamino, dialkylamino, amidino, guanidino, guanyl, aminosulfonyl, aminoalkoxy, aminoalkylthio, lower acylamino, or benzyloxycarbonyl;
  the —(CH₂)ₚ— alkylene chain is optionally substituted with one or more amino or hydroxyl groups;
  p is independently 0 to 6;
  q1 and q2 are each 0; and
m is 1 to 5;
and a pharmaceutically acceptable carrier or diluent.

In other aspects, in the polymer or oligomer of Formula IV',
x and y are NR³, z is C=O or C=S, and R³ is hydrogen;
A and B are independently optionally substituted o-, m-, or p-phenylene;
3NP is a nonpolar group independently selected from R⁴ or —U—(CH₂)ₚ—R⁴ wherein R⁴ is selected from a group consisting of hydrogen, C₁-C₄ alkyl, C₃-C₁₂ branched alkyl, C₃-C₈ cycloalkyl, phenyl optionally substituted with one or more C₁-C₄ alkyl groups and heteroaryl optionally substituted with one or more C₁-C₄ alkyl groups, and U and p are as defined below;
P is a polar group selected from IIIa, hydroxyethoxymethyl, methoxyethoxymethyl or polyoxyethylene —U—(CH₂)ₚ—V  (IIIa)

wherein
U is O, S, S(=O), S(=O)₂, NH, or absent;
V is selected from a group consisting of amino, hydroxyl, C₁-C₆ alkylamino, C₁-C₆ dialkylamino, NH(CH₂)ₚNH₂, N(CH₂CH₂NH₂)₂, amidine, guanidine, semicarbazone, and imidazole, piperidine, piperazine, 4-alkylpiperazine and phenyl optionally substituted with an amino, C₁-C₆ alkylamino, C₁-C₆ dialkylamino or lower acylamino optionally substituted with one or more amino, lower alkylamino or lower dialkylamino;
and the alkylene chain is optionally substituted with an amino or hydroxyl group;
p is independently 0 to 8; and,
m is 1 to about 500.

In yet other aspects, in the polymer or oligomer of Formula IV',
x and y are NH, z is C=O;
A and B are m or p-phenylene and either (i) A is substituted at the 2-position with a polar (P) group and B is substituted at the 5-position with a nonpolar (NP) group, or (ii) A is substituted at the 5-position with a polar (P) group and B is substituted at the 2-position with a nonpolar (NP) group, or (iii) A and B are both substituted at the 2-position with a polar (P) group and at the 5-position with a nonpolar (NP) group, or (iv) A is substituted at the 2-position with a polar (P) group and at the 5-position with a nonpolar (NP) group and B is unsubstituted;
NP is a nonpolar group independently selected from R⁴ or —U—(CH₂)ₚ—R⁴ wherein R⁴ is selected from a group consisting of hydrogen, methyl, ethyl, n-propyl, iso-propyl, iso-butyl, sec-butyl, tert-butyl, iso-pentyl, and sec-pentyl, and U and p are as defined below;
P is a polar group U—(CH₂)ₚ—V wherein U is absent or selected from a group consisting of O and S, and V is selected from a group consisting of amino, lower alkyl amino, lower dialkylamino, imidazole, guanidine, NH(CH₂)ₚNH₂, N(CH₂CH₂NH₂)₂, piperidine, piperazine, and 4-alkylpiperazine;
p is independently 0 to 8; and,
m is 1 to about 500;
or an acceptable salt or solvate thereof; and
a pharmaceutically acceptable carrier or diluent.

In some aspects, the invention is directed to a method of treating a microbial infection in an animal in need thereof, the method comprising administering to the animal an effective amount of a pharmaceutical composition comprising a polymer or oligomer of Formula XIV:

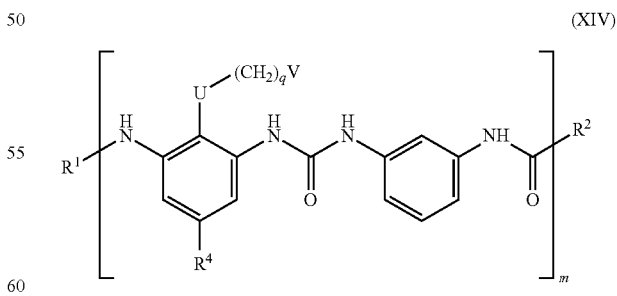

(XIV)

R⁴ is selected from a group consisting of methyl, ethyl, n-propyl, iso-propyl, n-butyl, iso-butyl, sec-butyl, tert-butyl, n-pentyl, iso-pentyl, and sec-pentyl, and U and p are as defined below;
U is absent, O or S, and V is selected from a group consisting of amino, lower alkyl amino, lower dialkylamino, imidazole, guanidine, NH(CH$_2$)$_p$NH$_2$, N(CH$_2$CH$_2$NH$_2$)$_2$, piperidine, piperazine, and 4-alkylpiperazine; and, p is 0 to 8;

m is 1 to about 30, or is 1 to about 50;

or an acceptable salt or solvate thereof; and a pharmaceutically acceptable carrier or diluent.

In yet other aspects, the invention is directed to a method of treating a microbial infection in an animal in need thereof, the method comprising administering to the animal an effective amount of a pharmaceutical composition comprising a polymer or oligomer of Formula XVII:

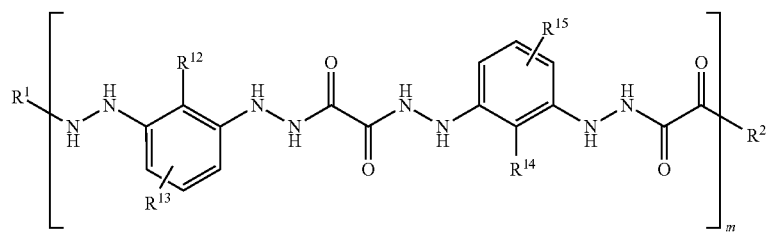

(XVII)

wherein:

either R$^{12}$ and R$^{14}$ are independently polar (P) groups and R$^{13}$ and R$^{15}$ are independently nonpolar (NP) groups substituted at one of the remaining unsubstituted carbon atoms, or R$^{12}$ and R$^{14}$ are independently nonpolar (NP) groups and R$^{13}$ and R$^{15}$ are independently polar (P) groups;

NP is a nonpolar group independently selected from R$^4$ or —U—R$^4$ wherein R$^4$ is selected from a the group consisting of methyl, ethyl, n-propyl, iso-propyl, n-butyl, iso-butyl, sec-butyl, tert-butyl, n-pentyl, iso-pentyl, and sec-pentyl, and U and p are as defined below;

P is a polar group U—(CH$_2$)$_p$—V wherein U is selected from a group consisting of O and S, and V is selected from a group consisting of amino, lower alkyl amino, lower dialkylamino, guanidine, pyridine, piperazine, and 4-alkylpiperazine;

p is independently 0 to 8; and, m is 1 to about 30, or 1 to about 50;

or an acceptable salt or solvate thereof; and a pharmaceutically acceptable carrier or diluent.

In, yet other aspects, the invention is directed to a method of treating a microbial infection in an animal in need thereof, the method comprising administering to the animal an effective amount of a pharmaceutical composition comprising a polymer or oligomer of Formula XVIII:

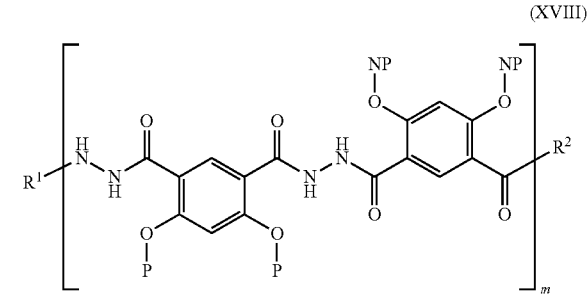

(XVIII)

wherein:

NP is a nonpolar group independently selected from R$^4$ or —(CH$_2$)$_p$—R$^4$ wherein R$^4$ is selected from a group consisting of hydrogen, methyl, ethyl, n-propyl, iso-propyl, n-butyl, iso-butyl, sec-butyl, tert-butyl, n-pentyl, iso-pentyl, and sec-pentyl, and p is as defined below;

P is a polar group (CH$_2$)$_p$—V wherein V is selected from a group consisting of amino, lower alkyl amino, lower dialkylamino, imidazole, guanidine, NH(CH$_2$)$_p$NH$_2$, N(CH$_2$CH$_2$NH$_2$)$_2$, piperidine, piperazine, and 4-alkylpiperazine;

p is independently 0 to 8; and, m is 1 to about 30, or 1 to about 50;

or an acceptable salt or solvate thereof; and a pharmaceutically acceptable carrier or diluent.

The polymers and oligomers of the invention can be used to treat a microbial infection caused by any type of microorganism, including, but not limited to, bacteria, algae, fungi, yeast, mycoplasmas, mycobacterial, parasites and protozoa. The polymers and oligomers of the present invention are therefore effective in treating bacterial infections, fungal infections, viral infections, yeast infections, mycoplasmid infections, mycobacterial infections, or protozoal infections.

The polymers and oligomers of the present invention have been shown to possess antiviral activity and can be used as antiviral agents.

Thus, in some aspects, the invention is directed to a method of treating a viral infection in an animal in need thereof, the method comprising administering to the animal an effective amount of a pharmaceutical composition comprising a polymer of oligomer described above, for example, a polymer or oligomer of Formula I, Formula I', Formula II, Formula Ia, Formula II', Formula IV, Formula IVa, Formula IVb, Formula IVc, Formula IV', —Formula VII, Formula IX, Formula XI, Formula XII, Formula XIII, Formula XIV, Formula XV, Formula XVI, Formula XVII, Formula XVIII, or Formula XX, as defined above.

The polymers and oligomers of the present invention can also be used in methods of treating fungal infections.

Immunocompromised individuals are at serious risk for developing systemic fungal infections and the high incidence of cancer and AIDS underscores the need for developing effective and safe antifungal therapies. Many of the existing antifungal drugs act on molecular targets involved in cell wall synthesis (Debono, M., and Gordee, R. S., *Ann. Rev. Microbiol.* 48:471-497 (1994)). However, many of these targets are also found in mammalian cells which can lead to unwanted side-effects, and current therapies are associated with serious clinical complications including hepatic and kidney toxicities. Furthermore, as with bacterial infections, drug-resistant fungi are emerging at an alarming rate (DeLucca, A. J., and Walsh, T. J., *Antimicob. Agents Chemother.* 43:1-11 (1999)). Therefore, there is a strong need for the development of novel approaches for systemic and topical agents that can rapidly, effectively and safely control fungal infections while minimizing the potential for the development of resistance to their mechanism of action.

The polymers and oligomers of the present invention have also been shown to possess antifungal activity and thus can be used as antifungal agents, for example, in a method of treating fungal infections in an animal.

Thus, in some aspects, the invention is directed to a method of treating a fungal infection in an animal in need thereof, the method comprising administering to the animal an effective amount of a pharmaceutical composition comprising a polymer or oligomer described above, for example, a polymer or oligomer of Formula I, Formula I', Formula II, Formula Ia, Formula II', Formula IV, Formula IVa, Formula IVb, Formula IVc, Formula IV', Formula VII, Formula IX, Formula XI, Formula XII, Formula XIII, Formula XIV, Formula XV, Formula XVI, Formula XVII, Formula XVIII, or Formula XX, as defined above.

The polymers and oligomers of the invention can also be used as antidotes for hemorrhagic complications associated with low molecular weight heparin therapy.

Heparin has been commonly used as an anticoagulant and antithrombotic agent in the hospital setting. However, there are several pharmacokinetic parameters of standard heparin (SH) that complicate therapy. For example, the high serum protein-binding activity of SH precludes subcutaneous administration and its rapid and unpredictable plasma clearance necessitates constant monitoring of activated partial thromboplastin time to assess effectiveness (Turpie, A. G. G., *Am. Heart J.* 135:S329-S335 (1998)). More recently, low molecular weight heparin derivatives (LMWH) have become the standard of care for the management of major vessel thrombotic conditions (Hirsh, J., and Levine, M. N., *Blood.* 79:1-17 (1992)). Nevertheless, LMWHs have gained popularity over standard heparin (SH) as antithrombotic agents because of their improved pharmacokinetics and more predictable anticoagulant responses to weight-adjusted doses. LMWHs are formed by enzymatic or chemical cleavage of heparin and are effective factor Xa inhibitors because they contain the high affinity pentasaccharide sequence. However, they are not effective thrombin inhibitors (Hirsh, J., and Levine, M. N., *Blood.* 79:1-17 (1992)).

Both SH and LMWH have a high net negative (anionic) charge. Hemorrhagic complications are associated with antithrombotic treatments with both agents and an overdose may result in serious bleeding. Protamine, by virtue of its positive charge, can neutralize the effects of the heparin but protamine therapy also has serious adverse, side-effects including hypotension, pulmonary hypertension and impairment of certain blood cells including platelets and lymphocytes (Wakefield, T. W., et al., *J. Surg. Res.* 63:280-286 (1996)). Therefore, there is a strong need for the development of safe and effective antidotes for hemorrhagic complications associated with SH and LMWH antithrombotic therapies.

The polymers and oligomers of the present invention have been shown to inhibit the anticoagulation effects of heparin, in particular, low molecular weight heparin, and can be used as antidotes for hemorrhagic complications associated with low molecular weight heparin therapy.

Thus, in some aspects, the invention is directed to a method of providing an antidote to low molecular weight heparin overdose in an animal in need thereof, the method comprising administering to the animal an effective amount of a pharmaceutical composition comprising a polymer or oligomer described above, for example, a polymer or oligomer of Formula I, Formula I', Formula II, Formula Ia, Formula II', Formula IV, Formula IVa, Formula IVb, Formula IVc, Formula IV', Formula VII, Formula IX, Formula XI, Formula XII, Formula XIII, Formula XIV, Formula XV, Formula XVI, Formula XVII, Formula XVIII, or Formula XX, as defined above.

In some aspects of the invention, the polymers and oligomers of the present invention are useful as disinfectants. For example, coatings and paints adhesives are all exposed to microbial contamination and are used in locations where microbial growth is undesirable. Thus, the polymers and oligomers of the present invention are incorporated into polishes, paints, sprays, or detergents formulated for application to surfaces to inhibit the growth of a bacterial species thereon. These surfaces include, but are not limited to surfaces, such as, countertops, desks, chairs, laboratory benches, tables, floors, bed stands, tools or equipment, doorknobs, and windows. Polymers and oligomers of the present invention are also incorporated into soaps and hand lotions. The present cleansers, polishes, paints, sprays, soaps, or detergents contain a polymer or oligomer of the invention that provides a bacteriostatic property to them. They can optionally contain suitable solvent(s), carrier(s), thickeners, pigments, fragrances, deodorizers, emulsifiers, surfactants, wetting agents, waxes, or oils. For example, in some aspects of the invention, the polymers or oligomers are incorporated into a formulation for external use as a pharmaceutically acceptable skin cleanser, particularly for the surfaces of human hands. Cleansers, polishes, paints, sprays, soaps, hand lotions, and detergents are the like containing the antimicrobial polymers and oligomers of the present invention are useful in homes and institutions, particularly but not exclusively in hospital settings for the prevention of nosocomial infections.

In other aspects of the invention, the polymers and oligomers of the invention are useful as preservatives and can be used in a method for killing or inhibiting the growth of a microbial species in a foodstuff and can be added to the foodstuff as a preservative. Foodstuffs that can be treated with a polymer or oligomer of the invention include, but are not limited to, non-acidic foods, such as mayonnaise or other egg products, potato products, and other vegetable or meat products. The polymer or oligomer for adding to the foodstuff can be part of any comestible formulation that can also include a suitable medium or carrier for convenient mixing or dissolving into a particular foodstuff. The medium or carrier is preferably one that will not interfere with the familiar flavor of the food of interest, such as are known by the artisan skilled in food processing techniques.

In yet other aspects of the invention, the polymers and oligomers of the present invention provide a surface-mediated microbicide that only kills organisms in contact with the surface and are useful as surface-mediated disinfectants or preservatives.

Any object that is exposed to or susceptible to bacterial or microbial contamination can be treated with the polymers and oligomers of the present invention to provide a microbial surface. To provide a microbial surface, a polymer or oligomer of the invention are attached to, applied on or incorporated into almost any substrate including but not limited to woods, paper, synthetic polymers (plastics), natural and synthetic fibers, natural and synthetic rubbers, cloth, glasses and ceramics by appropriate methods including covalent bonding, ionic interaction, coulombic interaction, hydrogen bonding or cross-linking. Examples of synthetic polymers include elastically deformable polymers which may be thermosetting or thermoplastic including, but not limited to polypropylene, polyethylene, polyvinyl chloride, polyethylene terephthalate, polyurethane, polyesters, such as polylactide, polyglycolide, rubbers such as polyisoprene, polybutadiene or latex, polytetrafluoroethylene, polysulfone and polyethylenesulfone polymers or copolymers. Examples of natural fibers include cotton, wool and linen.

The incidence of infection from food-borne pathogens is a continuing concern and antimicrobial packaging material, utensils and surfaces would be valuable. In the health care and medical device areas the utility of antimicrobial instruments, packaging and surfaces are obvious. Products used internally or externally in humans or animal health including, but not limited to, surgical gloves, implanted devices, sutures, catheters, dialysis membranes, water filters and implements, all can harbor and transmit pathogens.

Polymers and oligomers of the present invention are incorporated into any of these devices or implements to provide surface-medicated antimicrobial surfaces that will kill or inhibit the growth of organisms in contact with the surface. For example, the polymers and oligomers of the present invention can be incorporated into spinnable fibers for use in materials susceptible to bacterial contamination including, but not limited to, fabrics, surgical gowns, and carpets. Also, ophthalmic solutions and contact lenses easily become contaminated and cause ocular infections. Antimicrobial storage containers for contact lens and cleaning solutions incorporating polymers and oligomers of the present invention would thus be very valuable.

Thus, in some aspects, the present invention is directed to a method of killing or inhibiting the growth of a microorganism, the method comprising contacting the microorganism with an effective amount of a polymer or oligomer described above, for example, a polymer or oligomer of Formula I, Formula I', Formula II, Formula Ia, Formula II', Formula IV, Formula IVa, Formula IVb, Formula IVc, Formula IV', Formula VII, Formula IX, Formula XI, Formula XII, Formula XIII, Formula XIV, Formula XV, Formula XVI, Formula XVII, Formula XVIII, or Formula XX, as defined above.

In some aspects, the invention is directed to a polymer of Formula I, Formula I', Formula II, Formula II', Formula IV, Formula IV', Formula VII, Formula IX, Formula XI, Formula XII, Formula XIII, Formula XIV, Formula XV, Formula XVI, Formula XVII, Formula XVIII, or Formula XX, as defined above, wherein m is 1 to about 500; or m is 1 to about 100; or m is 1 to about 50.

In other aspects, the invention is directed to an oligomer of Formula I, Formula I', Formula II, Formula Ia, Formula II', Formula IV, Formula IVa, Formula IVb, Formula IVc, Formula IV', Formula VII, Formula IX, Formula XI, Formula XII, Formula XIII, Formula XIV, Formula XV, Formula XVI, Formula XVII, Formula XVIII, or Formula XX, as defined above, wherein m is 1 to about 30, or 1 to about 25, or 1 to about 20. In other aspects, m is 1 to about 10, or 1 to about 5, or 1 to about 3, 2 or 1.

Thus, for example, the present invention is directed to an oligomer of Formula I:

$$R^1\text{-}[\text{-}x\text{-}A_1\text{-}y\text{-}x\text{-}A_2\text{-}y\text{-}]_m\text{-}R^2 \quad (I)$$

or an acceptable salt or solvate thereof,
wherein:
x is $NR^8$, y is C=O, and $R^8$ is hydrogen;
$A_1$ is optionally substituted o-, m-, or p-phenylene and $A_2$ is —$(CH_2)_q$—, wherein q is 1, wherein one of $A_1$ and $A_2$ is substituted with one or two polar (PL) group(s), and the other of $A_1$ and $A_2$ is substituted with one or two non-polar (NPL) group(s); or
$A_2$ is optionally substituted o-, m-, or p-phenylene and $A_1$ is —$(CH_2)_q$—, wherein q is 1, wherein one of $A_1$ and $A_2$ is substituted with one or two polar (PL) group(s), and the other of $A_1$ and $A_2$ is substituted with one or two non-polar (NPL) group(s);

$R^1$ and $R^2$ are independently hydrogen, a polar (PL) group, or a non-polar (NPL) group;

NPL is —$(NR^{3'})_{q1NPL}$—$U^{NPL}$—$(CH_2)_{pNPL}$—$(NR^{3''})_{q2NPL}$—$R^{4'}$, wherein:
$R^{4'}$ is selected from the group consisting of $C_1$-$C_{10}$ alkyl, $C_3$-$C_{18}$ branched alkyl, $C_2$-$C_{10}$ alkenyl, $C_2$-$C_{10}$ alkynyl, and $C_6$-$C_{10}$ aryl, any of which is optionally substituted with one or more alkyl or halo groups;
$U^{NPL}$ is absent or selected from the group consisting of NH, —C(=O)—, O and S;
the —$(CH_2)_{pNPL}$— alkylene chain is optionally substituted with one or more amino groups;
pNPL is 0 to 8;
q1NPL and q2NPL are 0;

PL is —$(NR^{5'})_{q1PL}$—$U^{PL}$—$(CH_2)_{pPL}$—$(NR^{5''})_{q2PL}$—V, wherein:
$U^{PL}$ is absent or selected from the group consisting of O, S, NH, and —C(=O);
V is selected from the group consisting of amino, $C_1$-$C_6$ alkylamino, —$NH(CH_2)_pNH_2$ wherein p is 1 to 4, —$N(CH_2CH_2NH_2)_2$, diazamino, amidino, and guanidino, any of which is optionally substituted with one or more of amino, halo, cyano, nitro, hydroxy, —$NH(CH_2)_pNH_2$ wherein p is 1 to 4, —$N(CH_2CH_2NH_2)_2$, amidino, guanyl, guanidino, or aminoalkoxy;
the —$(CH_2)_{pPL}$— alkylene chain is optionally substituted with one or more amino groups;
pPL is 0 to 8;
q1PL and q2PL are 0; and
m is 4 or 5.

In other aspects, the invention is directed to an oligomer of Formula IIa:

$$R^1\text{-}x\text{-}A_1\text{-}x\text{-}y\text{-}A_2\text{-}y\text{-}x\text{-}A_1\text{-}x\text{-}R^2 \quad (IIa)$$

or an acceptable salt or solvate thereof,
wherein:
x is $NR^8$, O, S, or —$N(R^8)N(R^8)$—; and y is C=O, C=S, or O=S=O; wherein $R^8$ is hydrogen or alkyl;
$A_1$ and $A_2$ are independently optionally substituted arylene or optionally substituted heteroarylene, wherein $A_1$ and $A_2$ are independently optionally substituted with one or more polar (PL) group(s), one or more non-polar (NPL) group(s), or a combination of one or more polar (PL) group(s) and one or more non-polar (NPL) group(s);
$R^1$ is a polar group (PL) or a non-polar group (NPL); and $R^2$ is $R^1$;
NPL is a nonpolar group independently selected from the group consisting of —$B(OR^4)_2$ and —$(NR^{3'})_{q1NPL}$—$U^{NPL}$—$(CH_2)_{pNPL}$—$(NR^{3''})_{q2NPL}$—$R^{4'}$, wherein:
$R^3$, $R^{3'}$, and $R^{3''}$ are independently selected from the group consisting of hydrogen, alkyl, and alkoxy;
$R^4$ and $R^{4'}$ are independently selected from the group consisting of hydrogen, alkyl, alkenyl, alkynyl, cycloalkyl, aryl, and heteroaryl, any of which is optionally substituted with one or more alkyl or halo groups;
$U^{NPL}$ is absent or selected from the group consisting of O, S, S(=O), S(=O)$_2$, $NR^3$, —C(=O)—, —C(=O)—N=N—$NR^3$—, —C(=O)—$NR^3$—N=N—, —N=N—$NR^3$—, —C(=N—N(R$^3$)$_2$)—, —C(=$NR^3$)—, —C(=O)O—, —C(=O)S—, —C(=S)—, —O—P(=O)$_2$O—, —$R^3$O—, —$R^3$S—, —S—C=N— and —C(=O)—$NR^3$—O—, wherein groups with two chemically nonequivalent termini can adopt both possible orientations;

the —(CH$_2$)$_{pNPL}$—alkylene chain is optionally substituted with one or more amino or hydroxy groups, or is unsaturated;

pNPL is 0 to 8;

q1NPL and q2NPL are independently 0, 1 or 2;

PL is a polar group selected from the group consisting of halo, hydroxyethoxymethyl, methoxyethoxymethyl, polyoxyethylene, and —(NR$^{5'}$)$_{q1PL}$—U$^{PL}$—(CH$_2$)$_{pPL}$—(NR$^{5'}$)$_{q2PL}$—V, wherein:

R$^5$, R$^{5'}$, and R$^{5''}$ are independently selected from the group consisting of hydrogen, alkyl, and alkoxy;

U$^{PL}$ is absent or selected from the group consisting of O, S, S(=O), S(=O)$_2$, NR$^5$, —C(=O)—, —C(=O)—N=N—NR$^5$—, —C(=O)—NR$^5$—N=N—, —N=N—NR$^5$—, —C(=N—N(R$^5$)$_2$)—, —C(=NR$^5$)—, —C(=O)O—, —C(=O)S—, —C(=S)—, —O—P(=O)$_2$O—, —R$^5$O—, —R$^5$S—, —S—C=N— and —C(=O)—NR$^5$—O—, wherein groups with two chemically nonequivalent termini can adopt both possible orientations;

V is selected from the group consisting of nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkythio, lower acylamino, or benzyloxycarbonyl;

the —(CH$_2$)$_{pPL}$— alkylene chain is optionally substituted with one or more amino or hydroxy groups, or is unsaturated;

pPL is 0 to 8; and q1PL and q2PL are independently 0, 1 or 2.

Examples of oligomers of the present invention, including oligomers for use in the disclosed methods of the invention, include, but are not limited to, the following compounds:

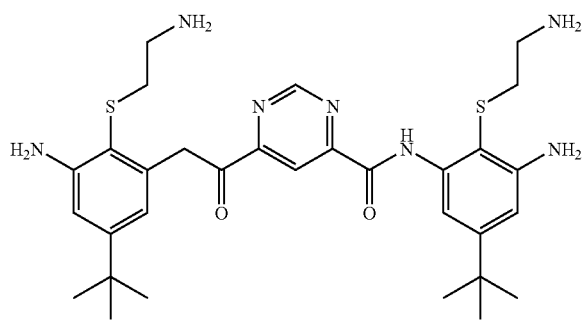

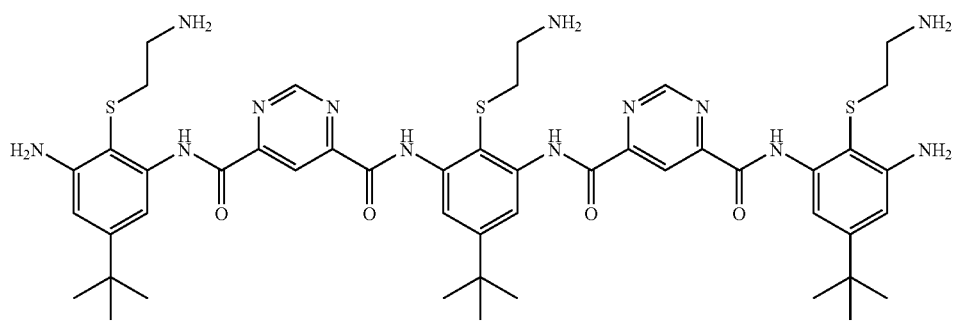

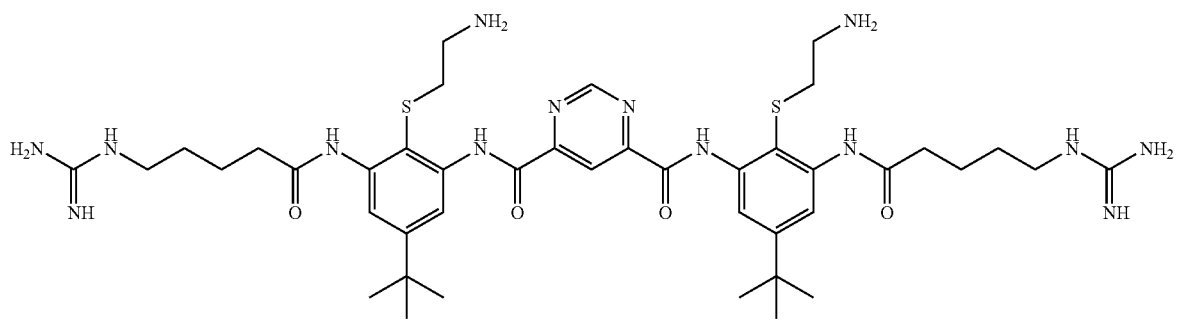

59
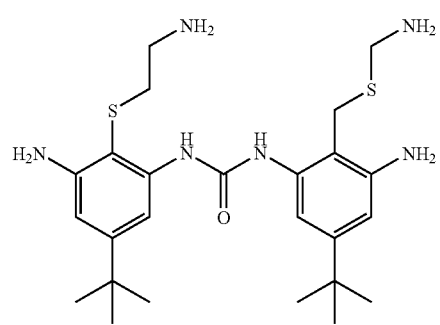
-continued
60
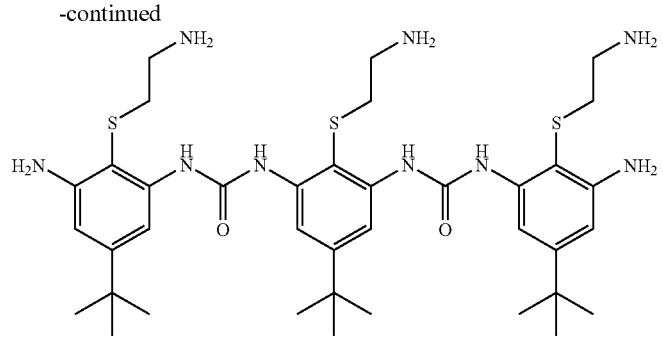
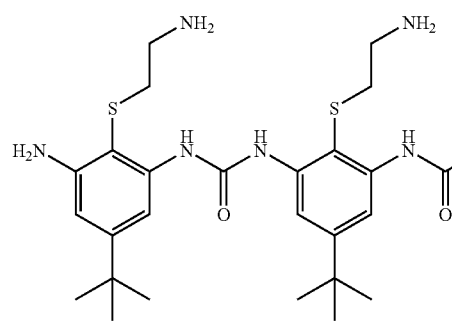
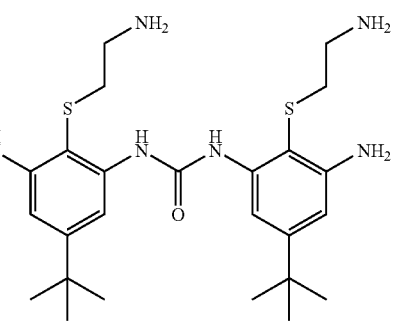
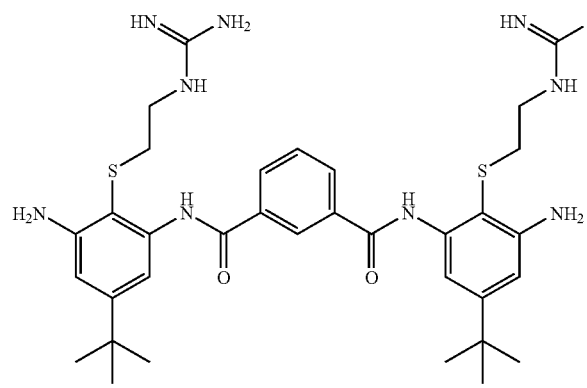
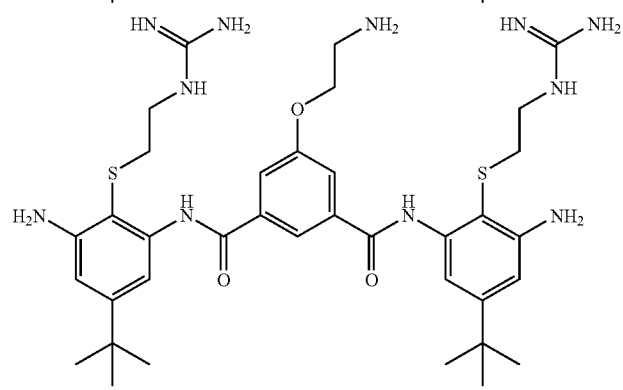
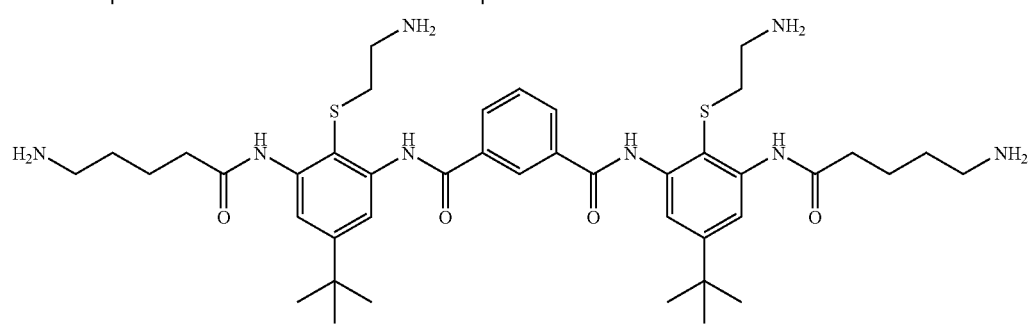

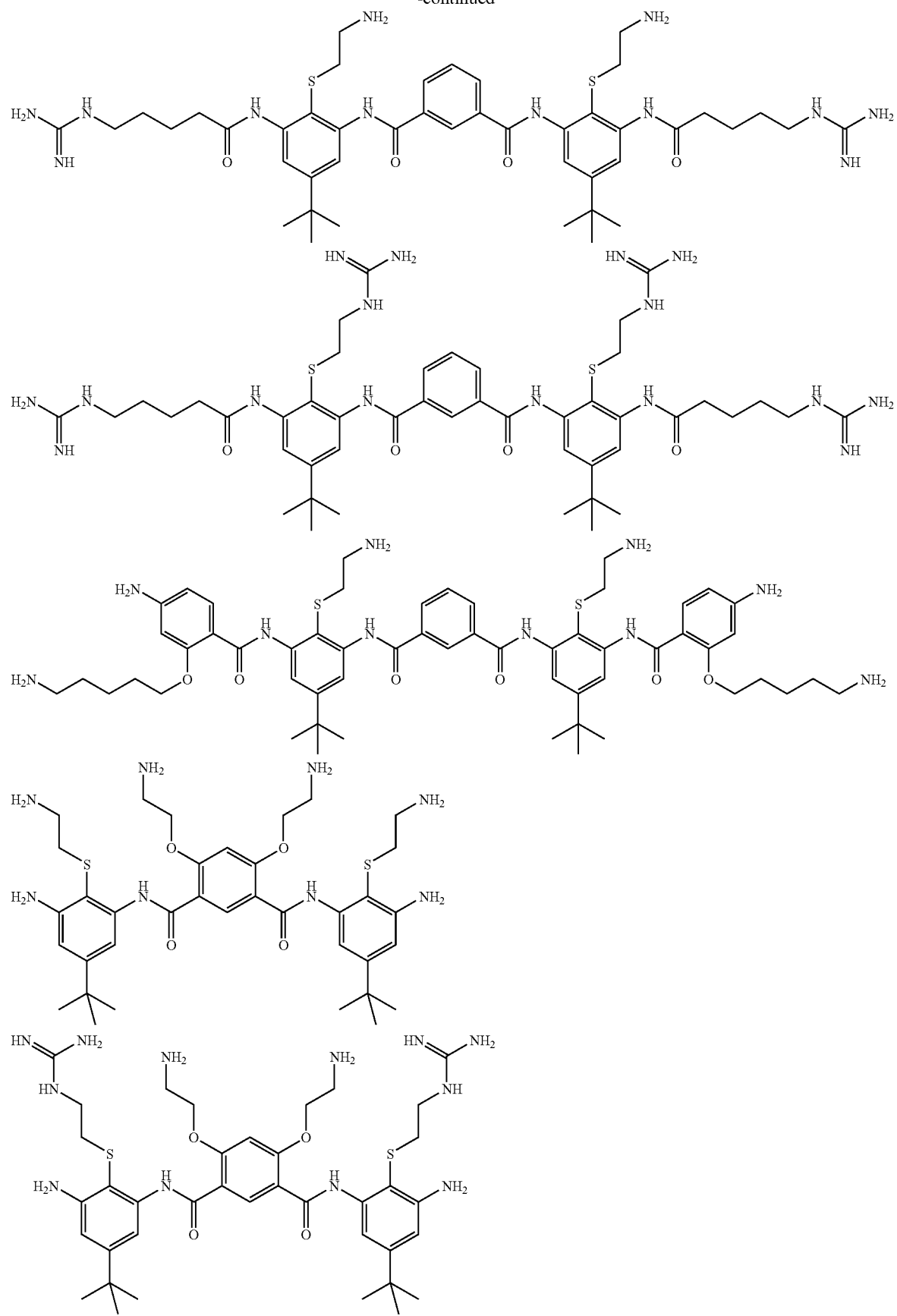

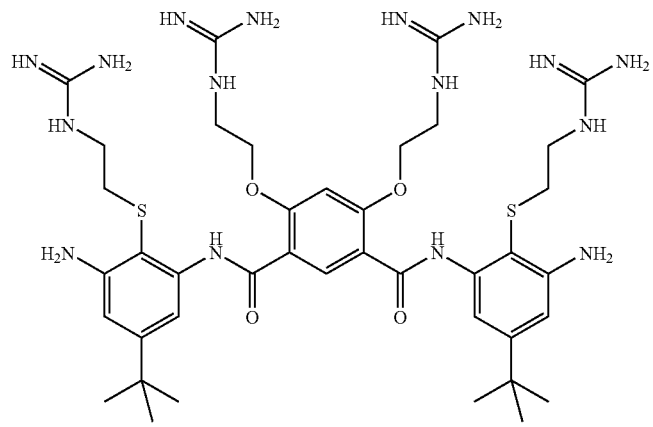
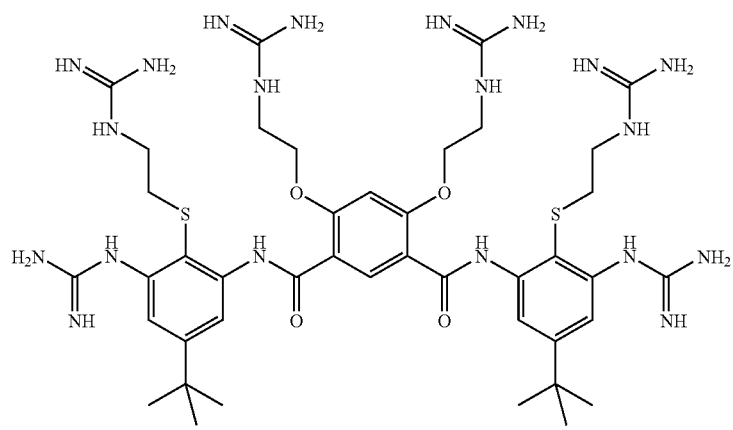
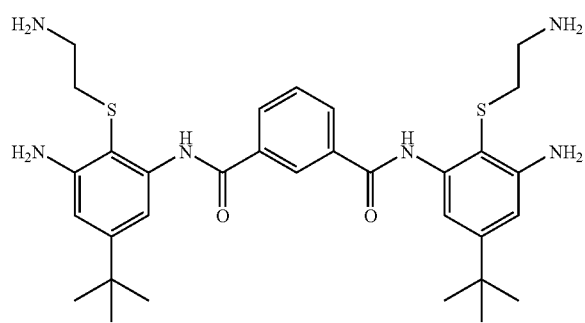
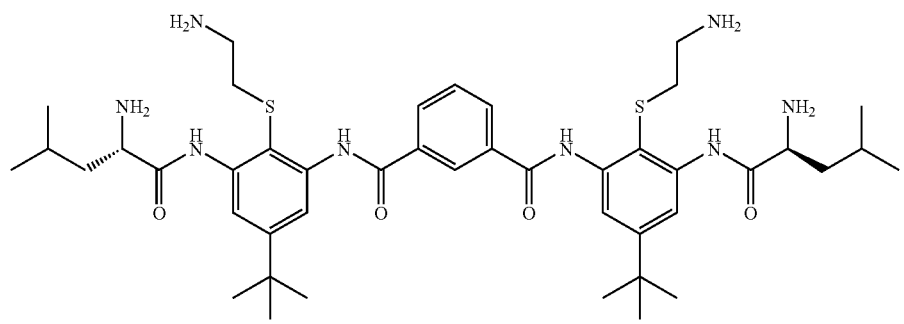

-continued
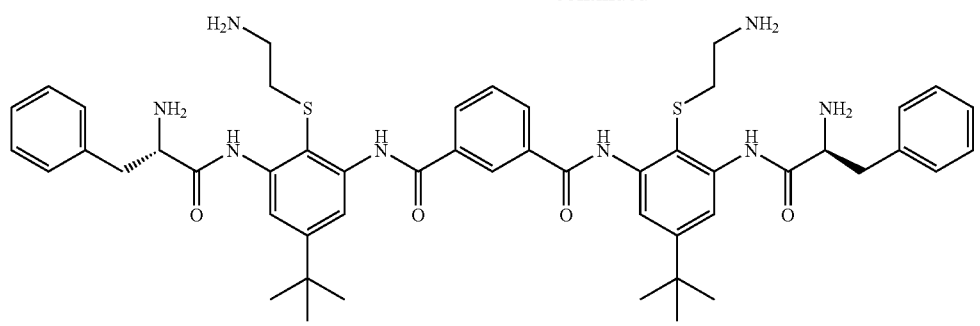
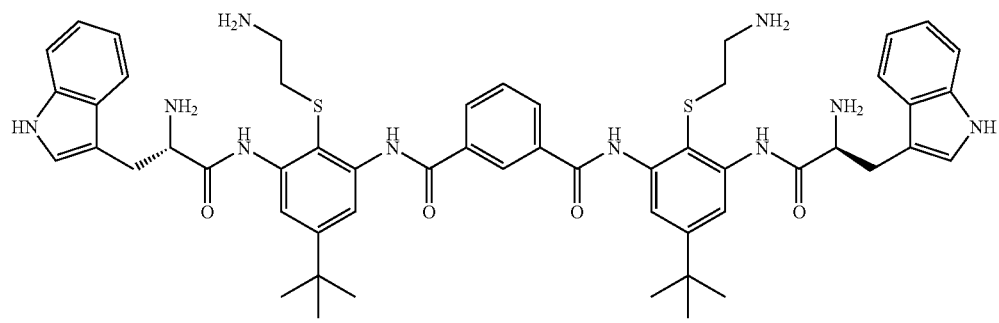
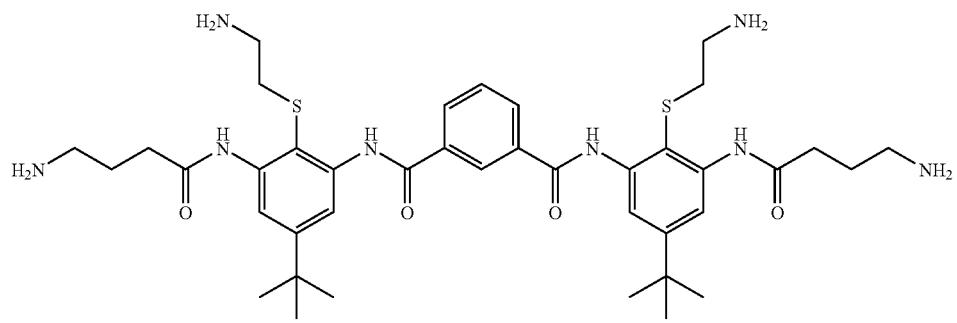
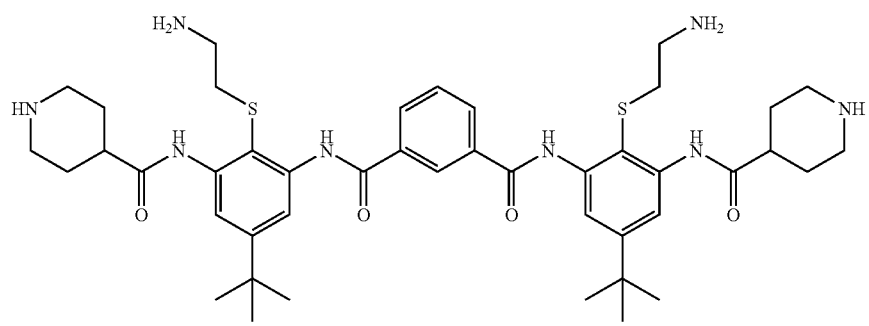
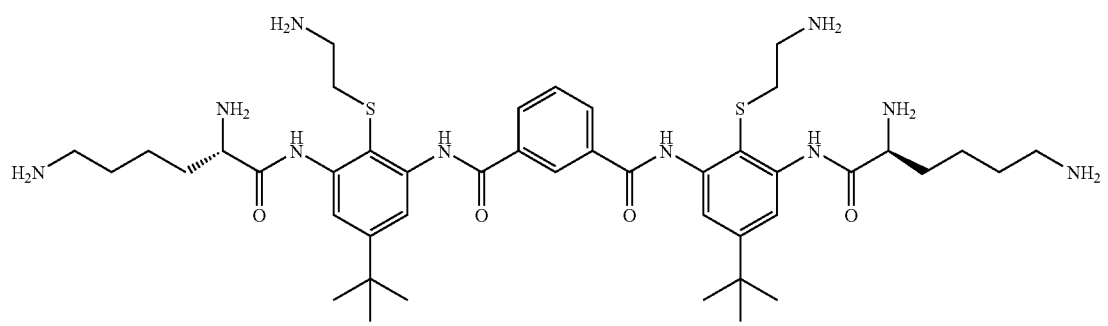

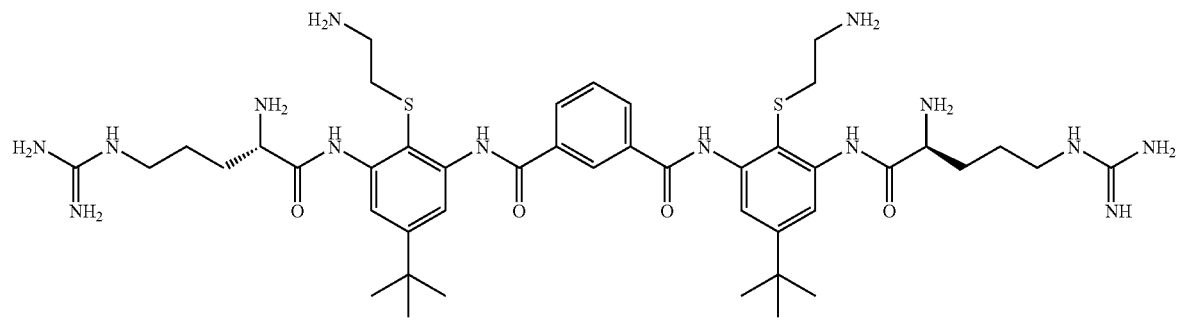
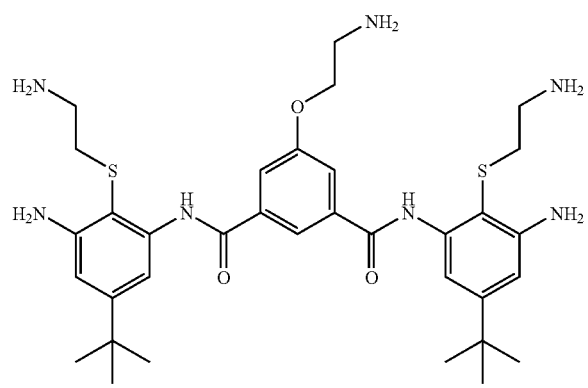
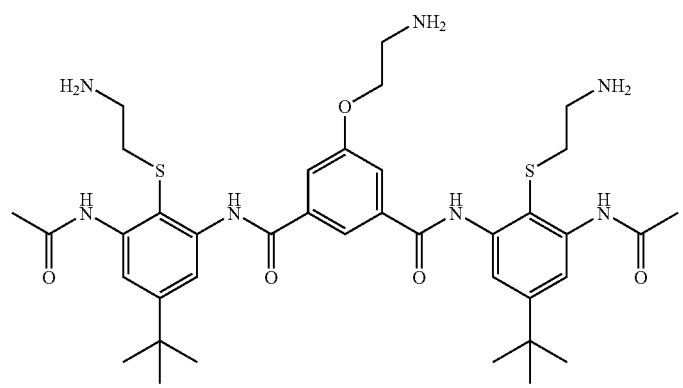
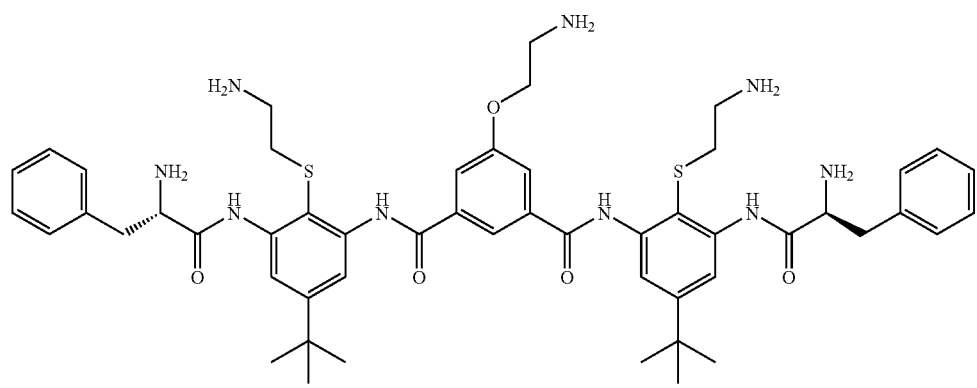

-continued
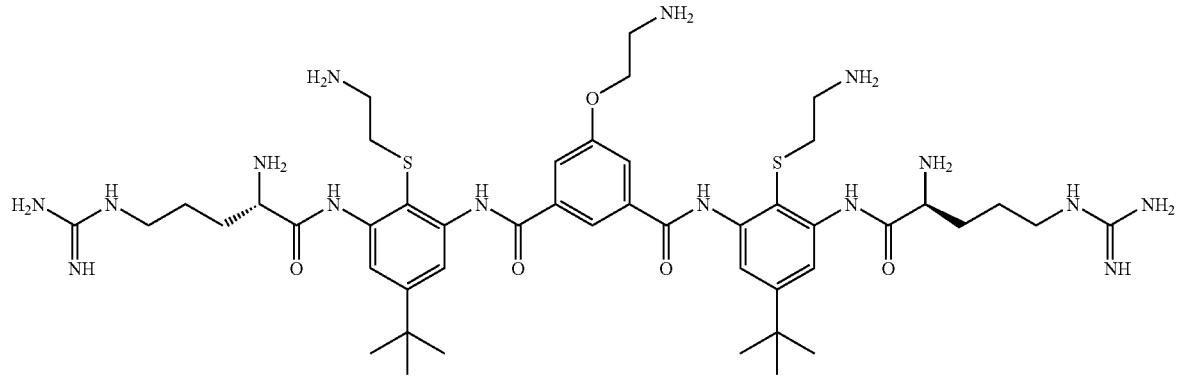
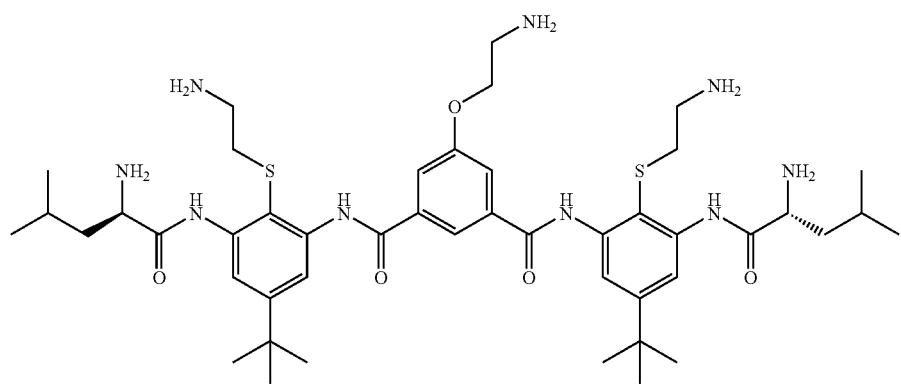
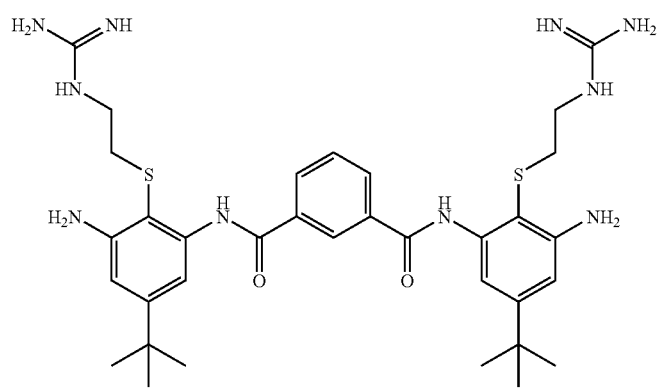
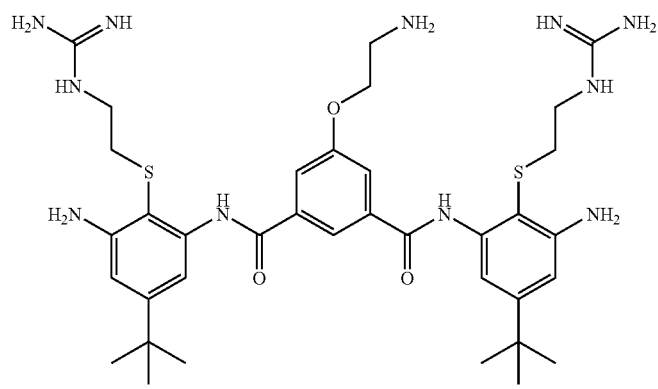

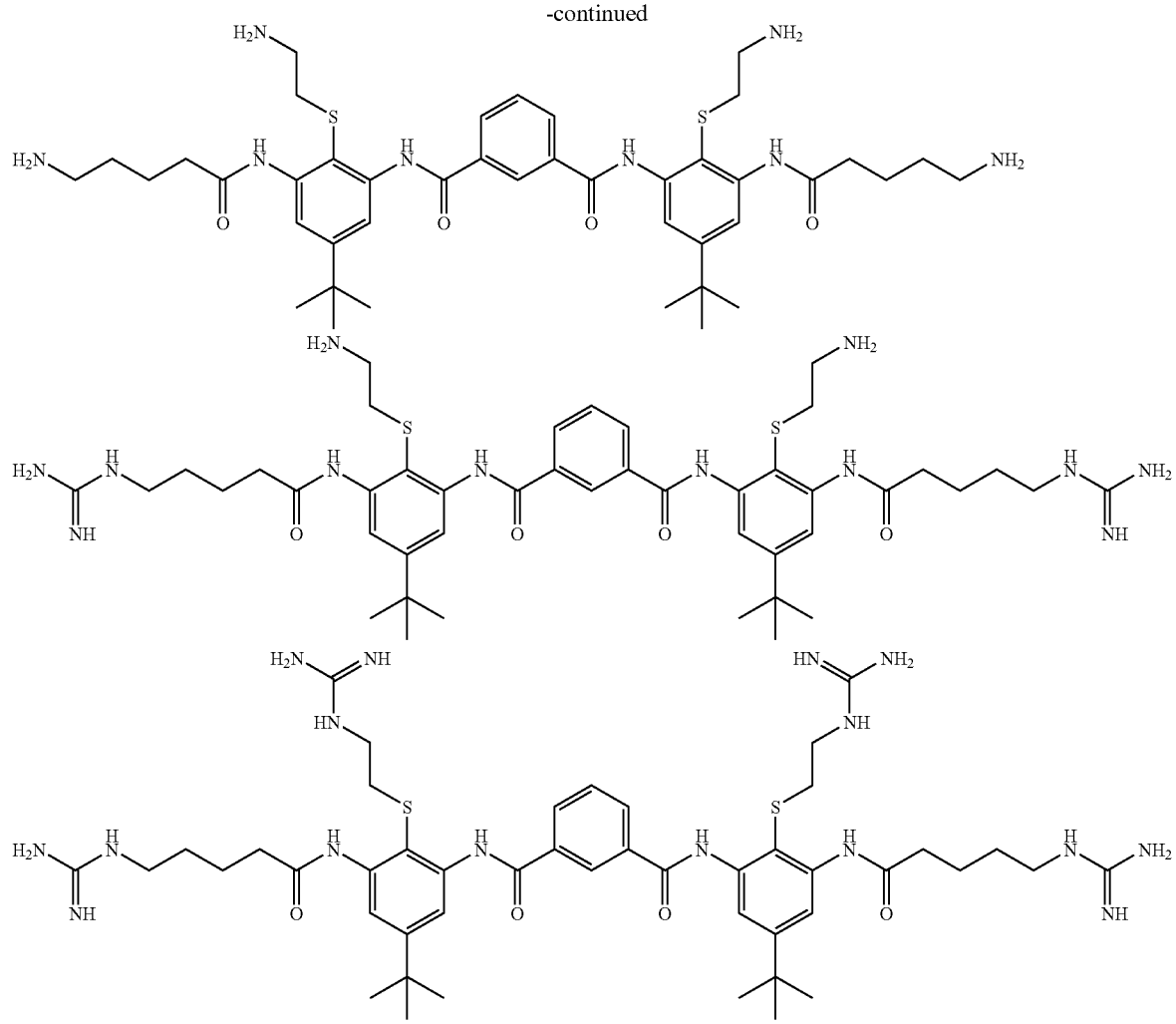

In some aspects of the invention, the polymers and oligomers of the present invention are derivatives referred to as prodrugs. The expression "prodrug" denotes a derivative of a known direct acting drug, which derivative has enhanced delivery characteristics and therapeutic value as compared to the drug, and is transformed into the active drug by an enzymatic or chemical process.

When any variable occurs more than one time in any constituent or in any of the polymers or oligomers recited for any of the general Formulae above (for example, Formulae I, II, or IV), its definition on each occurrence is independent of its definition at every other occurrence. Also, combinations of substituents and/or variables are permissible only if such combinations result in stable compounds.

It is understood that the present invention encompasses the use of stereoisomers, diastereomers and optical isomers of the polymers and oligomers of the present invention, as well as mixtures thereof, for treating microbial infections, killing or inhibiting the growth of a microorganism, and providing an antidote to low molecular weight heparin overdose in an animal. Additionally, it is understood that stereoisomers, diastereomers and optical isomers of the polymers and oligomers of the present invention, and mixtures thereof, are within the scope of the invention. By way of non-limiting example, the mixture may be a racemate or the mixture may comprise unequal proportions of one particular stereoisomer over the other. Additionally, the polymers and oligomers of the present invention may be provided as a substantially pure stereoisomers, diastereomers and optical isomers.

In another aspect of the invention, the polymers and oligomers of the present invention may be provided in the form of an acceptable salt (i.e., a pharmaceutically acceptable salt) for treating microbial infections, killing or inhibiting the growth of a microorganism, and providing an antidote to low molecular weight heparin overdose in an animal. Polymer or oligomer salts may be provided for pharmaceutical use, or as an intermediate in preparing the pharmaceutically desired form of the polymer or oligomer. One polymer or oligomer salt that may be considered to be acceptable is the hydrochloride acid addition salt. Hydrochloride acid addition salts are often acceptable salts when the pharmaceutically active agent has an amine group that can be protonated. Since a polymer or oligomer of the invention may be polyionic, such as a polyamine, the acceptable polymer or oligomer salt may be provided in the form of a poly(amine hydrochloride).

Polyamides and polyesters that are useful for the present invention can be prepared by typical condensation polymerization and addition polymerization processes. See, for example, G. Odian, *Principles of Polymerization*, John Wiley & Sons, Third Edition (1991), M. Steven, *Polymer*

*Chemistry*, Oxford University Press (1999). Most commonly the polyamides are prepared by (a) thermal dehydration of amine salts of carboxylic acids, (b) reaction of acid chlorides with amines and (c) aminolysis of esters. Methods (a) and (c) are of limited use in polymerizations of aniline derivatives which are generally prepared utilizing acid chlorides. The skilled chemist, however, will recognize that there are many alternative active acylating agents, for example phosphoryl anhydrides, active esters or azides, which may replace an acid chloride and which, depending of the particular polymer being prepared, may be superior to an acid chloride. The acid chloride route is probably the most versatile and baa been used extensively for the synthesis of aromatic polyamides

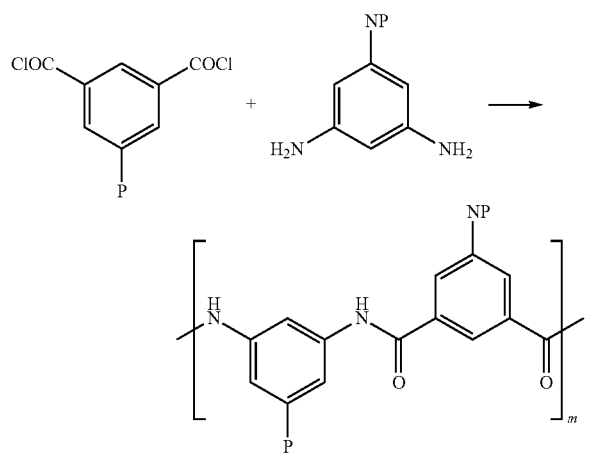

Homopolymers derived from substituted aminobenzoic acid derivatives can also prepared in a stepwise fashion. A stepwise process comprises coupling an N-protected amino acid to an amine (or hydroxy group) and subsequently removing the amine-protecting group and repeating the process. These techniques have been highly refined for synthesis of specific peptides, allow for the synthesis of specific sequences, and both solid-phase and solution techniques for peptide synthesis are directly applicable to the present invention. An alternative embodiment of the present invention is the corresponding polysulfonamides that can be prepared in analogous fashion by substituting sulfonyl chlorides for carboxylic acid chlorides.

The most common method for the preparation of polyureas is the reaction of diamines with diisocyanates. (Yamaguchi, I. et al., *Polym. Bull.* 44:247 (2000)) This exothermic reaction can be carried out by solution techniques or by interfacial techniques. One skilled in organic and polymer chemistry will appreciate that the diisocyanate can be replaced with a variety of other bis-acylating agents e.g., phosgene or N,N'-(diimidazolyl)carbonyl, with similar results. Polyurethanes are prepared by comparable techniques using a diisocyanate and a dialcohol or by reaction of a diamine with a bis-chloroformate.

The syntheses of appropriately substituted monomers are straightforward. Numerous pathways are available to incorporate polar and nonpolar side chains. Phenolic groups on the monomer can be alkylated. Alkylation of the commercially available phenol will be accomplished with standard Williamson ether synthesis for the non-polar side chain with ethyl bromide as the alkylating agent. Polar sidechains can be introduced with bifunctional alkylating agents such as BOC-NH(CH$_2$)$_2$Br. Alternatively, the phenol group can be alkylated to install the desired polar side chain function by employing the Mitsonobu reaction with BOC-NH(CH$_2$)$_2$—OH, triphenyl phosphine, and diethyl acetylenedicarboxylate. Standard conditions for reduction of the nitro groups and hydrolysis of the ester afford the amino acid. With the aniline and benzoic acid in hand, coupling can be effected under a variety of conditions. Alternatively, the hydroxy group of the (di)nitrophenol can be converted to a leaving group and a functionality introduced under nucleophilic aromatic substitution conditions (see FIG. 8, for example). Other potential scaffolds that can be prepared with similar sequences are methyl 2-nitro-4-hydroxybenzoate and methyl 2-hydroxy-4-nitrobenzoate.

The polymers and oligomers of the present invention are designed using computer-aided computational techniques, such as de novo design techniques, to embody the amphiphilic properties believed to be important for activity. In general, de novo design of oligomers is done by defining a three-dimensional framework of the backbone assembled from a repeating sequence of monomers using molecular dynamics and quantum force field calculations. Next, side groups are computationally grafted onto the backbone to maximize diversity and maintain drug-like properties. The best combinations of functional groups are then computationally selected to produce a cationic, amphiphilic structures. Representative compounds are synthesized from this selected library to verify structures and test their biological activity. Importantly, novel molecular dynamic and coarse grain modeling programs have been developed for this approach because existing force fields developed for biological molecules, such as peptides, were unreliable in these oligomer applications (Car, R., and Parrinello, M., *Phys. Rev. Lett.*, 55:2471-2474 (1985); Siepmann, J. I., and Frenkel, D., *Mol. Phys.* 75:59-70 (1992); Martin, M. G., and Siepmann, J. I., *J. Phys. Chem. B* 103:4508-4517 (1999); Brooks, B. R., et al., *J. Comp. Chem.* 4:187-217 (1983)). Several chemical structural series of oligomers and polymers have been prepared. See, for example, WO 02/100295 A2, the entire contents of which are incorporated herein by reference. The polymers and oligomers of the present invention are prepared in a similar manner (see below).

The general approach is as follows:

1) A polymer backbone that should fold into a given, well-defined three-dimensional structure is defined. Extensive theoretical studies are carried out to demonstrate that the polymers are able to adopt the desired secondary conformation. Model compounds (short oligomers) are prepared for structural analysis of folding by X-ray crystallography.

2) The backbone of the polymer is then decorated with appropriate functional groups to endow the oligomer or polymer with the desired facial amphiphilic character.

3) The desired oligomers and polymers are synthesized, and their biological activities are measured.

4) Biophysical studies are carried out to confirm that the polymers are binding to membranes in the desired conformation and that the mechanism of action is as expected from the design.

5) Based on the findings, structures are redesigned to optimize the potency and selectivity of the compounds, and steps 2-4 are re-iterated.

The goal of this approach is to capture the structural and biological properties of antimicrobial peptides within the framework of traditional polymers that can be prepared by inexpensive condensation reactions.

While the synthesis of a variety of polymer backbones is well understood, computer-aided computational techniques can provide valuable insight and guidance in the selection of potential antimicrobial polymers. The goal of these computations is to identify potential low energy conformations which have a geometrical repeat that matches a convenient sequence repeat of less than 6 monomer units. For example in α-amino acid oligomers, the geometrical repeat of the β-sheet is 2.0 residues. Once these repeating scaffolds are identified and the frequency of the repeat is calculated; polar and non-polar substituents can be incorporated into the monomers to confer amphiphilic properties into the molecule.

High level ab initio calculations are one technique which will identify accessible low energy conformations. Unfortunately, these techniques, while extremely powerful, are not practical with molecules the size of the present invention. Molecular Dynamics simulations provide an alternative that can be adapted efficiently to molecules envisioned in the present invention. Key elements in determining conformational energies are strong electrostatic interactions (i.e., intramolecular hydrogen bonding) between adjacent or more distant monomers and rigidification caused by the backbone torsions or by bulky functional groups. In order to simulate these interactions in molecular mechanics calculations the empirical parameters, i.e., a force field, must be determined for representative polymer backbones. Density functional theory (DFT) can be used to carry out ab initio calculations on small model compounds that share the basic structural connectivity of the polymer backbones and which will generate required torsional potentials. The procedure to carry out these computations is:

1. Select simple model compounds that share similar torsional patterns with the target polymer backbones.
2. For each compound, perform a full geometric optimization at the BLYP/6-31G(d) level of theory (multiple initial configurations ensure the global minimum is obtained).
3. Calculate the single-point energy at the most stable geometry obtained in step 2 above, using B3LYP/6-311G++(dp) or plane wave CPMD.
4. Constrain a relevant torsion to a set angle and repeat steps 2 and 3.
5. Repeat step 4 for several angles; the torsional energy is obtained by subtracting the non-bonded interactions.
6. Fit energies versus torsion angle to a cosine series whose coefficients are the force field parameters.

Molecular dynamic and coarse grain modeling programs can be used for the above design approach. See, for example, U.S. patent application Ser. No. 10/446,171, filed May 28, 2003, and U.S. patent application Ser. No. 10/459,698, filed Jun. 12, 2003. The contents of U.S. application Ser. No. 10/446,171 and U.S. application Ser. No. 10/459,698 are fully incorporated by reference herein.

After verifying the suitability of the force field by comparing computed predictions of the structure and thermodynamic properties to molecules that have similar torsional patterns and for which experimental data are available, the fitted torsions are then combined with bond stretching, bending, one-four, van der Waals, and electrostatic potentials borrowed from the CHARMM (Brooks, B. R., et al., *J. Comp. Chem.* 4:187-217 (1983)) and TraPPE (Martin, M. G., and Siepmann, J. I., *J. Phys. Chem. B* 103:4508-4517 (1999); Wick, C. D., et al., *J. Phys. Chem. B* 104:3093-3104 (2000)) molecular dynamics force fields. To identify conformations that can adopt periodic folding patterns with polar groups and apolar groups lined up on the opposite sides, initial structures can be obtained with the Gaussian package (Frisch, M., et al., *Gaussian* 98 (revision A.7) Gaussian Inc., Pittsburgh, Pa. 1998). Then, the parallelized plane-wave Car-Parrinello CP-MD (Car, R., and Parrinello, M., *Phys. Rev. Lett.* 55:2471-2474 (1985)) program, (cf. Röthlisberger, U., et al., *J. Chem. Phys.* 3692-3700 (1996)) is used to obtain energies at the minimum and constrained geometries. The conformations of the polymers without side-chains can be investigated in the gas phase. Both MD and MC methods will be used to sample the conformations. The former is useful for global motions of the polymer. With biasing techniques (Siepmann, J. I., and Frenkel, D., *Mol. Phys.* 75:59-70 (1992); Martin, M. G., and Siepmann, J. I., *J. Phys. Chem. B* 103:4508-4517 (1999); Vlugt, T. J. H., et al. *Mol. Phys.* 94:727-733 (1998)) the latter allows efficient sampling for polymers with multiple local minimum configurations that are separated by relatively large barriers.

The potential conformations are examined for positions to attach pendant groups that will impart amphiphilic character to the secondary structure, Polymers selected from the gas phase studies with suitable backbone conformations and with side-chains at the optimal positions to introduce amphiphilicity will be further evaluated in a model interfacial system, n-hexane/water, chosen because it is simple and cheap for calculations while it mimics well the lipid/water bilayer environment. Polymer secondary structures that require interpolymer interactions can be identified by repeating the above-mentioned calculations using a periodically repeated series of unit cells of various symmetries (so called variable cell molecular dynamics or Monte Carlo technique) with or without solvent. The results of these calculations will guide the selection of candidates for synthesis.

An embodiment of the present is a computation technique to identify polymer backbones which can produce facially amphiphilic polymers by:

(1) selecting a polymer backbones or scaffolds suitable for regiospecific introduction of polar (P) and nonpolar (NP) groups;
(2) determining parameters for molecular mechanics force field utilizing ab initio quantum mechanical calculations;
(3) calculating energetically accessible conformations of the backbone using molecular dynamics or molecular mechanics calculations;
(4) identifying energetically accessible conformations of the backbone wherein the periodicity of a geometrical/conformational repeat matches a sequence repeat;
(5) synthesizing monomers with polar and nonpolar substituents;
(6) synthesizing an antimicrobial polymer containing the monomers by solution or solid-phase synthesis.

An example of the design, synthesis, and testing of arylamide polymers and oligomers, a subgroup of polymers and oligomers disclosed in the present invention, is presented in Tew, G. N., et al., *Proc. Natl. Acad. Sci. USA* 99:5110-5114 (2002), the contents of which are fully incorporated by reference herein (Tew, G. N., et al., *Proc. Natl. Acad. Sci. USA* 99:5110-5114 (2002)). See also Example 12 below.

Oligomers of the present invention are synthesized by solid-phase synthetic procedures well know to those of skill in the art. See, for example, Tew et al. (Tew, G. N., et al., *Proc. Natl. Acad. Sci. USA* 99:5110-5114 (2002)). See also Barany, G., et al., *Int. J. Pept. Prot. Res.* 30:705-739 (1987); *Solid-phase Synthesis: A Practical Guide*, Kates, S. A., and Albericio, F., eds., Marcel Dekker, New York (2000); and Dörwald, F. Z., *Organic Synthesis on Solid Phase: Supports, Linkers, Reactions*, 2nd Ed., Wiley-VCH, Weinheim (2002).

The polymers and oligomers of the invention are synthesized in a range of molecular weights. Molecular weights for the polymers and oligomers range from about 300 Daltons to about 1,000,000 Daltons. Preferred polymers of the present invention have average molecular weights that range from about 400 Daltons to about 120,000 Daltons (about 2 to about 500 monomer units). Especially preferred polymers have average weights that range from about 1,000 Daltons to about 25,000 Daltons (about 5 to about 100 monomer units). Oligomers of the present invention have molecular weights that range from about 300 Daltons to about 6,000 Daltons (about 2 to about 25 monomer units), with preferred oligomers having molecular weights that range from about 300 Daltons to about 2,500 Daltons (about 2 to about 10 monomer units).

One of skill in the art will recognize that the synthetic processes for producing polymers and oligomers of the invention can be modified to produce different ranges in molecular weight. The polymer chemist will readily appreciate that the chain length of polymers can be varied by techniques know in the polymer art. Advancements in solid-phase and solution phase synthesis of amino acid oligomers have made available techniques to prepare homogeneous oligomers with defined sequence and size and these techniques can be adapted to the present invention.

The polymers and oligomers of the invention are tested for antimicrobial activity by methods well known to those of skill in the art. See, for example, Tew, G. N., et al. (Tew, G. N., et al., *Proc. Natl. Acad. Sci. USA* 99:5110-5114 (2002)). Antimicrobial testing can be carried out using the micro-broth dilution technique with *E. coli*, or, if desired, another bacterial strain, such as, for example, *B. subtilis, P. aeruginosa, K. pneumoniae, S. typhimurium, N. gonorrhoeae, B. megaterium, S. aureus, E. feacalis, M. luteus,* or *S. pyogenes*. Other specific bacterial strains that can be screened include ampicillin and streptomycin-resistant *E. coli* D31, vancomycin-resistant *Enterococcus faecium* A436, and methicillin-resistant *S. aureus* 5332. Any polymer or oligomer found to be active can be purified to homogeneity and re-tested to obtain an accurate $IC_{50}$. Secondary screens include *Klebsiella pneumoniae* Kpl, and *Salmonella typhimurium* S5, and *Pseudomonus aeruginosa* 10. Traditionally, the micro-broth dilution technique only evaluates a single data point between 18-24 hours; however, the measurements can be extended to 24 hr to monitor cell growth through the entire growth phase. These experiments are performed in LB medium (which is a rich medium typically used to grow cells for protein expression) and represent a critical initial screen for activity. Since salt concentration, proteins, and other solutes can affect the activities of antibiotics, materials that show no activity in rich medium can be re-tested in minimal medium (M9) to determine if rich medium is limiting activity. No relationship between the media and the activity has been observed which is consistent with the mode of action this is believed to be through general membrane disruption.

Standard assays can be performed to determine whether a polymer or oligomer is bacteriostatic or bactericidal. Such assays are well known to those of skill in the art and are performed, for example, by incubating *E. coli* cells overnight with the polymer or oligomer being tested, and then plating the mixture on agar plates according to procedures well known to those of skill in the art. See, for example, Tew, G. N., et al. (Tew, G. N., et al., *Proc. Natl. Acad. Sci. USA* 99:5110-5114 (2002)), and Liu, D., and DeGrado, W. F. (Liu, D., and DeGrado, W. F., *J. Amer. Chem. Soc.* 123:7553-7559 (2001)).

Assays for determining the antiviral and antifungal activity of polymers and oligomer are also well known to those of skill in the art. For examples of antiviral assays, see Belaid et al., (Belaid, A., et al., *J. Med. Virol.* 66:229-234 (2002)), Egal et al., (Egal, M., et al., *Int. J. Antimicrob. Agents* 13:57-60 (1999)), Andersen et al., (Andersen, J. H., et al., *Antiviral Rs.* 51:141-149 (2001)), and Bastian, A., and Schafer, H. (Bastian, A., and Schafer, H., *Regul. Pept.* 15:157-161 (2001)). See also Cole, A. M., et al., *Proc. Natl. Acad. Sci USA* 99:1813-1818 (2002). For examples of antifungal assays, see Edwards, J. R., et al., *Antimicrobial Agents Chemotherapy* 33:215-222 (1989), and Broekaert, W. F., et al., *FEMS Microbiol. Lett.* 69:55-60 (1990). The entire contents of each of these documents is fully incorporated herein by reference.

Assays for measuring the cytotoxic selectivity for polymers and oligomers toward bacteria and eukaryotic cells are well known to those of skill in the art. For example, cytotoxic selectivity can be assessed by determining the hemolytic activity of the polymer or oligomer. Hemolytic activity assays are performed by measuring the degree of hemolysis of human erythrocytes following incubation in the presence of the polymer or oligomer and determining HC50 values. HC50 values represent the concentration of compound that results in 50% hemoglobin release. See, for example, Liu, D., and DeGrado, W. F. (Liu, D., and DeGrado, W. F., *J. Amer. Chem. Soc.* 123:7553-7559 (2001)), and references cited therein. See also Javadpour, M. M., et al., *J. Med. Chem.* 39:3107-3113 (1996).

Vesicle leakage assays can also be used to confirm that a polymer or oligomer interact with and disrupt phospholipid bilayers, a model for cellular membranes. Vesicle leakage assays are well known to those of skill, in the art. See, for example, Tew, G. N., et al. (Tew, G. N., et al., *Proc. Natl. Acad. Sci. USA* 99:5110-5114 (2002)), and references cited therein.

Assays for determining the heparin-neutralizing activity of a polymer or oligomer are well known to those of skill in the art and are commonly performed using either an activated partial thromboplastin time assay (for example, by measuring the delay in clotting times for activated plasma in the presence of a fixed concentration of heparin, in the absence and presence of a test compound) or a Factor X assay. See, for example, Kandrotas (Kandrotas, R. J., *Clin. Pharmacokinet.* 22:359-374 (1992)), Wakefield et al. (Wakefield, T. W., et al., *J. Surg. Res.* 63:280-286 (1996)), and Diness, V., and Østergaard, P. B. (Diness, V. O., and Østergaard, P. B., *Thromb. Haemost.* 56:318-322 (1986)), and references cited therein. See also Wong, P. C., et al., *J. Pharm. Exp. Therap.* 292:351-357 (2000), and Ryn-McKenna, J. V., et al., *Thromb. Haemost.* 63:271-274 (1990).

The polymers and oligomers of the present invention can be used to kill or inhibit the growth of any of the following microbes or mixtures of the following microbes, or, alternatively, can be administered to treat local and/or systemic microbial infections or illnesses caused by the following microbes or mixtures of the following microbes: Gram-positive cocci, for example Staphylococci (*Staph. aureus, Staph. epidermidis*) and Streptococci (*Strept. agalactiae, Strept. faecalis, Strept. pneumoniae, Strept. pyogenes*); Gram-negative cocci (*Neisseria gonorrhoeae* and *Yersinia pestis*) and Gram-negative rods such as Enterobacteriaceae, for example *Escherichia coli, Hamophilus influenzae, Citrobacter* (*Citrob. freundii, Citrob. divernis*), *Salmonella* and *Shigella*, and *Francisella* (*Francisella tularensis*); Gram-positive rods such as *Bacillus* (*Bacillus anthracis, Bacillus thuringenesis*); furthermore *Klebsiella* (*Klebs. pneumoniae, Klebs. oxytoca*), *Enterobacter* (*Ent. aerogenes, Ent. agglomerans*), *Hafnia, Serratia* (*Serr. marcescens*), *Proteus* (*Pr. mirabilis, Pr. rettgeri, Pr. vulgaris*), *Providencia, Yersinia*, and the genus *Acinetobacter*. Furthermore, the anti-microbial spectrum of the polymers and oligomers of the invention covers the genus *Pseudomonas* (*Ps. aeruginosa, Ps. maltophilia*) and strictly anaerobic bacteria such as, for example, *Bacteroides fragilis*, representatives of the genus *Peptococcus, Peptostreptococcus* and the genus *Clostridium*; furthermore Mycoplasmas (*M. pneumoniae, M. hominis, Ureaplasma urealyticum*) as well as *Mycobacteria*, for example *Mycobacterium tuberculosis*. This list of microbes is purely illustrative and is in no way to be interpreted as restrictive.

Examples of microbial infections or illness that can be treated by administration of the polymers and oligomers of the invention include, but are not limited to, microbial infections or illnesses in humans such as, for example, otitis, pharyngitis, pneumonia, peritonitis, pyelonephritis, cystitis, endocarditis, systemic infections, bronchitis (acute and chronic), septic infections, illnesses of the upper airways, diffuse panbronchiolitis, pulmonary emphysema, dysentery, enteritis, liver abscesses, urethritis, prostatitis, epididymitis, gastrointestinal infections, bone and joint infections, cystic fibrosis, skin infections, postoperative wound infections, abscesses, phlegmon, wound infections, infected burns, burns, infections in the mouth, infections after dental operations, osteomyelitis, septic arthritis, cholecystitis, peritonitis with appendicitis, cholangitis, intraabdominal abscesses, pancreatitis, sinusitis, mastoiditis, mastitis, tonsileitis, typhoid, meningitis and infections of the nervous system, salpingitis, endometritis, genital infections, pelveoperitonitis and eye infections.

Examples of viral infections that can be treated by administration of the polymers and oligomers of the invention include, but are not limited to, viral infections caused by human immunodeficiency virus (HIV-1, HIV-2), hepatitis virus (e.g., hepatitis A, hepatitis B, hepatitis C, hepatitis D, and hepatitis E viruses), herpesviruses (e.g., herpes simplex virus types 1 and 2, varicella-zoster virus, cytomegalovirus, Epstein Barr virus, and human herpes viruses types 6, 7, and 8), influenza virus, respiratory syncytial virus (RSV), vaccinia virus, and adenoviruses. This list is purely illustrative and is in no way to be interpreted as restrictive.

Examples of fungal infections or illnesses that can be treated by administration of the polymers and oligomers of the present invention include, but are not limited to, fungal infections caused by Chytridiomycetes, Hyphochrytridiomycetes, Plasmodiophoromycetes, Oomycetes, Zygomycetes, Ascomycetes, and Basidiomycetes. Fungal infections which can be inhibited or treated with compositions of the polymers and oligomers provided herein include, but are not limited to: Candidiasis, including, but not limited to, onchomycosis, chronic mucocutaneous candidiasis, oral candidiasis, epiglottistis, esophagitis, gastrointestinal infections, genitourinary infections, for example, caused by any *Candida* species, including, but not limited to, *Candida albicans, Candida tropicalis, Candida (Torulopsis) glabrata, Candida parapsilosis, Candida lusitaneae, Candida rugosa* and *Candida pseudotropicalis*; Aspergillosis, including, but not limited to, granulocytopenia caused, for example, by, *Aspergillus* spp. Including, but not limited, to *Aspergillus fumigatus, Aspergillus favus, Aspergillus niger* and *Aspergillus terreus*; Zygomycosis, including, but not limited to, pulmonary, sinus and rhinocerebral infections caused by, for example, zygomycetes such as *Mucor, Rhizopus* spp., *Absidia, Rhizomucor, Cunningamella, Saksenaea, Basidobolus* and *Conidobolus*; Cryptococcosis, including, but not limited to, infections of the central nervous system, e.g., meningitis, and infections of the respiratory tract caused by, for example, *Cryptococcus neoformans*; Trichosporonosis caused by, for example, *Trichosporon beigelii*; Pseudallescheriasis caused by, for example, *Pseudallescheria boydii; Fusarium* infection caused by, for example, *Fusarium* such as *Fusarium solani, Fusarium moniliforme* and *Fusarium proliferartum*; and other infections such as those caused by, for example, *Penicillium* spp. (generalized subcutaneous abscesses), *Trichophyton* spp., for example, *Trichophyton mentagrophytes* and *Trichophyton* rubrum, *Stachybotrys* spp., for example, *S. chartarum, Drechslera, Bipolaris, Exserohilum* spp., *Paecilomyces lilacinum, Exophila jeanselmei* (cutaneous nodules), *Malassezia furfur* (folliculitis), *Alternaria* (cutaneous nodular lesions), *Aureobasidium pullulans* (splenic and disseminated infection), *Rhodotorula* spp. (disseminated infection), *Chaetomium* spp. (empyema), *Torulopsis* candida (fungernia), *Curvularia* spp. (nasopharnygeal infection), *Cunninghamella* spp. (pneumonia), *H. Capsulatum, B. dermatitidis, Coccidioides immitis, Sporothrix schenckii* and *Paracoccidioides brasiliensis, Geotrichum candidum* (disseminated infection). The polymers and oligomers of the present invention can also be used to kill or inhibit the growth of any of the fungi listed above. This list is purely illustrative and is in no way to be interpreted as restrictive.

The polymer or oligomer can be administered to a human subject. Thus, in some aspects of the invention, the polymer or oligomer is administered to a human.

The methods disclosed above also have veterinary applications and can be used to treat a wide variety of non-human vertebrates. Thus, in other aspects of the invention, the polymer or oligomer is administered in the above methods to non-human vertebrates, such as wild, domestic, or farm animals, including, but not limited to, cattle, sheep, goats, pigs, dogs, cats, and poultry such as chicken, turkeys, quail, pigeons, ornamental birds and the like.

The following are examples of microbial infections in non-human vertebrates that can be treated by administering a polymer or oligomer of the invention: Pig: coli diarrhoea, enterotoxaemia, sepsis, dysentery, salmonellosis, metritis-mastitis-agalactiae syndrome, mastitis; ruminants (cattle, sheep, goat): diarrhoea, sepsis, bronchopneumonia, salmonellosis, pasteurellosis, mycoplasmosis, genital infections; horse: bronchopneumonias, joint ill, puerperal and post-puerperal infections, salmonellosis; dog and cat: bronchopneumonia, diarrhoea, dermatitis, otitis, urinary tract infections, prostatitis; poultry (chicken, turkey, quail, pigeon, ornamental birds and others): mycoplasmosis, *E. coli* infections, chronic respiratory tract illnesses, salmonellosis, pasteurellosis, psittacosis. This list is purely illustrative and is in no way to be interpreted as restrictive.

For those applications in which the polymers and oligomers of the present invention are used as disinfectants and/or preservatives, e.g., in cleansers, polishers, paints, sprays, soaps, or detergents, the polymers and oligomers are incorporated into the cleanser, polisher, paint, spray, soap, or detergent formulation, optionally in combination with suitable solvent(s), carrier(s), thickeners, pigments, fragrances, deodorizers, emulsifiers, surfactants, wetting agents, waxes, or oils. If the polymer or oligomer is to be used as a preservative in a foodstuff, the polymer or oligomer can be added to the foodstuff as part of any comestible formulation that can also include a suitable medium or carrier for convenient mixing or dissolving into the foodstuff. The amount of polymer or oligomer added to or incorporated into the cleanser, polisher, soap, etc. formulation or into the foodstuff will be an amount sufficient to kill or inhibit the growth of the desired microbial species and can easily be determined by one of skill in the art.

For those applications in which the polymers and oligomers of the invention are used as surface-mediated microbicides, e.g., in some applications as disinfectants and as preservatives (e.g., including, but not limited to, medical devices such as catheters, bandages, and implanted devices, or food containers and food handling implements), the polymers and oligomers may be attached to, applied on or incorporated into almost any substrate including, but not limited to, woods, paper, synthetic polymers (plastics), natural and synthetic fibers, natural and synthetic rubbers, cloth, glasses and ceramics by appropriate methods, including covalent bonding, ionic interaction, coulombic interaction, hydrogen bonding or cross-linking.

Procedures for attaching, applying, and incorporating the polymers and oligomers of the invention into appropriate materials and substrates are disclosed in WIPO Publ. No. WO 02/100295, the contents of which are fully incorporated herein by reference. Appropriate substrates and materials are also disclosed in WO 02/100295.

The following examples are illustrative, but not limiting, of the methods and compositions of the present invention. Other suitable modifications and adaptations of the variety of conditions and parameters normally encountered and obvious to those skilled in the art are within the spirit and scope of the invention.

The polymers and oligomers of the present invention are administered in the conventional manner by any route where they are active. Administration can be systemic, topical, or oral. For example, administration can be, but is not limited to, parenteral, subcutaneous, intravenous, intramuscular, intraperitoneal, transdermal, oral, buccal, or ocular routes, or intravaginally, by inhalation, by depot injections, or by implants. Thus, modes of administration for the polymers and oligomers (either alone or in combination with other pharmaceuticals) can be, but are not limited to, sublingual, injectable (including short-acting, depot, implant and pellet forms injected subcutaneously or intramuscularly), or by use of vaginal creams, suppositories, pessaries, vaginal rings, rectal suppositories, intrauterine devices, and transdermal forms such as patches and creams.

Specific modes of administration will depend on the indication (e.g., whether the polymer or oligomer is administered to treat a microbial infection, or to provide an antidote for hemorrhagic conditions associated with heparin therapy). The mode of administration can depend on the pathogen or microbe to be targeted. The selection of the specific route of administration and the dose regimen is to be adjusted or titrated by the clinician according to methods known to the clinician in order to obtain the optimal clinical response. The amount of polymer or oligomer to be administered is that amount which is therapeutically effective. The dosage to be administered will depend on the characteristics of the subject being treated, e.g., the particular animal treated, age, weight, health, types of concurrent treatment, if any, and frequency of treatments, and can be easily determined by one of skill in the art (e.g., by the clinician).

The pharmaceutical formulations containing the polymers and oligomers and a suitable carrier can be solid dosage forms which include, but are not limited to, tablets, capsules, cachets, pellets, pills, powders and granules; topical dosage forms which include, but are not limited to, solutions, powders, fluid emulsions, fluid suspensions, semi-solids, ointments, pastes, creams, gels and jellies, and foams; and parenteral dosage forms which include, but are not limited to, solutions, suspensions, emulsions, and dry powder; comprising an effective amount of a polymer or oligomer as taught in this invention. It is also known in the art that the active ingredients can be contained in such formulations with pharmaceutically acceptable diluents, fillers, disintegrants, binders, lubricants, surfactants, hydrophobic vehicles, water soluble vehicles, emulsifiers, buffers, humectants, moisturizers, solubilizers, preservatives and the like. The means and methods for administration are known in the art and an artisan can refer to various pharmacologic references for guidance. For example, *Modern Pharmaceutics*, Banker & Rhodes, Marcel Dekker, Inc. (1979); and *Goodman & Gilman's The Pharmaceutical Basis of Therapeutics*, 6th Edition, MacMillan Publishing Co., New York (1980) can be consulted.

The polymers and oligomers can be formulated for parenteral administration by injection, e.g., by bolus injection or continuous infusion. The polymers and oligomers can be administered by continuous infusion subcutaneously over a period of about 15 minutes to about 24 hours. Formulations for injection can be presented in unit dosage form, e.g., in ampoules or in multi-dose containers, with an added preservative. The compositions can take such forms as suspensions, solutions or emulsions in oily or aqueous vehicles, and can contain formulatory agents such as suspending, stabilizing and/or dispersing agents.

For oral administration, the polymers and oligomers can be formulated readily by combining these compounds with pharmaceutically acceptable carriers well known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained by adding a solid excipient, optionally grinding the resulting mixture, and processing the mixture of granules, after adding suitable auxiliaries, if desired, to obtain tablets or dragee cores. Suitable excipients include, but are not limited to, fillers such as sugars, including, but not limited to, lactose, sucrose, mannitol, and sorbitol; cellulose preparations such as, but not limited to, maize starch, wheat starch, rice starch, potato starch, gelatin, gum tragacanth, methyl cellulose, hydroxypropylmethyl-cellulose, sodium carboxymethylcellulose, and polyvinylpyrrolidone (PVP). If desired, disintegrating agents can be added, such as, but not limited to, the cross-linked polyvinyl pyrrolidone, agar, or alginic acid or a salt thereof such as sodium alginate.

Dragee cores can be provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments can be added to the tablets or dragee coatings for identification or to characterize different combinations of active compound doses.

Pharmaceutical preparations which can be used orally include, but are not limited to, push-fit capsules made of gelatin, as well as soft, sealed capsules made of gelatin and a plasticizer, such as glycerol or sorbitol. The push-fit capsules can contain the active ingredients in admixture with filler such as, e.g., lactose, binders such as, e.g., starches, and/or lubricants such as, e.g., talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

For buccal administration, the polymer and oligomer compositions can take the form of, e.g., tablets or lozenges formulated in a conventional manner.

For administration by inhalation, the polymers and oligomers for use according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The polymers and oligomers can also be formulated in rectal compositions such as suppositories or retention enemas, e.g., containing conventional suppository bases such as cocoa butter or other glycerides.

In addition to the formulations described previously, the polymers and oligomers can also be formulated as a depot preparation. Such long acting formulations can be administered by implantation (for example subcutaneously or intramuscularly) or by intramuscular injection.

Depot injections can be administered at about 1 to about 6 months or longer intervals. Thus, for example, the compounds can be formulated with suitable polymeric or hydrophobic materials (for example as an emulsion in an acceptable oil) or ion exchange resins, or as sparingly soluble derivatives, for example, as a sparingly soluble salt.

In transdermal administration, the polymers and oligomers, for example, can be applied to a plaster, or can be applied by transdermal, therapeutic systems that are consequently supplied to the organism.

The pharmaceutical compositions of the polymers and oligomers also can comprise suitable solid or gel phase carriers or excipients. Examples of such carriers or excipients include but are not limited to calcium carbonate, calcium phosphate, various sugars, starches, cellulose derivatives, gelatin, and polymers such as, e.g., polyethylene glycols.

The polymers and oligomers can also be administered in combination with other active ingredients, such as, for example, adjuvants, protease inhibitors, or other compatible drugs or compounds where such combination is seen to be desirable or advantageous in achieving the desired effects of the methods described herein (e.g., controlling infection caused by harmful microorganisms, or treating hemorrhagic complications associated with heparin therapy.). For example, the polymers and oligomers of the present invention can be administered with other antibiotics, including, but not limited to, vancomycin, ciprofloxacin, merapenem, oxicillin, and amikacin.

The following examples will serve to further typify the nature of this invention but should not be construed as a limitation in the scope thereof, which scope is defined solely by the appended claims.

EXAMPLE 1

Synthesis of a Polyamide Polymer

Figure 8:
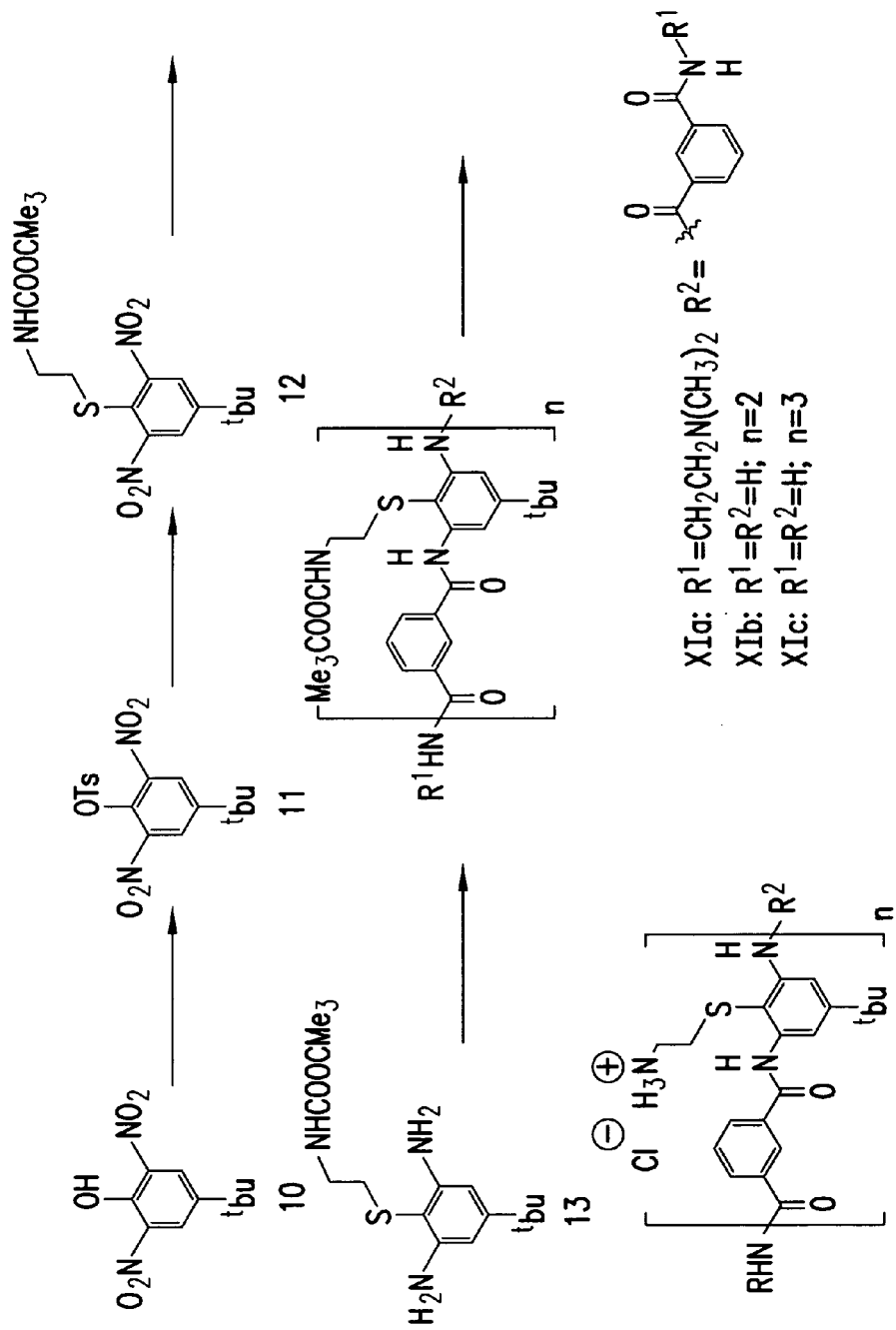
FIG. 8 shows a synthetic scheme for preparation of polyamide polymers (XIa) and oligomers (XIb and XIc).

The following protocol, illustrated in FIG. 8, was used to synthesize polyamide polymer XIa (FIG. 8).
2,6-Dinitro-4-t-butyl-phenyl(4-methyl)-benzenesulfonate (11)
2,6-dinitro-4-t-butyl-phenol (80 mmol; 10) and tosyl chloride (80 mmol) were dissolved in 300 ml $CH_2Cl_2$. Diisopropylethylamine (DIEA, 80 mmol) was added to the solution. The mixture was stirred at room temperature for 2 hours. The solution was washed with 10% citric acid, saturated aqueous NaCl (sat. NaCl), and dried with $MgSO_4$. The solvent was removed under reduced pressure, and the product was obtained as a bright yellow solid in quantitative yield. $^1$H NMR (500 MHz, $CDCl_3$): δ=8.12(s,2H), 7.80(d,2H), 7.40(d, 2H), 2.51(s,3H), 1.41(s, 9H). ESI-MS: m/z: 417.2 (M+$Na^+$)
2,6-Dinitro-4-t-butyl-1-(2-t-butoxycarbonylaminoethyl)sulfanyl benzene (12)
Compound 11 (13 mmol), 2-Boc-aminoethanthiol (16 mmol) and DIEA (13 mmol) were dissolved in 50 ml chloroform. The solution was stirred under nitrogen for 12 hours. The solution was washed with 0.5 M NaOH, 10% citric acid, sat. $Na_2CO_3$ and sat. NaCl, and dried with $MgSO_4$. The solution volume was reduced to 15 ml by rotary evaporation. After addition of 80 ml hexane the product crystallized as a bright yellow solid in. 94% yield. $^1$H NMR (500 MHz, $CDCl_3$): δ 7.81(s,2H), 4.87(s,1H), 3.31(t,2H), 310(t,2H), 1.44(s,9H), 1.39(s,9H). ESI-MS: m/z: 422.4(M+$Na^+$).
2,6-Diamino-4-t-butyl-1-(2-t-butoxycarbonylaminoethyl) sulfanylbenzene (13)
Dinitro compound 12 (20 mmol) and sodium acetate (200 mmol) were added to 50 ml EtOH. The mixture was heated to 78° C., and the solid dissolved completely. Stannous chloride dihydrate (200 mmol) was added to the solution, and the reaction mixture was stirred at 7° C. for 35 minutes. After removal of solvent under reduced pressure, the residue was dissolved in 800 ml EtOAc, and washed with 40% $KCO_3$. The organic phase was dried, evaporated and the residue column chromatographed ($SiO_2$) and eluted with a gradient of $CH_2Cl_2$/MeOH from 100:1 to 95:5 to produce 13 in 93% yield. $^1$H NMR. (500 MHz, $CDCl_3$): δ 6.21(s,2H), 5.41(s, 1H), 4.35(br,4H), 3.21(t,2H), 2.75(t,2H), 1.35 (s,9H), 1.24(s, 9H). ESI-MS: m/z:340.5($MH^+$)
General Method of Polymerization
Diamine 13 (0.1 mmol) was dissolved in 3 ml DMF. Isophthaloyl dichloride (0.1 mmol), triethylamine (0.2 mmol)) and N,N-dimethylethylenediamine (0.2/n mmol) were added while stirring. The mixture was stirred under nitrogen for 18 hours. After the volume of solvent was reduced to 1 ml, water was added to precipitate the polymer. The polymer was collected and dried under vacuum. The Boc group was removed by treatment with trifluoroacetic acid (TFA, 3 ml) for 1 hour. The deprotected polymer was dried under vacuum overnight.

EXAMPLE 2

Solid Phase Synthesis of Polyamide Oligomers

The following protocol, illustrated in FIG. 8, was used to synthesize polyamide oligomers XIb and XIc (FIG. 8).
Fmoc-PAL-PEG-resin (0.1 mmol) was swelled in DMF; then the Fmoc was removed with 20% piperidine in DMF for 20 min. The oligomer was then built up by alternately coupling 10 equivalents of isophthalic acid or diamine 13. In each case the couplings were carried out in DMF using 10 equivalents each of 2-(1H-benzotriazole-1-yl)-1,1,3,3,-tetramethyluronium hexafluorophosphate (HBTU) and N-hydroxybenzotriazole hydrate (HOBt), and 20 equivalents of DIEA for 24 hours at room temperature. The oligomers were cleaved from the resin by treatment with TFA/anisole (95:5) for 1 hour. Pure oligomers were obtained by HPLC on a reverse phase C4 column, with a linear gradient from 30% to 80% solvent B in 50 minutes (solvent A, 0.1% TFA in water; solvent B, acetonitrile/water/TFA 900:99:1). MALDI-TOF MS: compound 2: 756.5 (M+$H^+$), compound 3: 1125.6.(M+$H^+$).

EXAMPLE 3

General Method for Amide Polymerization

An oven-dried flask is charged with diamine dissolved in dimethylsulfoxide (DMSO). To this solution is added an equimolar quantity of the diacid chloride which is freshly prepared by stirring the dicarboxylic acid with excess thionyl chloride for 2 hr prior to addition to the diamine solution. A catalytic amount of 4-dimethylaminopyridine and four-fold molar excess of triethylamine are added to the stirring mixture. The reaction is stirred at room temperature overnight wider positive $N_2$ pressure. The DMSO solution is poured into water and the solid polymer is recovered by filtration. The degree of polymerization is controlled by the addition of various molar amounts of a monofunctional amine. The molar amount of the monofunctional amine is determined by the Flory equation (G. Odian, *Principles of Polymerization*, John Wiley & Sons, Third Edition (1991) p. 78-82).

EXAMPLE 4

General Method for Polyurea Polymerization

A dried flask is charged with equal molar ratios of the diamine and the diisocyanate in DMSO. The reaction is stirred at room temperature overnight under positive $N_2$ pressure. The reaction is poured into water or other and the solid polymer is recovered by filtration. The degree of polymerization is controlled by the addition of various molar amounts of a monofunctional amine. The molar amount of the monofunctional amine is determined by the Flory equation.

EXAMPLE 5

Antimicrobial Assays

Figure 9:
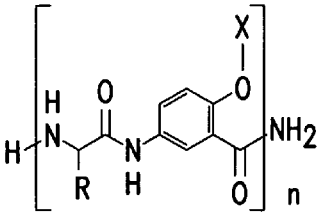
FIG. 9 shows antimicrobial data for polyamide oligomers of Formulae I and I'
Figure 11:
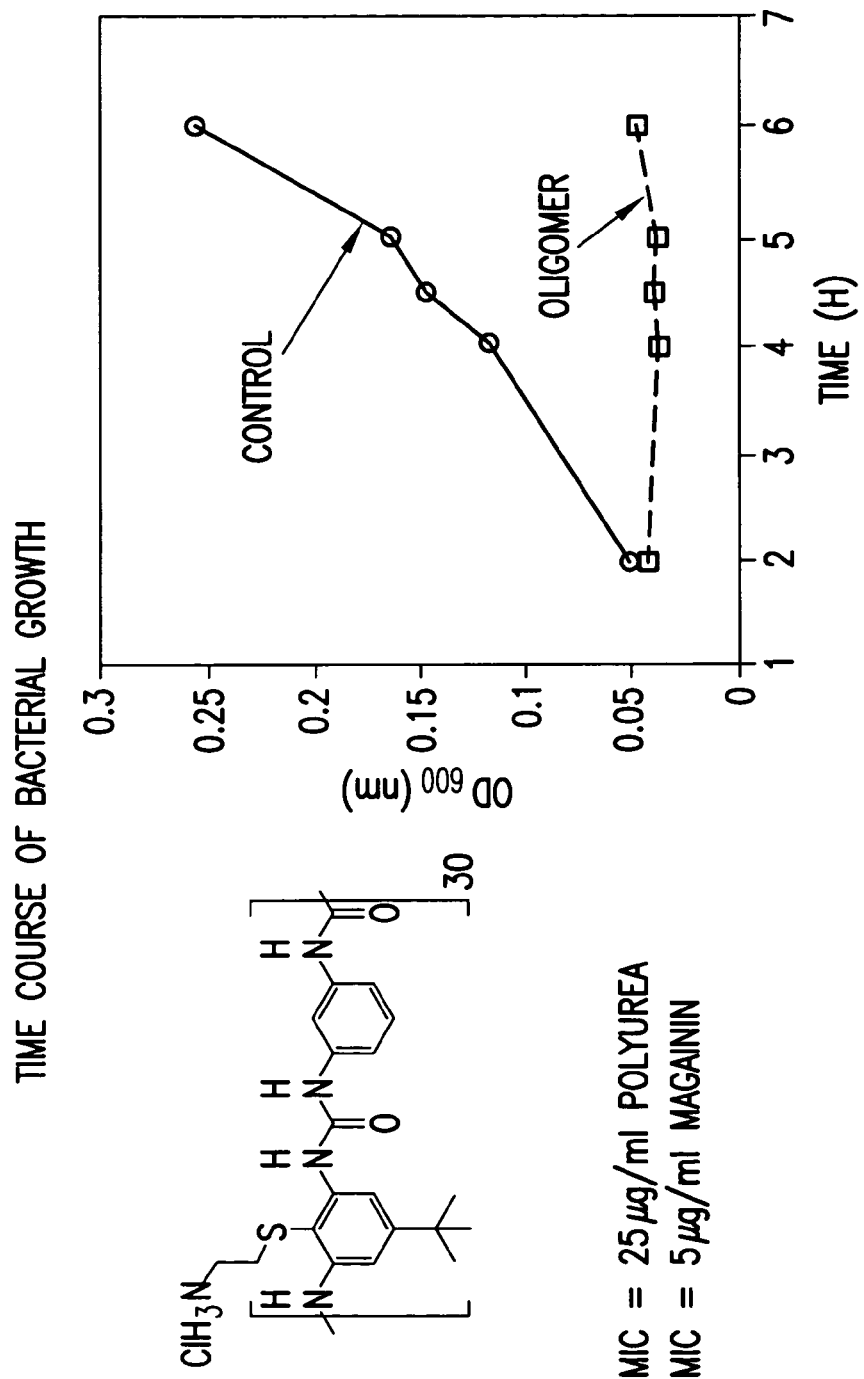
FIG. 11 shows the time course for antibacterial activity of a polyurea oligomer of Formulae IV and IV'.

Antimicrobial assays are carried out in suspension using BHI medium inoculated with bacteria ($10^6$ CFU/ml) in a 96-well format. A stock solution of the polymers was prepared in DMSO/water and used to prepare a ten fold dilution series. Minimal inhibitory concentrations (MIC) were obtained by incubating the compounds with the bacteria for 18 hours at 37° C., and measuring cell growth by monitoring at 590 nm. Antibacterial data for various polyamide and polyurea oligomers and polymers are presented in FIG. 8 and FIG. 9.

EXAMPLE 6

Hemolytic Activity

The toxicity to mammalian cells of polymers and oligomers of the present invention was evaluated using human blood obtained from healthy volunteers, anticoagulated with 0.1 volume of sodium citrate. The general procedure is as follows: Washed erythrocytes are suspended in either HEPES buffer, pH 7.4, containing 1 mM $Mg^{2+}$ and 1 mM $Ca^{2+}$ or in heated and unheated autologous serum obtained from clotted blood. Red cell agglutination is evaluated microscopically and red cell lysis is evaluated by measuring the amount of released hemoglobin spectroscopically. The effect of polymers on platelet function is studied by adding increasing concentrations of polymer to citrate-anticoagulated platelet-rich plasma. Platelet aggregation and secretion are then evaluated in a lumi-aggregometer (Chrono-Log).

EXAMPLE 7

Structure-Activity Relationships for a Series of Arylamide Polyamide Oligomers

A series of arylamide oligomers were designed, synthesized, and assayed for their ability to selectively lyse bacterial cells. Structure-activity relationships for antimicrobial efficacy and selectivity were then determined for the series of oligomers.

The arylamide oligomers were designed, synthesized, and tested for antimicrobial activity using the procedures as described above. The oligomers were also assayed for their ability to lyse mammalian cells by measuring hemolysis of human erythrocytes following one hour incubation in the presence of compound (Liu, D., and DeGrado, W. F., *J. Amer. Chem. Soc.*, 123:7553-7559 (2001). $HC_{50}$ values represent the concentration of compound that results in 50% hemoglobin release. The assay results are presented in Table 1.

TABLE 1

Arylamide structure - activity relationships

| Oligomer | Compound No. | MW | MIC E. coli (μg/ml) | $HC_{50}$ RBC (μg/ml) |
|---|---|---|---|---|
| 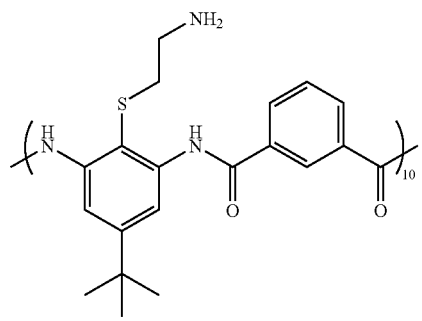 | 1 | ~6000 | 7.5–15 | 50 |

TABLE 1-continued

Arylamide structure - activity relationships

| Oligomer | Compound No. | MW | MIC E. coli (μg/ml) | HC$_{50}$ RBC (μg/ml) |
|---|---|---|---|---|
| [structure] | 2 | ~6000 | 125 | >200 |
| [structure] | 3 | ~6000 | >200 | |
| [structure] | 4 | ~6000 | >500 | >500 |
| [structure] | 5 | 779 | 25 | >200 |

TABLE 1-continued

Arylamide structure - activity relationships

| Oligomer | Compound No. | MW | MIC E. coli (μg/ml) | HC$_{50}$ RBC (μg/ml) |
|---|---|---|---|---|
| (structure) | 6 | 921 | 6 | 715 |

Many of the compounds synthesized initially were highly efficacious against bacteria but also had high hemolytic activity. However, it was found that selectivity could be improved while maintaining potent antimicrobial activity by decreasing the repeat length and modulating the positive charge through end-group substitutions (Table 1). Beginning with an arylamide oligomer having a repeat length of n=10 (Molecular Weight (MW) approximately 6000 Daltons), the tert-butyl analogue (compound 1) had relatively potent activity against E-coli but significant hemolytic activity. A reduction in hydrophobicity of the R group (compounds 2 and 3) or neutralization of the positive charge (compounds 4) significantly reduced activity against both E. coli and erythrocytes. By reducing the chain length to n=2 (MW 779 Daltons) and increasing the positive charge at the end-groups (compound 5), moderate antimicrobial activity was restored without significant hemolytic activity. A further modification of the positive charge at the end-groups (n=2, MW 921 Daltons) resulted in a highly potent and selective oligomer (compound 6).

EXAMPLE 8

Structure-Activity Relationships for a Series of Salicylamide Polyamide Oligomers A series of salicylamide oligomers were designed, synthesized, and assayed for their ability to selectively lyse bacterial cells. Structure-activity relationships for antimicrobial efficacy and selectivity were then determined for the series of oligomers.

The salicylamide oligomers were designed, synthesized, and tested for antimicrobial activity as described above. The oligomers were also assayed for their ability to lyse mammalian cells by measuring hemolysis of human erythrocytes following one hour incubation in the presence of compound (Liu, D., and DeGrado, W. F., *J. Amer. Chem. Soc.* 123:7553-7559 (2001)). HC$_{50}$ values represent the concentration of compound that results in 50% hemoglobin release. The assay results are presented in Table 2.

The structure-activity relationship for compounds in this salicylamide series showed the strong effect of chain length on antimicrobial activity and hydrophobicity of the end group on hemolytic activity (Table 2). For the salicylamide compounds having a leucine apolar group on the salicylic acid (compounds 1-3), a minimum chain length of 4 was required for antimicrobial activity. This chain length dependence may reflect a limit size requirement that is needed for accessing and disrupting the bacterial cell membrane. For similar salicylamides having a leucine apolar group (compounds 4-9), modification of the charge on the polar endgroup did not significantly affect antimicrobial activity but has a strong impact on hemolytic activity. The structure-activity relationship was used to design and synthesize two highly potent salicylamide compounds having no appreciable hemolytic activity (Compounds 6 and 7, Table 2).

TABLE 2

Salicylamide structure-activity relationships

| Oligomer | n | X | Compound | MW | MIC: E-coli μg/ml | HC$_{50}$ RBC μg/ml |
|---|---|---|---|---|---|---|
| (structure) | 2 | | 1 | 599 | >60 | >200 |
| | 3 | | 2 | 890 | >500 | >200 |
| | 4 | | 3 | 1181 | 30 | >200 |

TABLE 2-continued

Salicylamide structure-activity relationships

| Oligomer | n | X | Compound | MW | MIC: E-coli μg/ml | HC$_{50}$ RBC μg/ml |
|---|---|---|---|---|---|---|
| [structure: methylamino-urea-X-NH-salicylamide with O-ethyl-guanidine] | 4 | Leu | 4 | | 20 | >200 |
| | 5 | Leu | 5 | | 20 | >200 |
| [structure: repeating unit with O-butyl-NH$_2$ sidechain] | 4 | Leu | 6 | | 12 | >200 |
| | 5 | Leu | 7 | | 12 | >200 |
| [structure: repeating unit with O-pentyl-guanidine sidechain] | 4 | Leu | 8 | | 12 | 35 |
| | 5 | Leu | 9 | | 12 | 8 |

EXAMPLE 9

Antiviral Activity of Oligomers

Figure 12:
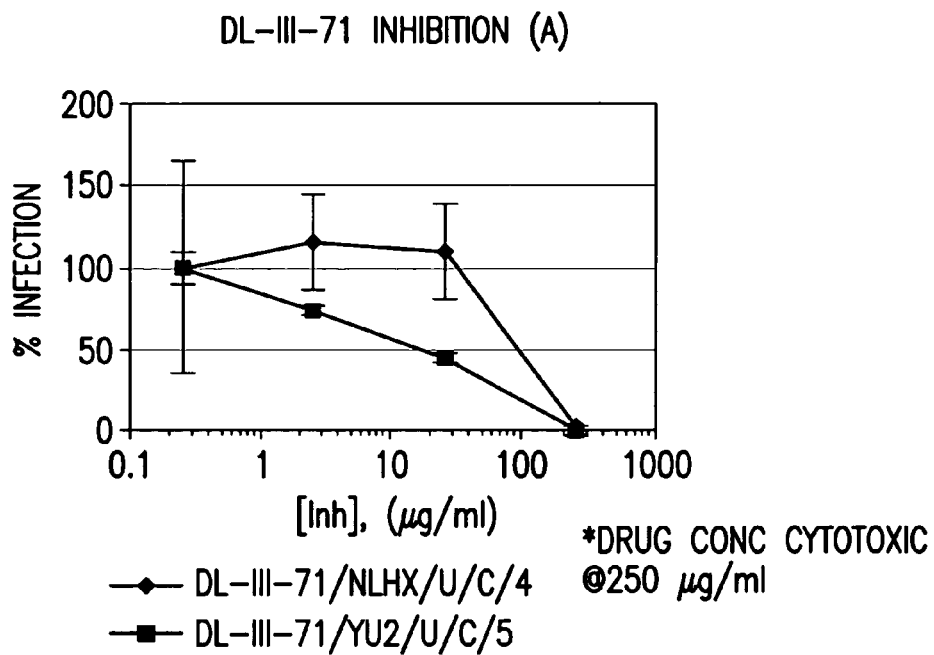
FIG. 12 shows the results of an experiment in which the antiviral activity of the compound 1 (DL-III-71) was tested by monitoring the percent infection by HLHX or YU2 viruses of U87/CD4/CCR5 and U87/CD4/CXCR4 cells.
Figure 13:
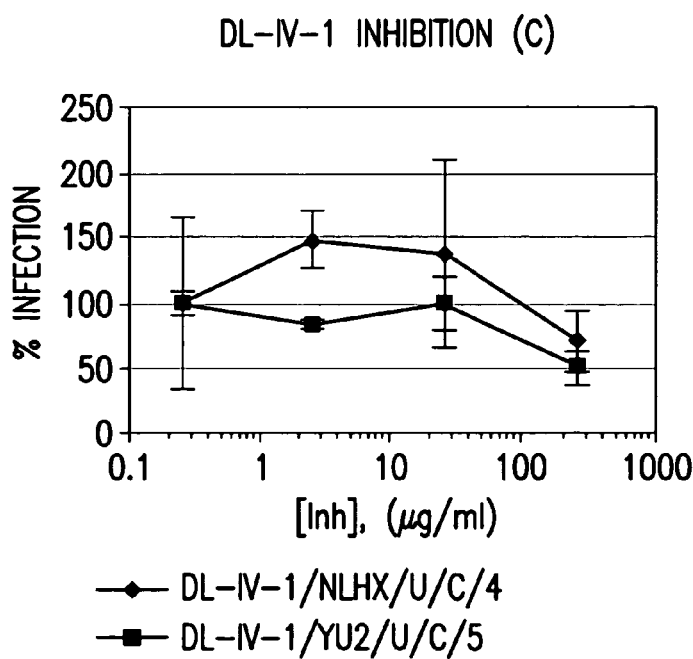
FIG. 13 shows the results of an experiment in which the antiviral activity of the compound 2 (DL-IV-1) was tested by monitoring the percent infection by HLHX or YU2 viruses of U87/CD4/CCR5 and U87/CD4/CXCR4 cells.

Three oligomers were synthesized as described above and tested for their ability to inhibit HIV replication in cell culture (Table 3, FIG. 12, and FIG. 13). Two viruses were used in the infection assays; NLHX or YU2 that use CXCR4 or CCR5 as co-receptor, respectively. U87/CD4/CCR5 or U87/CD4/CXCR4 cells were seeded in 48-well plates at 3×10$^4$ cells/well on the day prior to infection. Culture supernatants were removed from cells and replaced with pseudotyped luciferase reporter virus alone or pseudotyped luciferase reporter virus and defensin-like compound at indicated final concentrations. Virus and compound were removed from cells approximately 16 hours post-infection, the cells were washed and then culture media was replenished. Cells were lysed and assayed for luciferase activity 3 days post infection. Results are presented as a percent of luciferase activity observed in the absence of compound.

The results in FIG. 12 demonstrate that Compound 1 (DL-III-71) inhibits the infection of the CCR5 tropic virus but has little effect on CXCR4 tropic virus infection. The inhibition observed at 200 ug/ml on both viruses is likely a non-specific effect due to apparent cytotoxicity of the compound. Compound 2 (DL-IV-1) has little inhibitory effect on infection of the CXCR4 tropic virus but inhibits the infection of the CCR5 tropic virus by 50% at the highest dose tested (FIG. 13). No cytotoxicity was observed at any dose.

Figure 14:
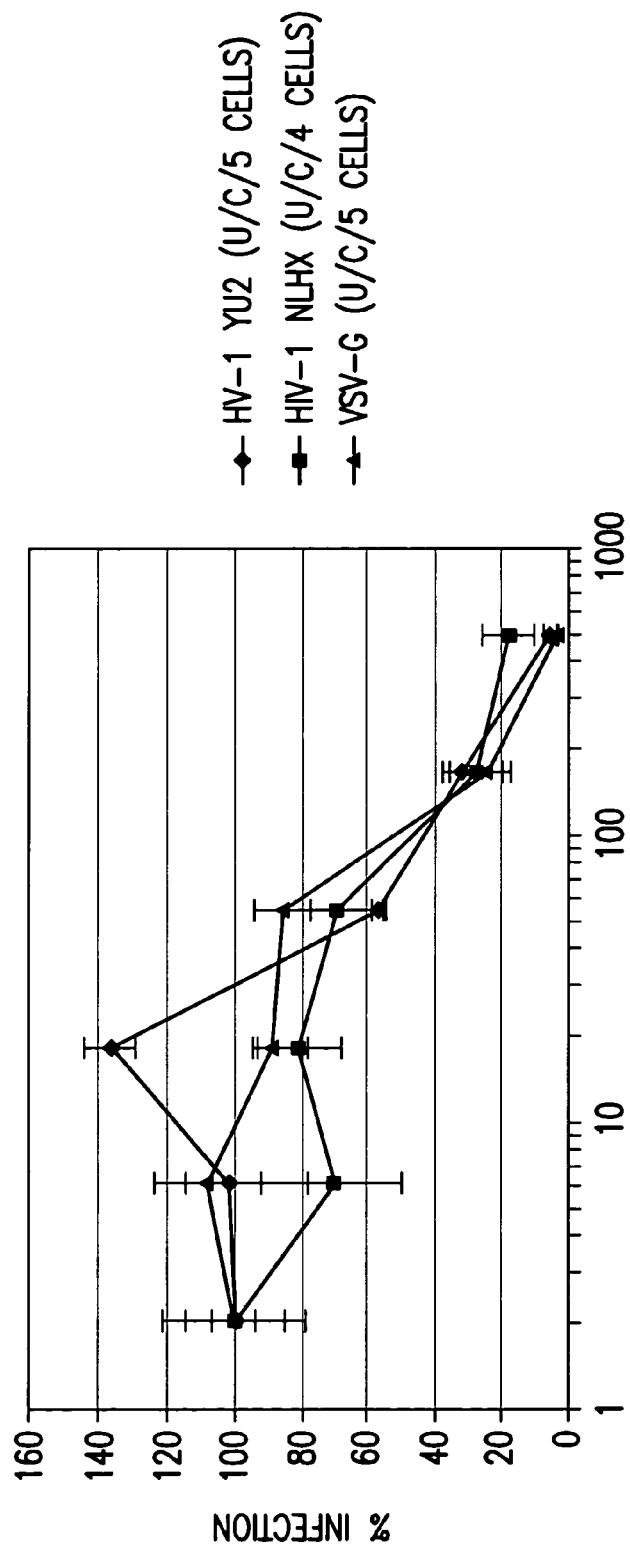
FIG. 14 shows the results of an experiment in which the antiviral activity of the compound 3 (Compound E) was tested by monitoring the percent infection by HLHX, YU2, or VSV-2 viruses of U87/CD4/CCR5 and U87/CD4/CXCR4 cells.

Compound 3 (Compound E, FIG. 14) was tested against 3 viruses; NLHX, YU2 and VSV-2, a non-HIV based virus pseudotype (FIG. 14). A similar level of inhibition was observed with all three Env types indicating that Compound 3 blocks HIV infection and is not specific for HIV. No cytotoxicity was evident at any concentration tested.

These results demonstrate that the amphiphilic oligomers effectively block HIV infection and their inhibitory properties for viral infection are not limited to HIV or HIV subtypes.

TABLE 3

| Compound No. | Structure |
|---|---|
| 1 (DL-III-71) | [structure: salicylamide oligomer with R1 = isobutyl, R2 = hexyl-NH$_2$, n = 4] |

TABLE 3-continued

| Compound No. | Structure |
|---|---|
| 2 (DL-IV-1) | 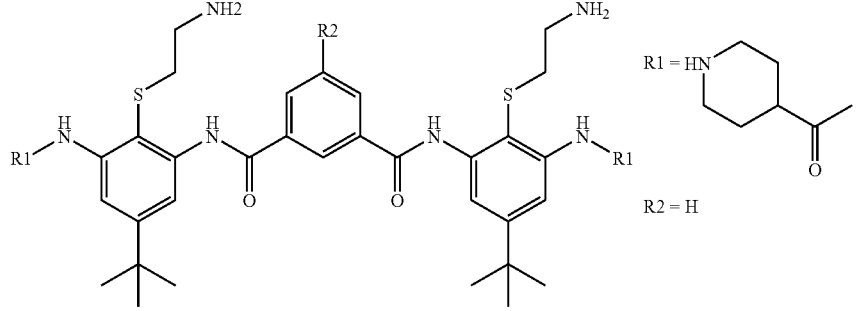 |
| 3 (Compound E) | 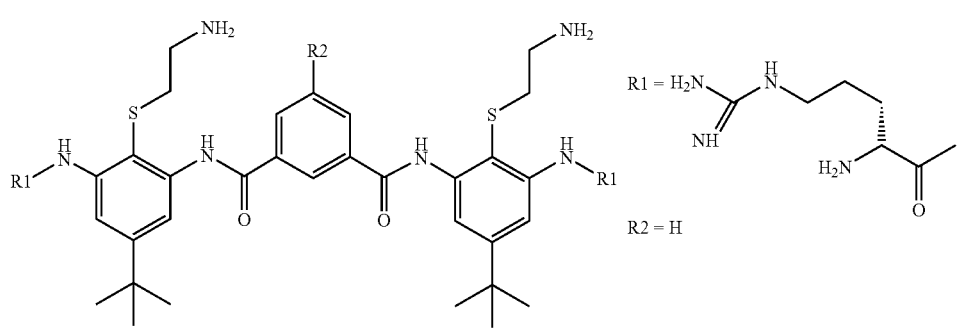 |

EXAMPLE 10

Antifungal Activity of Oligomers

Several different genera of fungi were tested for their sensitivity to a set of salicylamide and arylamide oligomers. Both non-filamentous (yeast) and filamentous fungi were tested and specific fungi that are associated with various types of human infections were chosen for the screen (Table 4). Five oligomers (3 arylamides and 2 salicylamides) which inhibit the growth of bacteria were tested for their antifungal activities (Table 5). The antifungal assays were done to determine the minimal inhibitory concentrations that resulted in complete inhibition of growth ($MIC_{100}$). All growth assays were done in a total of 1 ml volumes and growth was assessed by turbidity measurements. Other assay conditions are described in Table 6. Moderate inhibitory activity against *Candida albicans* and *Trichophyton mentagrophytes* was observed for all of the compounds tested (MIC=100 ug/ml) and the growth of *Aspergillus fumigatus* was moderately inhibited by oligomers 2, 4, and 5 (Table 7). However, all of the tested oligomers were very active against *Cryptococcus neoformans* with 4 of the 5 compounds exhibiting highly potent growth inhibitory activity (<1 ug/ml). Surprisingly, the MIC values for *C. neoformans* were significantly more potent than the MICs for *E. coli* for 4 of the 5 compounds tested. These data indicate that the amphiphilic oligomers synthesized for antibacterial properties also possess significant antifungal activities which could be developed for both pharmaceutical and material applications.

TABLE 4

| Organism | Clinical Features |
|---|---|
| Yeast | |
| *Candida albicans* ATCC 10231 | Mucosal infections (skin, GI, urinary tract, reproductive organs) |
| Filamentous fungi | |
| *Aspergillus fumigatus* ATCC 1028 | Allergic disease, sinusitis bronchopulmonary infections and systemic infections in immune-compromised individuals |
| *Cryptococcus neoformans* ATCC 24067 | Opportunistic pathogen causing systemic infections in immune-compromised individuals |
| *Trichophyton mentagrophytes* ATCC 9533 | Skin infections (dermatophytosis) |
| *Trichophyton rubrum* ATCC 10218 | Chronic infections of the skin and nails, most widely distributed dermatophyte |
| Control | |
| *E. coli* ATCC 25922 | Verify compound integrity and activity, verify assay conditions |

TABLE 5
| Oligomer | Structure |
|---|---|
| 1 | 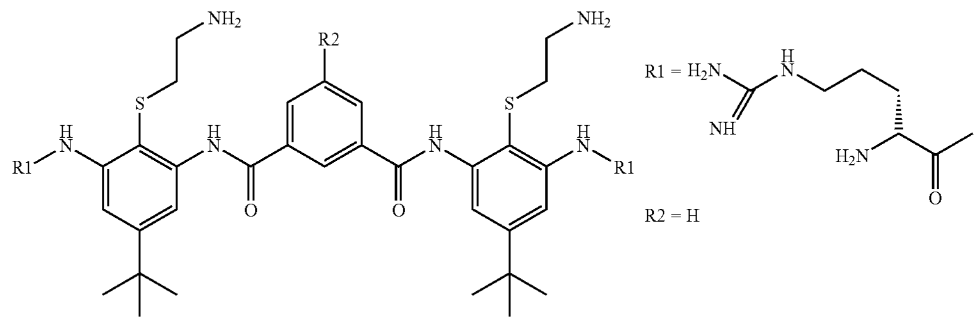 |
| 2 | 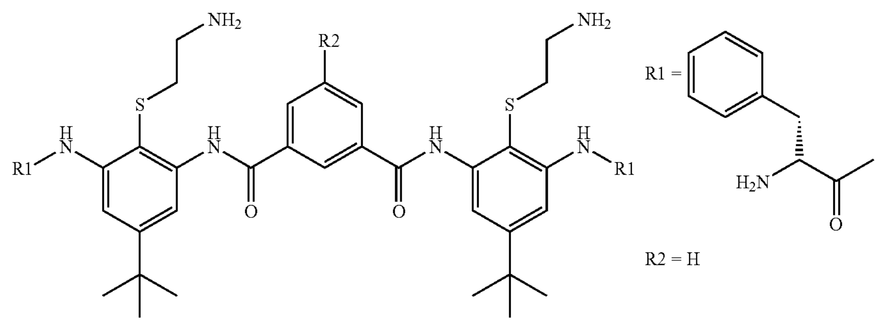 |
| 3 | 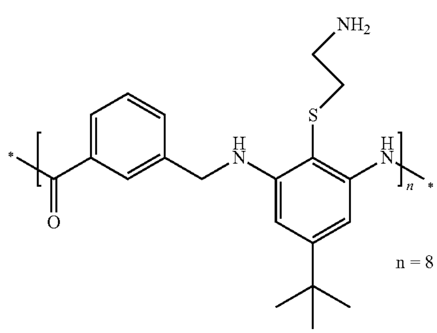 |
| 4 | 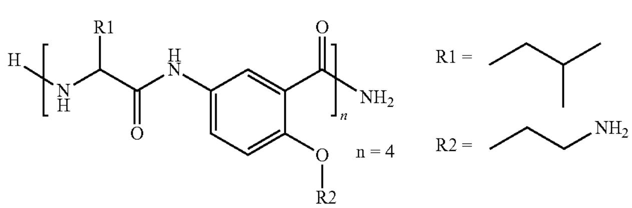 |
| 5 | 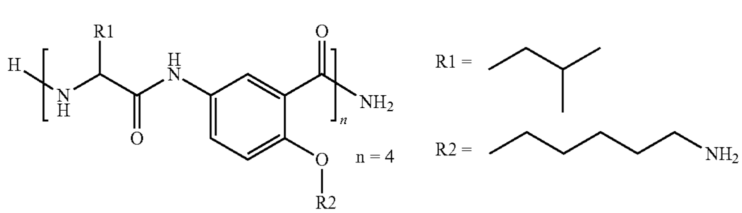 |
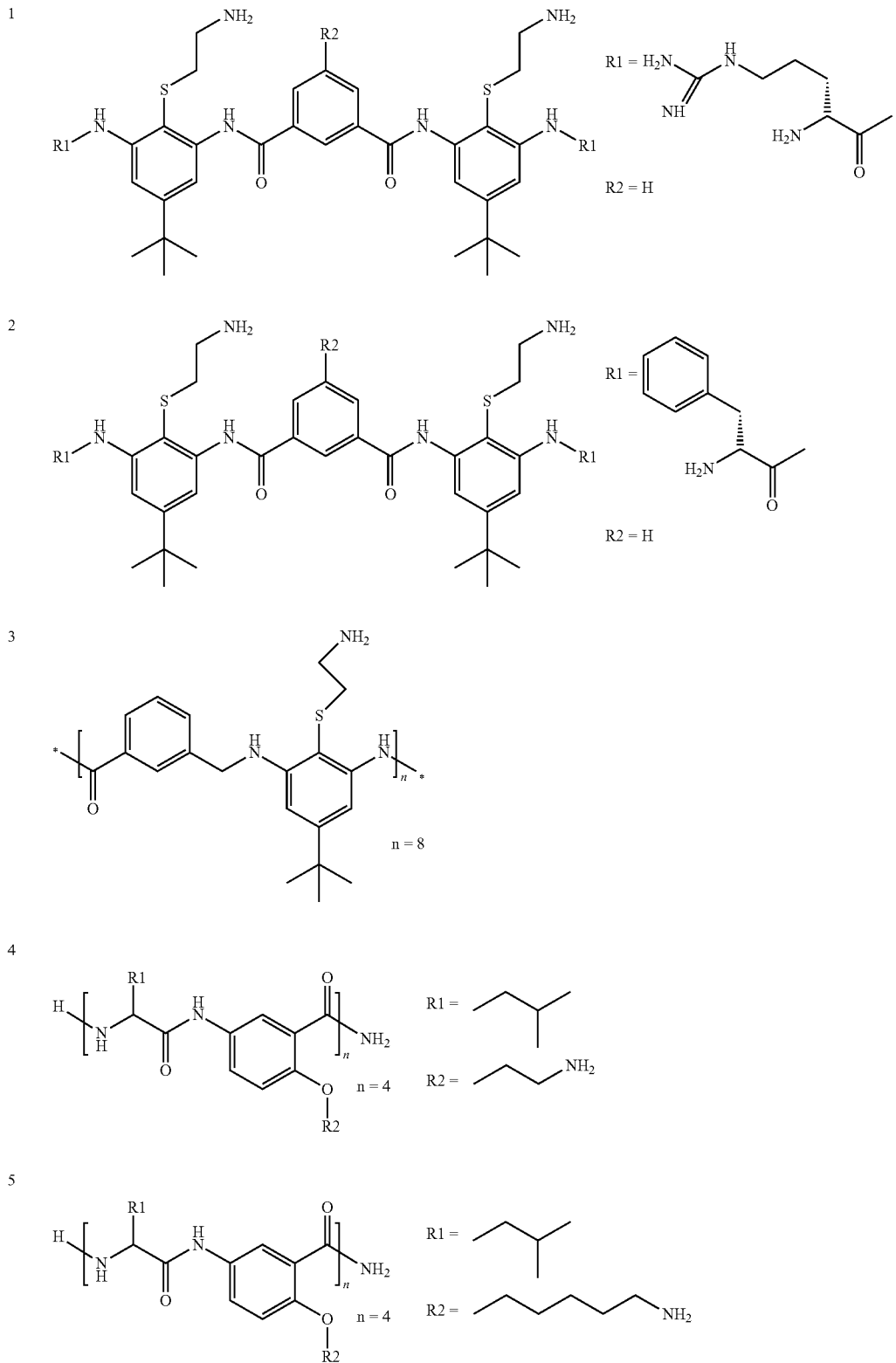

TABLE 6

| Method Conditions | Candida albicans | Aspergillus fumigatus | Cryptococcus neoformans | Trichophyton mentagrophytes | Trichophyton rubrum | E. coli (ATCC25922) |
|---|---|---|---|---|---|---|
| Culture Medium | Fluid Sabouraud Medium | Potatoe Dextrose Broth | Fluid Sabouraud Medium | Potatoe Dextrose Broth | Fluid Sabouraud Medium | Nutrient Broth |
| Incubation Time | 20 hours | 2 days | 2 days | 3 days | 3 days | 20 hours |
| Incubation Temp. | 37° C. | 28° C. | 37° C. | 28° C. | 28° C. | 37° C. |

TABLE 7

| | $MIC_{100}$ (ug/ml) | | | | | |
|---|---|---|---|---|---|---|
| | Candida albicans | Aspergillus fumigatus | Cryptococcus neoformans | Trichophyton mentagrophytes | Trichophyton rubrum | E. coli (ATCC25922) |
| Oligomer | | | | | | |
| 1 | 100 | >100 | 0.3 | 100 | >100 | 30 |
| 2 | 100 | 100 | <0.1 | 100 | >100 | 3 |
| 3 | 100 | >100 | 30 | 100 | >100 | 30 |
| 4 | 100 | 100 | 1 | 100 | >100 | 100 |
| 5 | 100 | 100 | 1 | 100 | >100 | 10 |
| Control | | | | | | |
| Amphotericin | 0.1 | 1 | 0.1 | 0.3 | 1 | 3 |
| Gentamycin | | | | | | |

EXAMPLE 11

Figure 15:
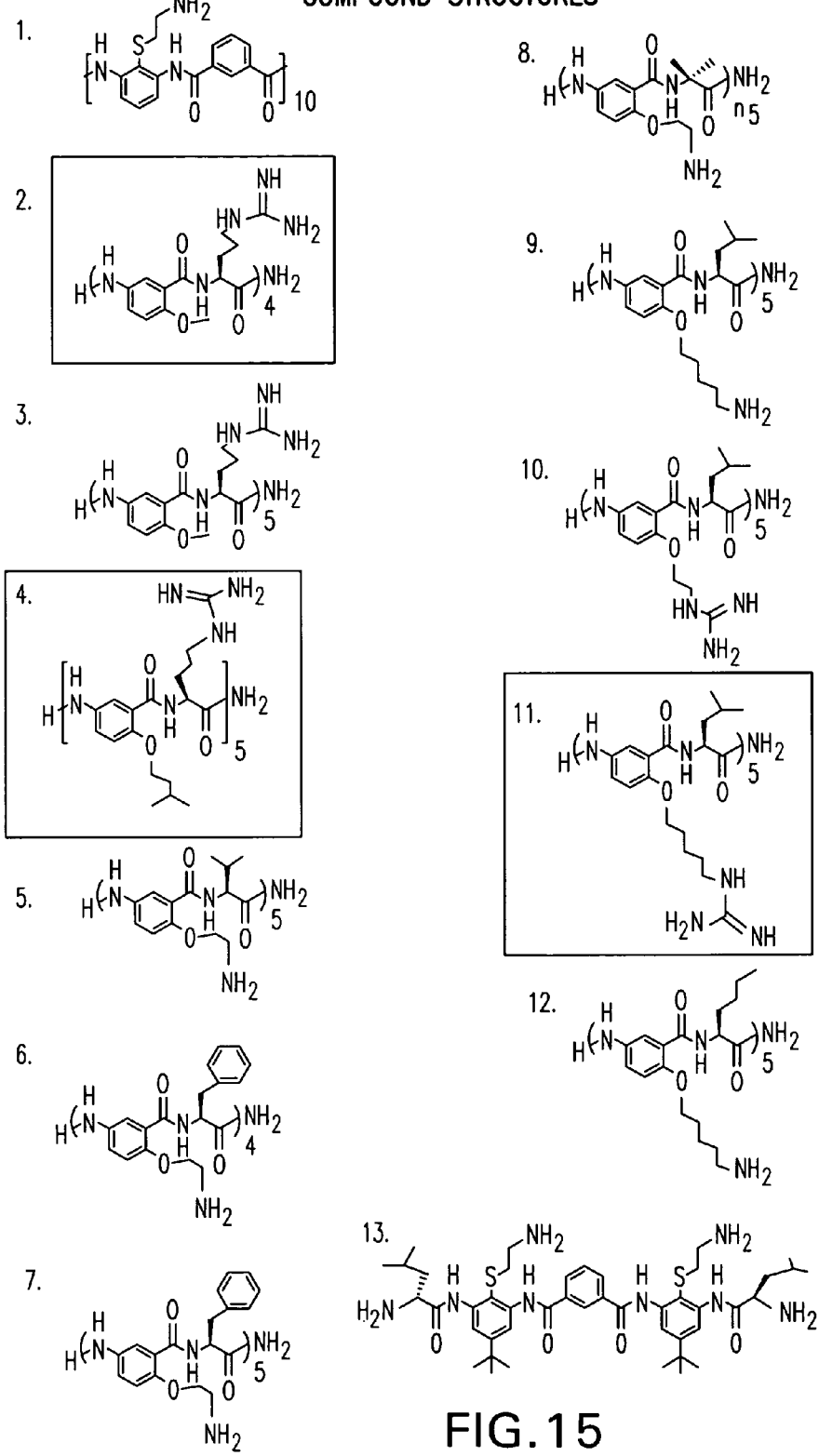
FIG. 15 shows the structure of oligomers used in the anticoagulation assays described in Example 11. Oligomers enclosed in boxes significantly antagonized the delay in plasma clotting caused by low molecular weight heparin.

Ability of Oligomers to Inhibit the Anticoagulation Effects of Low Molecular Weight Heparin Several of the amphiphilic polymers and oligomers that were synthesized for antimicrobial applications were tested for their ability to inhibit the anticoagulation effects of heparin. The structures for compounds that were tested in the collaboration appear in FIG. 15. It was assumed that heparin-neutralizing activity would largely be dependent on the charge and charge distribution characteristics of the compounds rather than oil their hydrophobic qualities.

Table 8 summarizes the effects of increasing concentrations of the oligomers on the delay in clotting times of activated plasma caused by a fixed concentration of heparin. Many of the oligomers when tested at a concentration of 4.4 ug/ml significantly antagonized the delay in clotting time induced by 1 unit (0.2 ug/ml) of heparin (compounds 2, 3, 11-19).

Dose-response data were collected for several of the compounds and heparin activity was antagonized at concentrations as low as 1.5 ug/ml of oligomer but not at 0.4 ug/ml. The near stoichiometric level of antagonism indicates high affinity binding between the oligomer and heparin molecules.

Figure 16:
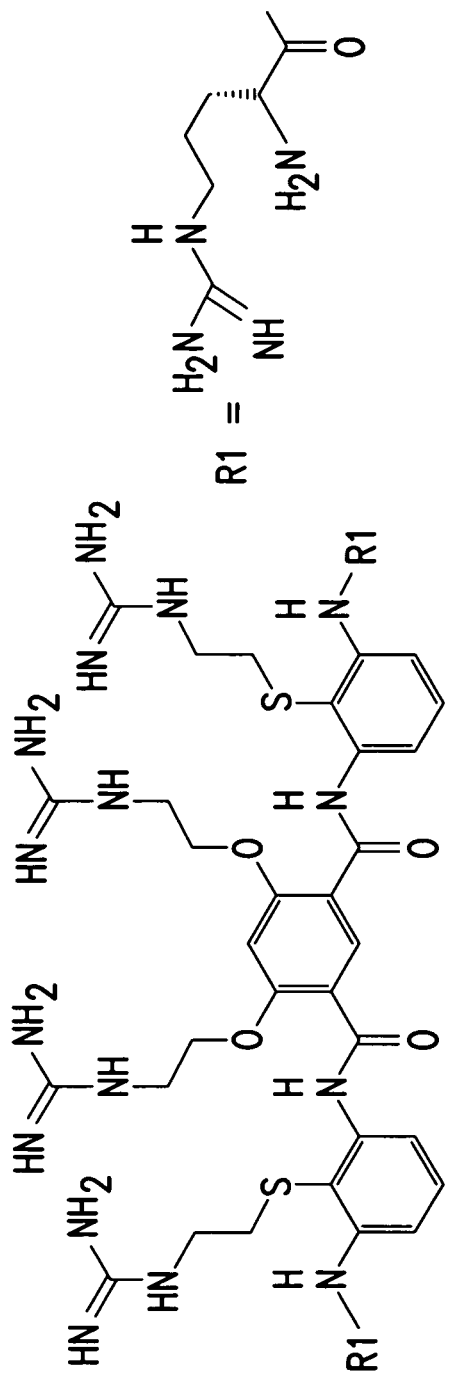
FIG. 16 shows the structure of the Pmx10073, the oligomer tested in the assays described In Example 11.

Antagonism of the delay in clotting time caused by low molecular weight heparin (LMWH) was also investigated (Table 9). Compounds 2, 4, 11, 18 and 19 (boxed in FIG. 16) when tested at 4.4 ug/ml significantly antagonized the delay in plasma clotting caused by LMWH (Innohep, 4.6 ug/ml final concentration). As with heparin, the near stoichiometric level of antagonism indicates a high affinity association between the effective oligomers and LMWH. A reduction in concentration of oligomer to 1.5 ug/ml resulted in a loss of the heparin-antagonizing activity. An indication of activity for compound 19 at 0.4 ug/ml is suspect because of the lack of a consistent dose-response effect. This initial survey has resulted in the identification of multiple oligomeric compounds of diverse structure (salicylamides, hydrazides and calixarenes) that potently inhibit the anticlotting activities of heparin and, most importantly, LMWH.

Figure 17:
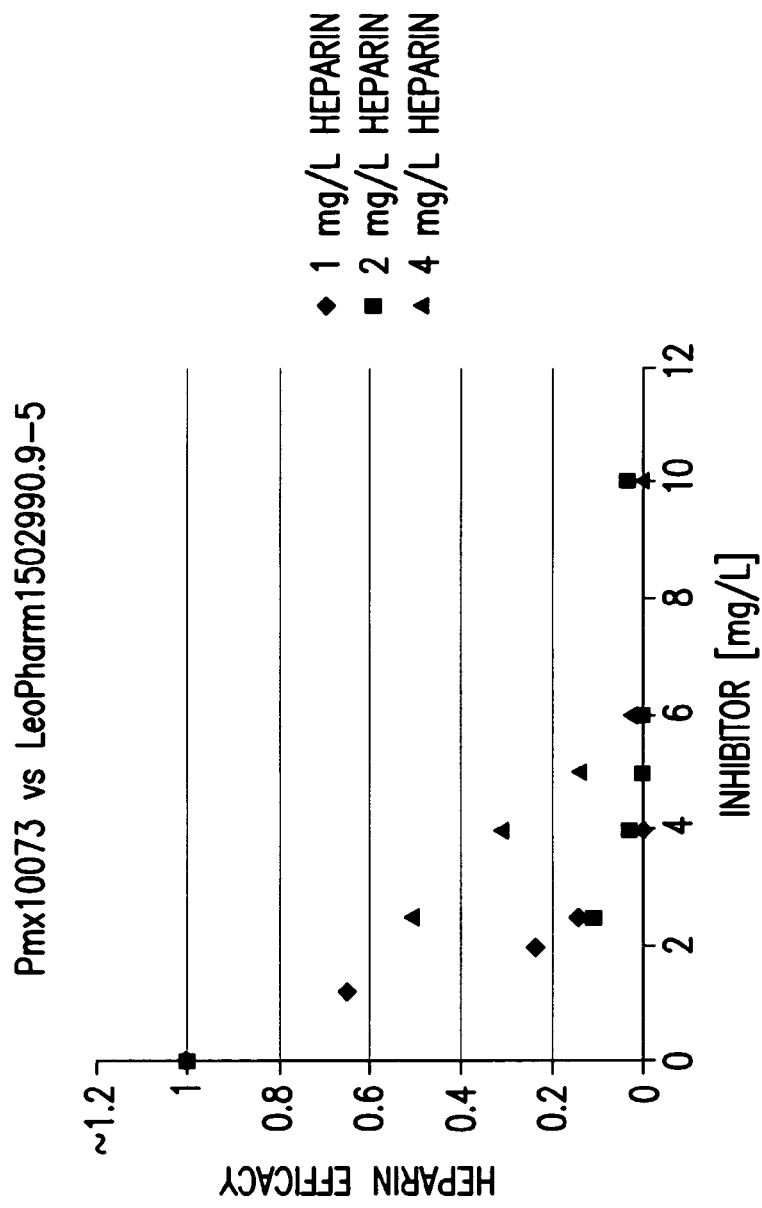
FIG. 17 illustrates the antagonism of low molecular weight heparin effects measured for the oligomer Pmx10073 on plasma clotting time in whole blood, as described in Example 11.
Figure 18:
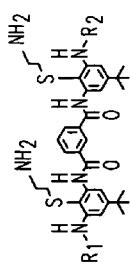
FIG. 18 shows the antibacterial activities and selectivities for arylamide oligomers described in Example 12.
Figure 20:
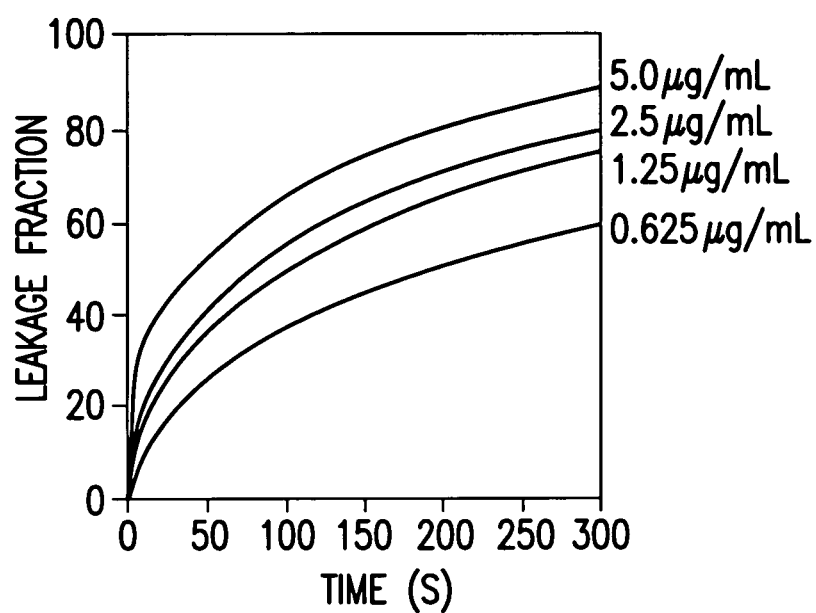
FIG. 20 shows the results of vesicle leakage assays performed with compound 8 in Example 12.

An arylamide oligomer was tested for its LMWH-antagonizing activity by measuring clotting time in whole blood. This compound, Pmx10073 (FIG. 17), is similar to the antimicrobial arylamides and was designed to antagonize LMWH. Pmx10073 has a high positive-charge density but lacks the hydrophobic side chains present on the arylamide series of compounds shown to be important for antibacterial activity. A dose-response for antagonism of the delay in clotting time induced by 3 different concentrations of LMWH (LeoPharm, 1 ug/ml) is shown in FIG. 18. Potent antagonism of LMWH activity is observed at all three concentrations of LMWH. Furthermore, the concentration of Pmx10073 which causes a 50% inhibition of LMWH activity is approximately 1.5 ug/ml in the presence of 1 or 2 ug/ml LMWH and shifts to 3 ug/ml in the presence of 4 ug/ml LMWH. This stoichiometric response is clearly indicative of a high affinity association between Pmx10073 and LMWH.

With regard to the results of the previous studies, the results with Pmx10073 further demonstrate LMWH-antagonizing activity of yet another structural class of oligomers arylamides) and confirms activity against LMWH produced by another manufacturer. One distinction is that the studies with Pmx10073 were done in whole blood. This is important in consideration of pharmaceutical applications because it indicates that potential serum protein binding by the compound is not an issue that could impact biological activity in vivo. The utility for pharmaceutical applications is further supported by selectivity experiments. The concentrations of compound that are cytotoxic for mammalian cells were determined and compared to efficacious concentrations. In hemolysis studies, using human red blood cells, 50% RBC lysis occurred at Pmx10073 concentrations of approximately 3100 ug/ml, a selectivity margin ([50% antagonism of LMWH effects on clotting time]/[50% RBC lysis]) of over 1000 fold. This superior safety index argues that in vivo efficacy can be achieved at concentrations that are far below cytotoxic levels. These data strongly support the development of amphiphilic oligomers and their derivatives as antidotes for hemorrhagic complications associated with LMWH treatment.

TABLE 8

Effects of Oligomers on Clotting Times of Activated Plasma in the Presence of Heparin.

Heparin (1 unit, 0.2 ug/ml)

| | Trial #1 | Trial #2 | Trial #3 | Trial #4 | Average | SD | SE |
|---|---|---|---|---|---|---|---|
| Oligomer (44.4 ug/ml) | | | | | | | |
| None | 180.0 | 205.1 | 263.2 | 266.2 | 228.6 | 42.9 | 21.5 |
| #1 | 153.6 | 158.6 | 136.1 | 151.6 | 150.0 | 9.7 | 4.9 |
| #2 | 46.6 | 31.6 | 35.1 | 33.2 | 36.7 | 6.8 | 3.4 |
| #3 | 38.7 | 34.1 | 38.6 | 35.6 | 36.8 | 2.3 | 1.1 |
| #4 | 31.6 | 29.6 | 29.6 | 26.1 | 29.2 | 2.3 | 1.1 |
| #5 | 35.1 | 35.1 | 33.6 | 33.2 | 34.3 | 1.0 | 0.5 |
| #6 | 36.1 | 35.6 | 34.1 | 29.7 | 33.9 | 2.9 | 1.5 |
| #7 | 27.1 | 32.6 | 30.6 | 31.1 | 30.4 | 2.3 | 1.2 |
| #8 | 36.6 | 34.6 | 34.6 | 34.1 | 35.0 | 1.1 | 0.6 |
| #9 | 31.7 | 33.8 | 33.8 | 33.1 | 33.1 | 1.0 | 0.5 |
| #10 | 40.7 | 35.6 | 36.7 | 33.7 | 38.7 | 3.0 | 1.5 |
| #11 | 78.6 | 71.6 | 61.6 | 60.1 | 68.0 | 8.7 | 4.4 |
| Oligomer (4.4 ug/ml) | | | | | | | |
| #1 | 170.0 | 184.6 | 221.6 | | 192.1 | 26.6 | 15.4 |
| #2 | 67.6 | 70.2 | 67.2 | 83.6 | 72.2 | 7.7 | 3.9 |
| #3 | 72.2 | 75.1 | 81.2 | 92.6 | 80.3 | 9.0 | 4.5 |
| #4 | 175.5 | 153.8 | 157.1 | 192.6 | 169.8 | 18.0 | 9.0 |
| #5 | 145.1 | 142.5 | 149.7 | 202.6 | 160.0 | 28.6 | 14.3 |
| #6 | 145.1 | 142.6 | 197.6 | 279.1 | 191.1 | 63.9 | 32.0 |
| #7 | 151.6 | 149.2 | 169.6 | 221.1 | 172.9 | 33.4 | 16.7 |
| #8 | 216.6 | 199.1 | 243.2 | >350 | 219.6 | | |
| #9 | >350 | | | | >350 | | |
| #10 | 113.8 | 317.6 | >450 | >450 | >400 | | |
| #11 | 45.1 | 42.2 | 36.1 | 39.7 | 40.8 | 3.8 | 1.9 |
| #12 | 70.2 | 83.1 | 90.1 | 100.7 | 86.0 | 12.8 | 6.4 |
| #13 | 81.2 | 88.2 | 94.1 | 106.2 | 92.4 | 10.6 | 5.3 |
| #14 | 40.5 | 34.2 | | 31.8 | 35.5 | 4.5 | 2.6 |
| #15 | 37.6 | 34.2 | 35.1 | 31.7 | 34.7 | 2.4 | 1.2 |
| #16 | 53.1 | 55.6 | | | 54.4 | 1.8 | 1.3 |
| #17 | 25.6 | 22.2 | | | 23.9 | 2.4 | 1.7 |
| #18 | 57.6 | | | | 57.6 | | |
| #19 | 29.0 | 26.7 | | | 27.9 | 1.6 | 1.2 |
| Oligomer (1.5 ug/ml) | | | | | | | |
| #14 | 42.7 | 39.1 | | | 40.9 | 2.5 | 1.8 |
| #15 | 39.7 | 42.7 | | | 41.2 | 2.1 | 1.5 |
| #17 | 43.1 | | | | 43.1 | | |
| #19 | 43.2 | 37.1 | | | 40.2 | 4.3 | 3.1 |
| Oligomer (0.4 ug/ml) | | | | | | | |
| #14 | 306.6 | >400 | | | >400 | | |
| #15 | >400 | | | | >400 | | |
| #17 | >400 | | | | >400 | | |
| #19 | >400 | | | | >400 | | |

TABLE 9

Effects of Oligomers on Clotting Times of Activated Plasma in the Presence LMWH.

LMWH (4.6 ug/ml)

| Oligomer (14.8 ug/ml) | |
|---|---|
| None | 178.9 |
| #1 | 261.7 |
| #2 | 48.4 |
| #3 | 109.2 |
| #4 | 44.9 |
| #5 | 86.2 |
| #6 | 140.1 |
| #7 | 167.2 |
| #8 | 159.7 |
| #9 | 62.7 |
| #10 | 97.6 |
| #11 | 54.1 |
| #12 | 167 |
| #13 | 189.2 |
| #14 | 182.2 |
| #15 | 74.2 |
| #16 | 118.7 |
| #17 | 112.7 |

TABLE 9-continued

Effects of Oligomers on Clotting Times of
Activated Plasma in the Presence LMWH.

| | LMWH (4.6 ug/ml) |
|---|---|
| #18 | 48.6 |
| #19 | 34 |
| Oligomer (1.5 ug/ml) | |
| #19 | 232.8 |
| Oligomer (0.4 ug/ml) | |
| #2 | 117.6 |
| #4 | 137.7 |
| #11 | 161.2 |
| #18 | 140.1 |
| #19 | 64.2 |
| No LMWH, No oligomer | |
| Plasma-1 | 28.6 |
| Plasma-2 | 26 |

EXAMPLE 12

Synthesis and Antibacterial Properties of a Second Series of Arylamide Oligomers A series of arylamide oligomers were designed, synthesized, and their antibacterial activities and selectivity determined. Antibacterial assays, hemolysis assays, and vesicle leakage experiments were carried out as described above, and as in Tew, G. N., et al., *Proc. Natl. Acad. Sci. USA* 99:5110 (2002) and Liu, D. et al., *Angew. Chem. Int. Ed. Engl.* 43:1158-1162 (2004).

Triarylamide 1 (FIG. 18, 1, and compound 1 in Example 6) was selected as a template for optimizing the selectivity of a second arylamide series of antimicrobial oligomers. Various amino acid side chains were introduced into triarylamide 1 to produce compounds 2-12. Amino acid side chains were chosen because their amino groups would introduce an additional positively charged center, while theit sidechains would provide a ready source of diversity. Compounds 2 through 12 were synthesized by following the procedures outlined below and tested using antibacterial and hemolysis assoays. The results are presented in FIG. 18 and FIG. 19.

Compounds 2-4, which have increasingly hydrophobic substituents, showed good activity against both Gram-negative and Gram-positive bacteria (MIC=6 to 12 µg/ml versus both *E. coli* and *S. aureus*; FIG. 18). However, these compounds also showed toxicity towards human red cells, which increased as a function of the hydrophobicity of the sidechain. In contrast, the introduction of more polar substituents in compounds 5 through 8 led to oligomers with significantly lower toxicity towards erythrocytes. Compound 8, which features the dibasic Arg substituent, was the most active of the series. This compound displayed antibacterial activity similar to the potent magainin analogue MSl-78, and significantly greater selectivity. Given these results, an additional polar, positively charged, aminoalkyl substituent was introduced from the central isophthaloyl group. This substitution enhanced the selectivity of the compounds without greatly altering their potency, irrespective of the amino acid component (FIG. 19). Indeed, the Arg-containing analogue, compound 12, did not lyse red cells at concentrations as high as 800 µM.

To confirm the mechanism of action of this series of compounds, compound 8 to induce leakage of a fluorescent dye, calcein, from large unilamellar vesicles (LUV) composed of 90% stearolyloleoyl-phosphatidylcholine (SOPC) and 10% stearolyloleoyl-phosphatidylserine (SOPS) was determined. Lysis occurred in a concentration-dependent manner, beginning at concentrations as low as 0.625 µg/ml. With concentrations of oligomer near the MIC for inhibition of bacterial growth, the vesicle leakage was close to 90% at 300 s.

Because the amino acid sidechain appeared to influence the selectivity of the compounds, the relationship between the selectivity ratio (the ratio of the MIC for a given bacteria versus the $IC_{50}$ for lysing human erythrocytes) and the hydrophobicity for each compound was determined. Hydrophobicity was determined by estimating the n-octanol/water partitioning coefficient, $K_{ow}$, a common measure of the hydrophobicity of a molecule. (See, for example, J. Sangster, *Octanol-Water Partitioning Coefficients: Fundamentals and Physical Chemistry*, John Wiley & Sons, Chichester, 1997; and C. Hansch, A. Leo, *Exploring QSAR. Vol. 1: Fundamentals and Applications In Chemistry and Biology*, American Chemical Society, Washington, 1995). The atom/fragment approach was used to estimate $K_{ow}$ (W. M. Meylan, P. H. Howard, *Perspectives in Drug Discovery and Design* 2000, 19, 67). It was found that the logarithm of the selectivity ratio varied linearly with log $K_{ow}$.

Hydrophobic moment distributions were obtained for a few selected compounds from extensive molecular dynamics simulations of the arylamides. (See Liu, D. et al., *Angew. Chem. Int. Ed. Engl.* 43:1158-1162 (2004)). Inspection of the plots of the hydrophobic moment distributions for three of the compounds (not shown) revealed that the conformational ensemble for the Arg case (Compound 8) had the largest hydrophobic moment and therefore the most amphiphilic conformations. Visual inspection of configurations obtained from molecular dynamics simulations for compounds 2 and 8 revealed that the benzene rings on the two sides that the Arg groups of compound 8 were attached to were roughly perpendicular to the interface, with the t-butyl groups sliding into the n-octane phase and the polar side chains exposed into the water phase, a conformation that maximizes both polar and non-polar interactions.

By varying the appending group so as to adjust the overall charge, hydrophobicity and hydrophobic moment, arylamide oligomers with both good activity and selectivity were obtained.

The oligomers in this Example were synthesized according to the following synthetic schemes and protocols.

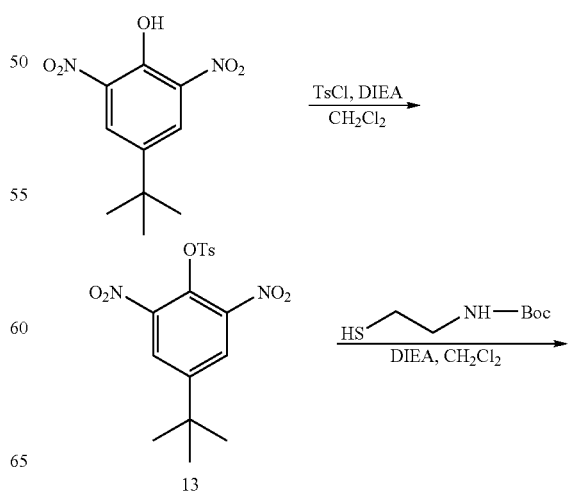

103
-continued
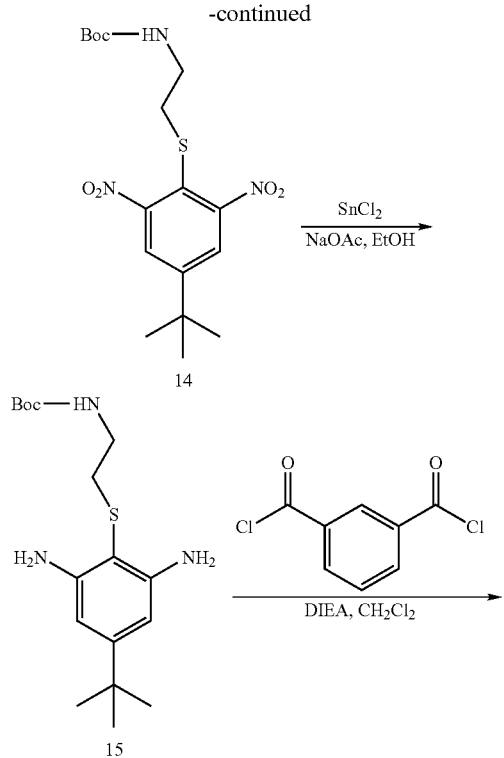
104
-continued
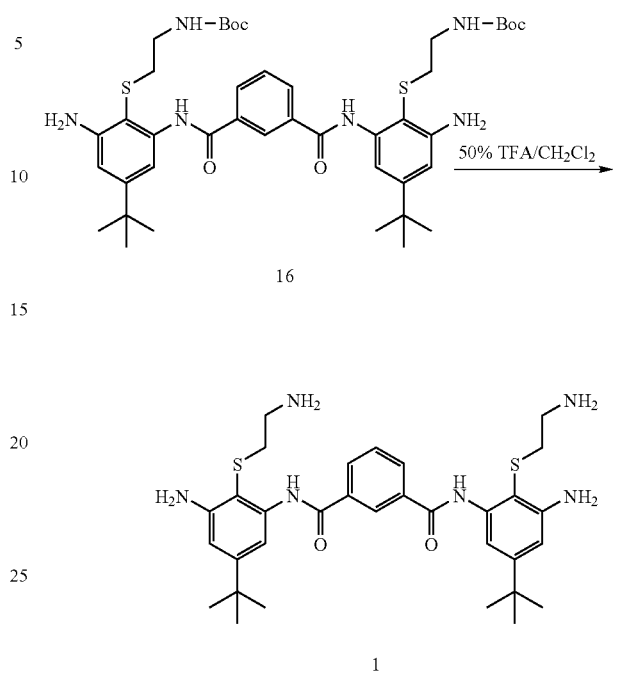
Scheme 2
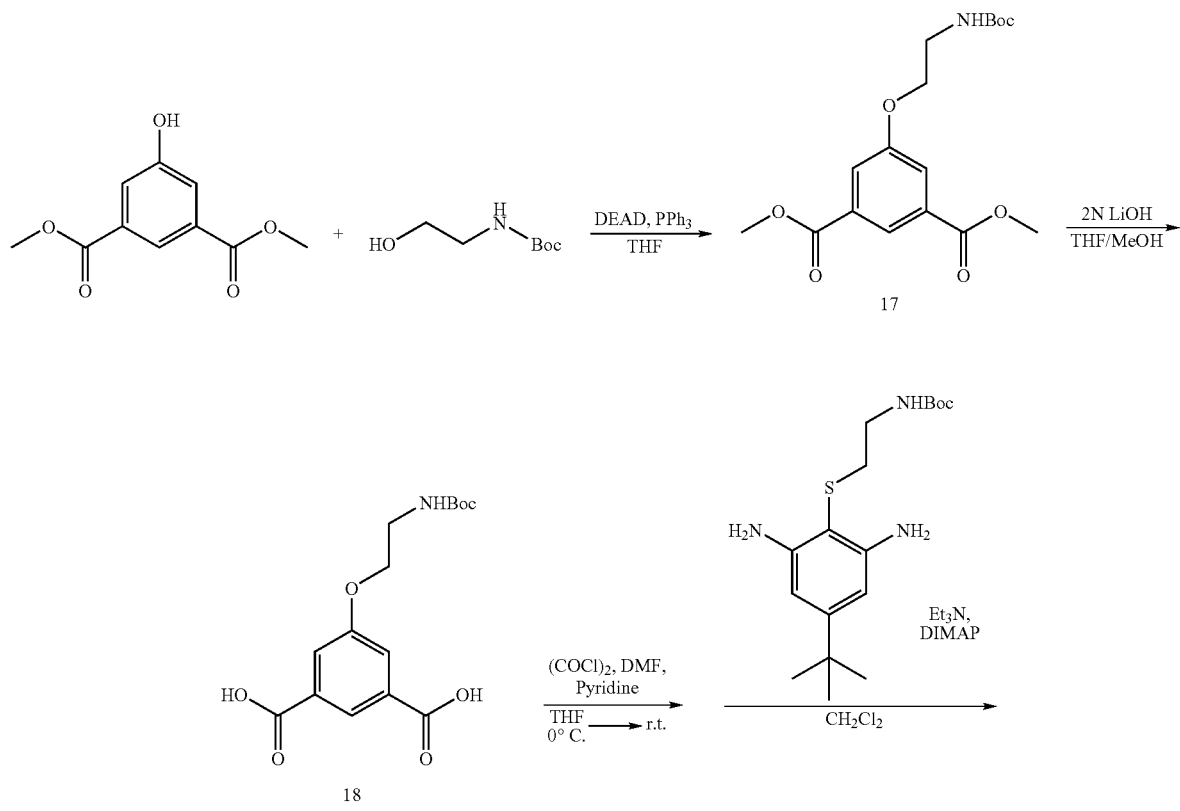

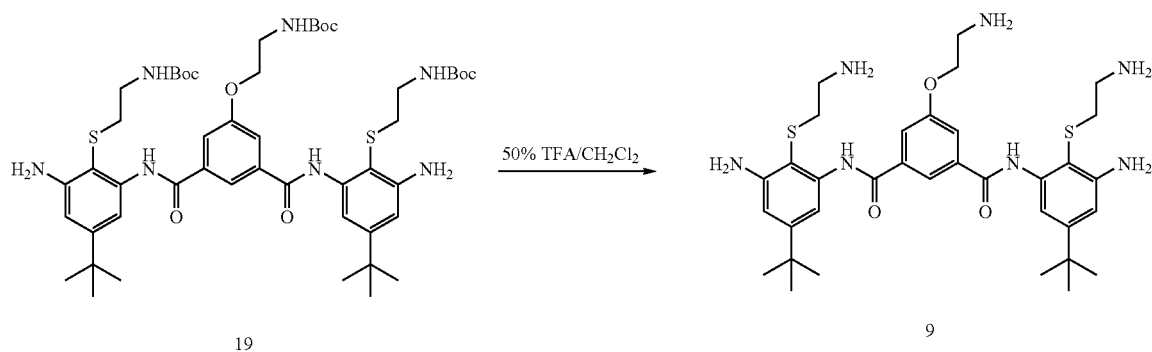
Scheme 3
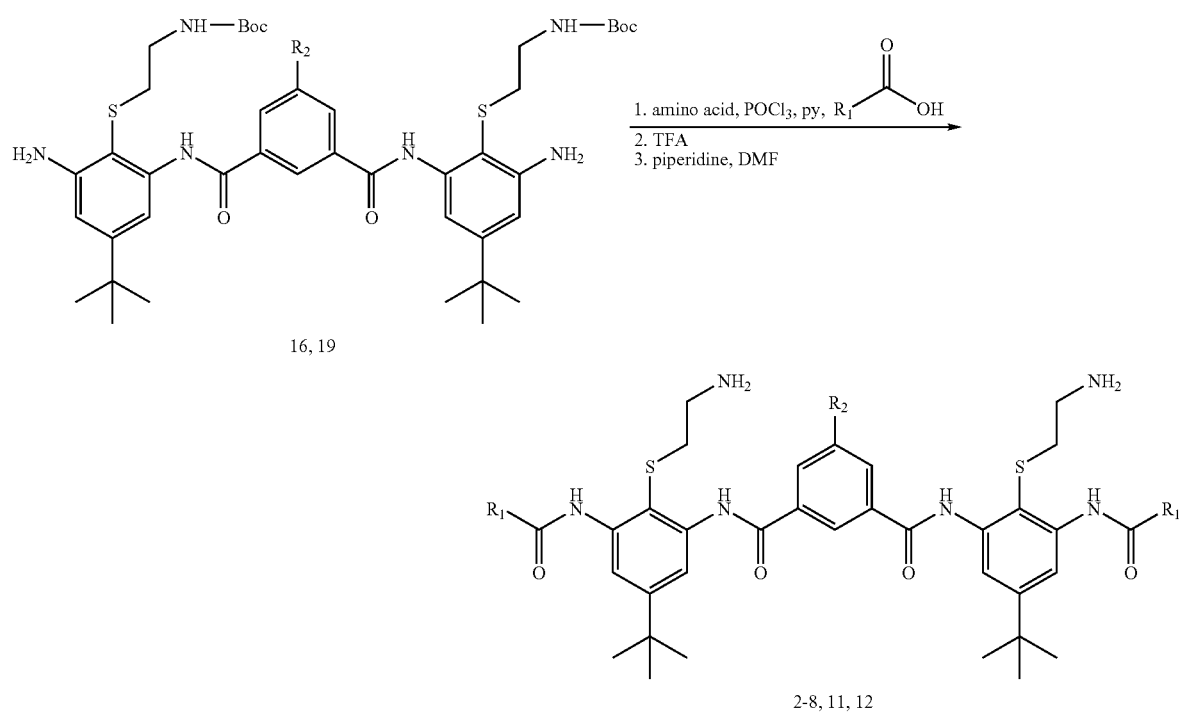
Scheme 4
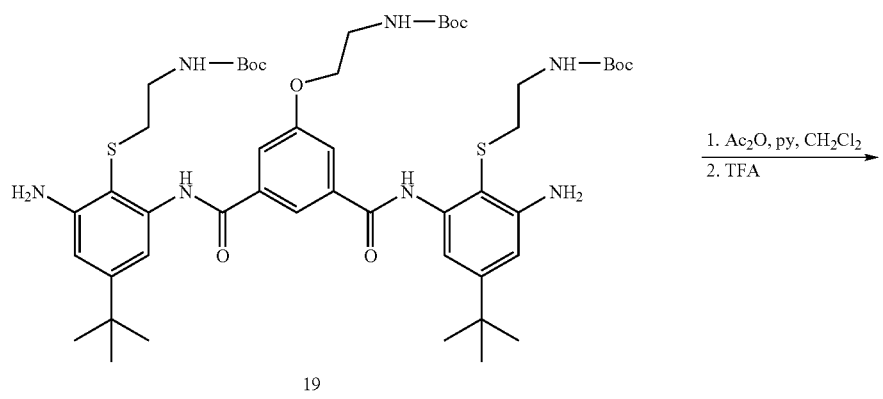

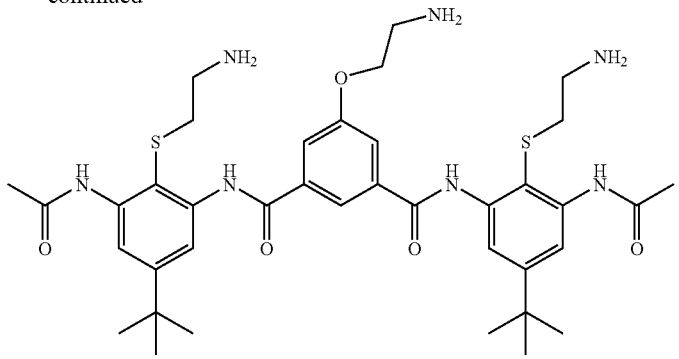

10

2,6-Dinitro-4-t-butyl-phenyl(4-methyl)-benzenesulfonate (13). 2,6-dinitro-4-t-butyl-phenol (80 mmol) and tosyl chloride (80 mmol) were dissolved in 300 ml $CH_2Cl_2$. Diisopropylethylamine (DIEA, 80 mmol) was added to the solution. The mixture was stirred at room temperature for 2 hours. The solution was washed with 10% citric acid, saturated aqueous NaCl, and dried with $MgSO_4$. The solvent was removed under reduced pressure, and the product was obtained as a bright yellow solid in quantitative yield. $^1H$ NMR (500 MHz, $CDCL_3$): δ=8.12 (s, 2H), 7.80 (d, 2H), 7.40 (d, 2H), 2.51(s, 3H), 1.41(s, 9H). ESI-MS: m/z ($M^+Na^+$): 417.07 (calcd), 417.2 (found).

2,6-Dinitro-4-t-butyl-1-(2-t-butoxycarbonylaminoethyl)-sulfanyl-benzene (14). Compound 1 (13 mmol), 2-Boc-aminoethanthiol (16 mmol) and DIEA (13 mmol) were dissolved in 50 ml chloroform. The solution was stirred under nitrogen for 12 hours. The solution was washed with 0.5 M NaOH, 10% citric acid, sat. $Na_2CO_3$ and sat. NaCl, and dried with $MgSO_4$. The solution volume was reduced to 15 ml by rotary evaporation. The product crystallized as a bright yellow solid after addition of 80 ml hexane. Yield: 94%. $^1H$ NMR (500 MHz, $CDCL_3$): δ=7.81(s, 2H), 4.87(s, 1H), 3.31(t, 2H), 3.10 (t, 2H), 1.44 (s, 9ff), 1.39(s, 9H). ESI-MS: m/z($M+Na^+$): 422.45 (calcd), 422.4 (found).

2,6-Diamino-4-t-butyl-1-(2-t-butoxycarbonylaminoethyl) sulfanyl-benzene (15). Dinitro compound 2 (20 mmol) and sodium acetate (200 mmol) were added to 50 ml EtOH. The mixture was heated to 78° C., and the solid dissolved completely. $SnCl_2$-$2H_2O$ (200 mmol) was added to the solution, and the reaction mixture was stirred at 78 C for 35 minutes. After removal of solvent under reduced pressure, the residue was dissolved in 800 ml EtOAc, and washed with 40% $KCO_3$. The solvent was reduced by rotary evaporation, and the product was purified by column chromatography (silica gel, $CH_2Cl_2$/MeOH 100:1 to 95:5). Yield: 93%. $^1H$ NMR (500 MHz, $CDCl_3$): δ=6.21(s, 2H), 5.41(s, 1H), 4.35(br, 4H), 3.21 (t, 2H), 2.75(t, 2H), 1.35(s, 9H), 1.24(s, 9H). ESI-MS: m/z ($MH^+$): 340.51(calcd), 340.5(found).

Synthesis of diamine 16 and 1

Diamine 15 (5 mmol) was dissolved in 50 mL $CH_2CL_2$ with DIEA. (10 mmol). Isophthaloyl dichloride (2.3 mmol) was dissolved in 10 mL $CH_2Cl_2$/DMF (4:1) and was added dropwise to the diamine solution under argon. The addition was finished in one hour. The mixture was stirred overnight. Solvent was removed using a rotovap. The product was purified by column chromatography (silica gel, Hexane/EtOAc 2:1 to 1:1). Yield 60%. $^1H$ NMR (500 MHz, $CDCl_3$): -=9.69 (s, 2H), 8.57 (s, 1H), 8.19 (d, 2H), 8.18 (s, 2H), 7.70 (t, 1H), 6.61 (s, 2H), 5.22 (b, 2H), 4.47 (b, 4H), 3.25 (m, 4H), 2.83 (t, 4H), 1.34 (s, 36H). MALDI-MS: m/z ($MNa^+$): 832.08 (calcd), 831.26(found). The Boc group of 16 was removed by treatment with 50% TFA/$CH_2CL_2$ to give compound 1. MALDI MS: m/z (MW) 608.86 (calcd), 609.26 (found).

Dimethyl 5-(((2-((t-butyloxy)carbonyl)amino)ethoxy) benzene-1,3-dicarboxylate (17). (See D. L. Boger, et al., Bioorg. Med. Chem. 1998, 6, 1347-1378).

To a solution of dimethyl 5-hydroxy isophthalate (5 g, 23.33 mmol), $PPh_3$ (6.73 g, 25.66 mmol), and t-butyl N-(2-hydroxyethyl)carbamate (4.05 ml, 25.66 mmol) in dry THF (60 ml) was added diethyl azodicarboxylate (11.64 ml, 25.66 mmol; 40% in toluene) dropwise at 0° C. The resulting mixture was warmed to room temperature and stirred for 24 hrs. The solvent was evaporated and the residue was dissolved with EtOAc. The organic layer was washed with $H_2O$, saturated NaCl(aq) and dried with $Na_2SO_4$. The solution was filtered and concentrated. The residue was purified by column chromatography (pet. Ether/$Et_2O$ 5:3) to give compound 17 (5.41 g, 71%). $^1H$ NMR(500 MHz, $CDCl_3$): δ 1.43(s, 9H), 3.54(m, 2H), 3.92(s, 6H), 4.08(t, 2H), 5.01(s, 1H), 7.71(s, 2H), 8.26(s, 1H). Electrospray ionization-MS: m/z ($MNa^+$): 376.1372 (calcd), 376.1363 (found).

5-(((2(t-butyloxy)carbonyl)amino)ethoxy)benzene-1, 3-dicarboxylic acid (18)

To a solution of compound 17 (1.66 g, 4.70 mmol) in MeOH/THF (10 ml:10 ml) was added 2N LiOH (9.28 ml, 18.80 ml). The resulting mixture was stirred for 24 hrs. The MeOH and THF was removed under reduced pressure. The aqueous solution was diluted with $H_2O$ (20 ml) and cooled down to 0° C. and acidified to pH3 with 3N HCl. The white precipitate was filtered and washed with $H_2O$. Compound 18 (1.46 g, 96%) was obtained without further purification (TLC indicated it is pure compound). $^1H$ NMR(500 MHz, DMSO-$d_6$): δ 1.37(s, 9H), 3.32(m, 2H), 4.08(t, 2H), 6.98(t, 1H), 7.64(s, 2H), 8.07(s,1H), 13.23(s, 2H). Electrospray ionization-MS: m/z ($MNa^+$): 348.1059 (calcd), 348.1062 (found).

Synthesis of diamine 19 and 9

To a solution of diacid compound 18 (200 mg, 0.615 mmol) in dry THF (10 ml) was added pyridine (149 µl, 1.845 mmol) and DMF (catalytic amount). The resulting mixture was cooled down to 0° C. and then oxalyl chloride (164 µl, 1.845 mmol) was added dropwise. After stirring for 45 mm at room temperature, the solvent, excess oxalyl chloride, and pyridine were removed under vacuum to give the crude acyl chloride which was directly used in the following without further purification. To a solution of diamine compound (630 mg, 1.845 mmol), $Et_3N$ (5 14111, 3.69 mmol), and DMAP (7.5 mg, 0062 mmol) in dry CH$_2$Cl$_2$ (10 ml) was added the crude acyl chloride in CH$_2$Cl$_2$ (20 ml) dropwise for 2 hrs. After a total of 7 hrs, the solvent was removed and then the residue was dissolved in EtOAc and washed with saturated NaHCO$_3$ (aq) and saturated NaCl(aq). After drying on Na$_2$SO$_4$, the organic layer was filtered and concentrated under reduced pressure. The residue was purified by column chromatography (Hexane/EtOAc 2:1) to give diamine 19 (369 mg, 62%). $^1$H NMR (500 MHz, DMSO-d$_6$): δ 1.25-1.29(36H), 1.38(s, 9H), 2.63(t, 4H), 3.00(br d, 4H), 3.38(m, 4H), 4.15(t, 4H), 5.50(s, 4H), 6.70(s, 2H), 6.85(s, 2H), 7.05(s, 1H), 7.27(s, 2H), 7.70(s, 2H), 8.10(s, 1H), 9.84(s, 2H). Electrospray ionization-MS: m/z (MNa$^+$) 990.4809 (calcd), 990.4828 (found). The Boc group of 19 was removed by treatment with 50% TFA/CH$_2$Cl$_2$ to give compound 9. Electrospray ionization-MS: m/z (MH$^+$) 667.3417 (calcd), 668.3447 (found).

General Method to Synthesize amino acid Appended arylamides (2-8, 11, 12). (See D. T. S. Rijkers, et al., *Tetrahedron* 1995, 51, 11235-11250)

Boc amino acids (Boc protecting group for both α-amino and side chain amino groups) were used for the synthesis except arginine. Fmoc D-Arg (pbf) was used for synthesis of 8 and 12. Diamine 16 or 19 (2 mmol) and protected amino acid (8 mmol) were dissolved in 30 mL anhydrous pyridine and was cooled down to –30 C with dry ice/acetone. POCL$^3$ (8 mmol) was added dropwise to the solution in 0.5 hour. The mixture was stirred for another 0.5 hour before the reaction was quenched with 50 mL ice water. The product was extracted with EtOAc (50 ml×1, 30 ml×3), washed with 10% citric acid (50 mL×1), sat. NaHCO$_3$ (50 mL×3) and sat. NaCl (50 mL×1). The protected product was purified by column chromatograph (silica gel, CH$_2$Cl$_2$/MeOH 100:1 to 98:2). Boc and pbf groups were removed by treatment of 20 ml TFA/TIS (95:5) for one hour. Fmoc group was removed by 30 mL 20% piperidine for one hour. The product was concentrated to an oil. Water (0.1% HCl, 100 mL) was added to the oil. The aqueous solution was washed with ether (50 mL×4) and dried on a lyophilizer. Further purification was carried out on HPLC. Yield 60%. MALDI-MS: m/z (MW): 2:835.18 (calcd), 835.33(found); 3:903.21 (calcd), 903.38 (found); 4:981.28 (calcd), 981.44(found); 5:779.07 (calcd), 779.26 (found); 6:831.15 (calcd), 831.35 (found); 7:865.21 (calcd), 865.44 (found); 8:921.23 (calcd), 921.91(found); 11:962.48 (calcd), 962.48 (found); 12:980.54 (calcd), 980.54 (found).

Synthesis of 10

To a solution of arylamide compound 19 (37 mg, 0.038 mmol) and DMAP (cat.) in dry CH$_2$Cl$_2$ (3 ml) was added pyridine (31 μl, 0.38 mmol). The resulting mixture was cooled down to 0° C. and treated with acetic anhydride (36 μl, 0.38 mmol) and then warmed to room temperature. After stirring for 12 hrs, the solvent was removed under reduced pressure. The residue was dissolved with EtOAc and washed with 10% citric acid(aq), saturated NaHCO$_3$(aq), and saturated NaCl(aq). After drying on Na$_2$SO$_4$, the organic layer was filtered and concentrated under reduced pressure. The residue was purified by column chromatography (Hexane/EtOAc 1:1.5 to 1:2) to give diacetylated compound (31 mg, 78%).

The Boc group of diacetylated compound was removed by treatment with 50% TFA/CH$_2$Cl$_2$ to give compound 10. Electrospray ionization-MS: m/z (MH$^+$): 752.3628 (calcd), 752.3661 (found).

Having now fully described this invention, it will be understood to those of ordinary skill in the art that the same can be performed within a wide and equivalent range of conditions, formulations, and other parameters without affecting the scope of the invention or any embodiment thereof. All documents, e.g., scientific publications, patents, patent applications and patent publications recited herein are hereby incorporated by reference in their entirety to the same extent as if each individual document was specifically and individually indicated to be incorporated by reference in its entirety. Where the document cited only provides the first page of the document, the entire document is intended, including the remaining pages of the document.

What is claimed is:

1. A method of treating a microbial infection in an animal in need thereof, said method comprising systemically administering to the animal an effective amount of a pharmaceutical composition comprising an amphiphilic oligomer of Formula II:

$$R^1\text{-}[\text{-}x\text{-}A_1\text{-}x\text{-}y\text{-}A_2\text{-}y\text{-}]_m\text{-}R^2 \qquad (II)$$

or an acceptable salt or solvate thereof, wherein:

x is NR$^8$, —N(R$^8$)N(R$^8$)—, or —C(R$^7$R$^7$')NR$^8$—, and y is C=O;

wherein R$^8$ is hydrogen; R$^7$ and R$^7$'are independently hydrogen or alkyl, or R$^7$ and R$^7$'together are —(CH$_2$)$_p$—, wherein p is 4 to 8;

A$_1$ and A$_2$ are independently o-, m-, or p-phenylene or one of A$_1$ and A$_2$ is o-, m-, or p-phenylene and the other of A$_1$ and A$_2$ is heteroarylene, wherein A$_1$ is substituted with one or more polar (PL) groups and is optionally substituted with one or more non-polar (NPL) groups and A$_2$ is independently optionally substituted with one or more polar (PL) groups, one or more non-polar (NPL) groups, or a combination of one or more polar (PL) groups and one or more non-polar (NPL) groups;

R$^1$ is (i) hydrogen, a polar group (PL), or a non-polar group (NPL), and R$^2$ is -x-A$_1$-x-R$^1$, wherein A$_1$ is as defined above; or (ii) hydrogen, a polar group (PL), or a non-polar group (NPL), and R$^2$ is -x-A'-x -R$^1$, wherein A' is arylene or heteroarylene and is optionally substituted with one or more polar (PL) groups, one or more non-polar (NPL) groups, or a combination of one or more polar (PL) groups and one or more non-polar (NPL) groups;

(iii) -y-A$_2$-y-R$^2$, and R$^2$ is hydrogen, a polar group (PL), or a non-polar group (NPL); or (iv) -y-A' and R$^2$ is -x-A', wherein A' is aryl or heteroaryl and is optionally substituted with one or more polar (PL) groups, one or more non-polar (NPL) groups, or a combination of one or more polar (PL) groups and one or more non-polar (NPL) groups; or (V) R$^1$ and R$^2$ are independently a polar group (PL) Or a non-polar group (NPL); or (vi) R$^1$ and R$^2$ together form a single bond;

NPL is a nonpolar group independently selected from the group consisting of —B(OR$^4$)$_2$ and —(NR$^{3'}$)$_{q1NPL}$—U$^{NPL}$—(CH$_2$)$_{pNPL}$—(NR$^{3''}$)$_{q2NPL}$—R$^{4'}$, wherein:

R$^3$, R$^{3'}$, and R$^{3''}$ are independently selected from the group consisting of hydrogen, alkyl, and alkoxy;

R$^4$ and R$^{4'}$are independently selected from the group consisting of hydrogen, alkyl, alkenyl, alkynyl, cycloalkyl, aryl, and heteroaryl, any of which is optionally substituted with one or more alkyl or halo groups;

U$^{NPL}$ is absent or selected from the group consisting of O, S, S(=O), S(=O)$_2$, NR$^3$, —C(=O)—, —C(=O)—N=N—NR$^3$—, —C(=O)—NR$^3$—N=N—, —N=N—NR$^3$—, —C(=N—N(R$^3$)$_2$)—, —C(=NR$^3$)—, —C(=O)O—, —C(=O)S—, —C(=S)—, —O—P(=O)$_2$O—, —R$^3$O—, —R³S—, —S—C≡N— and —C(=O)—NR³—O—, wherein groups with two chemically nonequivalent termini can adopt both possible orientations;

the —(CH₂)$_{pNPL}$- alkylene chain is optionally substituted with one or more amino or hydroxy groups, or is unsaturated;

pNPL is 0 to 8;

q1NPL and q2NPL are independently 0, 1 or 2;

PL is a polar group selected from the group consisting of halo, hydroxyethoxymethyl, methoxyethoxymethyl, polyoxyethylene, and —(NR⁵')$_{q1PL}$—U$^{PL}$—(CH₂)$_{pPL}$—(NR⁵')$_{q2PL}$—V, wherein:

R⁵, R⁵', and R⁵" are independently selected from the group consisting of hydrogen, alkyl, and alkoxy;

U$^{PL}$ is absent or selected from the group consisting of O, S, S(=O), S(=O)₂, NR⁵, —C(=O)—, —C(=O)—N=N—NR⁵—, —C(=O)—NR⁵—N=N—, —N=N—NR⁵—, —C(N=N(R³)₂)—, —C(=NR⁵)—, —C(=O)O—, —C(=O)S—, —C(=S)—, —O—P(=O)₂O—, —R⁵O—, —R⁵S—, —S—C≡N— and —C(=O)—NR⁵—O—, wherein groups with two chemically nonequivalent termini can adopt both possible orientations;

V is selected from the group consisting of nitro, cyano, amino, hydroxy, alkoxy, alkylthio, alkylamino, dialkylamino, —NH(CH₂)$_p$NH₂ wherein p is 1 to 4, —N(CH₂CH₂NH₂)₂, diazamino, amidino, guanidino, guanyl, semicarbazone, aryl, heterocycle and heteroaryl, any of which is optionally substituted with one or more of amino, halo, cyano, nitro, hydroxy, —NH(CH₂)$_p$NH₂ wherein p is 1 to 4, —N(CH₂CH₂NH₂)₂, amidino, guanidino, guanyl, aminosulfonyl, aminoalkoxy, aminoalkythio, lower acylamino, or benzyloxycarbonyl;

the —(CH₂)$_{pPL}$— alkylene chain is optionally substituted with one or more amino or hydroxy groups, or is unsaturated;

pPL is 0 to 8;

q1PL and q2PL are independently 0, 1 or 2; and m is 1, 2 or 3;

and a pharmaceutically acceptable carrier or diluent.

2. A method of treating a microbial infection in an animal in need thereof, said method comprising systemically administering to the animal an effective amount of a pharmaceutical composition comprising an amphiphilic oligomer of Formula II:

$$R^1\text{-}[\text{-}x\text{-}A_1\text{-}x\text{-}y\text{-}A_2\text{-}y\text{-}]_m\text{-}R^2 \quad (II)$$

or an acceptable salt or solvate thereof, wherein:

x is NR⁸, y is C=O, and R⁸ is hydrogen;

$A_1$ and $A_2$ are independently o-, m-, or p-phenylene or pyrimidinylene, wherein $A_1$ is substituted with one or more polar (PL) groups and is optionally substituted with one or more non-polar (NPL) groups and $A_2$ is independently optionally substituted with one or more polar (PL) groups, one or more non-polar (NPL) groups, or a combination of one or more polar (PL) groups and one or more non-polar (NPL) groups;

$R^1$ is hydrogen, a polar group (PL), or a non-polar group (NPL), and $R^2$ is -x-$A_1$-x-$R^1$, wherein $A_1$ is as defined above;

NPL is —(NR³')$_{q1NPL}$—U$^{NPL}$—(CH₂")$_{q2NPL}$—(NR³")$_{q2NPL}$—R⁴' wherein:

R³, R³', and R³" are independently selected from the group consisting of hydrogen, $C_1$-$C_6$ alkyl, and $C_1$-$C_6$ alkoxy;

R⁴' is selected from the group consisting of hydrogen, $C_1$-$C_{10}$ alkyl, $C_3$-$C_{18}$ branched alkyl, $C_2$-$C_{10}$ alkenyl, $C_2$-$C_{10}$ alkynyl, $C_3$-$C_8$ cycloalkyl, $C_6$-$C_{10}$ aryl, and heteroaryl, any of which is optionally substituted with one or more $C_1$-$C_6$ alkyl or halo groups;

U$^{NPL}$ is absent or selected from the group consisting of O, S, NH, —C(=O)—, —C(=O)—N=N—NH—, —C(=O)—NH—N=N—, —N=N—NH—, —C(=N—N(R³)₂)—, —C(=NR³)—, —C(=O)O—, —R³S— and —R³O—, wherein groups with two chemically nonequivalent termini can adopt both possible orientations;

the —(CH₂)$_{pNPL}$— alkylene chain is optionally substituted with one or more amino or hydroxy groups;

pNPL is 0 to 6;

q1NPL and q2NPL are 0;

PL is —(NR⁵')$_{q1PL}$—U$^{PL}$—(CH₂)$_{pPL}$—(NR⁵')$_{q2PL}$—V, wherein:

R⁵, R⁵', and R⁵" are independently selected from the group consisting of hydrogen, $C_1$-$C_6$ alkyl, and $C_1$-$C_6$ alkoxy;

U$^{PL}$ is absent or selected from the group consisting of O, S, NH, —C(=O)—, —C(=O)—N=N—NH—, —C(=O)—NH—N=N—, —N=N—NH—, —C(=N—N(R³)₂)—, —C(=NR⁵)—, —C(=O)O—, —R⁵O—, and —R⁵S—, wherein groups with two chemically nonequivalent termini can adopt both possible orientations;

V is selected from the group consisting of nitro, cyano, amino, hydroxy, $C_1$-$C_6$ alkoxy, $C_1$-$C_6$ alkylthio, $C_1$-$C_6$ alkylamino, $C_1$-$C_6$ dialkylamino, —NH(CH₂)$_p$NH₂ wherein p is 1 to 4, —N(CH₂CH₂NH₂)₂, diazamino, amidino, guanidino, guanyl, semicarbazone, $C_6$-$C_{10}$ aryl, heterocycle, and heteroaryl;

the —(CH₂)$_{pPL}$— alkylene chain is optionally substituted with one or more amino or hydroxy groups;

pPL is 0 to 6;

q1PL and q2PL are 0;

m is 1, 2 or 3, and a pharmaceutically acceptable carrier or diluent.

3. The method of claim 1, wherein x is NR⁸, y is C=O, and R⁸ is hydrogen.

4. The method of claim 1, wherein x is —N(R⁸)N(R⁸)—, y is C=O, and R⁸ is hydrogen.

5. The method of claim 1, wherein $A_1$ and $A_2$ are independently o-, m-, or p-phenylene.

6. The method of 5, wherein $A_1$ and $A_2$ are m-phenylene.

7. The method of claim 1, wherein one of $A_1$ and $A_2$ is o-, m- or p-phenylene, and the other of $A_1$ and $A_2$ is heteroarylene.

8. The method of claim 7, wherein one of $A_1$ and $A_2$ is m-phenylene, and the other of $A_1$ and $A_2$ is pyrimidinylene.

9. The method of claim 7, wherein one of $A_1$ is substituted with one or more polar (PL) groups and one or more nonpolar (NPL) groups and $A_2$ is unsubstituted.

10. The met god of claim 1 wherein $A_1$ and $A_2$ are m-phenyiene, and $A_1$ is substituted with one polar (PL) group and one nonpolar (NPL) group and $A_2$ is unsubstituted.

11. The method of claim 1, wherein $R^1$ is hydrogen, a polar group (PL), or a non-polar group (NPL), and $R^2$ is -x-$A_1$-x-$R^1$, wherein $A_1$ is as defined in claim 1.

12. The method of claim 11, wherein $R^1$ is a polar (PL) group and $R^2$ is -x-$A_1$-x-$R^1$, where $A_1$ is substituted with one or two polar (PL) groups and one non-polar (NPL) group.

13. The method of claim 1, wherein:
NPL is —(NR$^{3'}$)$_{q1NPL}$—U$^{NPL}$—(CH$_2$)$_{pNPL}$—(NR$^{3''}$)$_{q2NPL}$—R$^{4'}$, and R$^3$ R$^{3'}$R$^{3''}$R$^{4'}$U$^{NPL}$, pNPL, q1NPL and q2NPL are as defined in claim 1.

14. The method of claim 13, wherein R$^3$, R$^{3'}$, and R$^{3''}$ are independently hydrogen, C$_1$-C$_6$ alkyl, or C$_1$-C$_6$ alkoxy.

15. The method of claim 14, wherein R$^3$, R$^{3'}$, and R$^{3''}$ are hydrogen.

16. The method of claim 13, wherein R$^{4'}$ is C$_1$-C$_{10}$ alkyl, C$_3$-C$_{18}$ branched alkyl, C$_2$-C$_{10}$ alkenyl, C$_2$-C$_{10}$ alkynyl, or C$_6$-C$_{10}$ aryl.

17. The method of claim 16, wherein R$^{4'}$ is phenyl, methyl, ethyl, n-propyl, isopropyl, n-butyl, tent-butyl, or n-pentyl.

18. The method of claim 13, wherein U$^{NPL}$ is O, S, NH, —C(=O)—, —C(=O)—N=N—NH—, —C(=O)—NH—N=N—, —N=N—NH—, —C(=N—N(R$^3$)$_2$)—, —C(=NR$^3$)—, —C(=O)O—, —R$^3$S—or—R$^3$O—.

19. The method of claim 18, wherein U$^{NPL}$ is —C(=O)—.

20. The method of claim 13, wherein U$^{NPL}$ is absent.

21. The method of claim 1, wherein NPL is n-propyl, isopropyl, n-butyl, or tent-butyl.

22. The method of claim 13, wherein:
pNPL is 0 to 2; and q1NPL and q2NPL are independently 0 or 1.

23. The method of claim 13, wherein the —(CH$_2$)$_{pNPL}$— alkylene chain in NPL is substituted with one or more amino groups.

24. The method of claim 1, wherein:
PL is —(NR$^{5'}$)$_{q1PL}$—U$^{PL}$—(CH$_2$)$_{pPL}$—(NR$^{5''}$)$_{q2PL}$—V, and R$^5$, R$^{5'}$R$^{5''}$, V, U$^{PL}$, pPL, q1PL and q2PL are as defined in claim 1.

25. The method of claim 24, wherein R$^5$, R$^{5'}$, and R$^{5''}$ are independently hydrogen, C$_1$-C$_6$ alkyl, or alkoxy.

26. The method of claim 24, wherein U$^{PL}$ is O, S, NH, —C(=O)—, —C(=O)—N=N—NH—, —C(=O)—NH—N=N—, —N=N—NH—, —C(=N—N(R$^5$)$_2$)—, —C(=NR$^5$)—, —C(=O)O—, R$^5$S—or—R$^5$O—.

27. The method of claim 24, wherein U$^{PL}$ is O, S, —C(=O), or is absent.

28. The method of claim 24, wherein V is amino, C$_1$-C$_6$ alkylamino, —NH(CH$_2$)$_p$NH$_2$ wherein p is 1 to 4, —N(CH$_2$CH$_2$NH$_2$)$_2$ diazamino, amidino, or guanidino.

29. The method of claim 24, wherein pPL is 2 to 4, and q1PL and q2PL are 0.

30. The method of claim 24, wherein the —(CH$_2$)$_{pPL}$— alkylene chain in PL is substituted with one or more amino groups.

31. The method of claim 1, wherein:
x is NR$^8$, y is C=O, and R$^8$ is hydrogen;
A$_1$ and A$_2$ are m-phenyiene, wherein
 (i) A$_1$ is substituted with one polar (PL) group and one nonpolar (NPL) group and A$_2$ is unsubstituted; or
 (ii) A$_1$ is substituted with one polar (PL) group and one nonpolar (NPL) group and A$_2$ is substituted with one or two polar (PL) groups;
R$^1$ is hydrogen or a polar group (PL), and R$^2$ is -x-A$_1$-x-R$^1$, wherein A$_1$ is as defined above;
NPL is —(NR$^{3'}$)$_{q1NPL}$—U$^{NPL}$—(CH$_2$)$_{pNPL}$—(NR$^{3''}$)$_{q2NPL}$—R$^{4'}$, wherein:
R$^3$, R$^{3'}$, and R$^{3''}$ are independently selected from the group consisting of hydrogen, C$_1$-C$_6$ alkyl, and C$_1$-C$_6$ alkoxy;
R' is selected from the group consisting of hydrogen, C$_1$-C$_{10}$ alkyl, C$_3$-C$_{18}$ branched alkyl, C$_2$-C$_{10}$ alkenyl, C$_2$-C$_{10}$ alkynyl, C$_3$-C$_8$ cycloalkyl, C$_6$-C$_{10}$ aryl, and heteroaryl, any of which is optionally substituted with one or more C$_1$-C$_6$ alkyl or halo groups;

U$^{NPL}$ is absent or selected from the group consisting of O, S, NH, —C(=O)—, —R$^3$S—and —R$^3$O—, wherein groups with two chemically nonequivalent termini can adopt both possible orientations;
the 2(CH$_2$)$_{pNPL}$- alkylene chain is optionally substituted with one or more amino groups;
pNPL is 0 to 6;
q1NPL and q2NPL are 0;
PL is —(NR$^{5'}$)$_{q1PL}$—U$^{PL}$—(CH$_2$)$_{pPL}$—(NR$^{5'}$)$_{q2PL}$—V, wherein:
R$^5$, R$^{5'}$, and R$^{5''}$are independently selected from the group consisting of hydrogen, C$_1$-C$_6$ alkyl, and C$_1$-C$_6$ alkoxy;
U$^{PL}$ is absent or selected from the group consisting of O, S, NH, —C(=O)—, —R$^5$O—, and —R$^5$S—, wherein groups with two chemically nonequivalent termini can adopt both possible orientations;
V is selected from the group consisting of amino, hydroxy, C$_1$-C$_6$ alkylamino, —NH(CH$_2$)$_p$NH$_2$ wherein p is 1 to 4, —N(CH$_2$CH$_2$NH$_2$)$_2$, diazamino, amidino, and guanidine;
the —(CH$_2$)$_{pPL}$- alkylene chain is optionally substituted with one or more amino groups;
pPL is 0 to 6;
q1PL and q2PL are 0; and
m is 1,2 or 3.

32. A method of treating a microbial infection in an animal in need thereof, said method comprising systemically administering to the animal an effective amount of a pharmaceutical composition comprising an amphiphilic oligomer of Formula II:

$$R^1\text{-}[\text{-}_x\text{-}A_1\text{-}x\text{-}y\text{-}A_2\text{-}y\text{-}]_m\text{-}R^2 \qquad (II)$$

or an acceptable salt or solvate thereof, wherein:
x is NR$^8$, y is C=O, and R$^8$ is hydrogen;
A$_1$ and A$_2$ are m-phenylene or m-pyrimidinylene, wherein one of A$_1$ and A$_2$ is m-phenylene, and the other of A$_1$ and A$_2$ is pyrimidinylene, and wherein
 (i) A$_1$ is substituted with one polar (PL) group and one nonpolar (NPL) group and A$_2$ is unsubstituted; or
 (ii) A$_1$ is substituted with one polar (PL) group and one nonpolar (NPL) group and A$_2$ is substituted with one or two polar (PL) groups;
R$^1$ is hydrogen or a polar group (PL), and R$^2$ is -x-A$_1$-x-R$^1$, wherein A$_1$ is as defined above;
NPL is —(NR$^{3'}$)$_{q1NPL}$—U$^{NPL}$—(CH$_2$)$_{pNPL}$—(NR$^{3''}$)$_{q2NPL}$—R$^{4'}$, wherein:
R$^3$, R$^{3'}$, and R$^{3''}$are independently selected from the group consisting of hydrogen, C$_1$-C$_6$ alkyl, and C$_1$-C$_6$ alkoxy;
R$^{4'}$ is selected from the group consisting of hydrogen, C$_1$-C$_{10}$ alkyl, C$_3$-C$_{18}$ branched alkyl, C$_2$-C$_{10}$ alkenyl, C$_2$-C$_{10}$ alkynyl, C$_3$-C$_8$ cycloalkyl, C$_6$-C$_{10}$ aryl, acid beteroaryl, any of whiCh is optionally substituted with one or more C$_1$-C$_6$ alkyl or halo groups;
U$^{NPL}$ is absent or selected from the group consisting of O S, NH, —C(=O)—, —R$^3$S—and —R$^3$O—, wherein groups with two chemically nonequivalent termini can adopt both possible orientations;
the —(CH$_2$)$_{pNPL}$— alkylene chain is optionally substituted with one or more amino groups;

pNPL is 0 to 6;
q1NPL and q2NPL are 0;
PL is —(NR$^{5'}$)$_{q1PL}$—U$^{PL}$—(CH$_2$)$_{pPL}$—(NR$^{5'}$)$_{q2PL}$—V, wherein:
R$^5$, R$^{5'}$, and R$^{5''}$ are independently selected from the group consisting of hydrogen, C$_1$-C$_6$ alkyl, and C$_1$-C$_6$ alkoxy;
U$^{PL}$ is absent or selected from the group consisting of O, S, NH, —C(=O)—, —R$^5$O—, and —R$^5$S—, wherein groups with two chemically nonequivalent termini can adopt both possible orientations;
V is selected from the group consisting of amino, hydroxy, C$_1$-C$_6$ alkylamino, —NH(CH$_2$)$_p$NH$_2$ wherein p is 1 to 4, —N(CH$_2$CH$_2$NH$_2$)$_2$, diazamino, amidino, and guanidino;
the —(CH$_2$)$_{pPL}$— alkylene chain is optionally substituted with one or more amino groups;
pPL is 0 to 6;
q1PL and q2PL are 0; and
m is 1, 2 or 3,
and a pharmaceutically acceptable carrier or diluent.

33. The method of claim 32, wherein the amphiphilic oligomer is selected from the group consisting of:

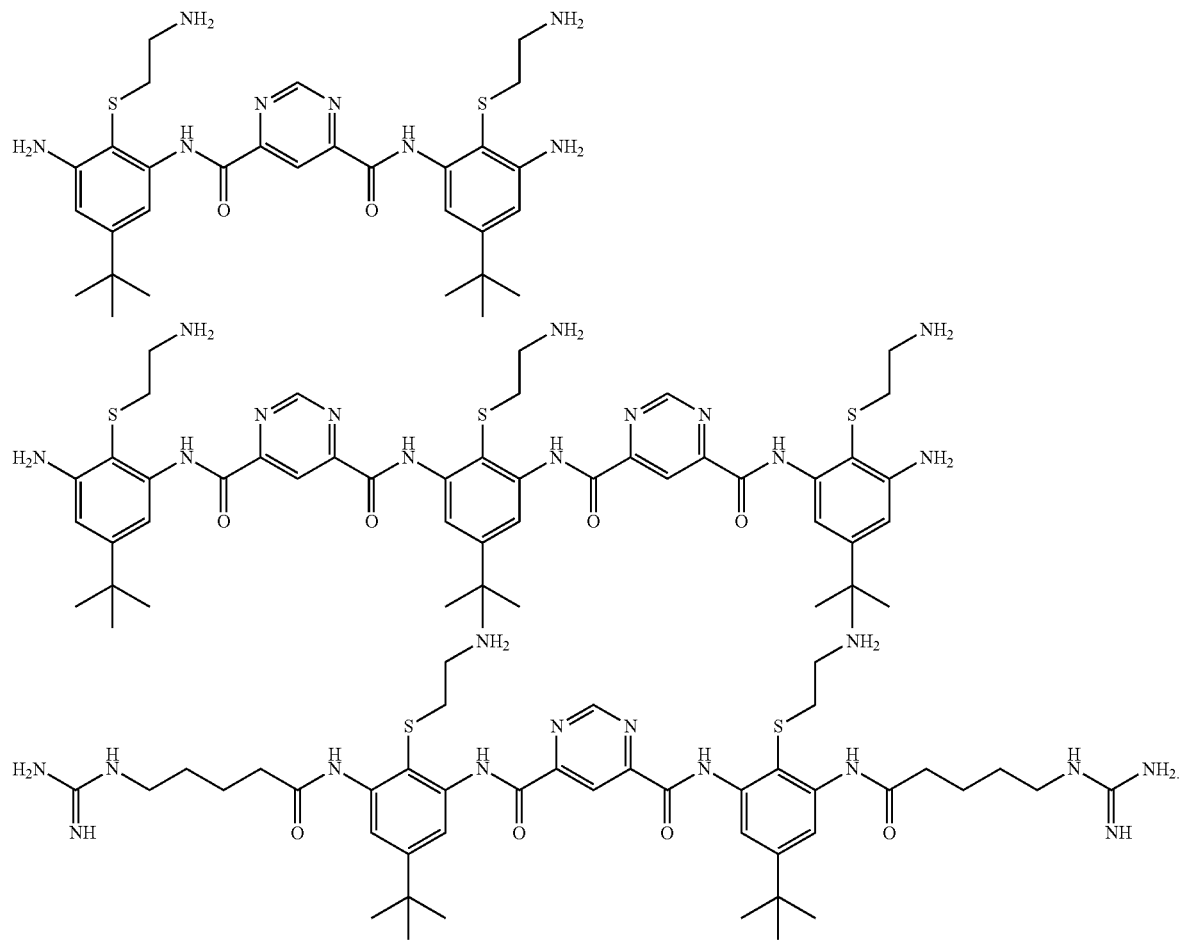

34. The method of claim 1, wherein the microbial infection is a bacterial infection, a fungal infection, or a viral infection.

35. The method of claim 1, wherein the heteroarylene selected from the group consisting of pyridinylene, pyrimidinylene, and pyrazinylene.

36. The method of claim 1, wherein:
x is NR$^8$, y is C=O, and R$^8$ is hydrogen;
one of A$_1$ and A$_2$ is m-phenylene, and the other of A$_1$ and A$_2$ is pyrimidinylene, wherein A$_1$ is substituted with one polar (PL) group and one nonpolar (NPL) group and A$_2$ is unsubstituted;
R$^1$ is a polar group (PL), and R$^2$ is -x-A$_1$-x-R$^1$;
NPL is a nonpolar group —(NR$^{3'}$)$_{q1NPL}$—U$^{NPL}$—(CH$_2$)$_{q2NPL}$—(NR$^{3''}$)$_{q2NPL}$—R$^{4'}$, wherein:
R$^{4'}$ is selected from the group consisting of hydrogen, alkyl, alkenyl, alkynyl, cycloalkyl, aryl, and heteroaryl, any of which is optionally substituted with one or more alkyl or halo groups;
U$^{NPL}$ is absent;
pNPL is 0, 1 or 2;
q1NPL and q2NPL are independently 0;
PL is a polar group —(NR$^{5'}$)$_{q1PL}$—U$^{PL}$—(CH$_2$)$_{pPL}$—(NR$^{5'}$)$_{q2PL}$—V, wherein:
U$^{PL}$ is selected from the group consisting of O, S, and —C(=O)—;
pPL is 0 to 4;
q1PL and q2PL are independently 0;

V is selected from the group consisting of nitro, cyano, amino, hydroxy, alkoxy, alkylthio, alkylamino, dialkylamino, —NH(CH$_2$)$_p$NH$_2$ wherein p is 1 to 4, —N(CH$_2$CH$_2$NH$_2$)$_2$, diazamino, amidino, guanidino, guanyl, semicarbazone, aryl, heterocycle and heteroaryl, any of which is optionally substituted with one or more of amino, halo, cyano, nitro, hydroxy, —NH(CH$_2$)$_p$NH$_2$ wherein p is 1 to 4, —N(CH$_2$CH$_2$NH$_2$)$_2$, amidino, guanidino, guanyl, aminosulfonyl, aminoalkoxy, aminoalkythio, lower acylamino, or benzyloxycarbonyl, and wherein the heterocycle is selected from the group consisting of piperidinyl, piperazinyl, pyrrolidinyl, pyrazolidinyl, and inorpholinyl; and m is 1, 2 or 3.

37. The method of claim 1, wherein:

x is NR$^8$, y is C=O, and R$^8$ is hydrogen;

one of A$_1$ and A$_2$ is m-phenylene, and the other of A$_1$ and A$_2$ is pyrimidinylene, wherein A$_1$ is substituted with one polar (PL) group and one nonpolar (NPL) group and A$_2$ is unsubstituted;

R$^1$ is a polar group (PL), and R$^2$ is -x-A$_1$-x-R$^1$;

NPL is a nonpolar group —(NR$^{3'}$)$_{q1NPL}$—U$^{NPL}$—(CH$_2$)$_{pNPL}$—(NR$^{3''}$)$_{q2NPL}$—R$^{4'}$, wherein:

R$^{4'}$ is selected from the group consisting of hydrogen, alkyl, alkenyl, alkynyl, cycloalkyl, aryl, and heteroaryl, any of which is optionally substituted with one or more alkyl or halo groups;

U$^{NPL}$ is absent;

pNPL is 0, 1 or 2;

q1NPL and q2NPL are independently 0;

PL is a polar group —(NR$^{5'}$)$_{q1PL}$—U$^{PL}$—(CH$_2$)$_{pPL}$—(NR$^{5'}$)$_{q2PL}$—V, wherein:

U$^{PL}$ is selected from the group consisting of O, S, and —C(=O)—;

pPL is 0 to 4;

q1PL and q2PL are independently 0;

V is selected from the group consisting of amino and guanidino; and m is 1,2 or 3.

38. The method of claim 1, wherein:

x is NR$^8$, y is C=O, and R$^8$ is hydrogen;

one of A$_1$ and A$_2$ is o-, m-, or p-phenylene, and the other of A$_1$ and A$_2$ is heteroarylene, wherein A$_1$ is substituted with one polar (PL) group and one nonpolar (NPL) group and A$_2$ is unsubstituted, and wherein the heteroarylene is selected from the group consisting of pyridinylene, pyrimidinylene, or pyrazinylene;

R$^1$ is a polar group (PL), and R$^2$ is -x-A$_1$-x-R$^1$;

NPL is a nonpolar group —(NR$^{3'}$)$_{q1NPL}$—U$^{NPL}$—(CH$_2$)$_{pNPL}$—(NR$^{3'}$)$_{q2NPL}$—R$^{4'}$, wherein:

R$^{4'}$ is selected from the group consisting of hydrogen, alkyl, alkenyl, alkynyl, cycloalkyl, aryl, and heteroaryl, any of which is optionally substituted with one or more alkyl or halo groups;

U$^{NPL}$ is absent;

pNPL is 0, 1 or 2;

q1NPL and q2NPL are independently 0;

PL is a polar group(NR$^{5'}$)$_{q1PL}$—U$^{PL}$—(CH$_2$)$_{pPL}$—(NR$^{5'}$)$_{q2PL}$—V, wherein:

U$^{PL}$ is selected from the group consisting of O, S, and —C(=O)—;

pPL is 0 to 4;

q1PL and q2PL are independently 0;

V is selected from the group consisting of amino and guanidino; and m is 1,2 or 3.

39. The method of claim 1, comprising systemic administration to the animal of an effective amount of a pharmaceutical composition comprising an amphiphilic oligomer of Formula II, wherein said pharmaceutical composition is administered orally.

40. The method of claim 1, comprising systemic administration to the animal of an effective amount of a pharmaceutical composition comprising an amphiphilic oligomer of Formula II, wherein said administration is parenteral, subcutaneous, intravenous, intramuscular, intraperitoneal, buccal, intravaginal, by ocular routes, by inhalation, by depot injections, or by implants.

41. The method of claim 2, comprising systemic administration to the animal of an effective amount of a pharmaceutical composition comprising an amphiphilic oligomer of Folimla II, wherein said pharmaceutical composition is administered orally.

42. The method of claim 2, comprising systemic administration to the animal of an effective amount of a pharmaceutical composition comprising an amphiphilic oligomer of Formula II, wherein said administration is parenteral, subcutaneous, intravenous, intramuscular, intraperitoneal, buccal, intravaginal, by ocular routes, by inhalation, by depot injections, or by implants.

43. The method of claim 32, comprising systemic administration to the animal of an effective amount of a pharmaceutical composition comprising an amphiphilic oligomer of Formula II, wherein said pharmaceutical composition is administered orally.

44. The method of claim 32, comprising systemic administration to the animal of an effective amount of a pharmaceutical composition comprising an amphiphilic oligomer of Formula II, wherein said administration is parenteral, subcutaneous, intravenous, intramuscular, intraperitoneal, buccal, intravaginal, by ocular routes, by inhalation, by depot injections, or by implants.

* * * * *

UNITED STATES PATENT AND TRADEMARK OFFICE
CERTIFICATE OF CORRECTION

PATENT NO. : 9,241,917 B2
APPLICATION NO. : 10/801951
DATED : January 26, 2016
INVENTOR(S) : DeGrado et al.

It is certified that error appears in the above-identified patent and that said Letters Patent is hereby corrected as shown below:

In the Specification

Column 1, Lines 19-22, replace with the following:
This invention was made with government support under grant number GM065803 awarded by the National Institutes of Health and grant number DMR0079909 awarded by the National Science Foundation. The government has certain rights in the invention.

Signed and Sealed this
Tenth Day of May, 2022

Katherine Kelly Vidal
*Director of the United States Patent and Trademark Office*